US012071481B2

(12) United States Patent
Jefferson et al.

(10) Patent No.: US 12,071,481 B2
(45) Date of Patent: Aug. 27, 2024

(54) ANTI-CD47 ANTIBODIES AND USES THEREOF

(71) Applicant: D-10 Therapeutics, Inc., Torrance, CA (US)

(72) Inventors: Louis Jefferson, Huntersville, NC (US); Metasebya Solomon, Los Angeles, CA (US)

(73) Assignee: D-10 Therapeutics, Inc., Torrance, CA (US)

( * ) Notice: Subject to any disclaimer, the term of this patent is extended or adjusted under 35 U.S.C. 154(b) by 0 days.

(21) Appl. No.: 17/560,763

(22) Filed: Dec. 23, 2021

(65) Prior Publication Data

US 2022/0204613 A1 Jun. 30, 2022

Related U.S. Application Data

(60) Provisional application No. 63/129,716, filed on Dec. 23, 2020.

(51) Int. Cl.
*C07K 16/28* (2006.01)
*A61P 7/00* (2006.01)

(52) U.S. Cl.
CPC ............ *C07K 16/2803* (2013.01); *A61P 7/00* (2018.01); *C07K 2317/24* (2013.01); *C07K 2317/31* (2013.01); *C07K 2317/565* (2013.01); *C07K 2317/92* (2013.01)

(58) Field of Classification Search
CPC ............ C07K 16/2803; C07K 2317/24; C07K 2317/31; C07K 2317/565; C07K 2317/92; A61P 7/00
See application file for complete search history.

(56) References Cited

U.S. PATENT DOCUMENTS

2020/0377593 A1 12/2020 Liu et al.

FOREIGN PATENT DOCUMENTS

| WO | WO-2017053423 A1 | 3/2017 | |
|----|------------------|--------|--|
| WO | WO-2017181033 A1 | 10/2017 | |
| WO | WO-2019034895 A1 | 2/2019 | |
| WO | WO-2019144895 A1 * | 8/2019 | ............. A61P 35/00 |
| WO | WO-2019185717 A1 | 10/2019 | |
| WO | WO-2020043188 A1 | 3/2020 | |
| WO | WO-2020114399 A1 | 6/2020 | |

OTHER PUBLICATIONS

Lazar et al., Mol. Cell. Biol., 8:1247-1252, 1988 (Year: 1988).*
Bowie et al., Science, 1990, 247:1306-1310 (Year: 1990).*
Burgess et al., J. Cell Biol. 111:2129-2138, 1990 (Year: 1990).*
Greenspan et al. 1999, Nature Biotechnology, 17:936-937 (Year: 1999).*
Bork, Genome Research, 2000, 10:398-400 (Year: 2000).*
Brittain, et al. "Integrin-associated protein is an adhesion receptor on sickle red blood cells for immobilized thrombospondin," Blood, Apr. 1, 2001, 97(7):2159-2164.
Edris, B. et al. "Antibody therapy targeting the CD47 protein is effective in a model of aggressive metastatic leiomyosarcoma," PNAS, Apr. 24, 2012, 109(17):6656-6661.
International Search Report and Written Opinion for International Application No. PCT/US2021/065056, mailed Jul. 4, 2022, 27 pages.
Lu, Q., et al. "Potential New Cancer Immunotherapy: Anti-CD47-SIRPα Antibodies", OncoTargets and Therapy, 2020, 13:9323-9331.
Rudikoff, S. et al. "Single amino acid substitution altering antigen-binding specificity", PNAS USA, Mar. 1982, 79:1979-1983.

* cited by examiner

*Primary Examiner* — Vanessa L. Ford
*Assistant Examiner* — Danaya L Middleton
(74) *Attorney, Agent, or Firm* — COOLEY LLP

(57) ABSTRACT

Provided herein are anti-CD47 antibodies and antigen-binding portions thereof and methods for using the same.

22 Claims, 6 Drawing Sheets

Specification includes a Sequence Listing.

```
                         SEQUENCE LISTING

<160> NUMBER OF SEQ ID NOS: 244

<210> SEQ ID NO 1
<211> LENGTH: 417
<212> TYPE: DNA
<213> ORGANISM: Artificial Sequence
<220> FEATURE:
<223> OTHER INFORMATION: Heavy chain variable domain

<400> SEQUENCE: 1
atgaaatgca gctgggttat cttcttcctg atggcagtgg ttacaggggt caattcagag      60
gttcagctgc agcagtctgg gacagaactt gtgaagccag gggcctcagt caggttgtcc     120
tgcacagctt ctggcctcga cattaaagac acctatatgc actggttgaa acagaggcct     180
gaacagggcc tggagtggat tgggaggatt gatcctgcga gtggcaatgc taaacatgac     240
ccgaagttcc agggcaaggc cactataaca tcagacccat cctccaacac agccaattta     300
cagctcacca gcctaacatc tgaggacagt gccgtctatt actgtgcctc cggctatggt     360
cactacgtcg gtgctatgga ctactgggt caaggtacct cagtcaccgt ctcctca        417
```

<210> SEQ ID NO 2
<211> LENGTH: 360
<212> TYPE: DNA
<213> ORGANISM: Artificial Sequence
<220> FEATURE:
<223> OTHER INFORMATION: Heavy chain variable domain

<400> SEQUENCE: 2

```
gaggttcagc tgcagcagtc tgggacagaa cttgtgaagc caggggcctc agtcaggttg    60
tcctgcacag cttctggcct cgacattaaa gacacctata tgcactggtt gaaacagagg   120
cctgaacagg gcctggagtg gattgggagg attgatcctg cgagtggcaa tgctaaacat   180
gacccgaagt tccagggcaa ggccactata acatcagacc catcctccaa cacagccaat   240
ttacagctca ccagcctaac atctgaggac agtgccgtct attactgtgc ctccggctat   300
ggtcactacg tcggtgctat ggactactgg ggtcaaggta cctcagtcac cgtctcctca   360
```

<210> SEQ ID NO 3
<211> LENGTH: 57
<212> TYPE: DNA
<213> ORGANISM: Artificial Sequence
<220> FEATURE:
<223> OTHER INFORMATION: Heavy chain signal sequence

<400> SEQUENCE: 3

```
atgaaatgca gctgggttat cttcttcctg atggcagtgg ttacaggggt caattca       57
```

<210> SEQ ID NO 4
<211> LENGTH: 90
<212> TYPE: DNA
<213> ORGANISM: Artificial Sequence
<220> FEATURE:
<223> OTHER INFORMATION: Heavy chain FR1

<400> SEQUENCE: 4

```
gaggttcagc tgcagcagtc tgggacagaa cttgtgaagc caggggcctc agtcaggttg    60
tcctgcacag cttctggcct cgacattaaa                                     90
```

<210> SEQ ID NO 5
<211> LENGTH: 15
<212> TYPE: DNA
<213> ORGANISM: Artificial Sequence
<220> FEATURE:
<223> OTHER INFORMATION: Heavy chain CDR1

<400> SEQUENCE: 5

```
gacacctata tgcac                                                     15
```

<210> SEQ ID NO 6
<211> LENGTH: 42
<212> TYPE: DNA
<213> ORGANISM: Artificial Sequence
<220> FEATURE:
<223> OTHER INFORMATION: Heavy chain FR2

<400> SEQUENCE: 6

```
tggttgaaac agaggcctga acagggcctg gagtggattg gg                       42
```

<210> SEQ ID NO 7
<211> LENGTH: 51
<212> TYPE: DNA
<213> ORGANISM: Artificial Sequence
<220> FEATURE:

<223> OTHER INFORMATION: Heavy chain CDR2

<400> SEQUENCE: 7
aggattgatc ctgcgagtgg caatgctaaa catgacccga agttccaggg c        51

<210> SEQ ID NO 8
<211> LENGTH: 96
<212> TYPE: DNA
<213> ORGANISM: Artificial Sequence
<220> FEATURE:
<223> OTHER INFORMATION: Heavy chain FR3

<400> SEQUENCE: 8
aaggccacta taacatcaga cccatcctcc aacacagcca atttacagct caccagccta        60
acatctgagg acagtgccgt ctattactgt gcctcc                                 96

<210> SEQ ID NO 9
<211> LENGTH: 33
<212> TYPE: DNA
<213> ORGANISM: Artificial Sequence
<220> FEATURE:
<223> OTHER INFORMATION: Heavy chain CDR3

<400> SEQUENCE: 9
ggctatggtc actacgtcgg tgctatggac tac                            33

<210> SEQ ID NO 10
<211> LENGTH: 33
<212> TYPE: DNA
<213> ORGANISM: Artificial Sequence
<220> FEATURE:
<223> OTHER INFORMATION: Heavy chain FR4

<400> SEQUENCE: 10
tggggtcaag gtacctcagt caccgtctcc tca                            33

<210> SEQ ID NO 11
<211> LENGTH: 139
<212> TYPE: PRT
<213> ORGANISM: Artificial Sequence
<220> FEATURE:
<223> OTHER INFORMATION: Heavy chain variable domain

<400> SEQUENCE: 11

Met Lys Cys Ser Trp Val Ile Phe Phe Leu Met Ala Val Val Thr Gly
1               5                   10                  15

Val Asn Ser Glu Val Gln Leu Gln Gln Ser Gly Thr Glu Leu Val Lys
            20                  25                  30

Pro Gly Ala Ser Val Arg Leu Ser Cys Thr Ala Ser Gly Leu Asp Ile
        35                  40                  45

Lys Asp Thr Tyr Met His Trp Leu Lys Gln Arg Pro Glu Gln Gly Leu
    50                  55                  60

Glu Trp Ile Gly Arg Ile Asp Pro Ala Ser Gly Asn Ala Lys His Asp
65                  70                  75                  80

Pro Lys Phe Gln Gly Lys Ala Thr Ile Thr Ser Asp Pro Ser Ser Asn
                85                  90                  95

Thr Ala Asn Leu Gln Leu Thr Ser Leu Thr Ser Glu Asp Ser Ala Val
            100                 105                 110

Tyr Tyr Cys Ala Ser Gly Tyr Gly His Tyr Val Gly Ala Met Asp Tyr
        115                 120                 125

Trp Gly Gln Gly Thr Ser Val Thr Val Ser Ser
    130                 135

```
              130                 135
```

<210> SEQ ID NO 12
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 12

```
Glu Val Gln Leu Gln Gln Ser Gly Thr Glu Leu Val Lys Pro Gly Ala
1               5                   10                  15

Ser Val Arg Leu Ser Cys Thr Ala Ser Gly Leu Asp Ile Lys Asp Thr
            20                  25                  30

Tyr Met His Trp Leu Lys Gln Arg Pro Glu Gln Gly Leu Glu Trp Ile
        35                  40                  45

Gly Arg Ile Asp Pro Ala Ser Gly Asn Ala Lys His Asp Pro Lys Phe
    50                  55                  60

Gln Gly Lys Ala Thr Ile Thr Ser Asp Pro Ser Ser Asn Thr Ala Asn
65                  70                  75                  80

Leu Gln Leu Thr Ser Leu Thr Ser Glu Asp Ser Ala Val Tyr Tyr Cys
                85                  90                  95

Ala Ser Gly Tyr Gly His Tyr Val Gly Ala Met Asp Tyr Trp Gly Gln
            100                 105                 110

Gly Thr Ser Val Thr Val Ser Ser
        115                 120
```

<210> SEQ ID NO 13
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 13

```
Met Lys Cys Ser Trp Val Ile Phe Phe Leu Met Ala Val Val Thr Gly
1               5                   10                  15

Val Asn Ser
```

<210> SEQ ID NO 14
<211> LENGTH: 30
<212> TYPE: PRT
<213> ORGANISM: Artificial Sequence
<220> FEATURE:
<223> OTHER INFORMATION: Heavy chain FR1

<400> SEQUENCE: 14

```
Glu Val Gln Leu Gln Gln Ser Gly Thr Glu Leu Val Lys Pro Gly Ala
1               5                   10                  15

Ser Val Arg Leu Ser Cys Thr Ala Ser Gly Leu Asp Ile Lys
            20                  25                  30
```

<210> SEQ ID NO 15
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 15

```
Asp Thr Tyr Met His
1               5
```

```
<210> SEQ ID NO 16
<211> LENGTH: 14
<212> TYPE: PRT
<213> ORGANISM: Artificial Sequence
<220> FEATURE:
<223> OTHER INFORMATION: Heavy chain FR2

<400> SEQUENCE: 16

Trp Leu Lys Gln Arg Pro Glu Gln Gly Leu Glu Trp Ile Gly
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 17

Arg Ile Asp Pro Ala Ser Gly Asn Ala Lys His Asp Pro Lys Phe Gln
1               5                   10                  15

Gly

<210> SEQ ID NO 18
<211> LENGTH: 32
<212> TYPE: PRT
<213> ORGANISM: Artificial Sequence
<220> FEATURE:
<223> OTHER INFORMATION: Heavy chain FR3

<400> SEQUENCE: 18

Lys Ala Thr Ile Thr Ser Asp Pro Ser Ser Asn Thr Ala Asn Leu Gln
1               5                   10                  15

Leu Thr Ser Leu Thr Ser Glu Asp Ser Ala Val Tyr Tyr Cys Ala Ser
                20                  25                  30

<210> SEQ ID NO 19
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 19

Gly Tyr Gly His Tyr Val Gly Ala Met Asp Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Heavy chain FR4

<400> SEQUENCE: 20

Trp Gly Gln Gly Thr Ser Val Thr Val Ser Ser
1               5                   10

<210> SEQ ID NO 21
<211> LENGTH: 381
<212> TYPE: DNA
<213> ORGANISM: Artificial Sequence
<220> FEATURE:
<223> OTHER INFORMATION: Light chain variable domain
```

<400> SEQUENCE: 21

```
atgagggtcc ttgctgagct cctggggctg ctgctgttct gcttttagg tgtgagatgt      60 gacatccaga tgaaccagtc tccatccagt ctgtctgcat cccttggaga cacaattacc    120
atcacttgcc atgccagtca gaacattaat gtttggttaa gctggtacca gcagaaacca    180
ggaaatattc ctaaactatt gatctataag gcttccaatt tgcacacagg cgtcccatca    240
aggtttagtg gcagtggatc tggaacaggt ttcacattaa ccatcagcag cctgcagcct    300
gaggacattg ccacttacta ctgtcaacag agtcggaatt atccgtacac gttcggaggg    360
gggaccaagc tggaaataaa a                                              381
```

<210> SEQ ID NO 22
<211> LENGTH: 321
<212> TYPE: DNA
<213> ORGANISM: Artificial Sequence
<220> FEATURE:
<223> OTHER INFORMATION: Light chain variable domain

<400> SEQUENCE: 22

```
gacatccaga tgaaccagtc tccatccagt ctgtctgcat cccttggaga cacaattacc     60
atcacttgcc atgccagtca gaacattaat gtttggttaa gctggtacca gcagaaacca    120
ggaaatattc ctaaactatt gatctataag gcttccaatt tgcacacagg cgtcccatca    180
aggtttagtg gcagtggatc tggaacaggt ttcacattaa ccatcagcag cctgcagcct    240
gaggacattg ccacttacta ctgtcaacag agtcggaatt atccgtacac gttcggaggg    300
gggaccaagc tggaaataaa a                                              321
```

<210> SEQ ID NO 23
<211> LENGTH: 60
<212> TYPE: DNA
<213> ORGANISM: Artificial Sequence
<220> FEATURE:
<223> OTHER INFORMATION: Light chain signal sequence

<400> SEQUENCE: 23

```
atgagggtcc ttgctgagct cctggggctg ctgctgttct gcttttagg tgtgagatgt      60
```

<210> SEQ ID NO 24
<211> LENGTH: 69
<212> TYPE: DNA
<213> ORGANISM: Artificial Sequence
<220> FEATURE:
<223> OTHER INFORMATION: Light chain FR1

<400> SEQUENCE: 24

```
gacatccaga tgaaccagtc tccatccagt ctgtctgcat cccttggaga cacaattacc     60
atcacttgc                                                            69
```

<210> SEQ ID NO 25
<211> LENGTH: 33
<212> TYPE: DNA
<213> ORGANISM: Artificial Sequence
<220> FEATURE:
<223> OTHER INFORMATION: Light chain CDR1

<400> SEQUENCE: 25

```
catgccagtc agaacattaa tgtttggtta agc                                  33
```

<210> SEQ ID NO 26
<211> LENGTH: 45

```
<212> TYPE: DNA
<213> ORGANISM: Artificial Sequence
<220> FEATURE:
<223> OTHER INFORMATION: Light chain FR2

<400> SEQUENCE: 26
tggtaccagc agaaaccagg aaatattcct aaactattga tctat            45

<210> SEQ ID NO 27
<211> LENGTH: 21
<212> TYPE: DNA
<213> ORGANISM: Artificial Sequence
<220> FEATURE:
<223> OTHER INFORMATION: Light chain CDR2

<400> SEQUENCE: 27
aaggcttcca atttgcacac a                                      21

<210> SEQ ID NO 28
<211> LENGTH: 96
<212> TYPE: DNA
<213> ORGANISM: Artificial Sequence
<220> FEATURE:
<223> OTHER INFORMATION: Light chain FR3

<400> SEQUENCE: 28
ggcgtcccat caaggtttag tggcagtgga tctggaacag gtttcacatt aaccatcagc    60
agcctgcagc ctgaggacat tgccacttac tactgt                             96

<210> SEQ ID NO 29
<211> LENGTH: 27
<212> TYPE: DNA
<213> ORGANISM: Artificial Sequence
<220> FEATURE:
<223> OTHER INFORMATION: Light chain CDR3

<400> SEQUENCE: 29
caacagagtc ggaattatcc gtacacg                                27

<210> SEQ ID NO 30
<211> LENGTH: 30
<212> TYPE: DNA
<213> ORGANISM: Artificial Sequence
<220> FEATURE:
<223> OTHER INFORMATION: Light chain FR4

<400> SEQUENCE: 30
ttcggagggg ggaccaagct ggaaataaaa                             30

<210> SEQ ID NO 31
<211> LENGTH: 127
<212> TYPE: PRT
<213> ORGANISM: Artificial Sequence
<220> FEATURE:
<223> OTHER INFORMATION: Light chain variable domain

<400> SEQUENCE: 31

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Lys Pro Gly Asn Ile Pro
```

```
                50                  55                  60
Lys Leu Leu Ile Tyr Lys Ala Ser Asn Leu His Thr Gly Val Pro Ser
 65                  70                  75                  80

Arg Phe Ser Gly Ser Gly Ser Gly Thr Gly Phe Thr Leu Thr Ile Ser
                 85                  90                  95

Ser Leu Gln Pro Glu Asp Ile Ala Thr Tyr Tyr Cys Gln Gln Ser Arg
                100                 105                 110

Asn Tyr Pro Tyr Thr Phe Gly Gly Gly Thr Lys Leu Glu Ile Lys
        115                 120                 125

<210> SEQ ID NO 32
<211> LENGTH: 107
<212> TYPE: PRT
<213> ORGANISM: Artificial Sequence
<220> FEATURE:
<223> OTHER INFORMATION: Light chain variable domain

<400> SEQUENCE: 32

Asp Ile Gln Met Asn Gln Ser Pro Ser Ser Leu Ser Ala Ser Leu Gly
 1               5                  10                  15

Asp Thr Ile Thr Ile Thr Cys His Ala Ser Gln Asn Ile Asn Val Trp
                 20                  25                  30

Leu Ser Trp Tyr Gln Gln Lys Pro Gly Asn Ile Pro Lys Leu Leu Ile
         35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Ser Arg Asn Tyr Pro Tyr
                 85                  90                  95

Thr Phe Gly Gly Gly Thr Lys Leu Glu Ile Lys
                100                 105

<210> SEQ ID NO 33
<211> LENGTH: 20
<212> TYPE: PRT
<213> ORGANISM: Artificial Sequence
<220> FEATURE:
<223> OTHER INFORMATION: Light chain signal sequence

<400> SEQUENCE: 33

Met Arg Val Leu Ala Glu Leu Leu Gly Leu Leu Leu Phe Cys Phe Leu
 1               5                  10                  15

Gly Val Arg Cys
        20

<210> SEQ ID NO 34
<211> LENGTH: 23
<212> TYPE: PRT
<213> ORGANISM: Artificial Sequence
<220> FEATURE:
<223> OTHER INFORMATION: Light chain FR1

<400> SEQUENCE: 34

Asp Ile Gln Met Asn Gln Ser Pro Ser Ser Leu Ser Ala Ser Leu Gly
 1               5                  10                  15

Asp Thr Ile Thr Ile Thr Cys
        20

<210> SEQ ID NO 35
```

```
<211> LENGTH: 11
<212> TYPE: PRT
<213> ORGANISM: Artificial Sequence
<220> FEATURE:
<223> OTHER INFORMATION: Light chain CDR1

<400> SEQUENCE: 35

His Ala Ser Gln Asn Ile Asn Val Trp Leu Ser
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Light chain FR2

<400> SEQUENCE: 36

Trp Tyr Gln Gln Lys Pro Gly Asn Ile Pro Lys Leu Leu Ile Tyr
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Light chain CDR2

<400> SEQUENCE: 37

Lys Ala Ser Asn Leu His Thr
1               5

<210> SEQ ID NO 38
<211> LENGTH: 32
<212> TYPE: PRT
<213> ORGANISM: Artificial Sequence
<220> FEATURE:
<223> OTHER INFORMATION: Light chain FR3

<400> SEQUENCE: 38

Gly Val Pro Ser Arg Phe Ser Gly Ser Gly Ser Gly Thr Gly Phe Thr
1               5                   10                  15

Leu Thr Ile Ser Ser Leu Gln Pro Glu Asp Ile Ala Thr Tyr Tyr Cys
            20                  25                  30

<210> SEQ ID NO 39
<211> LENGTH: 9
<212> TYPE: PRT
<213> ORGANISM: Artificial Sequence
<220> FEATURE:
<223> OTHER INFORMATION: Light chain CDR3

<400> SEQUENCE: 39

Gln Gln Ser Arg Asn Tyr Pro Tyr Thr
1               5

<210> SEQ ID NO 40
<211> LENGTH: 10
<212> TYPE: PRT
<213> ORGANISM: Artificial Sequence
<220> FEATURE:
<223> OTHER INFORMATION: Light chain FR4

<400> SEQUENCE: 40

Phe Gly Gly Gly Thr Lys Leu Glu Ile Lys
1               5                   10
```

-continued

<210> SEQ ID NO 41
<211> LENGTH: 423
<212> TYPE: DNA
<213> ORGANISM: Artificial Sequence
<220> FEATURE:
<223> OTHER INFORMATION: Heavy chain variable domain

<400> SEQUENCE: 41

```
atggaatgga gttggatatt tctctttctc ctgtcaggaa ctgcaggtgt ccactctgag      60
gtccagctgc agcagtctgg acctgaactg gtaaagcctg gggcttcagt gaagctgtcc     120
tgcaaggctt ctggatacac attcactagc tctgttatgc actgggtgaa gcagaagcct     180
gggcagggcc ttgagtggct tggatatatt aatccttata gtgatggaac taaattcaat     240
gagaagtaca aaaccaaggc cacactgact tcagacaaat cctccagcac agcctacatg     300
gaactcagca gcctgacctc tgaggactct gcggtctatt actgtgcaag aggccttata     360
gggactagat acgactcctg gtttgcttac tggggccaag ggactctggt cactgtctct     420
gca                                                                    423
```

<210> SEQ ID NO 42
<211> LENGTH: 366
<212> TYPE: DNA
<213> ORGANISM: Artificial Sequence
<220> FEATURE:
<223> OTHER INFORMATION: Heavy chain variable domain

<400> SEQUENCE: 42

```
gaggtccagc tgcagcagtc tggacctgaa ctggtaaagc tggggcttc agtgaagctg       60
tcctgcaagg cttctggata cacattcact agctctgtta tgcactgggt gaagcagaag     120
cctgggcagg ccttgagtg gcttggatat attaatcctt atagtgatgg aactaaattc      180
aatgagaagt acaaaaccaa ggccacactg acttcagaca aatcctccag cacagcctac     240
atggaactca gcagcctgac ctctgaggac tctgcggtct attactgtgc aagaggcctt     300
atagggacta gatacgactc ctggtttgct tactggggcc aagggactct ggtcactgtc     360
tctgca                                                                 366
```

<210> SEQ ID NO 43
<211> LENGTH: 57
<212> TYPE: DNA
<213> ORGANISM: Artificial Sequence
<220> FEATURE:
<223> OTHER INFORMATION: Heavy chain signal sequence

<400> SEQUENCE: 43

```
atggaatgga gttggatatt tctctttctc ctgtcaggaa ctgcaggtgt ccactct         57
```

<210> SEQ ID NO 44
<211> LENGTH: 90
<212> TYPE: DNA
<213> ORGANISM: Artificial Sequence
<220> FEATURE:
<223> OTHER INFORMATION: Heavy chain FR1

<400> SEQUENCE: 44

```
gaggtccagc tgcagcagtc tggacctgaa ctggtaaagc tggggcttc agtgaagctg       60
tcctgcaagg cttctggata cacattcact                                       90
```

<210> SEQ ID NO 45
<211> LENGTH: 15

```
<212> TYPE: DNA
<213> ORGANISM: Artificial Sequence
<220> FEATURE:
<223> OTHER INFORMATION: Heavy chain CDR1

<400> SEQUENCE: 45
agctctgtta tgcac                                                       15

<210> SEQ ID NO 46
<211> LENGTH: 42
<212> TYPE: DNA
<213> ORGANISM: Artificial Sequence
<220> FEATURE:
<223> OTHER INFORMATION: Heavy chain FR2

<400> SEQUENCE: 46
tgggtgaagc agaagcctgg gcagggcctt gagtggcttg ga                         42

<210> SEQ ID NO 47
<211> LENGTH: 51
<212> TYPE: DNA
<213> ORGANISM: Artificial Sequence
<220> FEATURE:
<223> OTHER INFORMATION: Heavy chain CDR2

<400> SEQUENCE: 47
tatattaatc cttatagtga tggaactaaa ttcaatgaga agtacaaaac c               51

<210> SEQ ID NO 48
<211> LENGTH: 96
<212> TYPE: DNA
<213> ORGANISM: Artificial Sequence
<220> FEATURE:
<223> OTHER INFORMATION: Heavy chain FR3

<400> SEQUENCE: 48
aaggccacac tgacttcaga caaatcctcc agcacagcct acatggaact cagcagcctg      60
acctctgagg actctgcggt ctattactgt gcaaga                                96

<210> SEQ ID NO 49
<211> LENGTH: 39
<212> TYPE: DNA
<213> ORGANISM: Artificial Sequence
<220> FEATURE:
<223> OTHER INFORMATION: Heavy chain CDR3

<400> SEQUENCE: 49
ggccttatag ggactagata cgactcctgg tttgcttac                             39

<210> SEQ ID NO 50
<211> LENGTH: 33
<212> TYPE: DNA
<213> ORGANISM: Artificial Sequence
<220> FEATURE:
<223> OTHER INFORMATION: Heavy chain FR4

<400> SEQUENCE: 50
tggggccaag ggactctggt cactgtctct gca                                   33

<210> SEQ ID NO 51
<211> LENGTH: 141
<212> TYPE: PRT
<213> ORGANISM: Artificial Sequence
<220> FEATURE:
<223> OTHER INFORMATION: Heavy chain variable domain
```

<400> SEQUENCE: 51

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Ser Ser Val Met His Trp Val Lys Gln Lys Pro Gly Gln Gly Leu
    50                  55                  60

Glu Trp Leu Gly Tyr Ile Asn Pro Tyr Ser Asp Gly Thr Lys Phe Asn
65              70                  75                  80

Glu Lys Tyr Lys Thr Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ala
    130                 135                 140

<210> SEQ ID NO 52
<211> LENGTH: 122
<212> TYPE: PRT
<213> ORGANISM: Artificial Sequence
<220> FEATURE:
<223> OTHER INFORMATION: Heavy chain variable domain

<400> SEQUENCE: 52

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Val Met His Trp Val Lys Gln Lys Pro Gly Gln Gly Leu Glu Trp Leu
        35                  40                  45

Gly Tyr Ile Asn Pro Tyr Ser Asp Gly Thr Lys Phe Asn Glu Lys Tyr
    50                  55                  60

Lys Thr Lys Ala Thr Leu Thr Ser Asp Lys Ser Ser Ser Thr Ala Tyr
65              70                  75                  80

Met Glu Leu Ser Ser Leu Thr Ser Glu Asp Ser Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ala
        115                 120

<210> SEQ ID NO 53
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 53

Met Glu Trp Ser Trp Ile Phe Leu Phe Leu Leu Ser Gly Thr Ala Gly
1               5                   10                  15

Val His Ser

<210> SEQ ID NO 54
<211> LENGTH: 30
<212> TYPE: PRT
<213> ORGANISM: Artificial Sequence
<220> FEATURE:
<223> OTHER INFORMATION: Heavy chain FR1

<400> SEQUENCE: 54

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr
            20                  25                  30

<210> SEQ ID NO 55
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 55

Ser Ser Val Met His
1               5

<210> SEQ ID NO 56
<211> LENGTH: 14
<212> TYPE: PRT
<213> ORGANISM: Artificial Sequence
<220> FEATURE:
<223> OTHER INFORMATION: Heavy chain FR2

<400> SEQUENCE: 56

Trp Val Lys Gln Lys Pro Gly Gln Gly Leu Glu Trp Leu Gly
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 57

Tyr Ile Asn Pro Tyr Ser Asp Gly Thr Lys Phe Asn Glu Lys Tyr Lys
1               5                   10                  15

Thr

<210> SEQ ID NO 58
<211> LENGTH: 32
<212> TYPE: PRT
<213> ORGANISM: Artificial Sequence
<220> FEATURE:
<223> OTHER INFORMATION: Heavy chain FR3

<400> SEQUENCE: 58

Lys Ala Thr Leu Thr Ser Asp Lys Ser Ser Ser Thr Ala Tyr Met Glu
1               5                   10                  15

Leu Ser Ser Leu Thr Ser Glu Asp Ser Ala Val Tyr Tyr Cys Ala Arg
            20                  25                  30

<210> SEQ ID NO 59
<211> LENGTH: 13
<212> TYPE: PRT
<213> ORGANISM: Artificial Sequence
<220> FEATURE:
<223> OTHER INFORMATION: Heavy chain CDR3

<400> SEQUENCE: 59

Gly Leu Ile Gly Thr Arg Tyr Asp Ser Trp Phe Ala Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Heavy chain FR4

<400> SEQUENCE: 60

Trp Gly Gln Gly Thr Leu Val Thr Val Ser Ala
1               5                   10

<210> SEQ ID NO 61
<211> LENGTH: 378
<212> TYPE: DNA
<213> ORGANISM: Artificial Sequence
<220> FEATURE:
<223> OTHER INFORMATION: Light chain variable domain

<400> SEQUENCE: 61
atgtcctctg ctcagttcct tggtctcctg ttgctctgtt ttcaaggtat cagatgtgat      60
atccagatga cacagaatgc atcctccctg tctgcctctc tgggagacag agtcaccatc     120
agttgcagga caagtcagga cattaacaat tatttaaatt ggtatcagca gaaaccagat     180
ggaactgtta aactcctgat ctattacaca tcaagattac actcaggagt cccatcaagg     240
ttcagtggca gtgggtctgg aacagattat tctctctcca ttcgctacct ggagcaagaa     300
gatattgcca cttactttg ccaccagggt aatacacttc cgtacacgtt cggaggggg     360 accaaactgg aaataaaa                                                   378

<210> SEQ ID NO 62
<211> LENGTH: 321
<212> TYPE: DNA
<213> ORGANISM: Artificial Sequence
<220> FEATURE:
<223> OTHER INFORMATION: Light chain variable domain

<400> SEQUENCE: 62
gatatccaga tgacacagaa tgcatcctcc ctgtctgcct ctctgggaga cagagtcacc      60
atcagttgca ggacaagtca ggacattaac aattatttaa attggtatca gcagaaacca     120
gatggaactg ttaaactcct gatctattac acatcaagat acactcagg agtcccatca      180 aggttcagtg gcagtgggtc tggaacagat tattctctct ccattcgcta cctggagcaa     240
gaagatattg ccacttactt tgccaccag ggtaatacac ttccgtacac gttcggaggg      300
gggaccaaac tggaaataaa a                                               321

<210> SEQ ID NO 63
<211> LENGTH: 57
<212> TYPE: DNA
<213> ORGANISM: Artificial Sequence
<220> FEATURE:
<223> OTHER INFORMATION: Light chain signal sequence

<400> SEQUENCE: 63
atgtcctctg ctcagttcct tggtctcctg ttgctctgtt ttcaaggtat cagatgt        57

<210> SEQ ID NO 64

```
<211> LENGTH: 69
<212> TYPE: DNA
<213> ORGANISM: Artificial Sequence
<220> FEATURE:
<223> OTHER INFORMATION: Light chain FR1

<400> SEQUENCE: 64
gatatccaga tgacacagaa tgcatcctcc ctgtctgcct ctctgggaga cagagtcacc    60
atcagttgc                                                            69

<210> SEQ ID NO 65
<211> LENGTH: 33
<212> TYPE: DNA
<213> ORGANISM: Artificial Sequence
<220> FEATURE:
<223> OTHER INFORMATION: Light chain CDR1

<400> SEQUENCE: 65
aggacaagtc aggacattaa caattattta aat                                 33

<210> SEQ ID NO 66
<211> LENGTH: 45
<212> TYPE: DNA
<213> ORGANISM: Artificial Sequence
<220> FEATURE:
<223> OTHER INFORMATION: Light chain FR2

<400> SEQUENCE: 66
tggtatcagc agaaaccaga tggaactgtt aaactcctga tctat                    45

<210> SEQ ID NO 67
<211> LENGTH: 21
<212> TYPE: DNA
<213> ORGANISM: Artificial Sequence
<220> FEATURE:
<223> OTHER INFORMATION: Light chain CDR2

<400> SEQUENCE: 67
tacacatcaa gattacactc a                                              21

<210> SEQ ID NO 68
<211> LENGTH: 96
<212> TYPE: DNA
<213> ORGANISM: Artificial Sequence
<220> FEATURE:
<223> OTHER INFORMATION: Light chain FR3

<400> SEQUENCE: 68
ggagtcccat caaggttcag tggcagtggg tctggaacag attattctct ctccattcgc    60
tacctggagc aagaagatat tgccacttac ttttgc                              96

<210> SEQ ID NO 69
<211> LENGTH: 27
<212> TYPE: DNA
<213> ORGANISM: Artificial Sequence
<220> FEATURE:
<223> OTHER INFORMATION: Light chain CDR3

<400> SEQUENCE: 69
caccagggta atacacttcc gtacacg                                        27

<210> SEQ ID NO 70
<211> LENGTH: 30
<212> TYPE: DNA
<213> ORGANISM: Artificial Sequence
```

```
<220> FEATURE:
<223> OTHER INFORMATION: Light chain FR4

<400> SEQUENCE: 70
ttcggagggg ggaccaaact ggaaataaaa                                                  30

<210> SEQ ID NO 71
<211> LENGTH: 126
<212> TYPE: PRT
<213> ORGANISM: Artificial Sequence
<220> FEATURE:
<223> OTHER INFORMATION: Light chain variable domain

<400> SEQUENCE: 71

Met Ser Ser Ala Gln Phe Leu Gly Leu Leu Leu Cys Phe Gln Gly
1               5                   10                  15

Ile Arg Cys Asp Ile Gln Met Thr Gln Asn Ala Ser Ser Leu Ser Ala
            20                  25                  30

Ser Leu Gly Asp Arg Val Thr Ile Ser Cys Arg Thr Ser Gln Asp Ile
        35                  40                  45

Asn Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Ser Ile Arg Tyr
                85                  90                  95

Leu Glu Gln Glu Asp Ile Ala Thr Tyr Phe Cys His Gln Gly Asn Thr
            100                 105                 110

Leu Pro Tyr Thr Phe Gly Gly Gly Thr Lys Leu Glu Ile Lys
        115                 120                 125

<210> SEQ ID NO 72
<211> LENGTH: 107
<212> TYPE: PRT
<213> ORGANISM: Artificial Sequence
<220> FEATURE:
<223> OTHER INFORMATION: Light chain variable domain

<400> SEQUENCE: 72

Asp Ile Gln Met Thr Gln Asn Ala Ser Ser Leu Ser Ala Ser Leu Gly
1               5                   10                  15

Asp Arg Val Thr Ile Ser Cys Arg Thr Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Ser Ile Arg Tyr Leu Glu Gln
65                  70                  75                  80

Glu Asp Ile Ala Thr Tyr Phe Cys His Gln Gly Asn Thr Leu Pro Tyr
                85                  90                  95

Thr Phe Gly Gly Gly Thr Lys Leu Glu Ile Lys
            100                 105

<210> SEQ ID NO 73
<211> LENGTH: 19
<212> TYPE: PRT
<213> ORGANISM: Artificial Sequence
<220> FEATURE:
<223> OTHER INFORMATION: Light chain signal sequence
```

```
<400> SEQUENCE: 73

Met Ser Ser Ala Gln Phe Leu Gly Leu Leu Leu Leu Cys Phe Gln Gly
1               5                   10                  15

Ile Arg Cys

<210> SEQ ID NO 74
<211> LENGTH: 23
<212> TYPE: PRT
<213> ORGANISM: Artificial Sequence
<220> FEATURE:
<223> OTHER INFORMATION: Light chain FR1

<400> SEQUENCE: 74

Asp Ile Gln Met Thr Gln Asn Ala Ser Ser Leu Ser Ala Ser Leu Gly
1               5                   10                  15

Asp Arg Val Thr Ile Ser Cys
            20

<210> SEQ ID NO 75
<211> LENGTH: 11
<212> TYPE: PRT
<213> ORGANISM: Artificial Sequence
<220> FEATURE:
<223> OTHER INFORMATION: Light chain CDR1

<400> SEQUENCE: 75

Arg Thr Ser Gln Asp Ile Asn Asn Tyr Leu Asn
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Light chain FR2

<400> SEQUENCE: 76

Trp Tyr Gln Gln Lys Pro Asp Gly Thr Val Lys Leu Leu Ile Tyr
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: Light chain CDR2

<400> SEQUENCE: 77

Tyr Thr Ser Arg Leu His Ser
1               5

<210> SEQ ID NO 78
<211> LENGTH: 32
<212> TYPE: PRT
<213> ORGANISM: Artificial Sequence
<220> FEATURE:
<223> OTHER INFORMATION: Light chain FR3

<400> SEQUENCE: 78

Gly Val Pro Ser Arg Phe Ser Gly Ser Gly Ser Gly Thr Asp Tyr Ser
1               5                   10                  15

Leu Ser Ile Arg Tyr Leu Glu Gln Glu Asp Ile Ala Thr Tyr Phe Cys
            20                  25                  30
```

```
<210> SEQ ID NO 79
<211> LENGTH: 8
<212> TYPE: PRT
<213> ORGANISM: Artificial Sequence
<220> FEATURE:
<223> OTHER INFORMATION: Light chain CDR3

<400> SEQUENCE: 79

His Gln Gly Asn Thr Leu Pro Tyr
1               5

<210> SEQ ID NO 80
<211> LENGTH: 323
<212> TYPE: PRT
<213> ORGANISM: Homo sapiens

<400> SEQUENCE: 80

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
            50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
                115                 120                 125

Leu Lys Tyr Arg Val Val Ser Trp Phe Ser Pro Asn Glu Asn Ile Leu
            130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Lys Thr Ile Gln Pro Pro Arg Lys
                290                 295                 300

Ala Val Glu Glu Pro Leu Asn Ala Phe Lys Glu Ser Lys Gly Met Met
```

Asn Asp Glu

<210> SEQ ID NO 81
<211> LENGTH: 417
<212> TYPE: DNA
<213> ORGANISM: Artificial Sequence
<220> FEATURE:
<223> OTHER INFORMATION: Heavy chain variable domain

<400> SEQUENCE: 81

```
atggaatgga gttggatatt tctctttctc ctgtcaggaa ctgcaggtgt ccactctgag    60
gtccagctgc agcagtctgg acctgagctg gtacagcctg ggcttcagt  gaggatgtcc   120
tgcaaggctt ctggatacac gttcactagc tatgttatgc actgggtgaa gcagaagcct   180
gggcagggcc ttgagtggat tggatatatt aatccttaca atgatggtac taagtataat   240
gagaagttca aggcaaggc  cacactgact tcagacaaat cctccagcac agcctacatg   300
gagctcagca gcctgacctc tgaggactct gcggtctatt actgtgcaag aggaaggaat   360
aggtacgacg gttggtttac ttactggggc caagggactc tggtcactgt ctctgca      417
```

<210> SEQ ID NO 82
<211> LENGTH: 360
<212> TYPE: DNA
<213> ORGANISM: Artificial Sequence
<220> FEATURE:
<223> OTHER INFORMATION: Heavy chain variable domain

<400> SEQUENCE: 82

```
gaggtccagc tgcagcagtc tggacctgag ctggtacagc ctggggcttc agtgaggatg    60
tcctgcaagg cttctggata cacgttcact agctatgtta tgcactgggt gaagcagaag   120
cctgggcagg gccttgagtg gattggatat attaatcctt acaatgatgg tactaagtat   180
aatgagaagt tcaaaggcaa ggccacactg acttcagaca aatcctccag cacagcctac   240
atggagctca gcagcctgac ctctgaggac tctgcggtct attactgtgc aagaggaagg   300
aataggtacg acggttggtt tacttactgg ggccaaggga ctctggtcac tgtctctgca   360
```

<210> SEQ ID NO 83
<211> LENGTH: 323
<212> TYPE: PRT
<213> ORGANISM: Macaca fascicularis

<400> SEQUENCE: 83

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Ala Pro Ala Asn
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

```
Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Met Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys
        290                 295                 300

Ala Val Glu Glu Pro Leu Asn Ala Phe Lys Glu Ser Lys Gly Met Met
305                 310                 315                 320

Asn Asp Glu

<210> SEQ ID NO 84
<211> LENGTH: 90
<212> TYPE: DNA
<213> ORGANISM: Artificial Sequence
<220> FEATURE:
<223> OTHER INFORMATION: Heavy chain FR1

<400> SEQUENCE: 84
gaggtccagc tgcagcagtc tggacctgag ctggtacagc ctggggcttc agtgaggatg    60
tcctgcaagg cttctggata cacgttcact                                     90

<210> SEQ ID NO 85
<211> LENGTH: 15
<212> TYPE: DNA
<213> ORGANISM: Artificial Sequence
<220> FEATURE:
<223> OTHER INFORMATION: Heavy chain CDR1

<400> SEQUENCE: 85
agctatgtta tgcac                                                     15

<210> SEQ ID NO 86
<211> LENGTH: 42
<212> TYPE: DNA
<213> ORGANISM: Artificial Sequence
<220> FEATURE:
<223> OTHER INFORMATION: Heavy chain FR2

<400> SEQUENCE: 86
tgggtgaagc agaagcctgg gcagggcctt gagtggattg ga                       42
```

<210> SEQ ID NO 87
<211> LENGTH: 51
<212> TYPE: DNA
<213> ORGANISM: Artificial Sequence
<220> FEATURE:
<223> OTHER INFORMATION: Heavy chain CDR2

<400> SEQUENCE: 87
tatattaatc cttacaatga tggtactaag tataatgaga agttcaaagg c          51

<210> SEQ ID NO 88
<211> LENGTH: 96
<212> TYPE: DNA
<213> ORGANISM: Artificial Sequence
<220> FEATURE:
<223> OTHER INFORMATION: Heavy chain FR3

<400> SEQUENCE: 88
aaggccacac tgacttcaga caaatcctcc agcacagcct acatggagct cagcagcctg    60
acctctgagg actctgcggt ctattactgt gcaaga                             96

<210> SEQ ID NO 89
<211> LENGTH: 33
<212> TYPE: DNA
<213> ORGANISM: Artificial Sequence
<220> FEATURE:
<223> OTHER INFORMATION: Heavy chain CDR3

<400> SEQUENCE: 89
ggaaggaata ggtacgacgg ttggtttact tac                               33

<210> SEQ ID NO 90
<211> LENGTH: 33
<212> TYPE: DNA
<213> ORGANISM: Artificial Sequence
<220> FEATURE:
<223> OTHER INFORMATION: Heavy chain FR4

<400> SEQUENCE: 90
tggggccaag ggactctggt cactgtctct gca                               33

<210> SEQ ID NO 91
<211> LENGTH: 139
<212> TYPE: PRT
<213> ORGANISM: Artificial Sequence
<220> FEATURE:
<223> OTHER INFORMATION: Heavy chain variable domain

<400> SEQUENCE: 91

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Gln
            20                  25                  30

Pro Gly Ala Ser Val Arg Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser
                85                  90                  95

Thr Ala Tyr Met Glu Leu Ser Ser Leu Thr Ser Glu Asp Ser Ala Val 100                 105                 110
Tyr Tyr Cys Ala Arg Gly Arg Asn Arg Tyr Asp Gly Trp Phe Thr Tyr
        115                 120                 125
Trp Gly Gln Gly Thr Leu Val Thr Val Ser Ala
    130                 135

<210> SEQ ID NO 92
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 92

Glu Val Gln Leu Gln Gln Ser Gly Pro Glu Leu Val Gln Pro Gly Ala
1               5                   10                  15

Ser Val Arg Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Arg Asn Arg Tyr Asp Gly Trp Phe Thr Tyr Trp Gly Gln
            100                 105                 110

Gly Thr Leu Val Thr Val Ser Ala
        115                 120

<210> SEQ ID NO 93
<211> LENGTH: 30
<212> TYPE: PRT
<213> ORGANISM: Artificial Sequence
<220> FEATURE:
<223> OTHER INFORMATION: Heavy chain FR1

<400> SEQUENCE: 93

Glu Val Gln Leu Gln Gln Ser Gly Pro Glu Leu Val Gln Pro Gly Ala
1               5                   10                  15

Ser Val Arg Met Ser Cys Lys Ala Ser Gly Tyr Thr Phe Thr
            20                  25                  30

<210> SEQ ID NO 94
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 94

Ser Tyr Val Met His
1               5

<210> SEQ ID NO 95
<211> LENGTH: 14
<212> TYPE: PRT
<213> ORGANISM: Artificial Sequence
<220> FEATURE:
<223> OTHER INFORMATION: Heavy chain FR2

<400> SEQUENCE: 95

Trp Val Lys Gln Lys Pro Gly Gln Gly Leu Glu Trp Ile Gly
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 96

Tyr Ile Asn Pro Tyr Asn Asp Gly Thr Lys Tyr Asn Glu Lys Phe Lys
1               5                   10                  15
Gly

<210> SEQ ID NO 97
<211> LENGTH: 15
<212> TYPE: PRT
<213> ORGANISM: Artificial Sequence
<220> FEATURE:
<223> OTHER INFORMATION: AA Junction

<400> SEQUENCE: 97

Cys Ala Ser Gly Tyr Gly His Tyr Val Gly Ala Met Asp Tyr Trp
1               5                   10                  15

<210> SEQ ID NO 98
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 98

Gly Arg Asn Arg Tyr Asp Gly Trp Phe Thr Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: AA Junction

<400> SEQUENCE: 99

Cys Gln Gln Ser Arg Asn Tyr Pro Tyr Thr Phe
1               5                   10

<210> SEQ ID NO 100
<211> LENGTH: 378
<212> TYPE: DNA
<213> ORGANISM: Artificial Sequence
<220> FEATURE:
<223> OTHER INFORMATION: Light chain variable domain

<400> SEQUENCE: 100
atgtcctctg ctcagttcct tggtctcctg ttgctctgtt ttcaaggtat cagatgtgat      60
atccagatga cacagactac attctccctg tctgcctctc tgggagacag agtcaccatc    120
agttgcaggg caagtcagga cattagtaat tatttaaact ggtatcagca gaaaccagat    180
ggaactgtta aactcctgat ctactacaca tcaagattac actcaggagt cccatcaagg    240
ttcagtggca gtgggtctgg aacagattat tctctcacca ttagcaacct ggagcaagaa    300

```
gatattgcca cttactttg ccaacaggt aatacgcttc cgtacacgtt cggagggggg      360
accaagctgg aaataaaa                                                   378
```

<210> SEQ ID NO 101
<211> LENGTH: 321
<212> TYPE: DNA
<213> ORGANISM: Artificial Sequence
<220> FEATURE:
<223> OTHER INFORMATION: Light chain variable domain

<400> SEQUENCE: 101

```
gatatccaga tgacacagac tacattctcc ctgtctgcct ctctgggaga cagagtcacc       60
atcagttgca gggcaagtca ggacattagt aattatttaa actggtatca gcagaaacca      120
gatggaactg ttaaactcct gatctactac acatcaagat acactcagg agtcccatca       180 aggttcagtg gcagtgggtc tggaacagat tattctctca ccattagcaa cctggagcaa      240
gaagatattg ccacttactt ttgccaacag gtaatacgc ttccgtacac gttcggaggg       300
gggaccaagc tggaaataaa a                                                321
```

<210> SEQ ID NO 102
<211> LENGTH: 57
<212> TYPE: DNA
<213> ORGANISM: Artificial Sequence
<220> FEATURE:
<223> OTHER INFORMATION: Light chain signal sequence

<400> SEQUENCE: 102

```
atgtcctctg ctcagttcct tggtctcctg ttgctctgtt ttcaaggtat cagatgt          57
```

<210> SEQ ID NO 103
<211> LENGTH: 69
<212> TYPE: DNA
<213> ORGANISM: Artificial Sequence
<220> FEATURE:
<223> OTHER INFORMATION: Light chain FR1

<400> SEQUENCE: 103

```
gatatccaga tgacacagac tacattctcc ctgtctgcct ctctgggaga cagagtcacc       60
atcagttgc                                                              69
```

<210> SEQ ID NO 104
<211> LENGTH: 33
<212> TYPE: DNA
<213> ORGANISM: Artificial Sequence
<220> FEATURE:
<223> OTHER INFORMATION: Light chain CDR1

<400> SEQUENCE: 104

```
agggcaagtc aggacattag taattattta aac                                    33
```

<210> SEQ ID NO 105
<211> LENGTH: 45
<212> TYPE: DNA
<213> ORGANISM: Artificial Sequence
<220> FEATURE:
<223> OTHER INFORMATION: Light chain FR2

<400> SEQUENCE: 105

```
tggtatcagc agaaaccaga tggaactgtt aaactcctga tctac                       45
```

<210> SEQ ID NO 106
<211> LENGTH: 96

```
<212> TYPE: DNA
<213> ORGANISM: Artificial Sequence
<220> FEATURE:
<223> OTHER INFORMATION: Light chain FR3

<400> SEQUENCE: 106
ggagtcccat caaggttcag tggcagtggg tctggaacag attattctct caccattagc      60
aacctggagc aagaagatat tgccacttac ttttgc                               96

<210> SEQ ID NO 107
<211> LENGTH: 27
<212> TYPE: DNA
<213> ORGANISM: Artificial Sequence
<220> FEATURE:
<223> OTHER INFORMATION: Light chain CDR3

<400> SEQUENCE: 107
caacagggta atacgcttcc gtacacg                                         27

<210> SEQ ID NO 108
<211> LENGTH: 30
<212> TYPE: DNA
<213> ORGANISM: Artificial Sequence
<220> FEATURE:
<223> OTHER INFORMATION: Light chain FR4

<400> SEQUENCE: 108
ttcggagggg ggaccaagct ggaaataaaa                                      30

<210> SEQ ID NO 109
<211> LENGTH: 126
<212> TYPE: PRT
<213> ORGANISM: Artificial Sequence
<220> FEATURE:
<223> OTHER INFORMATION: Light chain variable domain

<400> SEQUENCE: 109
```

Met Ser Ser Ala Gln Phe Leu Gly Leu Leu Leu Leu Cys Phe Gln Gly
1               5                   10                  15

Ile Arg Cys Asp Ile Gln Met Thr Gln Thr Thr Phe Ser Leu Ser Ala
            20                  25                  30

Ser Leu Gly Asp Arg Val Thr Ile Ser Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Lys
        115                 120                 125

```
<210> SEQ ID NO 110
<211> LENGTH: 107
<212> TYPE: PRT
<213> ORGANISM: Artificial Sequence
<220> FEATURE:
<223> OTHER INFORMATION: Light chain variable domain

<400> SEQUENCE: 110
```

```
Asp Ile Gln Met Thr Gln Thr Thr Phe Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 111
<211> LENGTH: 23
<212> TYPE: PRT
<213> ORGANISM: Artificial Sequence
<220> FEATURE:
<223> OTHER INFORMATION: Light chain FR1

<400> SEQUENCE: 111

Asp Ile Gln Met Thr Gln Thr Thr Phe Ser Leu Ser Ala Ser Leu Gly
1               5                   10                  15

Asp Arg Val Thr Ile Ser Cys
            20

<210> SEQ ID NO 112
<211> LENGTH: 11
<212> TYPE: PRT
<213> ORGANISM: Artificial Sequence
<220> FEATURE:
<223> OTHER INFORMATION: Light chain CDR1

<400> SEQUENCE: 112

Arg Ala Ser Gln Asp Ile Ser Asn Tyr Leu Asn
1               5                   10

<210> SEQ ID NO 113
<211> LENGTH: 15
<212> TYPE: PRT
<213> ORGANISM: Artificial Sequence
<220> FEATURE:
<223> OTHER INFORMATION: Light chain FR2

<400> SEQUENCE: 113

Trp Tyr Gln Gln Lys Pro Asp Gly Thr Val Lys Leu Leu Ile Tyr
1               5                   10                  15

<210> SEQ ID NO 114
<211> LENGTH: 32
<212> TYPE: PRT
<213> ORGANISM: Artificial Sequence
<220> FEATURE:
<223> OTHER INFORMATION: Light chain FR3

<400> SEQUENCE: 114

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30
```

```
<210> SEQ ID NO 115
<211> LENGTH: 9
<212> TYPE: PRT
<213> ORGANISM: Artificial Sequence
<220> FEATURE:
<223> OTHER INFORMATION: Light chain CDR3

<400> SEQUENCE: 115

Gln Gln Gly Asn Thr Leu Pro Tyr Thr
1               5

<210> SEQ ID NO 116
<211> LENGTH: 17
<212> TYPE: PRT
<213> ORGANISM: Artificial Sequence
<220> FEATURE:
<223> OTHER INFORMATION: AA Junction

<400> SEQUENCE: 116

Cys Ala Arg Gly Leu Ile Gly Thr Arg Tyr Asp Ser Trp Phe Ala Tyr
1               5                   10                  15

Trp

<210> SEQ ID NO 117
<211> LENGTH: 423
<212> TYPE: DNA
<213> ORGANISM: Artificial Sequence
<220> FEATURE:
<223> OTHER INFORMATION: Heavy chain variable domain

<400> SEQUENCE: 117
atggaatgga gttggatatt tctctttctc ctgtcaggaa ctgcaggtgt ccactctgag     60
gtccagctgc agcagtctgg acctgagctg gtaaagcctg gggcttcagt gaagatgtcc    120
tgcaaggctt ctggatacac attcactagc tatgttatgc actgggtgaa gcagaagcct    180
gggcagggcc ttgagtggat gggatatatt aatccttaca atgatggtac taagtacaat    240
gagaagttca aggcaaggc cacactgact tcagacaaat cctccaacac agcctacatg     300
gagttcagca gcctgacctc tgaggactct gcggtctatt actgtgcaag aatagactac    360
ggtactatcc acacgtcctg gtttgcttac tggggccaag gactctggt cactgtctct     420 gca                                                                  423

<210> SEQ ID NO 118
<211> LENGTH: 366
<212> TYPE: DNA
<213> ORGANISM: Artificial Sequence
<220> FEATURE:
<223> OTHER INFORMATION: Heavy chain variable domain

<400> SEQUENCE: 118
gaggtccagc tgcagcagtc tggacctgag ctggtaaagc ctggggcttc agtgaagatg     60
tcctgcaagg cttctggata cacattcact agctatgtta tgcactgggt gaagcagaag    120
cctgggcagg ccttgagtg atgggatat attaatcctt acaatgatgg tactaagtac      180
aatgagaagt tcaaaggcaa ggccacactg acttcagaca atcctccaa cacagcctac     240 atggagttca gcagcctgac ctctgaggac tctgcggtct attactgtgc aagaatagac    300
tacggtacta tccacacgtc ctggtttgct tactggggcc aagggactct ggtcactgtc    360
tctgca                                                               366
```

-continued

```
<210> SEQ ID NO 119
<211> LENGTH: 11
<212> TYPE: PRT
<213> ORGANISM: Artificial Sequence
<220> FEATURE:
<223> OTHER INFORMATION: AA Junction

<400> SEQUENCE: 119

Cys His Gln Gly Asn Thr Leu Pro Tyr Thr Phe
1               5                   10

<210> SEQ ID NO 120
<211> LENGTH: 90
<212> TYPE: DNA
<213> ORGANISM: Artificial Sequence
<220> FEATURE:
<223> OTHER INFORMATION: Heavy chain FR1

<400> SEQUENCE: 120
gaggtccagc tgcagcagtc tggacctgag ctggtaaagc ctggggcttc agtgaagatg       60
tcctgcaagg cttctggata cacattcact                                       90

<210> SEQ ID NO 121
<211> LENGTH: 42
<212> TYPE: DNA
<213> ORGANISM: Artificial Sequence
<220> FEATURE:
<223> OTHER INFORMATION: Heavy chain FR2

<400> SEQUENCE: 121
tgggtgaagc agaagcctgg gcagggcctt gagtggatgg ga                         42

<210> SEQ ID NO 122
<211> LENGTH: 51
<212> TYPE: DNA
<213> ORGANISM: Artificial Sequence
<220> FEATURE:
<223> OTHER INFORMATION: Heavy chain CDR2

<400> SEQUENCE: 122
tatattaatc cttacaatga tggtactaag tacaatgaga agttcaaagg c                51

<210> SEQ ID NO 123
<211> LENGTH: 96
<212> TYPE: DNA
<213> ORGANISM: Artificial Sequence
<220> FEATURE:
<223> OTHER INFORMATION: Heavy chain FR3

<400> SEQUENCE: 123
aaggccacac tgacttcaga caaatcctcc aacacagcct acatggagtt cagcagcctg       60
acctctgagg actctgcggt ctattactgt gcaaga                                96

<210> SEQ ID NO 124
<211> LENGTH: 39
<212> TYPE: DNA
<213> ORGANISM: Artificial Sequence
<220> FEATURE:
<223> OTHER INFORMATION: Heavy chain CDR3

<400> SEQUENCE: 124
atagactacg gtactatcca cacgtcctgg tttgcttac                             39

<210> SEQ ID NO 125
<211> LENGTH: 33
```

-continued

```
<212> TYPE: DNA
<213> ORGANISM: Artificial Sequence
<220> FEATURE:
<223> OTHER INFORMATION: Heavy chain FR4

<400> SEQUENCE: 125
tggggccaag ggactctggt cactgtctct gca                                     33

<210> SEQ ID NO 126
<211> LENGTH: 141
<212> TYPE: PRT
<213> ORGANISM: Artificial Sequence
<220> FEATURE:
<223> OTHER INFORMATION: Heavy chain variable domain

<400> SEQUENCE: 126
```

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Met Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Asn
                85                  90                  95

Thr Ala Tyr Met Glu Phe Ser Ser Leu Thr Ser Glu Asp Ser Ala Val
            100                 105                 110

Tyr Tyr Cys Ala Arg Ile Asp Tyr Gly Thr Ile His Thr Ser Trp Phe
        115                 120                 125

Ala Tyr Trp Gly Gln Gly Thr Leu Val Thr Val Ser Ala
    130                 135                 140

```
<210> SEQ ID NO 127
<211> LENGTH: 122
<212> TYPE: PRT
<213> ORGANISM: Artificial Sequence
<220> FEATURE:
<223> OTHER INFORMATION: Heavy chain variable domain

<400> SEQUENCE: 127
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Asn Thr Ala Tyr
65                  70                  75                  80

Met Glu Phe Ser Ser Leu Thr Ser Glu Asp Ser Ala Val Tyr Tyr Cys
                85                  90                  95

Ala Arg Ile Asp Tyr Gly Thr Ile His Thr Ser Trp Phe Ala Tyr Trp
            100                 105                 110

Gly Gln Gly Thr Leu Val Thr Val Ser Ala
        115                 120

<210> SEQ ID NO 128
<211> LENGTH: 30
<212> TYPE: PRT
<213> ORGANISM: Artificial Sequence
<220> FEATURE:
<223> OTHER INFORMATION: Heavy chain FR1

<400> SEQUENCE: 128

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr
            20                  25                  30

<210> SEQ ID NO 129
<211> LENGTH: 14
<212> TYPE: PRT
<213> ORGANISM: Artificial Sequence
<220> FEATURE:
<223> OTHER INFORMATION: Heavy chain FR2

<400> SEQUENCE: 129

Trp Val Lys Gln Lys Pro Gly Gln Gly Leu Glu Trp Met Gly
1               5                   10

<210> SEQ ID NO 130
<211> LENGTH: 32
<212> TYPE: PRT
<213> ORGANISM: Artificial Sequence
<220> FEATURE:
<223> OTHER INFORMATION: Heavy chain FR3

<400> SEQUENCE: 130

Lys Ala Thr Leu Thr Ser Asp Lys Ser Ser Asn Thr Ala Tyr Met Glu
1               5                   10                  15

Phe Ser Ser Leu Thr Ser Glu Asp Ser Ala Val Tyr Tyr Cys Ala Arg
            20                  25                  30

<210> SEQ ID NO 131
<211> LENGTH: 13
<212> TYPE: PRT
<213> ORGANISM: Artificial Sequence
<220> FEATURE:
<223> OTHER INFORMATION: Heavy chain CDR3

<400> SEQUENCE: 131

Ile Asp Tyr Gly Thr Ile His Thr Ser Trp Phe Ala Tyr
1               5                   10

<210> SEQ ID NO 132
<211> LENGTH: 15
<212> TYPE: PRT
<213> ORGANISM: Artificial Sequence
<220> FEATURE:
<223> OTHER INFORMATION: AA Junction

<400> SEQUENCE: 132

Cys Ala Arg Gly Arg Asn Arg Tyr Asp Gly Trp Phe Thr Tyr Trp
1               5                   10                  15

<210> SEQ ID NO 133
<211> LENGTH: 378
<212> TYPE: DNA
<213> ORGANISM: Artificial Sequence
<220> FEATURE:
<223> OTHER INFORMATION: Light chain variable domain

<400> SEQUENCE: 133

```
atgtcctctg ctcagttcct tggtctcctg ttgctctgtt ttcaaggtac cagatgtgat      60
atccagatga cacacactac atcctccctg tctgcctctc tgggagacag agtcaccatc     120
agttgcaggg caagtcagga cattagcaat tatttaaact ggtatcagca gaaaccagat     180
ggaactgtta aactcctgat ctactacaca tcaagattac actcaggagt cccatcaagg     240
ttcagtggca gtgggtctgg aacagattat tctctcacca ttagcaacct ggagcaagaa     300
gatattgcca cttacttttg ccaacagggt aatacgcttc cgtggacgtt cggtggaggc     360
accaaactgg aaatcaaa                                                   378
```

<210> SEQ ID NO 134
<211> LENGTH: 321
<212> TYPE: DNA
<213> ORGANISM: Artificial Sequence
<220> FEATURE:
<223> OTHER INFORMATION: Light chain variable domain

<400> SEQUENCE: 134

```
gatatccaga tgacacacac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat acactcagg agtcccatca      180
aggttcagtg gcagtgggtc tggaacagat tattctctca ccattagcaa cctggagcaa     240
gaagatattg ccacttactt ttgccaacag ggtaatacgc ttccgtggac gttcggtgga     300
ggcaccaaac tggaaatcaa a                                               321
```

<210> SEQ ID NO 135
<211> LENGTH: 57
<212> TYPE: DNA
<213> ORGANISM: Artificial Sequence
<220> FEATURE:
<223> OTHER INFORMATION: Light chain signal sequence

<400> SEQUENCE: 135

```
atgtcctctg ctcagttcct tggtctcctg ttgctctgtt ttcaaggtac cagatgt         57
```

<210> SEQ ID NO 136
<211> LENGTH: 69
<212> TYPE: DNA
<213> ORGANISM: Artificial Sequence
<220> FEATURE:
<223> OTHER INFORMATION: Light chain FR1

<400> SEQUENCE: 136

```
gatatccaga tgacacacac tacatcctcc ctgtctgcct ctctgggaga cagagtcacc      60
atcagttgc                                                              69
```

<210> SEQ ID NO 137
<211> LENGTH: 33
<212> TYPE: DNA
<213> ORGANISM: Artificial Sequence
<220> FEATURE:
<223> OTHER INFORMATION: Light chain CDR1

<400> SEQUENCE: 137

```
agggcaagtc aggacattag caattattta aac                                   33
```

<210> SEQ ID NO 138

```
<211> LENGTH: 45
<212> TYPE: DNA
<213> ORGANISM: Artificial Sequence
<220> FEATURE:
<223> OTHER INFORMATION: Light chain FR2

<400> SEQUENCE: 138
tggtatcagc agaaaccaga tggaactgtt aaactcctga tctac            45

<210> SEQ ID NO 139
<211> LENGTH: 11
<212> TYPE: PRT
<213> ORGANISM: Artificial Sequence
<220> FEATURE:
<223> OTHER INFORMATION: AA Junction

<400> SEQUENCE: 139

Cys Gln Gln Gly Asn Thr Leu Pro Tyr Thr Phe
1               5                   10

<210> SEQ ID NO 140
<211> LENGTH: 96
<212> TYPE: DNA
<213> ORGANISM: Artificial Sequence
<220> FEATURE:
<223> OTHER INFORMATION: Light chain FR3

<400> SEQUENCE: 140
ggagtcccat caaggttcag tggcagtggg tctggaacag attattctct caccattagc    60
aacctggagc aagaagatat tgccacttac ttttgc                              96

<210> SEQ ID NO 141
<211> LENGTH: 27
<212> TYPE: DNA
<213> ORGANISM: Artificial Sequence
<220> FEATURE:
<223> OTHER INFORMATION: Light chain CDR3

<400> SEQUENCE: 141
caacagggta atacgcttcc gtggacg                                        27

<210> SEQ ID NO 142
<211> LENGTH: 30
<212> TYPE: DNA
<213> ORGANISM: Artificial Sequence
<220> FEATURE:
<223> OTHER INFORMATION: Light chain FR4

<400> SEQUENCE: 142
ttcggtggag gcaccaaact ggaaatcaaa                                     30

<210> SEQ ID NO 143
<211> LENGTH: 126
<212> TYPE: PRT
<213> ORGANISM: Artificial Sequence
<220> FEATURE:
<223> OTHER INFORMATION: Light chain variable domain

<400> SEQUENCE: 143

Met Ser Ser Ala Gln Phe Leu Gly Leu Leu Leu Leu Cys Phe Gln Gly
1               5                   10                  15

Thr Arg Cys Asp Ile Gln Met Thr His Thr Thr Ser Ser Leu Ser Ala
                20                  25                  30

Ser Leu Gly Asp Arg Val Thr Ile Ser Cys Arg Ala Ser Gln Asp Ile
            35                  40                  45
```

Ser Asn Tyr Leu Asn Trp Tyr Gln Gln Lys Pro Asp Gly Thr Val Lys
            50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys
            115                 120                 125

<210> SEQ ID NO 144
<211> LENGTH: 107
<212> TYPE: PRT
<213> ORGANISM: Artificial Sequence
<220> FEATURE:
<223> OTHER INFORMATION: Light chain variable domain

<400> SEQUENCE: 144

Asp Ile Gln Met Thr His Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 145
<211> LENGTH: 19
<212> TYPE: PRT
<213> ORGANISM: Artificial Sequence
<220> FEATURE:
<223> OTHER INFORMATION: Light chain signal sequence

<400> SEQUENCE: 145

Met Ser Ser Ala Gln Phe Leu Gly Leu Leu Leu Cys Phe Gln Gly
 1               5                  10                  15

Thr Arg Cys

<210> SEQ ID NO 146
<211> LENGTH: 23
<212> TYPE: PRT
<213> ORGANISM: Artificial Sequence
<220> FEATURE:
<223> OTHER INFORMATION: Light chain FR1

<400> SEQUENCE: 146

Asp Ile Gln Met Thr His Thr Thr Ser Ser Leu Ser Ala Ser Leu Gly
 1               5                  10                  15

Asp Arg Val Thr Ile Ser Cys
            20

<210> SEQ ID NO 147
<211> LENGTH: 15
<212> TYPE: PRT
<213> ORGANISM: Artificial Sequence
<220> FEATURE:
<223> OTHER INFORMATION: Light chain FR2

<400> SEQUENCE: 147

Trp Tyr Gln Gln Lys Pro Asp Gly Thr Val Lys Leu Leu Ile Tyr
1               5                   10                  15

<210> SEQ ID NO 148
<211> LENGTH: 32
<212> TYPE: PRT
<213> ORGANISM: Artificial Sequence
<220> FEATURE:
<223> OTHER INFORMATION: Light chain FR3

<400> SEQUENCE: 148

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 149
<211> LENGTH: 9
<212> TYPE: PRT
<213> ORGANISM: Artificial Sequence
<220> FEATURE:
<223> OTHER INFORMATION: Light chain CDR3

<400> SEQUENCE: 149

Gln Gln Gly Asn Thr Leu Pro Trp Thr
1               5

<210> SEQ ID NO 150
<211> LENGTH: 17
<212> TYPE: PRT
<213> ORGANISM: Artificial Sequence
<220> FEATURE:
<223> OTHER INFORMATION: AA Junction

<400> SEQUENCE: 150

Cys Ala Arg Ile Asp Tyr Gly Thr Ile His Thr Ser Trp Phe Ala Tyr
1               5                   10                  15

Trp

<210> SEQ ID NO 151
<211> LENGTH: 423
<212> TYPE: DNA
<213> ORGANISM: Artificial Sequence
<220> FEATURE:
<223> OTHER INFORMATION: Heavy chain variable domain

<400> SEQUENCE: 151
atggaatgga gttggatatt tctctttctc ctgtcaggaa ctgcaggtgt ccactctgag      60
gtccagctgc agcagtctgg acctgagttg gtaaagcctg ggcttcagt gaagctgtcc     120 tgcaaggctt ctggatacac attcactagt tctgttattc actgggtgaa gcagaagcct    180
gggcagggcc ttgagtggct tggatatatt aatccttata gtgatggaac taaattcaat    240
gagaagtgca aaatcaaggc cacactgact tcagacaaat cctccagcac agcctacatg    300
gaactcagca gcctgacctc tgaggactct gcggtctatt actgtgcaag aggccttata    360
gggactagat acgactcctg gtttgcttac tggggccaag gactctggt cactgtctct    420

```
gca                                                                    423

<210> SEQ ID NO 152
<211> LENGTH: 366
<212> TYPE: DNA
<213> ORGANISM: Artificial Sequence
<220> FEATURE:
<223> OTHER INFORMATION: Heavy chain variable domain

<400> SEQUENCE: 152
gaggtccagc tgcagcagtc tggacctgag ttggtaaagc ctggggcttc agtgaagctg     60
tcctgcaagg cttctggata cacattcact agttctgtta ttcactgggt gaagcagaag    120
cctgggcagg gccttgagtg gcttggatat attaatcctt atagtgatgg aactaaattc    180
aatgagaagt gcaaaatcaa ggccacactg acttcagaca atcctccag cacagcctac     240 atggaactca gcagcctgac ctctgaggac tctgcggtct attactgtgc aagaggcctt    300
atagggacta gatacgactc ctggtttgct tactggggcc aagggactct ggtcactgtc    360
tctgca                                                                366

<210> SEQ ID NO 153
<211> LENGTH: 90
<212> TYPE: DNA
<213> ORGANISM: Artificial Sequence
<220> FEATURE:
<223> OTHER INFORMATION: Heavy chain FR1

<400> SEQUENCE: 153
gaggtccagc tgcagcagtc tggacctgag ttggtaaagc ctggggcttc agtgaagctg     60
tcctgcaagg cttctggata cacattcact                                       90

<210> SEQ ID NO 154
<211> LENGTH: 15
<212> TYPE: DNA
<213> ORGANISM: Artificial Sequence
<220> FEATURE:
<223> OTHER INFORMATION: Heavy chain CDR1

<400> SEQUENCE: 154
agttctgtta ttcac                                                       15

<210> SEQ ID NO 155
<211> LENGTH: 42
<212> TYPE: DNA
<213> ORGANISM: Artificial Sequence
<220> FEATURE:
<223> OTHER INFORMATION: Heavy chain FR2

<400> SEQUENCE: 155
tgggtgaagc agaagcctgg gcagggcctt gagtggcttg ga                         42

<210> SEQ ID NO 156
<211> LENGTH: 51
<212> TYPE: DNA
<213> ORGANISM: Artificial Sequence
<220> FEATURE:
<223> OTHER INFORMATION: Heavy chain CDR2

<400> SEQUENCE: 156
tatattaatc cttatagtga tggaactaaa ttcaatgaga agtgcaaaat c               51

<210> SEQ ID NO 157
```

<211> LENGTH: 96
<212> TYPE: DNA
<213> ORGANISM: Artificial Sequence
<220> FEATURE:
<223> OTHER INFORMATION: Heavy chain FR3

<400> SEQUENCE: 157
aaggccacac tgacttcaga caaatcctcc agcacagcct acatggaact cagcagcctg    60
acctctgagg actctgcggt ctattactgt gcaaga    96

<210> SEQ ID NO 158
<211> LENGTH: 39
<212> TYPE: DNA
<213> ORGANISM: Artificial Sequence
<220> FEATURE:
<223> OTHER INFORMATION: Heavy chain CDR3

<400> SEQUENCE: 158
ggccttatag ggactagata cgactcctgg tttgcttac    39

<210> SEQ ID NO 159
<211> LENGTH: 33
<212> TYPE: DNA
<213> ORGANISM: Artificial Sequence
<220> FEATURE:
<223> OTHER INFORMATION: Heavy chain FR4

<400> SEQUENCE: 159
tggggccaag ggactctggt cactgtctct gca    33

<210> SEQ ID NO 160
<211> LENGTH: 141
<212> TYPE: PRT
<213> ORGANISM: Artificial Sequence
<220> FEATURE:
<223> OTHER INFORMATION: Heavy chain variable domain

<400> SEQUENCE: 160

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Ser Ser Val Ile His Trp Val Lys Gln Lys Pro Gly Gln Gly Leu
    50                  55                  60

Glu Trp Leu Gly Tyr Ile Asn Pro Tyr Ser Asp Gly Thr Lys Phe Asn
65                  70                  75                  80

Glu Lys Cys Lys Ile Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ala
    130                 135                 140

<210> SEQ ID NO 161
<211> LENGTH: 122
<212> TYPE: PRT
<213> ORGANISM: Artificial Sequence
<220> FEATURE:

<223> OTHER INFORMATION: Heavy chain variable domain

<400> SEQUENCE: 161

Glu Val Gln Leu Gln Gln Ser Gly Pro Glu Leu Val Lys Pro Gly Ala
1               5                   10                  15
Ser Val Lys Leu Ser Cys Lys Ala Ser Gly Tyr Thr Phe Thr Ser Ser
            20                  25                  30
Val Ile His Trp Val Lys Gln Lys Pro Gly Gln Gly Leu Glu Trp Leu
        35                  40                  45
Gly Tyr Ile Asn Pro Tyr Ser Asp Gly Thr Lys Phe Asn Glu Lys Cys
    50                  55                  60
Lys Ile Lys Ala Thr Leu Thr Ser Asp Lys Ser Ser Thr Ala Tyr
65                  70                  75                  80
Met Glu Leu Ser Ser Leu Thr Ser Glu Asp Ser Ala Val Tyr Tyr Cys
                85                  90                  95
Ala Arg Gly Leu Ile Gly Thr Arg Tyr Asp Ser Trp Phe Ala Tyr Trp
            100                 105                 110
Gly Gln Gly Thr Leu Val Thr Val Ser Ala
        115                 120

<210> SEQ ID NO 162
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 162

Ser Ser Val Ile His
1               5

<210> SEQ ID NO 163
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 163

Tyr Ile Asn Pro Tyr Ser Asp Gly Thr Lys Phe Asn Glu Lys Cys Lys
1               5                   10                  15
Ile

<210> SEQ ID NO 164
<211> LENGTH: 378
<212> TYPE: DNA
<213> ORGANISM: Artificial Sequence
<220> FEATURE:
<223> OTHER INFORMATION: Light chain 1 variable domain

<400> SEQUENCE: 164

```
atgtcctctg ctcagttcct tggtctcctg ttgctctgtt ttcaaggtat cagatgtgat    60
atccagatga cacagaatgg atcctccctg tctgcctctc tgggagacag agtcaccatc   120
agttgcagga caagtcagga cattaacaat tatttaaatt ggtatcagca gaaacaagat   180
ggaactgtta aactcctgat ctactacaca tcaagattac actcaggagt cccatcaagg   240
ttcagtggca gtgggtctgg aacagattat tctctcacca ttcgcaacct ggagcaagaa   300
gatattgcca cttactttg ccaacagggt aatacgcttc cgtacacgtt cggagggggg   360
accaaactgg aaataaaa                                                 378
```

<210> SEQ ID NO 165
<211> LENGTH: 321
<212> TYPE: DNA
<213> ORGANISM: Artificial Sequence
<220> FEATURE:
<223> OTHER INFORMATION: Light chain 1 variable domain

<400> SEQUENCE: 165

```
gatatccaga tgacacagaa tggatcctcc ctgtctgcct ctctgggaga cagagtcacc    60
atcagttgca ggacaagtca ggacattaac aattatttaa attggtatca gcagaaacaa   120
gatggaactg ttaaactcct gatctactac acatcaagat acactcagg agtcccatca    180 aggttcagtg gcagtgggtc tggaacagat tattctctca ccattcgcaa cctggagcaa   240
gaagatattg ccacttactt ttgccaacag gtaatacgc ttccgtacac gttcggaggg    300
gggaccaaac tggaaataaa a                                              321
```

<210> SEQ ID NO 166
<211> LENGTH: 69
<212> TYPE: DNA
<213> ORGANISM: Artificial Sequence
<220> FEATURE:
<223> OTHER INFORMATION: Light chain 1 FR1

<400> SEQUENCE: 166

```
gatatccaga tgacacagaa tggatcctcc ctgtctgcct ctctgggaga cagagtcacc    60
atcagttgc                                                            69
```

<210> SEQ ID NO 167
<211> LENGTH: 45
<212> TYPE: DNA
<213> ORGANISM: Artificial Sequence
<220> FEATURE:
<223> OTHER INFORMATION: Light chain 1 FR2

<400> SEQUENCE: 167

```
tggtatcagc agaaacaaga tggaactgtt aaactcctga tctac                    45
```

<210> SEQ ID NO 168
<211> LENGTH: 96
<212> TYPE: DNA
<213> ORGANISM: Artificial Sequence
<220> FEATURE:
<223> OTHER INFORMATION: Light chain 1 FR3

<400> SEQUENCE: 168

```
ggagtcccat caaggttcag tggcagtggg tctggaacag attattctct caccattcgc    60
aacctggagc aagaagatat tgccacttac ttttgc                              96
```

<210> SEQ ID NO 169
<211> LENGTH: 126
<212> TYPE: PRT
<213> ORGANISM: Artificial Sequence
<220> FEATURE:
<223> OTHER INFORMATION: Light chain 1 variable domain

<400> SEQUENCE: 169

```
Met Ser Ser Ala Gln Phe Leu Gly Leu Leu Leu Cys Phe Gln Gly
1               5                   10                  15

Ile Arg Cys Asp Ile Gln Met Thr Gln Asn Gly Ser Ser Leu Ser Ala
            20                  25                  30
```

```
Ser Leu Gly Asp Arg Val Thr Ile Ser Cys Arg Thr Ser Gln Asp Ile
        35                  40                  45

Asn Asn Tyr Leu Asn Trp Tyr Gln Gln Lys Gln Asp Gly Thr Val Lys
 50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Ser Leu Thr Ile Arg Asn
                 85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Lys
        115                 120                 125

<210> SEQ ID NO 170
<211> LENGTH: 107
<212> TYPE: PRT
<213> ORGANISM: Artificial Sequence
<220> FEATURE:
<223> OTHER INFORMATION: Light chain 1 variable domain

<400> SEQUENCE: 170

Asp Ile Gln Met Thr Gln Asn Gly Ser Ser Leu Ser Ala Ser Leu Gly
 1               5                  10                  15

Asp Arg Val Thr Ile Ser Cys Arg Thr Ser Gln Asp Ile Asn Asn Tyr
            20                  25                  30

Leu Asn Trp Tyr Gln Gln Lys Gln Asp Gly Thr Val Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Arg Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Lys
            100                 105

<210> SEQ ID NO 171
<211> LENGTH: 23
<212> TYPE: PRT
<213> ORGANISM: Artificial Sequence
<220> FEATURE:
<223> OTHER INFORMATION: Light chain 1 FR1

<400> SEQUENCE: 171

Asp Ile Gln Met Thr Gln Asn Gly Ser Ser Leu Ser Ala Ser Leu Gly
 1               5                  10                  15

Asp Arg Val Thr Ile Ser Cys
            20

<210> SEQ ID NO 172
<211> LENGTH: 15
<212> TYPE: PRT
<213> ORGANISM: Artificial Sequence
<220> FEATURE:
<223> OTHER INFORMATION: Light chain 1 FR2

<400> SEQUENCE: 172

Trp Tyr Gln Gln Lys Gln Asp Gly Thr Val Lys Leu Leu Ile Tyr
 1               5                  10                  15
```

```
<210> SEQ ID NO 173
<211> LENGTH: 32
<212> TYPE: PRT
<213> ORGANISM: Artificial Sequence
<220> FEATURE:
<223> OTHER INFORMATION: Light chain 1 FR3

<400> SEQUENCE: 173

Gly Val Pro Ser Arg Phe Ser Gly Ser Gly Ser Gly Thr Asp Tyr Ser
1               5                   10                  15

Leu Thr Ile Arg Asn Leu Glu Gln Glu Asp Ile Ala Thr Tyr Phe Cys
            20                  25                  30

<210> SEQ ID NO 174
<211> LENGTH: 381
<212> TYPE: DNA
<213> ORGANISM: Artificial Sequence
<220> FEATURE:
<223> OTHER INFORMATION: Light chain 2 variable domain

<400> SEQUENCE: 174
atgagggtcc ttgctgagct cctggggctg ctgctgttct gcttttttagg tgtgagatgt      60 gacatccaga tgaaccagtc tccatccagt ctgtctgcat cccttggaga cacaattacc     120
atcacttgcc atgccagtca gaacattaat gtttggttaa gctggtacca gcagaaacca     180
ggaaatattc ctaaactatt gatctataag gcttccaact tgcacacagg cgtcccatca     240
agatttagtg gcagtggatc tggaacaggt ttcacattaa ccatcagcag cctgcagcct     300
gaagacattg ccacttacta ctgtcaacag ggtcaaagtt atcctctcac gttcggtgct     360
gggaccaagc tggagctgaa a                                                381

<210> SEQ ID NO 175
<211> LENGTH: 321
<212> TYPE: DNA
<213> ORGANISM: Artificial Sequence
<220> FEATURE:
<223> OTHER INFORMATION: Light chain 2 variable domain

<400> SEQUENCE: 175
gacatccaga tgaaccagtc tccatccagt ctgtctgcat cccttggaga cacaattacc      60
atcacttgcc atgccagtca gaacattaat gtttggttaa gctggtacca gcagaaacca     120
ggaaatattc ctaaactatt gatctataag gcttccaact tgcacacagg cgtcccatca     180
agatttagtg gcagtggatc tggaacaggt ttcacattaa ccatcagcag cctgcagcct     240
gaagacattg ccacttacta ctgtcaacag ggtcaaagtt atcctctcac gttcggtgct     300
gggaccaagc tggagctgaa a                                                321

<210> SEQ ID NO 176
<211> LENGTH: 21
<212> TYPE: DNA
<213> ORGANISM: Artificial Sequence
<220> FEATURE:
<223> OTHER INFORMATION: Light chain 2 CDR2

<400> SEQUENCE: 176
aaggcttcca acttgcacac a                                                 21

<210> SEQ ID NO 177
<211> LENGTH: 96
<212> TYPE: DNA
<213> ORGANISM: Artificial Sequence
<220> FEATURE:
```

<223> OTHER INFORMATION: Light chain 2 FR3

<400> SEQUENCE: 177

```
ggcgtcccat caagatttag tggcagtgga tctggaacag gtttcacatt aaccatcagc    60
agcctgcagc ctgaagacat tgccacttac tactgt                              96
```

<210> SEQ ID NO 178
<211> LENGTH: 27
<212> TYPE: DNA
<213> ORGANISM: Artificial Sequence
<220> FEATURE:
<223> OTHER INFORMATION: Light chain 2 CDR3

<400> SEQUENCE: 178

```
caacagggtc aaagttatcc tctcacg                                        27
```

<210> SEQ ID NO 179
<211> LENGTH: 30
<212> TYPE: DNA
<213> ORGANISM: Artificial Sequence
<220> FEATURE:
<223> OTHER INFORMATION: Light chain 2 FR4

<400> SEQUENCE: 179

```
ttcggtgctg ggaccaagct ggagctgaaa                                     30
```

<210> SEQ ID NO 180
<211> LENGTH: 127
<212> TYPE: PRT
<213> ORGANISM: Artificial Sequence
<220> FEATURE:
<223> OTHER INFORMATION: Light chain 2 variable domain

<400> SEQUENCE: 180

```
Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Lys Pro Gly Asn Ile Pro
    50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Gly Phe Thr Leu Thr Ile Ser
                85                  90                  95

Ser Leu Gln Pro Glu Asp Ile Ala Thr Tyr Tyr Cys Gln Gln Gly Gln
            100                 105                 110

Ser Tyr Pro Leu Thr Phe Gly Ala Gly Thr Lys Leu Glu Leu Lys
        115                 120                 125
```

<210> SEQ ID NO 181
<211> LENGTH: 107
<212> TYPE: PRT
<213> ORGANISM: Artificial Sequence
<220> FEATURE:
<223> OTHER INFORMATION: Light chain 2 variable domain

<400> SEQUENCE: 181

```
Asp Ile Gln Met Asn Gln Ser Pro Ser Ser Leu Ser Ala Ser Leu Gly
1               5                   10                  15
```

```
Asp Thr Ile Thr Ile Thr Cys His Ala Ser Gln Asn Ile Asn Val Trp
                20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
            100                 105
```

<210> SEQ ID NO 182
<211> LENGTH: 9
<212> TYPE: PRT
<213> ORGANISM: Artificial Sequence
<220> FEATURE:
<223> OTHER INFORMATION: Light chain 2 CDR3

<400> SEQUENCE: 182

```
Gln Gln Gly Gln Ser Tyr Pro Leu Thr
1               5
```

<210> SEQ ID NO 183
<211> LENGTH: 9
<212> TYPE: PRT
<213> ORGANISM: Artificial Sequence
<220> FEATURE:
<223> OTHER INFORMATION: Light chain 2 FR4

<400> SEQUENCE: 183

```
Phe Gly Ala Gly Thr Lys Leu Glu Leu
1               5
```

<210> SEQ ID NO 184
<211> LENGTH: 11
<212> TYPE: PRT
<213> ORGANISM: Artificial Sequence
<220> FEATURE:
<223> OTHER INFORMATION: AA Junction

<400> SEQUENCE: 184

```
Cys Gln Gln Gly Asn Thr Leu Pro Trp Thr Phe
1               5                   10
```

<210> SEQ ID NO 185
<211> LENGTH: 15
<212> TYPE: PRT
<213> ORGANISM: Artificial Sequence
<220> FEATURE:
<223> OTHER INFORMATION: AA Junction

<400> SEQUENCE: 185

```
Cys Ala Ser Gly Tyr Gly His Tyr Val Gly Ala Met Asp Tyr Trp
1               5                   10                  15
```

<210> SEQ ID NO 186
<211> LENGTH: 11
<212> TYPE: PRT
<213> ORGANISM: Artificial Sequence
<220> FEATURE:
<223> OTHER INFORMATION: AA Junction

<400> SEQUENCE: 186

Cys Gln Gln Ser Arg Asn Tyr Pro Tyr Thr Phe
1               5                   10

<210> SEQ ID NO 187
<211> LENGTH: 11
<212> TYPE: PRT
<213> ORGANISM: Artificial Sequence
<220> FEATURE:
<223> OTHER INFORMATION: AA Junction

<400> SEQUENCE: 187

Cys Gln Gln Gly Gln Ser Tyr Pro Tyr Thr Phe
1               5                   10

<210> SEQ ID NO 188
<211> LENGTH: 468
<212> TYPE: PRT
<213> ORGANISM: Artificial Sequence
<220> FEATURE:
<223> OTHER INFORMATION: U0959FD090-chimeric-VH-PTM1

<400> SEQUENCE: 188

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Ser Ser Val Ile His Trp Val Lys Gln Lys Pro Gly Gln Gly Leu
    50                  55                  60

Glu Trp Leu Gly Tyr Ile Asn Pro Tyr Ser Glu Gly Thr Lys Phe Asn
65                  70                  75                  80

Glu Lys Ser Lys Ile Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ala Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser

```
                275                 280                 285
Gln Glu Asp Pro Glu Val Gln Phe Asn Trp Tyr Val Asp Gly Val Glu
            290                 295                 300
Val His Asn Ala Lys Thr Lys Pro Arg Glu Glu Gln Phe Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Gly Leu Pro Ser Ser
            340                 345                 350
Ile Glu Lys Thr Ile Ser Lys Ala Lys Gly Gln Pro Arg Glu Pro Gln
                355                 360                 365
Val Tyr Thr Leu Pro Pro Ser Gln Glu Glu Met Thr Lys Asn Gln Val
            370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Arg Leu Thr
            420                 425                 430
Val Asp Lys Ser Arg Trp Gln Glu Gly Asn Val Phe Ser Cys Ser Val
            435                 440                 445
Met His Glu Ala Leu His Asn His Tyr Thr Gln Lys Ser Leu Ser Leu
    450                 455                 460
Ser Leu Gly Lys
465

<210> SEQ ID NO 189
<211> LENGTH: 468
<212> TYPE: PRT
<213> ORGANISM: Artificial Sequence
<220> FEATURE:
<223> OTHER INFORMATION: U0959FD090-chimeric-VH-PTM2

<400> SEQUENCE: 189

Met Gly Trp Ser Cys Ile Ile Leu Phe Leu Val Ala Thr Ala Thr Gly
1               5                   10                  15
Val His Ser Glu Val Gln Leu Gln Gln Ser Gly Pro Glu Leu Val Lys
            20                  25                  30
Pro Gly Ala Ser Val Lys Leu Ser Cys Lys Ala Ser Gly Tyr Thr Phe
        35                  40                  45
Thr Ser Ser Val Ile His Trp Val Lys Gln Lys Pro Gly Gln Gly Leu
    50                  55                  60
Glu Trp Leu Gly Tyr Ile Asn Pro Tyr Ser Asp Ala Thr Lys Phe Asn
65                  70                  75                  80
Glu Lys Ser Lys Ile Lys Ala Thr Leu Thr Ser Asp Lys Ser Ser Ser
                85                  90                  95
Thr Ala Tyr Met Glu Leu Ser Ser Leu Thr Ser Glu Asp Ser Ala Val
            100                 105                 110
Tyr Tyr Cys Ala Arg Gly Leu Ile Gly Thr Arg Tyr Asp Ser Trp Phe
        115                 120                 125
Ala Tyr Trp Gly Gln Gly Thr Leu Val Thr Val Ser Ala Ala Ser Thr
    130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
```

```
                    165                 170                 175
Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Asp Val Ser
                275                 280                 285

Gln Glu Asp Pro Glu Val Gln Phe Asn Trp Tyr Val Asp Gly Val Glu
                290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Gln Glu Glu Met Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
                435                 440                 445

Met His Glu Ala Leu His Asn His Tyr Thr Gln Lys Ser Leu Ser Leu
                450                 455                 460

Ser Leu Gly Lys
465

<210> SEQ ID NO 190
<211> LENGTH: 468
<212> TYPE: PRT
<213> ORGANISM: Artificial Sequence
<220> FEATURE:
<223> OTHER INFORMATION: U0959FD090-VH1

<400> SEQUENCE: 190

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Ser Val Ile His Trp Val Arg Gln Ala Pro Gly Gln Gly Leu
```

```
                50                  55                  60
Glu Trp Met Gly Tyr Ile Asn Pro Tyr Ser Asp Gly Thr Lys Phe Asn
 65                  70                  75                  80

Glu Lys Cys Lys Ile Arg Val Thr Met Thr Arg Asp Thr Ser Ile Ser
                 85                  90                  95

Thr Ala Tyr Met Glu Leu Ser Arg Leu Arg Ser Asp Asp Thr Ala Val
                100                 105                 110

Tyr Tyr Cys Ala Arg Gly Leu Ile Gly Thr Arg Tyr Asp Ser Trp Phe
                115                 120                 125

Ala Tyr Trp Gly Gln Gly Thr Leu Val Thr Val Ser Ser Ala Ser Thr
                130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Lys Thr Tyr Thr Cys
                210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

Gln Glu Asp Pro Glu Val Gln Phe Asn Trp Tyr Val Asp Gly Val Glu
                290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Gln Glu Glu Met Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
                435                 440                 445

Met His Glu Ala Leu His Asn His Tyr Thr Gln Lys Ser Leu Ser Leu
                450                 455                 460

Ser Leu Gly Lys
465
```

<210> SEQ ID NO 191
<211> LENGTH: 468
<212> TYPE: PRT
<213> ORGANISM: Artificial Sequence
<220> FEATURE:
<223> OTHER INFORMATION: U0959FD090-VH1-PTM

<400> SEQUENCE: 191

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Ser Val Ile His Trp Val Arg Gln Ala Pro Gly Gln Gly Leu
    50                  55                  60

Glu Trp Met Gly Tyr Ile Asn Pro Tyr Ser Glu Gly Thr Lys Phe Asn
65                  70                  75                  80

Glu Lys Ser Lys Ile Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
            435                 440                 445

Met His Glu Ala Leu His Asn His Tyr Thr Gln Lys Ser Leu Ser Leu
450                 455                 460

Ser Leu Gly Lys
465

<210> SEQ ID NO 192
<211> LENGTH: 468
<212> TYPE: PRT
<213> ORGANISM: Artificial Sequence
<220> FEATURE:
<223> OTHER INFORMATION: U0959FD090-VH2

<400> SEQUENCE: 192

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Ser Val Ile His Trp Val Arg Gln Ala Pro Gly Gln Gly Leu
    50                  55                  60

Glu Trp Leu Gly Tyr Ile Asn Pro Tyr Ser Asp Gly Thr Lys Phe Asn
65                  70                  75                  80

Glu Lys Cys Lys Ile Arg Ala Thr Met Thr Ser Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
        290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
450                 455                 460

Ser Leu Gly Lys
465

<210> SEQ ID NO 193
<211> LENGTH: 468
<212> TYPE: PRT
<213> ORGANISM: Artificial Sequence
<220> FEATURE:
<223> OTHER INFORMATION: U0959FD090-VH3

<400> SEQUENCE: 193

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Ser Val Ile His Trp Val Lys Gln Ala Pro Gly Gln Gly Leu
    50                  55                  60

Glu Trp Leu Gly Tyr Ile Asn Pro Tyr Ser Asp Gly Thr Lys Phe Asn
65                  70                  75                  80

Glu Lys Cys Lys Ile Arg Val Thr Leu Thr Ser Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465

<210> SEQ ID NO 194
<211> LENGTH: 468
<212> TYPE: PRT
<213> ORGANISM: Artificial Sequence
<220> FEATURE:
<223> OTHER INFORMATION: U0959FD090-VH4

<400> SEQUENCE: 194

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Ser Val Ile His Trp Val Lys Gln Ala Pro Gly Gln Gly Leu
        50                  55                  60

Glu Trp Leu Gly Tyr Ile Asn Pro Tyr Ser Asp Gly Thr Lys Phe Asn
 65                  70                  75                  80

Glu Lys Cys Lys Ile Arg Ala Thr Met Thr Ser Asp Lys Ser Ile Ser
                85                  90                  95

Thr Ala Tyr Met Glu Leu Ser Arg Leu Arg Ser Asp Asp Thr Ala Val
                100                 105                 110

Tyr Tyr Cys Ala Arg Gly Leu Ile Gly Thr Arg Tyr Asp Ser Trp Phe
            115                 120                 125

Ala Tyr Trp Gly Gln Gly Thr Leu Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465

<210> SEQ ID NO 195
<211> LENGTH: 1410
<212> TYPE: DNA
<213> ORGANISM: Artificial Sequence
<220> FEATURE:
<223> OTHER INFORMATION: U0959FD090-chimeric-VH-PTM1

<400> SEQUENCE: 195

| atgggctggt | cttgtattat | tctgtttctg | gtcgcaactg | ctacaggcgt | gcattctgaa | 60 |
| gtgcagctgc | agcagagcgg | cccagagctc | gtcaaacctg | gagccagcgt | gaagctgagc | 120 |
| tgtaaagctt | ctggatacac | ctttaccagc | tctgtgatcc | actgggtgaa | gcagaagcct | 180 |
| ggccagggcc | tggaatggct | gggctacatc | aaccccctaca | gcgagggcac | aaagttcaac | 240 |
| gagaagtcca | agatcaaggc | caccctgacc | tccgataaga | gcagcagcac | cgcctatatg | 300 |
| gaactgagca | gcctgacatc | tgaggacagc | gccgtgtact | actgcgcccg | gggcctgatc | 360 |
| ggcacaagat | acgactcttg | gttcgcctac | tggggacaag | gcaccctggt | gaccgtgtcc | 420 |
| gctgccagca | ccaagggccc | ttccgtgttt | cccctggccc | cttgctcccg | gtccacatct | 480 |
| gagagcaccg | ccgccctggg | ctgtctggtg | aaggactact | cccagagcc | cgtgaccgtg | 540 |
| agctggaaca | gcggcgccct | gacaagcggc | gtgcacacat | tcccgccgt | gctgcagagc | 600 |
| tccggcctgt | actccctgtc | tagcgtggtg | acagtgcctt | cctctagcct | gggcaccaag | 660 |
| acatatacct | gtaacgtgga | ccacaagcca | agcaatacca | aggtggataa | gcgggtggag | 720 |
| tctaagtacg | gccctccttg | ccctccatgt | cctgctccag | agtttctggg | cggcccttcc | 780 |
| gtgttcctgt | tccacccaa | accaaggac | acactgatga | tctctagaac | accagaggtg | 840 |
| acctgcgtgt | ggtggacgt | gagccaggag | gatcccgagg | tgcagttcaa | ctggtacgtg | 900 |
| gatggcgtgg | aggtgcacaa | tgccaagacc | aagccaagag | aggagcagtt | taactctaca | 960 |
| tacagggtgg | tgagcgtgct | gaccgtgctg | caccaggatt | ggctcaacgg | caaggagtat | 1020 |
| aagtgcaagg | tgtccaataa | gggcctgccc | tcctctatcg | agaagacaat | ctctaaggct | 1080 |
| aagggccagc | caagagagcc | tcaggtgtac | accctgcctc | caagccagga | ggagatgaca | 1140 |
| aagaaccagg | tgtccctgac | atgtctggtg | aagggcttct | atccctccga | catcgccgtg | 1200 |
| gagtgggagt | ctaatggcca | gcctgagaac | aattacaaga | ccacccccc | tgtgctggac | 1260 |
| tctgatggca | gcttctttct | gtattccagg | ctgaccgtgg | ataagtctcg | gtggcaggag | 1320 |
| ggcaacgtgt | tcagctgctc | tgtgatgcac | gaagccctgc | ataatcacta | tactcagaaa | 1380 |
| agtctgtcac | tgtcactggg | aaagtgataa | | | | 1410 |

<210> SEQ ID NO 196
<211> LENGTH: 1410
<212> TYPE: DNA
<213> ORGANISM: Artificial Sequence
<220> FEATURE:
<223> OTHER INFORMATION: U0959FD090-chimeric-VH-PTM2

<400> SEQUENCE: 196

| atgggctggt | cttgtattat | tctgtttctg | gtcgcaactg | ctacaggcgt | gcattctgag | 60 |
| gtgcagctgc | agcagagcgg | acctgagctg | gtgaagccag | cgccagcgt | gaaactgagc | 120 |
| tgtaaagctt | ctggctacac | cttccaccagc | tctgtgatcc | actgggtcaa | gcagaagcct | 180 |

```
ggacaaggcc tggaatggct gggctacatc aaccccctaca gcgacgccac caagttcaac    240
gagaagagca agatcaaggc cacactgacc tctgataagt ccagctccac cgcctacatg    300
gaactgtcta gcctgacaag cgaggacagc gccgtgtact actgcgccag aggcctcatc    360
ggcacccggt acgacagctg gtttgcctat tggggccagg gcacactggt tacagtgtcc    420
gctgccagca ccaagggccc ttccgtgttt cccctggccc cttgctcccg gtccacatct    480
gagagcaccg ccgccctggg ctgtctggtg aaggactact cccagagcc cgtgaccgtg    540 agctggaaca gcggcgccct gacaagcggc gtgcacacat tcccgccgt gctgcagagc    600 tccggcctgt actccctgtc tagcgtggtg acagtgcctt cctctagcct gggcaccaag    660
acatatacct gtaacgtgga ccacaagcca agcaatacca aggtggataa gcgggtggag    720
tctaagtacg gccctccttg ccctccatgt cctgctccag agtttctggg cggcccttcc    780
gtgttcctgt ttccacccaa accaaggac acactgatga tctctagaac accagaggtg    840
acctgcgtgt ggtggacgt gagccaggag gatcccgagg tgcagttcaa ctggtacgtg    900
gatggcgtgg aggtgcacaa tgccaagacc aagccaagag aggagcagtt taactctaca    960
tacagggtgt gagcgtgct gaccgtgctg caccaggatt ggctcaacgg caaggagtat    1020
aagtgcaagg tgtccaataa gggcctgccc tcctctatcg agaagacaat ctctaaggct    1080
aagggccagc caagagagcc tcaggtgtac accctgcctc caagccagga ggagatgaca    1140
aagaaccagg tgtccctgac atgtctggtg aagggcttct atccctccga catcgccgtg    1200
gagtgggagt ctaatggcca gcctgagaac aattacaaga ccacacccccc tgtgctggac    1260 tctgatggca gcttctttct gtattccagg ctgaccgtgg ataagtctcg gtggcaggag    1320
ggcaacgtgt tcagctgctc tgtgatgcac gaagccctgc ataatcacta tactcagaaa    1380
agtctgtcac tgtcactggg aaagtgataa                                      1410

<210> SEQ ID NO 197
<211> LENGTH: 1410
<212> TYPE: DNA
<213> ORGANISM: Artificial Sequence
<220> FEATURE:
<223> OTHER INFORMATION: U0959FD090-VH1

<400> SEQUENCE: 197
atgggctggt cttgtattat tctgtttctg gtcgcaactg ctacaggcgt gcattctcaa     60
gtgcagctgg ttcagagcgg cgccgaggtg aagaaacctg gagcttccgt gaaagtgtcc    120
tgcaaggcct ctggctacac cttcaccagc agcgtgatcc actgggtgcg gcaggccct    180 ggccagggcc tggaatggat gggctacatc aaccccctaca gcgatggcac aaagttcaac    240
gagaagtgca agatccgggt gaccatgacc agagatacat ctatcagcac cgcttatatg    300
gaactgagca gactgagaag cgacgacacc gccgtgtact actgtgccag aggcctgatc    360
ggcacacgct acgacagctg gtttgcctac tggggccagg gaacactggt caccgtgtct    420
agcgccagca ccaagggccc ttccgtgttt cccctggccc cttgctcccg gtccacatct    480
gagagcaccg ccgccctggg ctgtctggtg aaggactact cccagagcc cgtgaccgtg    540 agctggaaca gcggcgccct gacaagcggc gtgcacacat tcccgccgt gctgcagagc    600 tccggcctgt actccctgtc tagcgtggtg acagtgcctt cctctagcct gggcaccaag    660
acatatacct gtaacgtgga ccacaagcca agcaatacca aggtggataa gcgggtggag    720
tctaagtacg gccctccttg ccctccatgt cctgctccag agtttctggg cggcccttcc    780
```

| | |
|---|---:|
| gtgttcctgt tttccacccaa accaaaggac acactgatga tctctagaac accagaggtg | 840 |
| acctgcgtgg tggtggacgt gagccaggag gatcccgagg tgcagttcaa ctggtacgtg | 900 |
| gatggcgtgg aggtgcacaa tgccaagacc aagccaagag aggagcagtt taactctaca | 960 |
| tacagggtgt tgagcgtgct gaccgtgctg caccaggatt ggctcaacgg caaggagtat | 1020 |
| aagtgcaagg tgtccaataa gggcctgccc tcctctatcg agaagacaat ctctaaggct | 1080 |
| aagggccagc caagagagcc tcaggtgtac accctgcctc caagccagga ggagatgaca | 1140 |
| aagaaccagg tgtccctgac atgtctggtg aagggcttct atccctccga catcgccgtg | 1200 |
| gagtgggagt ctaatggcca gcctgagaac aattacaaga ccacacccc tgtgctggac | 1260 |
| tctgatggca gcttctttct gtattccagg ctgaccgtgg ataagtctcg gtggcaggag | 1320 |
| ggcaacgtgt tcagctgctc tgtgatgcac gaagccctgc ataatcacta tactcagaaa | 1380 |
| agtctgtcac tgtcactggg aaagtgataa | 1410 |

<210> SEQ ID NO 198
<211> LENGTH: 1410
<212> TYPE: DNA
<213> ORGANISM: Artificial Sequence
<220> FEATURE:
<223> OTHER INFORMATION: U0959FD090-VH1-PTM

<400> SEQUENCE: 198

| | |
|---|---:|
| atgggctggt cttgtattat tctgtttctg gtcgcaactg ctacaggcgt gcattctcaa | 60 |
| gtgcagctgg tccagagcgg cgccgaggtg aaaaagcctg gcgcttctgt gaaggtgtcc | 120 |
| tgcaaggcct ctggctacac cttcaccagc agcgtgatcc actgggtgcg gcaggcccct | 180 |
| ggacagggcc tggaatggat gggctacatc aaccccctaca gcgagggcac aaagttcaac | 240 |
| gagaaaagca gatcagagt gaccatgacc agagatacct ccatcagcac agcttacatg | 300 |
| gaactgagcc gcctgcggag cgacgacacc gccgtgtact actgtgccag aggcctgatc | 360 |
| ggcacaagat acgacagctg gtttgcctat tggggccagg gaaccctggt tacagtgtct | 420 |
| agcgccagca ccaagggccc ttccgtgttt cccctggccc cttgctcccg gtccacatct | 480 |
| gagagcaccg ccgccctggg ctgtctggtg aaggactact cccagagcc cgtgaccgtg | 540 |
| agctggaaca gcggcgccct gacaagcggc gtgcacacat tcccgccgt gctgcagagc | 600 |
| tccggcctgt actccctgtc tagcgtggtg acagtgcctt cctctagcct gggcaccaag | 660 |
| acatatacct gtaacgtgga ccacaagcca agcaatacca aggtggataa gcgggtggag | 720 |
| tctaagtacg gccctccttg ccctccatgt cctgctccag agtttctggg cggcccttcc | 780 |
| gtgttcctgt ttccacccaa accaaaggac acactgatga tctctagaac accagaggtg | 840 |
| acctgcgtgg tggtggacgt gagccaggag gatcccgagg tgcagttcaa ctggtacgtg | 900 |
| gatggcgtgg aggtgcacaa tgccaagacc aagccaagag aggagcagtt taactctaca | 960 |
| tacagggtgt tgagcgtgct gaccgtgctg caccaggatt ggctcaacgg caaggagtat | 1020 |
| aagtgcaagg tgtccaataa gggcctgccc tcctctatcg agaagacaat ctctaaggct | 1080 |
| aagggccagc caagagagcc tcaggtgtac accctgcctc caagccagga ggagatgaca | 1140 |
| aagaaccagg tgtccctgac atgtctggtg aagggcttct atccctccga catcgccgtg | 1200 |
| gagtgggagt ctaatggcca gcctgagaac aattacaaga ccacacccc tgtgctggac | 1260 |
| tctgatggca gcttctttct gtattccagg ctgaccgtgg ataagtctcg gtggcaggag | 1320 |
| ggcaacgtgt tcagctgctc tgtgatgcac gaagccctgc ataatcacta tactcagaaa | 1380 |
| agtctgtcac tgtcactggg aaagtgataa | 1410 |

<210> SEQ ID NO 199
<211> LENGTH: 1410
<212> TYPE: DNA
<213> ORGANISM: Artificial Sequence
<220> FEATURE:
<223> OTHER INFORMATION: U0959FD090-VH2

<400> SEQUENCE: 199

| | | | | |
|---|---|---|---|---|
| atgggctggt | cttgtattat | tctgtttctg | gtcgcaactg ctacaggcgt gcattctcaa | 60 |
| gtgcagctgg | tccagagcgg | cgccgagtg | aagaagcctg gcgcttctgt gaaagtgtct | 120 |
| tgtaaagcct | ctggatacac | cttcaccagc | agcgtgatcc actgggtgcg gcaggcccct | 180 |
| ggacagggcc | tggaatggct | gggctacatc | aaccctaca gcgatggcac aaagttcaac | 240 |
| gagaagtgca | agatccgggc | cacaatgacc | tccgatacaa gcatcagcac cgcttatatg | 300 |
| gaactgagca | gactgagaag | cgacgacacc | gccgtgtact actgcgccag aggcctgatc | 360 |
| ggcacaagat | acgacagctg | gtttgcctac | tggggccagg gcaccctggt gaccgtgtcc | 420 |
| agcgccagca | ccaagggccc | ttccgtgttt | cccctggccc cttgctcccg gtccacatct | 480 |
| gagagcaccg | ccgccctggg | ctgtctggtg | aaggactact cccagagcc cgtgaccgtg | 540 |
| agctggaaca | gcggcgccct | gacaagcggc | gtgcacacat tcccgccgt gctgcagagc | 600 |
| tccggcctgt | actccctgtc | tagcgtggtg | acagtgcctt cctctagcct gggcaccaag | 660 |
| acatatacct | gtaacgtgga | ccacaagcca | agcaatacca aggtggataa gcgggtggag | 720 |
| tctaagtacg | gccctccttg | ccctccatgt | cctgctccag agtttctggg cggcccttcc | 780 |
| gtgttcctgt | ttccacccaa | accaaggac | acactgatga tctctagaac accagaggtg | 840 |
| acctgcgtgg | tggtggacgt | gagccaggag | gatcccgagg tgcagttcaa ctggtacgtg | 900 |
| gatggcgtgg | aggtgcacaa | tgccaagacc | aagccaagag aggagcagtt taactctaca | 960 |
| tacagggtgg | tgagcgtgct | gaccgtgctg | caccaggatt ggctcaacgg caaggagtat | 1020 |
| aagtgcaagg | tgtccaataa | gggcctgccc | tcctctatcg agaagacaat ctctaaggct | 1080 |
| aagggccagc | caagagagcc | tcaggtgtac | accctgcctc caagccagga ggagatgaca | 1140 |
| aagaaccagg | tgtccctgac | atgtctggtg | aagggcttct atccctccga catcgccgtg | 1200 |
| gagtgggagt | ctaatggcca | gcctgagaac | aattacaaga ccacacccc tgtgctggac | 1260 |
| tctgatggca | gcttcttct | gtattccagg | ctgaccgtgg ataagtctcg gtggcaggag | 1320 |
| ggcaacgtgt | tcagctgctc | tgtgatgcac | gaagccctgc ataatcacta tactcagaaa | 1380 |
| agtctgtcac | tgtcactggg | aaagtgataa | | 1410 |

<210> SEQ ID NO 200
<211> LENGTH: 1410
<212> TYPE: DNA
<213> ORGANISM: Artificial Sequence
<220> FEATURE:
<223> OTHER INFORMATION: U0959FD090-VH3

<400> SEQUENCE: 200

| | | | | |
|---|---|---|---|---|
| atgggctggt | cttgtattat | tctgtttctg | gtcgcaactg ctacaggcgt gcattctcaa | 60 |
| gtgcagctcg | tgcagagcgg | cgccgagtg | aaaaagcctg gcgcttctgt gaaggtgtct | 120 |
| tgtaaagcct | ctggctacac | cttcaccagc | agcgtgatcc actgggttaa gcaggcccct | 180 |
| ggacagggcc | tggaatggct | gggctacatc | aaccctaca gcgatggcac aaagttcaac | 240 |
| gagaagtgca | agatccgggt | gaccctgacc | tccgatacaa gcatcagcac cgcttatatg | 300 |

| | |
|---|---|
| gaactgagca gactgcggag cgacgacacc gccgtgtact actgcgccag aggcctgatc | 360 |
| ggaacaagat acgacagctg gtttgcctac tggggccagg gcacactggt caccgtgtcc | 420 |
| agcgccagca ccaagggccc ttccgtgttt cccctggccc cttgctcccg gtccacatct | 480 |
| gagagcaccg ccgccctggg ctgtctggtg aaggactact cccagagcc cgtgaccgtg | 540 |
| agctggaaca gcggcgccct gacaagcggc gtgcacacat tcccgccgt gctgcagagc | 600 |
| tccggcctgt actccctgtc tagcgtggtg acagtgcctt cctctagcct gggcaccaag | 660 |
| acatatacct gtaacgtgga ccacaagcca agcaatacca aggtggataa gcgggtggag | 720 |
| tctaagtacg gccctccttg ccctccatgt cctgctccag agtttctggg cggcccttcc | 780 |
| gtgttcctgt ttccacccaa accaaaggac acactgatga tctctagaac accagaggtg | 840 |
| acctgcgtgg tggtggacgt gagccaggag gatcccgagg tgcagttcaa ctggtacgtg | 900 |
| gatggcgtgg aggtgcacaa tgccaagacc aagccaagag aggagcagtt taactctaca | 960 |
| tacagggtgg tgagcgtgct gaccgtgctg caccaggatt ggctcaacgg caaggagtat | 1020 |
| aagtgcaagg tgtccaataa gggcctgccc tcctctatcg agaagacaat ctctaaggct | 1080 |
| aagggccagc caagagagcc tcaggtgtac accctgcctc caagccagga ggagatgaca | 1140 |
| aagaaccagg tgtccctgac atgtctggtg aagggcttct atccctccga catcgccgtg | 1200 |
| gagtgggagt ctaatggcca gcctgagaac aattacaaga ccacaccccc tgtgctggac | 1260 |
| tctgatggca gcttctttct gtattccagg ctgaccgtgg ataagtctcg gtggcaggag | 1320 |
| ggcaacgtgt tcagctgctc tgtgatgcac gaagccctgc ataatcacta tactcagaaa | 1380 |
| agtctgtcac tgtcactggg aaagtgataa | 1410 |

<210> SEQ ID NO 201
<211> LENGTH: 1410
<212> TYPE: DNA
<213> ORGANISM: Artificial Sequence
<220> FEATURE:
<223> OTHER INFORMATION: U0959FD090-VH4

<400> SEQUENCE: 201

| | |
|---|---|
| atgggctggt cttgtattat tctgtttctg gtcgcaactg ctacaggcgt gcattctcaa | 60 |
| gtgcagctgg ttcagagcgg cgccgaggtg aaaaagcctg gcgcttctgt gaaggtgtct | 120 |
| tgtaaagcct ctggctacac cttcaccagc agcgtgatcc actgggtcaa gcaggcccct | 180 |
| ggacagggac tggaatggct gggctacatc aacccctaca gcgatggcac aaagttcaac | 240 |
| gagaagtgca agatccgggc cacaatgacc tccgataaga gcatcagcac cgcttatatg | 300 |
| gaactgagca gactgcggag cgacgacacc gccgtgtact actgcgccag aggcctgatc | 360 |
| ggcacaagat acgacagctg gtttgcctac tggggccagg gcaccctggt gaccgtgtcc | 420 |
| agcgccagca ccaagggccc ttccgtgttt cccctggccc cttgctcccg gtccacatct | 480 |
| gagagcaccg ccgccctggg ctgtctggtg aaggactact cccagagcc cgtgaccgtg | 540 |
| agctggaaca gcggcgccct gacaagcggc gtgcacacat tcccgccgt gctgcagagc | 600 |
| tccggcctgt actccctgtc tagcgtggtg acagtgcctt cctctagcct gggcaccaag | 660 |
| acatatacct gtaacgtgga ccacaagcca agcaatacca aggtggataa gcgggtggag | 720 |
| tctaagtacg gccctccttg ccctccatgt cctgctccag agtttctggg cggcccttcc | 780 |
| gtgttcctgt ttccacccaa accaaaggac acactgatga tctctagaac accagaggtg | 840 |
| acctgcgtgg tggtggacgt gagccaggag gatcccgagg tgcagttcaa ctggtacgtg | 900 |
| gatggcgtgg aggtgcacaa tgccaagacc aagccaagag aggagcagtt taactctaca | 960 |

```
tacagggtgg tgagcgtgct gaccgtgctg caccaggatt ggctcaacgg caaggagtat    1020
aagtgcaagg tgtccaataa gggcctgccc tcctctatcg agaagacaat ctctaaggct    1080
aagggccagc caagagagcc tcaggtgtac accctgcctc caagccagga ggagatgaca    1140
aagaaccagg tgtccctgac atgtctggtg aagggcttct atccctccga catcgccgtg    1200
gagtgggagt ctaatggcca gcctgagaac aattacaaga ccacacccccc tgtgctggac    1260 tctgatggca gcttctttct gtattccagg ctgaccgtgg ataagtctcg gtggcaggag    1320
ggcaacgtgt tcagctgctc tgtgatgcac gaagccctgc ataatcacta tactcagaaa    1380
agtctgtcac tgtcactggg aaagtgataa                                    1410
```

<210> SEQ ID NO 202
<211> LENGTH: 233
<212> TYPE: PRT
<213> ORGANISM: Artificial Sequence
<220> FEATURE:
<223> OTHER INFORMATION: U0959FD090-VL1

<400> SEQUENCE: 202

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Asp Ile
        35                  40                  45

Asn Asn Tyr Leu Asn Trp Tyr Gln Gln Lys Pro Gly Lys Ala Pro Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Gly Asn Thr
            100                 105                 110

Leu Pro Tyr Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 203
<211> LENGTH: 233
<212> TYPE: PRT
<213> ORGANISM: Artificial Sequence
<220> FEATURE:
<223> OTHER INFORMATION: U0959FD090-VL2

<400> SEQUENCE: 203

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Asp Ile
        35                  40                  45

Asn Asn Tyr Leu Asn Trp Tyr Gln Gln Lys Pro Gly Lys Ala Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Phe Cys Gln Gln Gly Asn Thr
            100                 105                 110

Leu Pro Tyr Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 204
<211> LENGTH: 233
<212> TYPE: PRT
<213> ORGANISM: Artificial Sequence
<220> FEATURE:
<223> OTHER INFORMATION: U0959FD090-VL3

<400> SEQUENCE: 204

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Asp Ile
        35                  40                  45

Asn Asn Tyr Leu Asn Trp Tyr Gln Gln Lys Pro Gly Lys Ala Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Phe Cys Gln Gln Gly Asn Thr
            100                 105                 110

Leu Pro Tyr Thr Phe Gly Gly Thr Lys Val Glu Ile Lys Arg Thr
            115                 120                 125

Val Ala Ala Pro Ser Val Phe Ile Phe Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 205
<211> LENGTH: 233
<212> TYPE: PRT
<213> ORGANISM: Artificial Sequence
<220> FEATURE:
<223> OTHER INFORMATION: U0959FD090-VL4

<400> SEQUENCE: 205

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Ser Cys Arg Thr Ser Gln Asp Ile
        35                  40                  45

Asn Asn Tyr Leu Asn Trp Tyr Gln Gln Lys Pro Gly Lys Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Phe Cys Gln Gln Gly Asn Thr
            100                 105                 110

Leu Pro Tyr Thr Phe Gly Gly Gly Thr Lys Val Glu Ile Lys Arg Thr
        115                 120                 125

Val Ala Ala Pro Ser Val Phe Ile Phe Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 206
<211> LENGTH: 705
<212> TYPE: DNA
<213> ORGANISM: Artificial Sequence
<220> FEATURE:
<223> OTHER INFORMATION: U0959FD090-VL1

<400> SEQUENCE: 206

| | | | | | |
|---|---|---|---|---|---|
| atgggctggt | catgtattat | tctgtttctg | gtcgcaactg | ctacaggggt | ccatagtgat | 60 |
| attcagatga | cacagagccc | ctcttctctg | agcgctagcg | tgggcgatag | agtgaccatc | 120 |
| acatgtagaa | cctcccagga | catcaacaac | tacctgaact | ggtaccagca | gaaaccaggc | 180 |
| aaggcccta | agctgctgat | ctactacacc | agccggctgc | acagcggcgt | ccccagcaga | 240 |
| ttcagcggct | ccggatctgg | caccgacttc | acctttacca | tcagcagcct | gcagcctgag | 300 |
| gacatcgcca | cctactactg | ccagcaaggc | aatacccctgc | cttatacatt | cggcggcgga | 360 |
| acaaaggtgg | aaatcaagag | gacagtggcc | gccccaagcg | tgttcatctt | tccccttcc | 420 |
| gacgagcagc | tgaagtctgg | caccgccagc | gtggtgtgcc | tgctgaacaa | cttctaccct | 480 |
| cgggaggcca | aggtccagtg | gaaggtggat | aacgccctgc | agtctggcaa | tagccaggag | 540 |
| tccgtgaccg | agcaggactc | taaggatagc | acatattccc | tgtctagcac | cctgacactg | 600 |
| agcaaggccg | attacgagaa | gcacaaggtg | tatgcctgtg | aagtcaccca | tcagggctg | 660 |
| tcatcacccg | tcactaagtc | attcaatcgc | ggagaatgct | gataa | | 705 |

<210> SEQ ID NO 207
<211> LENGTH: 705
<212> TYPE: DNA
<213> ORGANISM: Artificial Sequence
<220> FEATURE:
<223> OTHER INFORMATION: U0959FD090-VL2

<400> SEQUENCE: 207

| | | | | | |
|---|---|---|---|---|---|
| atgggctggt | catgtattat | tctgtttctg | gtcgcaactg | ctacaggggt | ccatagtgat | 60 |
| attcagatga | cccagagccc | ctcctccctg | agcgcttctg | tgggcgatag | agtgaccatc | 120 |
| acctgtagaa | caagccagga | catcaacaac | tacctgaact | ggtaccagca | gaaacctggc | 180 |
| aaggccgtca | agctgctgat | ctactacacc | agccggctgc | acagcggagt | gccatctaga | 240 |
| ttcagcggct | ctggcagcgg | caccgacttc | acctttacca | tcagcagcct | gcagcctgag | 300 |
| gacatcgcca | catacttctg | ccagcaaggc | aatacccctgc | cttatacatt | cggcggcgga | 360 |
| acaaaggtgg | aaatcaagag | gacagtggcc | gccccaagcg | tgttcatctt | tccccttcc | 420 |
| gacgagcagc | tgaagtctgg | caccgccagc | gtggtgtgcc | tgctgaacaa | cttctaccct | 480 |
| cgggaggcca | aggtccagtg | gaaggtggat | aacgccctgc | agtctggcaa | tagccaggag | 540 |
| tccgtgaccg | agcaggactc | taaggatagc | acatattccc | tgtctagcac | cctgacactg | 600 |
| agcaaggccg | attacgagaa | gcacaaggtg | tatgcctgtg | aagtcaccca | tcagggctg | 660 |
| tcatcacccg | tcactaagtc | attcaatcgc | ggagaatgct | gataa | | 705 |

<210> SEQ ID NO 208
<211> LENGTH: 705
<212> TYPE: DNA
<213> ORGANISM: Artificial Sequence
<220> FEATURE:
<223> OTHER INFORMATION: U0959FD090-VL3

<400> SEQUENCE: 208

| | | | | | |
|---|---|---|---|---|---|
| atgggctggt | catgtattat | tctgtttctg | gtcgcaactg | ctacaggggt | ccatagtgat | 60 |

```
attcagatga cccagtcccc atctagcctg agcgccagcg tgggcgatag agtgaccatc 120
acctgtagaa ccagccagga catcaacaac tacctgaact ggtatcagca gaaacctggc 180
aaggccgtga agctgctgat ctactacaca tctagactgc acagcggcgt ccccagccgg 240
ttcagcggat ctggcagcgg caccgactac acatttacca tcagctccct gcagcctgag 300
gacatcgcta catacttctg ccagcaaggc aataccctgc cttacacctt cggcggaggc 360
```
acaaaggtgg aaatcaagag gacagtggcc gccccaagcg tgttcatctt tccccccttcc 420
gacgagcagc tgaagtctgg caccgccagc gtggtgtgcc tgctgaacaa cttctaccct 480
cgggaggcca aggtccagtg gaaggtggat aacgccctgc agtctggcaa tagccaggag 540
tccgtgaccg agcaggactc taaggatagc acatattccc tgtctagcac cctgacactg 600
agcaaggccg attacgagaa gcacaaggtg tatgcctgtg aagtcaccca tcaggggctg 660
tcatcacccg tcactaagtc attcaatcgc ggagaatgct gataa 705

<210> SEQ ID NO 209
<211> LENGTH: 705
<212> TYPE: DNA
<213> ORGANISM: Artificial Sequence
<220> FEATURE:
<223> OTHER INFORMATION: U0959FD090-VL4

<400> SEQUENCE: 209
atgggctggt catgtattat tctgtttctg gtcgcaactg ctacaggggt ccatagtgat 60
attcagatga cccagtcccc atcttccctg agcgccagcg tgggcgatag agtgaccatc 120
tcttgtagaa caagccagga catcaacaac tacctgaact ggtatcagca gaaacctggc 180
aagaccgtga agctgctgat ctactacacc agccggctgc acagcggcgt ccccagcaga 240
ttcagcggat ctggcagcgg caccgactac acatttacca tcagcagcct gcagcctgag 300
gacatcgcca catacttctg ccagcaaggc aataccctgc cttacacctt cggcggaggc 360
acaaaggtgg aaatcaagag gacagtggcc gccccaagcg tgttcatctt tccccccttcc 420
gacgagcagc tgaagtctgg caccgccagc gtggtgtgcc tgctgaacaa cttctaccct 480
cgggaggcca aggtccagtg gaaggtggat aacgccctgc agtctggcaa tagccaggag 540
tccgtgaccg agcaggactc taaggatagc acatattccc tgtctagcac cctgacactg 600
agcaaggccg attacgagaa gcacaaggtg tatgcctgtg aagtcaccca tcaggggctg 660
tcatcacccg tcactaagtc attcaatcgc ggagaatgct gataa 705

<210> SEQ ID NO 210
<211> LENGTH: 423
<212> TYPE: DNA
<213> ORGANISM: Artificial Sequence
<220> FEATURE:
<223> OTHER INFORMATION: Heavy chain variable domain
<400> SEQUENCE: 210
atgggctggt cttgtattat tctgtttctg gtcgcaactg ctacaggcgt gcattctcaa 60
gtgcagctgg tccagagcgg cgccgaggtg aaaaagcctg gcgcttctgt gaaggtgtcc 120
tgcaaggcct ctggctacac cttcaccagc agcgtgatcc actgggtgcg gcaggcccct 180
ggacagggcc tggaatggat gggctacatc aacccctaca gcgagggcac aaagttcaac 240
gagaaaagca agatcagagt gaccatgacc agagatacct ccatcagcac agcttacatg 300
gaactgagcc gcctgcggag cgacgacacc gccgtgtact actgtgccag aggcctgatc 360

| ggcacaagat acgacagctg gtttgcctat tggggccagg aaccctggt tacagtgtct | 420 |
| agc | 423 |

<210> SEQ ID NO 211
<211> LENGTH: 366
<212> TYPE: DNA
<213> ORGANISM: Artificial Sequence
<220> FEATURE:
<223> OTHER INFORMATION: Heavy chain variable domain

<400> SEQUENCE: 211

| caagtgcagc tggtccagag cggcgccgag gtgaaaaagc ctggcgcttc tgtgaaggtg | 60 |
| tcctgcaagg cctctggcta caccttcacc agcagcgtga tccactgggt gcggcaggcc | 120 |
| cctggacagg gcctggaatg gatgggctac atcaaccct acagcgaggg cacaaagttc | 180 |
| aacgagaaaa gcaagatcag agtgaccatg accagagata cctccatcag cacagcttac | 240 |
| atggaactga ccgcctgcg gagcgacgac accgccgtgt actactgtgc cagaggcctg | 300 |
| atcggcacaa gatacgacag ctggtttgcc tattggggcc aggggaaccct ggttacagtg | 360 |
| tctagc | 366 |

<210> SEQ ID NO 212
<211> LENGTH: 141
<212> TYPE: PRT
<213> ORGANISM: Artificial Sequence
<220> FEATURE:
<223> OTHER INFORMATION: Heavy chain variable domain

<400> SEQUENCE: 212

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Ser Val Ile His Trp Val Arg Gln Ala Pro Gly Gln Gly Leu
    50                  55                  60

Glu Trp Met Gly Tyr Ile Asn Pro Tyr Ser Glu Gly Thr Lys Phe Asn
65                  70                  75                  80

Glu Lys Ser Lys Ile Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Leu Ile Gly Thr Arg Tyr Asp Ser Trp Phe
        115                 120                 125

Ala Tyr Trp Gly Gln Gly Thr Leu Val Thr Val Ser Ser
    130                 135                 140

<210> SEQ ID NO 213
<211> LENGTH: 122
<212> TYPE: PRT
<213> ORGANISM: Artificial Sequence
<220> FEATURE:
<223> OTHER INFORMATION: Heavy chain variable domain

<400> SEQUENCE: 213

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser

-continued

```
                20                  25                  30

Val Ile His Trp Val Arg Gln Ala Pro Gly Gln Gly Leu Glu Trp Met
            35                  40                  45

Gly Tyr Ile Asn Pro Tyr Ser Glu Gly Thr Lys Phe Asn Glu Lys Ser
    50                  55                  60

Lys Ile Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ser
        115                 120

<210> SEQ ID NO 214
<211> LENGTH: 30
<212> TYPE: PRT
<213> ORGANISM: Artificial Sequence
<220> FEATURE:
<223> OTHER INFORMATION: Heavy chain FR1

<400> SEQUENCE: 214

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 215
<211> LENGTH: 14
<212> TYPE: PRT
<213> ORGANISM: Artificial Sequence
<220> FEATURE:
<223> OTHER INFORMATION: Heavy chain FR2

<400> SEQUENCE: 215

Trp Val Arg Gln Ala Pro Gly Gln Gly Leu Glu Trp Met Gly
1               5                   10

<210> SEQ ID NO 216
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 216

Tyr Ile Asn Pro Tyr Ser Glu Gly Thr Lys Phe Asn Glu Lys Ser Lys
1               5                   10                  15

Ile

<210> SEQ ID NO 217
<211> LENGTH: 32
<212> TYPE: PRT
<213> ORGANISM: Artificial Sequence
<220> FEATURE:
<223> OTHER INFORMATION: Heavy chain FR3

<400> SEQUENCE: 217

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30
```

<210> SEQ ID NO 218
<211> LENGTH: 11
<212> TYPE: PRT
<213> ORGANISM: Artificial Sequence
<220> FEATURE:
<223> OTHER INFORMATION: Heavy chain FR4

<400> SEQUENCE: 218

Trp Gly Gln Gly Thr Leu Val Thr Val Ser Ser
1               5                   10

<210> SEQ ID NO 219
<211> LENGTH: 378
<212> TYPE: DNA
<213> ORGANISM: Artificial Sequence
<220> FEATURE:
<223> OTHER INFORMATION: Light chain variable domain

<400> SEQUENCE: 219
atgggctggt catgtattat tctgtttctg gtcgcaactg ctacaggggt ccatagtgat      60
attcagatga cacagagccc ctcttctctg agcgctagcg tgggcgatag agtgaccatc     120
acatgtagaa cctcccagga catcaacaac tacctgaact ggtaccagca gaaaccaggc     180
aaggccccta agctgctgat ctactacacc agccggctgc acagcggcgt ccccagcaga     240
ttcagcggct ccggatctgg caccgacttc acctttacca tcagcagcct gcagcctgag     300
gacatcgcca cctactactg ccagcaaggc aataccctgc cttatacatt cggcggcgga     360
acaaaggtgg aaatcaag                                                   378

<210> SEQ ID NO 220
<211> LENGTH: 321
<212> TYPE: DNA
<213> ORGANISM: Artificial Sequence
<220> FEATURE:
<223> OTHER INFORMATION: Light chain variable domain

<400> SEQUENCE: 220
gatattcaga tgacacagag cccctcttct ctgagcgcta gcgtgggcga tagagtgacc      60
atcacatgta gaacctccca ggacatcaac aactacctga actggtacca gcagaaacca     120
ggcaaggccc ctaagctgct gatctactac accagccggc tgcacagcgg cgtccccagc     180
agattcagcg gctccggatc tggcaccgac ttcaccttta ccatcagcag cctgcagcct     240
gaggacatcg ccacctacta ctgccagcaa ggcaataccc tgccttatac attcggcggc     300
ggaacaaagg tggaaatcaa g                                               321

<210> SEQ ID NO 221
<211> LENGTH: 126
<212> TYPE: PRT
<213> ORGANISM: Artificial Sequence
<220> FEATURE:
<223> OTHER INFORMATION: Light chain variable domain

<400> SEQUENCE: 221

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Thr Ser Gln Asp Ile
            35                  40                  45

```
Asn Asn Tyr Leu Asn Trp Tyr Gln Gln Lys Pro Gly Lys Ala Pro Lys
         50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Phe Thr Phe Thr Ile Ser Ser
                 85                  90                  95

Leu Gln Pro Glu Asp Ile Ala Thr Tyr Tyr Cys Gln Gln Gly Asn Thr
            100                 105                 110

Leu Pro Tyr Thr Phe Gly Gly Gly Thr Lys Val Glu Ile Lys
        115                 120                 125

<210> SEQ ID NO 222
<211> LENGTH: 107
<212> TYPE: PRT
<213> ORGANISM: Artificial Sequence
<220> FEATURE:
<223> OTHER INFORMATION: Light chain variable domain

<400> SEQUENCE: 222

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Asp Ile Asn Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Tyr
                 85                  90                  95

Thr Phe Gly Gly Gly Thr Lys Val Glu Ile Lys
            100                 105

<210> SEQ ID NO 223
<211> LENGTH: 23
<212> TYPE: PRT
<213> ORGANISM: Artificial Sequence
<220> FEATURE:
<223> OTHER INFORMATION: Light chain FR1

<400> SEQUENCE: 223

Asp Ile Gln Met Thr Gln Ser Pro Ser Ser Leu Ser Ala Ser Val Gly
 1               5                  10                  15

Asp Arg Val Thr Ile Thr Cys
             20

<210> SEQ ID NO 224
<211> LENGTH: 15
<212> TYPE: PRT
<213> ORGANISM: Artificial Sequence
<220> FEATURE:
<223> OTHER INFORMATION: Light chain FR2

<400> SEQUENCE: 224

Trp Tyr Gln Gln Lys Pro Gly Lys Ala Pro Lys Leu Leu Ile Tyr
 1               5                  10                  15

<210> SEQ ID NO 225
<211> LENGTH: 32
<212> TYPE: PRT
```

<213> ORGANISM: Artificial Sequence
<220> FEATURE:
<223> OTHER INFORMATION: Light chain FR3

<400> SEQUENCE: 225

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 226
<211> LENGTH: 10
<212> TYPE: PRT
<213> ORGANISM: Artificial Sequence
<220> FEATURE:
<223> OTHER INFORMATION: Light chain FR4

<400> SEQUENCE: 226

Phe Gly Gly Gly Thr Lys Val Glu Ile Lys
1               5                   10

<210> SEQ ID NO 227
<211> LENGTH: 378
<212> TYPE: DNA
<213> ORGANISM: Artificial Sequence
<220> FEATURE:
<223> OTHER INFORMATION: Light chain variable domain

<400> SEQUENCE: 227

```
atgggctggt catgtattat tctgtttctg gtcgcaactg ctacaggggt ccatagtgat      60
attcagatga cccagagccc ctcctccctg agcgcttctg tgggcgatag agtgaccatc     120
acctgtagaa caagccagga catcaacaac tacctgaact ggtaccagca gaaacctggc     180
aaggccgtca agctgctgat ctactacacc agccggctgc acagcggagt gccatctaga     240
ttcagcggct ctggcagcgg caccgacttc acctttacca tcagcagcct gcagcctgag     300
gacatcgcca catacttctg ccagcaaggc aatacccctg cttatacatt cggcggcgga     360
acaaaggtgg aaatcaag                                                   378
```

<210> SEQ ID NO 228
<211> LENGTH: 321
<212> TYPE: DNA
<213> ORGANISM: Artificial Sequence
<220> FEATURE:
<223> OTHER INFORMATION: Light chain variable domain

<400> SEQUENCE: 228

```
gatattcaga tgacccagag ccccctcctcc ctgagcgctt ctgtgggcga tagagtgacc      60
atcacctgta gaacaagcca ggacatcaac aactacctga ctggtaccag cagaaacct      120
ggcaaggccg tcaagctgct gatctactac accagccggc tgcacagcgg agtgccatct      180
agattcagcg gctctggcag cggcaccgac ttcaccttta ccatcagcag cctgcagcct      240
gaggacatcg ccacatactt ctgccagcaa ggcaataccc tgccttatac attcggcggc      300
ggaacaaagg tggaaatcaa g                                                321
```

<210> SEQ ID NO 229
<211> LENGTH: 126
<212> TYPE: PRT
<213> ORGANISM: Artificial Sequence
<220> FEATURE:
<223> OTHER INFORMATION: Light chain variable domain

<400> SEQUENCE: 229

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Asp Ile
        35                  40                  45

Asn Asn Tyr Leu Asn Trp Tyr Gln Gln Lys Pro Gly Lys Ala Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Phe Cys Gln Gln Gly Asn Thr
            100                 105                 110

Leu Pro Tyr Thr Phe Gly Gly Gly Thr Lys Val Glu Ile Lys
        115                 120                 125

<210> SEQ ID NO 230
<211> LENGTH: 107
<212> TYPE: PRT
<213> ORGANISM: Artificial Sequence
<220> FEATURE:
<223> OTHER INFORMATION: Light chain variable domain

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asn Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Val Glu Ile Lys
            100                 105

<210> SEQ ID NO 231
<211> LENGTH: 15
<212> TYPE: PRT
<213> ORGANISM: Artificial Sequence
<220> FEATURE:
<223> OTHER INFORMATION: Light chain FR2

<400> SEQUENCE: 231

Trp Tyr Gln Gln Lys Pro Gly Lys Ala Val Lys Leu Leu Ile Tyr
1               5                   10                  15

<210> SEQ ID NO 232
<211> LENGTH: 32
<212> TYPE: PRT
<213> ORGANISM: Artificial Sequence
<220> FEATURE:
<223> OTHER INFORMATION: Light chain FR3

<400> SEQUENCE: 232

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Phe Cys
            20                  25                  30

<210> SEQ ID NO 233
<211> LENGTH: 378
<212> TYPE: DNA
<213> ORGANISM: Artificial Sequence
<220> FEATURE:
<223> OTHER INFORMATION: Light chain variable domain

<400> SEQUENCE: 233
atgggctggt catgtattat tctgtttctg gtcgcaactg ctacaggggt ccatagtgat      60
attcagatga cccagtcccc atctagcctg agcgccagcg tgggcgatag agtgaccatc     120
acctgtagaa ccagccagga catcaacaac tacctgaact ggtatcagca gaaacctggc     180
aaggccgtga agctgctgat ctactacaca tctagactgc acagcggcgt ccccagccgg     240
ttcagcggat ctggcagcgg caccgactac acatttacca tcagctccct gcagcctgag     300
gacatcgcta catacttctg ccagcaaggc aatacccggc ttacaccctt cggcggaggc     360
acaaaggtgg aaatcaag                                                   378

<210> SEQ ID NO 234
<211> LENGTH: 321
<212> TYPE: DNA
<213> ORGANISM: Artificial Sequence
<220> FEATURE:
<223> OTHER INFORMATION: Light chain variable domain

<400> SEQUENCE: 234
gatattcaga tgacccagtc cccatctagc ctgagcgcca gcgtgggcga tagagtgacc      60
atcacctgta gaaccagcca ggacatcaac aactacctga actggtatca gcagaaacct     120
ggcaaggccg tgaagctgct gatctactac acatctagac tgcacagcgg cgtccccagc     180
cggttcagcg gatctggcag cggcaccgac tacacattta ccatcagctc cctgcagcct     240
gaggacatcg ctacatactt ctgccagcaa ggcaataccc tgccttacac cttcggcgga     300
ggcacaaagg tggaaatcaa g                                               321

<210> SEQ ID NO 235
<211> LENGTH: 126
<212> TYPE: PRT
<213> ORGANISM: Artificial Sequence
<220> FEATURE:
<223> OTHER INFORMATION: Light chain variable domain

<400> SEQUENCE: 235

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Asp Ile
        35                  40                  45

Asn Asn Tyr Leu Asn Trp Tyr Gln Gln Lys Pro Gly Lys Ala Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Thr Phe Thr Ile Ser Ser

```
                        85                  90                  95

Leu Gln Pro Glu Asp Ile Ala Thr Tyr Phe Cys Gln Gln Gly Asn Thr
                100                 105                 110

Leu Pro Tyr Thr Phe Gly Gly Gly Thr Lys Val Glu Ile Lys
            115                 120                 125

<210> SEQ ID NO 236
<211> LENGTH: 107
<212> TYPE: PRT
<213> ORGANISM: Artificial Sequence
<220> FEATURE:
<223> OTHER INFORMATION: Light chain variable domain

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asn Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Val Glu Ile Lys
            100                 105

<210> SEQ ID NO 237
<211> LENGTH: 32
<212> TYPE: PRT
<213> ORGANISM: Artificial Sequence
<220> FEATURE:
<223> OTHER INFORMATION: Light chain FR3

<400> SEQUENCE: 237

Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Phe Cys
            20                  25                  30

<210> SEQ ID NO 238
<211> LENGTH: 122
<212> TYPE: PRT
<213> ORGANISM: Artificial Sequence
<220> FEATURE:
<223> OTHER INFORMATION: U0959FD090-chimeric-VH-PTM1

<400> SEQUENCE: 238

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Val Ile His Trp Val Lys Gln Lys Pro Gly Gln Gly Leu Glu Trp Leu
        35                  40                  45

Gly Tyr Ile Asn Pro Tyr Ser Glu Gly Thr Lys Phe Asn Glu Lys Ser
    50                  55                  60

Lys Ile Lys Ala Thr Leu Thr Ser Asp Lys Ser Ser Thr Ala Tyr
65                  70                  75                  80
```

```
Met Glu Leu Ser Ser Leu Thr Ser Glu Asp Ser Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ala
        115                 120

<210> SEQ ID NO 239
<211> LENGTH: 122
<212> TYPE: PRT
<213> ORGANISM: Artificial Sequence
<220> FEATURE:
<223> OTHER INFORMATION: U0959FD090-chimeric-VH-PTM2

<400> SEQUENCE: 239

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Val Ile His Trp Val Lys Gln Lys Pro Gly Gln Gly Leu Glu Trp Leu
            35                  40                  45

Gly Tyr Ile Asn Pro Tyr Ser Asp Ala Thr Lys Phe Asn Glu Lys Ser
    50                  55                  60

Lys Ile Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ala
        115                 120

<210> SEQ ID NO 240
<211> LENGTH: 122
<212> TYPE: PRT
<213> ORGANISM: Artificial Sequence
<220> FEATURE:
<223> OTHER INFORMATION: U0959FD090-VH1

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Val Ile His Trp Val Arg Gln Ala Pro Gly Gln Gly Leu Glu Trp Met
            35                  40                  45

Gly Tyr Ile Asn Pro Tyr Ser Asp Gly Thr Lys Phe Asn Glu Lys Cys
    50                  55                  60

Lys Ile Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ser
        115                 120
```

-continued

```
<210> SEQ ID NO 241
<211> LENGTH: 122
<212> TYPE: PRT
<213> ORGANISM: Artificial Sequence
<220> FEATURE:
<223> OTHER INFORMATION: U0959FD090-VH2

<400> SEQUENCE: 241

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Val Ile His Trp Val Arg Gln Ala Pro Gly Gln Gly Leu Glu Trp Leu
        35                  40                  45

Gly Tyr Ile Asn Pro Tyr Ser Asp Gly Thr Lys Phe Asn Glu Lys Cys
    50                  55                  60

Lys Ile Arg Ala Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ser
        115                 120

<210> SEQ ID NO 242
<211> LENGTH: 122
<212> TYPE: PRT
<213> ORGANISM: Artificial Sequence
<220> FEATURE:
<223> OTHER INFORMATION: U0959FD090-VH3

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Val Ile His Trp Val Lys Gln Ala Pro Gly Gln Gly Leu Glu Trp Leu
        35                  40                  45

Gly Tyr Ile Asn Pro Tyr Ser Asp Gly Thr Lys Phe Asn Glu Lys Cys
    50                  55                  60

Lys Ile Arg Val Thr Leu Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ser
        115                 120

<210> SEQ ID NO 243
<211> LENGTH: 122
<212> TYPE: PRT
<213> ORGANISM: Artificial Sequence
<220> FEATURE:
<223> OTHER INFORMATION: U0959FD090-VH4

<400> SEQUENCE: 243

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Ser
            20                  25                  30

Val Ile His Trp Val Lys Gln Ala Pro Gly Gln Gly Leu Glu Trp Leu
        35                  40                  45

Gly Tyr Ile Asn Pro Tyr Ser Asp Gly Thr Lys Phe Asn Glu Lys Cys
    50                  55                  60

Lys Ile Arg Ala Thr Met Thr Ser Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ile Gly Thr Arg Tyr Asp Ser Trp Phe Ala Tyr Trp
            100                 105                 110

Gly Gln Gly Thr Leu Val Thr Val Ser Ser
        115                 120

<210> SEQ ID NO 244
<211> LENGTH: 107
<212> TYPE: PRT
<213> ORGANISM: Artificial Sequence
<220> FEATURE:
<223> OTHER INFORMATION: U0959FD090-VL4

<400> SEQUENCE: 244

Asp Ile Gln Met Thr Gln Ser Pro Ser Ser Leu Ser Ala Ser Val Gly
1               5                   10                  15

Asp Arg Val Thr Ile Ser Cys Arg Thr Ser Gln Asp Ile Asn Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Val Glu Ile Lys
            100                 105
```

ANTI-CD47 ANTIBODIES AND USES THEREOF

CROSS-REFERENCE TO RELATED APPLICATIONS

This application claims the benefit of U.S. Provisional Patent Application No. 63/129,716, filed on Dec. 23, 2020, the disclosure of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: D10T_001_01US_SeqList_ST25.txt, date recorded: Dec. 23, 2021, file size ~160,632 bytes).

TECHNICAL FIELD

The disclosure relates to therapeutic antibody molecules and treatments for inherited disorders of red blood cells.

BACKGROUND

Sickle cell disease (SCD) is a group of inherited red blood cell (RBC) disorders. RBCs with normal hemoglobin (hemoglobin A or HbA) are disk-shaped, flexible and can move easily through blood vessels. SCD is caused by mutations in the hemoglobin beta (HBB) gene, which lead to production of abnormal hemoglobins. One type of mutation leads to production of hemoglobin S (HbS). HbS arises from a mutation substituting thymine for adenine in the sixth codon of the beta-chain gene: GAG to GTG. This causes coding of valine instead of glutamate in position 6 of the Hb beta chain. Individuals who are homozygous for the HbS mutation experience more severe forms of SCD than individuals who are heterozygous. Oxygenated HbS is much less soluble than oxygenated HbA, causing RBCs with HbS to become rigid and shaped like a sickle. These sickle cells adhere to vascular endothelium and obstruct small blood vessels. The obstructions can lead to pain, inflammation and increased levels of infection and stroke. Sickle cells also do not survive as long as normal RBCs, which can lead to anemia.

In the United States, SCD affects about 100,000 people. An estimated 2,000,000 Americans have sickle traits. In the United States, approximately 2,000 children are born with SCD each year. Globally, the SCD incidence is estimated at 250,000 to 300,000 births annually. Currently, treatment for SCD includes hydroxyurea, blood transfusion, and bone marrow transplants. Hydroxyurea increases production of normal-shaped fetal hemoglobin providing relief of certain SCD symptoms. However, hydroxyurea compromises the immune system. Hematopoietic Stem Cell Transplantation (HSCT) is the only cure for SCD, but it poses life-threatening risks. There is a need for therapies for SCD that have a reduced risk of adverse side effects.

SUMMARY

Provided herein is an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; (b) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (c) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (d) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (e) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (g) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

Provided herein is an anti-CD47 antibody or an antigen-binding portion thereof, wherein the antibody or antigen-binding portion cross-competes for binding to CD47 with an antibody comprising a heavy chain variable (VH) domain and a light chain variable (VL) domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; (b) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (c) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (d) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (e) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (g) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

Further provided herein is an anti-CD47 antibody or an antigen-binding portion thereof, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR3 comprises SEQ ID NO: 19; and/or wherein the LCDR3 comprises SEQ ID NO: 39; (b) wherein the HCDR3 comprises SEQ ID NO: 59; and/or wherein the LCDR3 comprises SEQ ID NO: 79; (c) wherein the HCDR3 comprises SEQ ID NO: 98; and/or wherein the LCDR3 comprises SEQ ID NO: 115; (d) wherein the HCDR3 comprises SEQ ID NO: 131; and/or wherein the LCDR3 comprises SEQ ID NO: 149; e) wherein the HCDR3 comprises SEQ ID NO: 59; and/or wherein the LCDR3 comprises SEQ ID NO: 115; or (f) wherein the HCDR3 comprises SEQ ID NO: 59; and/or wherein the LCDR3 comprises SEQ ID NO: 182.

Also provided herein is an anti-CD47 antibody or an antigen-binding portion thereof, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR2 comprises SEQ ID NO: 216; and/or wherein the LCDR2 comprises SEQ ID NO: 77; (b) wherein the HCDR2 comprises SEQ ID NO: 17; and/or wherein the LCDR2 comprises SEQ ID NO: 37; (c) wherein the HCDR2 comprises SEQ ID NO: 57; and/or wherein the LCDR2 comprises SEQ ID NO: 77; (d) wherein the HCDR2 comprises SEQ ID NO: 96; and/or wherein the LCDR2 comprises SEQ ID NO: 77; (e) wherein the HCDR2 comprises SEQ ID NO: 163; and/or wherein the LCDR2 comprises SEQ ID NO: 77; or (f) wherein the HCDR2 comprises SEQ ID NO: 163; and/or wherein the LCDR2 comprises SEQ ID NO: 37.

Additionally provided herein is an anti-CD47 antibody or an antigen-binding portion thereof, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR1 comprises SEQ ID NO: 15; and/or wherein the LCDR1 comprises SEQ ID NO: 35; (b) wherein the HCDR1 comprises SEQ ID NO: 55; and/or wherein the LCDR1 comprises SEQ ID NO: 75; (c) wherein the HCDR1 comprises SEQ ID NO: 94; and/or wherein the LCDR1 comprises SEQ ID NO: 112; (d) wherein the HCDR1 comprises SEQ ID NO: 162; and/or wherein the LCDR1 comprises SEQ ID NO: 75; or (e) wherein the HCDR1 comprises SEQ ID NO: 162; and/or wherein the LCDR1 comprises SEQ ID NO: 35.

Provided herein is an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3; (b) the VH domain amino acid sequence comprises HCDR1 of SEQ ID NO: 15, HCDR2 of SEQ ID NO: 17 and HCDR3 of SEQ ID NO: 19, or a variant thereof having 1, 2 or 3 conservative amino acid substitutions in HCDR1, HCDR2, and/or HCDR3; and the VL domain amino acid sequence comprises LCDR1 of SEQ ID NO: 35, LCDR2 of SEQ ID NO: 37 and LCDR3 of SEQ ID NO: 39, or a variant thereof having 1, 2 or 3 conservative amino acid substitutions in LCDR1, LCDR2, and/or LCDR3; (c) the VH domain amino acid sequence comprises HCDR1 of SEQ ID NO: 55, HCDR2 of SEQ ID NO: 57 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 79, or a variant thereof having 1, 2 or 3 conservative amino acid substitutions in LCDR1, LCDR2, and/or LCDR3; (d) the VH domain amino acid sequence comprises HCDR1 of SEQ ID NO: 94, HCDR2 of SEQ ID NO: 96 and HCDR3 of SEQ ID NO: 98, or a variant thereof having 1, 2 or 3 conservative amino acid substitutions in HCDR1, HCDR2, and/or HCDR3; and the VL domain amino acid sequence comprises LCDR1 of SEQ ID NO: 112, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3; (e) the VH domain amino acid sequence comprises HCDR1 of SEQ ID NO: 94, HCDR2 of SEQ ID NO: 96 and HCDR3 of SEQ ID NO: 131, or a variant thereof having 1, 2 or 3 conservative amino acid substitutions in HCDR1, HCDR2, and/or HCDR3; and the VL domain amino acid sequence comprises LCDR1 of SEQ ID NO: 112, LCDR2 of SEQ ID NO: 77 and LCDR3 of SEQ ID NO: 149, or a variant thereof having 1, 2 or 3 conservative amino acid substitutions in LCDR1, LCDR2, and/or LCDR3; (f) the VH domain amino acid sequence comprises HCDR1 of SEQ ID NO: 162, HCDR2 of SEQ ID NO: 163 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3; or (g) the VH domain amino acid sequence comprises HCDR1 of SEQ ID NO: 162, HCDR2 of SEQ ID NO: 163 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 35, LCDR2 of SEQ ID NO: 37 and LCDR3 of SEQ ID NO: 182, or a variant thereof having 1, 2 or 3 conservative amino acid substitutions in LCDR1, LCDR2, and/or LCDR3.

Provided herein is an anti-CD47 antibody or an antigen-binding portion thereof, wherein the antibody or antigen-binding portion comprises a VH domain and a VL domain, wherein the VH domain amino acid sequence comprises (a) SEQ ID NO: 213, or an amino acid sequence that is at least 95%, 96%, 97%, 98% or 99% identical to the amino acid sequence of SEQ ID NO: 213; (b) SEQ ID NO: 12, or an amino acid sequence that is at least 95%, 96%, 97%, 98% or 99% identical to the amino acid sequence of SEQ ID NO: 12; (c) SEQ ID NO: 52, or an amino acid sequence that is at least 95%, 96%, 97%, 98% or 99% identical to the amino acid sequence of SEQ ID NO: 52; (d) SEQ ID NO: 92, or an amino acid sequence that is at least 95%, 96%, 97%, 98% or 99% identical to the amino acid sequence of SEQ ID NO: 92; (e) SEQ ID NO: 127, or an amino acid sequence that is at least 95%, 96%, 97%, 98% or 99% identical to the amino acid sequence of SEQ ID NO: 127; or (f) SEQ ID NO: 161, or an amino acid sequence that is at least 95%, 96%, 97%, 98% or 99% identical to the amino acid sequence of SEQ ID NO: 161.

Provided herein is an anti-CD47 antibody or an antigen-binding portion thereof, wherein the antibody or antigen-binding portion comprises a VH domain and a VL domain, wherein the VL domain amino acid sequence comprises (a) SEQ ID NO: 222, or an amino acid sequence that is at least 95%, 96%, 97%, 98% or 99% identical to the amino acid sequence of SEQ ID NO: 222; (b) SEQ ID NO: 230, or an amino acid sequence that is at least 95%, 96%, 97%, 98% or 99% identical to the amino acid sequence of SEQ ID NO: 230; (c) SEQ ID NO: 236, or an amino acid sequence that is at least 95%, 96%, 97%, 98% or 99% identical to the amino acid sequence of SEQ ID NO: 236; (d) SEQ ID NO: 32, or an amino acid sequence that is at least 95%, 96%, 97%, 98% or 99% identical to the amino acid sequence of SEQ ID NO: 32; (e) SEQ ID NO: 72, or an amino acid sequence that is at least 95%, 96%, 97%, 98% or 99% identical to the amino acid sequence of SEQ ID NO: 72; (f) SEQ ID NO: 110, or an amino acid sequence that is at least 95%, 96%, 97%, 98% or 99% identical to the amino acid sequence of SEQ ID NO: 110; (g) SEQ ID NO: 144, or an amino acid sequence that is at least 95%, 96%, 97%, 98% or 99% identical to the amino acid sequence of SEQ ID NO: 144; (h) SEQ ID NO: 170, or an amino acid sequence that is at least 95%, 96%, 97%, 98% or 99% identical to the amino acid sequence of SEQ ID NO: 170; or (i) SEQ ID NO: 181, or an amino acid sequence that is at least 95%, 96%, 97%, 98% or 99% identical to the amino acid sequence of SEQ ID NO: 181.

Provided herein is an anti-CD47 antibody or an antigen-binding portion thereof, wherein (a) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 222, or an amino acid sequence that is at least 95%, 96%, 97%, 98% or 99% identical to the amino acid sequence of SEQ ID NO: 222; (b) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 230, or an amino acid sequence that is at least 95%, 96%, 97%, 98% or 99% identical to the amino acid sequence of SEQ ID NO: 230; (c) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 236, or an amino acid sequence that is at least 95%, 96%, 97%, 98% or 99% identical to the amino acid sequence of SEQ ID NO: 236; (d) the VH domain amino acid sequence comprises SEQ ID NO: 12, or an amino acid sequence that is at least 95%, 96%, 97%, 98% or 99% identical to the amino acid sequence of SEQ ID NO: 12; and the VL domain amino acid sequence comprises SEQ ID NO: 32, or an amino acid sequence that is at least 95%, 96%, 97%, 98% or 99% identical to the amino acid sequence of SEQ ID NO: 32; (e) the VH domain amino acid sequence comprises SEQ ID NO: 52, or an amino acid sequence that is at least 95%, 96%, 97%, 98% or 99% identical to the amino acid sequence of SEQ ID NO: 52; and the VL domain amino acid sequence comprises SEQ ID NO: 72, or an amino acid sequence that is at least 95%, 96%, 97%, 98% or 99% identical to the amino acid sequence of SEQ ID NO: 72; (f) the VH domain amino acid sequence comprises SEQ ID NO: 92, or an amino acid sequence that is at least 95%, 96%, 97%, 98% or 99% identical to the amino acid sequence of SEQ ID NO: 92; and the VL domain amino acid sequence comprises SEQ ID NO: 110, or an amino acid sequence that is at least 95%, 96%, 97%, 98% or 99% identical to the amino acid sequence of SEQ ID NO: 110; (g) the VH domain amino acid sequence comprises SEQ ID NO: 127, or an amino acid sequence that is at least 95%, 96%, 97%, 98% or 99% identical to the amino acid sequence of SEQ ID NO: 127; and the VL domain amino acid sequence comprises SEQ ID NO: 144, or an amino acid sequence that is at least 95%, 96%, 97%, 98% or 99% identical to the amino acid sequence of SEQ ID NO: 144; (h) the VH domain amino acid sequence comprises SEQ ID NO: 161, or an amino acid sequence that is at least 95%, 96%, 97%, 98% or 99% identical to the amino acid sequence of SEQ ID NO: 161; and the VL domain amino acid sequence comprises SEQ ID NO: 170, or an amino acid sequence that is at least 95%, 96%, 97%, 98% or 99% identical to the amino acid sequence of SEQ ID NO: 170; or (i) the VH domain amino acid sequence comprises SEQ ID NO: 161, or an amino acid sequence that is at least 95%, 96%, 97%, 98% or 99% identical to the amino acid sequence of SEQ ID NO: 161; and the VL domain amino acid sequence comprises SEQ ID NO: 181, or an amino acid sequence that is at least 95%, 96%, 97%, 98% or 99% identical to the amino acid sequence of SEQ ID NO: 181.

Provided herein is an anti-CD47 antibody or an antigen-binding portion thereof, wherein (a) the VH domain amino acid sequence comprises SEQ ID NO: 213; and the VL domain amino acid sequence comprises SEQ ID NO: 222; (b) the VH domain amino acid sequence comprises SEQ ID NO: 213; and the VL domain amino acid sequence comprises SEQ ID NO: 230; (c) the VH domain amino acid sequence comprises SEQ ID NO: 213; and the VL domain amino acid sequence comprises SEQ ID NO: 236; (d) the VH domain amino acid sequence comprises SEQ ID NO: 12; and the VL domain amino acid sequence comprises SEQ ID NO: 32; (e) the VH domain amino acid sequence comprises SEQ ID NO: 52; and the VL domain amino acid sequence comprises SEQ ID NO: 72; (f) the VH domain amino acid sequence comprises SEQ ID NO: 92; and the VL domain amino acid sequence comprises SEQ ID NO: 110; (g) the VH domain amino acid sequence comprises SEQ ID NO: 127; and the VL domain amino acid sequence comprises SEQ ID NO: 144; (h) the VH domain amino acid sequence comprises SEQ ID NO: 161; and the VL domain amino acid sequence comprises SEQ ID NO: 170; or (i) the VH domain amino acid sequence comprises SEQ ID NO: 161; and the VL domain amino acid sequence comprises SEQ ID NO: 181.

In some embodiments, the anti-CD47 antibody is anti-human CD47.

In some embodiments, the anti-CD47 antibody is monoclonal. In some embodiments, the antibody or antigen-binding portion is chimeric or humanized. In some embodiments, the VH domain, the VL domain, or both the VH domain and the VL domain comprise one or more human framework region amino acid sequences.

In some embodiments, the anti-CD47 antigen-binding portion is a Fab, a F(ab')$_2$, a Fab', a Fv, a scFv, a Fd, a diabody, a triabody, a tetrabody or a bis-scFv.

In some embodiments, the anti-CD47 antibody or antigen-binding portion is multispecific. In some embodiments, the anti-CD47 antibody or antigen-binding portion is bispecific.

In some embodiments, the anti-CD47 antibody or antigen-binding portion comprises an immunoglobulin constant region. In some embodiments, the immunoglobulin constant region is IgG, IgE, IgM, IgD, IgA or IgY. In some embodiments, the immunoglobulin constant region is IgG1, IgG2, IgG3, IgG4, IgA1 or IgA2. In some embodiments, the immunoglobulin constant region is immunologically inert. In some embodiments, the immunoglobulin constant region is a wild-type human IgG1 constant region, a wild-type human IgG2 constant region, a wild-type human IgG4 constant region, a human IgG1 constant region comprising the amino acid substitutions L234A, L235A and G237A, a human IgG1 constant region comprising the amino acid substitutions L234A, L235A, G237A and P331S or a human IgG4 constant region comprising the amino acid substitution S228P, wherein numbering is according to the EU numbering system.

In some embodiments, the anti-CD47 antibody or antigen-binding portion inhibits or reduces the binding of CD47 to thrombospondin 1 (TSP-1).

Provided herein is an immunoconjugate comprising an anti-CD47 antibody or antigen-binding portion described herein linked to a therapeutic agent. In some embodiments, the therapeutic agent is a small molecule drug.

Also provided herein is a pharmaceutical composition comprising an anti-CD47 antibody or an anti-CD47 antigen-binding portion, an immunoconjugate or a pharmaceutical composition described herein, and a pharmaceutically acceptable carrier, diluent or excipient.

Provided herein is a nucleic acid molecule encoding: (a) the VH domain amino acid sequence; (b) the VL domain amino acid sequence; or (c) both the VH domain and the VL domain amino acid sequences, of an anti-CD47 antibody or antigen-binding portion described herein. In some embodiments, the nucleic acid molecule comprises SEQ ID NO: 1, SEQ ID NO: 2, SEQ ID NO: 21, SEQ ID NO: 22, SEQ ID NO: 41, SEQ ID NO: 42, SEQ ID NO: 61, SEQ ID NO: 62, SEQ ID NO: 81, SEQ ID NO: 82, SEQ ID NO: 100, SEQ ID NO: 101, SEQ ID NO: 117, SEQ ID NO: 118, SEQ ID NO: 133, SEQ ID NO: 134, SEQ ID NO: 151, SEQ ID NO: 152, SEQ ID NO: 164, SEQ ID NO: 165, SEQ ID NO: SEQ ID NO: 174, SEQ ID NO: 175, SEQ ID NO: 210, SEQ ID NO: 211, SEQ ID NO: 219, SEQ ID NO: 220, SEQ ID NO: 227, SEQ ID NO: 228, SEQ ID NO: 233 or SEQ ID NO: 234. Also provided herein is an expression vector comprising a nucleic acid molecule described herein. Further provided herein is a recombinant host cell comprising nucleic acid molecule described herein or an expression vector described herein.

Provided herein is a method of producing an anti-CD47 antibody or an antigen-binding portion thereof, the method comprising: culturing a recombinant host cell comprising an expression vector described herein under conditions whereby the nucleic acid molecule is expressed, thereby producing the antibody or antigen-binding portion; and isolating the antibody or antigen-binding portion from the host cell or culture.

Provided herein is a method for treating or reducing the severity of sickle cell disease (SCD) in a subject, the method comprising administering to the subject a therapeutically effective amount of an anti-CD47 antibody or anti-CD47 antigen-binding portion, an immunoconjugate or a pharmaceutical composition described herein.

Further provided herein is a method for ameliorating, treating or reducing the severity of a symptom of SCD in a subject, the method comprising administering to the subject a therapeutically effective amount of an anti-CD47 antibody or an anti-CD47 antigen-binding portion, an immunoconjugate or a pharmaceutical composition described herein. In some embodiments, the symptom of SCD is pain, fatigue, anemia, infection or swelling of extremities.

Also provided herein is a method for ameliorating, treating or reducing the severity of a vaso-occlusive crisis or acute chest syndrome in a subject with SCD, the method comprising administering to the subject a therapeutically effective amount of an anti-CD47 antibody or an anti-CD47 antigen-binding portion, an immunoconjugate or a pharmaceutical composition described herein.

In some embodiments of the methods provided herein, the method comprises administering to the subject an additional therapeutic agent. In some embodiments, the additional therapeutic agent is a small molecule drug.

In some embodiments of the methods provided herein, the subject was previously treated with myeloablative therapy.

Provided herein is a method for inhibiting or reducing the binding of a CD47-expressing cell to TSP-1, the method comprising contacting the CD47-expressing cell with an anti-CD47 antibody or an anti-CD47 antigen-binding portion, an immunoconjugate or a pharmaceutical composition described herein. In some embodiments, the CD47-expressing cell is a CD47-expressing red blood cell (RBC). In some embodiments, the CD47-expressing RBC is a CD47-expressing RBC from a subject with SCD.

Provided herein is an anti-CD47 antibody or an anti-CD47 antigen-binding portion, an immunoconjugate or a pharmaceutical composition described herein, for use in the treatment of SCD.

Provided herein is an anti-CD47 antibody or an anti-CD47 antigen-binding portion, an immunoconjugate or a pharmaceutical composition described herein, for use as a medicament.

BRIEF DESCRIPTION OF THE DRAWINGS

FIG. 5A: chimeric-VH+VL-1. FIG. 5B: VH1-PTM+VL1. FIG. 5C: VH1-PTM+VL2. FIG. 5D: VH1-PTM+VL3.

DETAILED DESCRIPTION

Figure 1A:
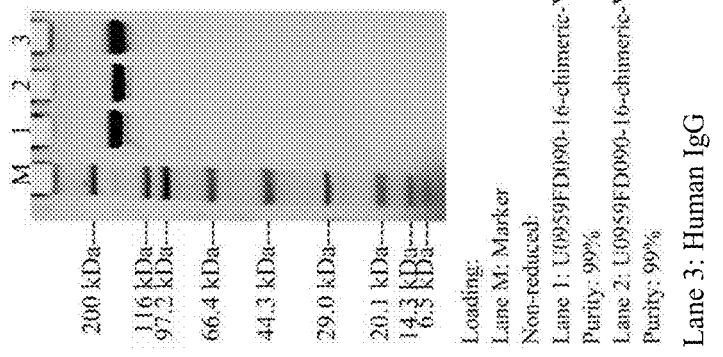
FIG. 1A and FIG. 1B show SDS-PAGE results of chimeric anti-CD47 antibodies under reduced (FIG. 1A) and non-reduced (FIG. 1B) conditions. Two combinations of heavy chain and light chain sequences were tested.

Provided herein are anti-CD47 antibodies and antigen-binding fragments thereof. Further provided herein are immunoconjugates and compositions comprising such antibodies and antigen-binding fragments and nucleic acid molecules encoding such antibodies and antigen-binding fragments. Also provided herein are methods for making such antibodies and antigen-binding fragments and methods for using such antibodies and antigen-binding fragments to treat symptoms and disorders related to sickle cell disease (SCD) in subjects in need thereof.

CD47 (also known as integrin associated protein (IAP), Cluster of Differentiation 47, MER6 and OA3) is a transmembrane protein that belongs to the immunoglobulin superfamily. CD47 binds to several known partners, including thrombospondin-1 (TSP-1), signal-regulatory protein alpha (SIRPα) and membrane integrins. CD47 is associated with a range of cellular processes, including apoptosis, proliferation, adhesion, and migration of cells. TSP-1 is a vascular adhesive glycoprotein secreted by multiple cell types and is encoded in humans by the THBS1 gene. TSP-1 is found in the extracellular matrix of blood vessels, as well as in plasma. TSP-1 mediates cell-to-cell and cell-to-matrix interactions. This cell-to-cell interaction is pathological when TSP-1 binds to the CD47 receptor of red blood cells (RBCs; also known as erythrocytes) of people with the point mutation of the sixth codon of the hemoglobin beta gene on Chromosome 11 causing SCD. CD47 has been shown to mediate the adhesion of sickle RBCs to immobilized TSP under both flow and static conditions. This leads to the adhesion of the RBC to the blood vessel wall, contributing to vaso-occlusive crises in SCD (Brittain et al., (2001) Blood 97, 2159-2164).

Antibodies

Provided herein are antibodies and antigen-binding fragments thereof that specifically bind CD47. Antibodies and antigen-binding fragments disclosed herein specifically bind human CD47. In some embodiments, antibodies and antigen-binding fragments may cross-react with CD47 from species other than human, for example, cynomolgus monkey (*Macaca fascicularis*) CD47 and/or rhesus monkey (*Macaca* mulatta) CD47. In some embodiments, an antibody may be specific for only human CD47 and may exhibit no non-human cross-reactivity. Exemplary amino acid sequences of human and cynomolgus CD47 are provided in Table 1.

TABLE 1

Exemplary CD47 amino acid sequences

| | |
|---|---|
| Human CD47 | MWPLVAALLLGSACCGSAQLLFNKTKSVEFTFCNDT VVIPCFVTNMEAQNTTEVYVKWKFKGRDIYTFDGAL NKSTVPTDFSSAKIEVSQLLKGDASLKMDKSDAVSH TGNYTCEVTELTREGETIIELKYRVVSWFSPNENIL IVIFPIFAILLFWGQFGIKTLKYRSGGMDEKTIALL VAGLVITVIVIVGAILFVPGEYSLKNATGLGLIVTS TGILILLHYYVFSTAIGLTSFVIAILVIQVIAYILA VVGLSLCIAACIPMHGPLLISGLSILALAQLLGLVY MKFVASNQKTIQPPRKAVEEPLNAFKESKGMMNDE (SEQ ID NO: 80) |
| Cynomolgus monkey CD47 | MWPLVAALLLGSACCGSAQLLFNKTKSVEFTFCNDT VVIPCFVTNMEAQNTTEVYVKWKFKGRDIYTFDGAL NKSTAPANFSSAKIEVSQLLKGDASLKMDKSDAVSH TGNYTCEVTELTREGETIIELKYRVVSWFSPNENIL IVIFPIFAILLFWGQFGIKTLKYRSGGMDEKTIALL VAGLMITVIVIVGAILFVPGEYSLKNATGLGLIVTS TGILILLHYYVFSTAIGLTSFVIAILVIQVIAYILA VVGLSLCIAACIPMHGPLLISGLSILALAQLLGLVY MKFVASNQKTIQPPRKAVEEPLNAFKESKGMMNDE (SEQ ID NO: 83) |

As used herein, the term "antibody" refers to immunoglobulin (Ig) molecules and immunologically active portions or fragments of immunoglobulin molecules, i.e., molecules that contain an antigen-binding site that specifically binds (immunoreacts with) an antigen (e.g., CD47). By "specifically binds" or "immunoreacts with" is meant that the antibody reacts with one or more antigenic determinants of the desired antigen and does not react with other polypeptides. In some embodiments, an antibody is said to specifically bind an antigen when it preferentially recognizes its target antigen in a complex mixture of proteins and/or macromolecules. In some embodiments, an antibody "specifically binds" CD47 if the antibody binds CD47 with greater affinity, greater avidity, more readily and/or for greater duration than it binds other polypeptides.

The term "antibody" broadly refers to an immunoglobulin (Ig) molecule, generally, comprising four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art.

In a full-length antibody, each heavy chain comprises a heavy chain variable domain (abbreviated herein as VH domain) and a heavy chain constant region. The heavy chain constant region comprises three domains, CH1, CH2 and CH3. Each light chain comprises a light chain variable domain (abbreviated herein as VL domain) and a light chain constant region. The light chain constant region comprises one domain, CL. The VH and VL domains can be further subdivided into regions of hypervariability, termed complementarity determining regions (CDRs), interspersed with regions that are more conserved, termed framework regions (FRs). Each VH domain and VL domain is composed of three CDRs and four FRs, arranged from amino-terminus to carboxyl-terminus in the following order: FR1, CDR1, FR2, CDR2, FR3, CDR3, FR4.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is according to the EU numbering system. The Fc region of an immunoglobulin generally comprises two constant domains, CH2 and CH3. An Fc region can be present in dimer or monomeric form. The Fc region binds to various cell receptors, such as Fc receptors, and other immune molecules, such as complement proteins.

Immunoglobulin molecules can be of any type (e.g., IgG, IgE, IgM, IgD, IgA or IgY) and class (e.g., IgG1, IgG2, IgG3, IgG4, IgA1 or IgA2) or subclass. IgG, IgD, and IgE antibodies generally contain two identical heavy chains and two identical light chains and two antigen combining domains, each composed of a VH) and a VL. Generally IgA antibodies are composed of two monomers, each monomer composed of two heavy chains and two light chains (as for IgG, IgD, and IgE antibodies); in this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies). Thus, the IgM molecule has ten antigen binding domains, each again composed of a VH and a VL. A cell surface form of IgM has a two heavy chain/two light chain structure similar to IgG, IgD and IgE antibodies.

The term "antigen-binding portion" or "antigen-binding fragment" of an antibody (or "antibody portion" or "antibody fragment"), as used herein, refers to one or more fragments of an antibody that retain the ability to specifically bind to an antigen (e.g., CD47). It has been shown that the antigen-binding function of an antibody can be performed by portions or fragments of a full-length antibody. Examples of binding fragments encompassed within the term "antigen binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb (domain antibody) fragment (Ward et al., (1989) *Nature* 341:544-546; WO 90/05144 µl, each herein incorporated by reference in its entirety), which comprises a single variable domain; and (vi) an isolated complementarity determining region (CDR). The disclosure also encompasses a Fab' fragment. Fab' fragments can be formed by the reduction of F(ab')2 fragments. Fab' is derived from F(ab')$_2$; therefore, it may contain a small portion of Fc. Furthermore, although the two domains of the Fv fragment, VL and VH, are coded for by separate genes, they can be joined, using recombinant methods, by a synthetic linker that enables them to be made as a single protein chain in which the VL and VH domains pair to form monovalent molecules (known as single chain Fv (scFv). See e.g., Bird et al. (1988) *Science* 242:423-426; Huston et al. (1988) *Proc. Natl. Acad. Sci. USA* 85:5879-5883. Such single chain antibodies are also intended to be encompassed within the term "antigen-binding portion" of an antibody. In some embodiments, scFv molecules may be incorporated into a fusion protein. In some embodiments, provided herein is a single chain camelid antibody. In some embodiments, provided herein is a shark heavy chain antibody (V-NAR). See, English et al. (2020) *Antibody Therapeutics*, 3(1):1-9. Examples of antigen-binding portions are known in the art (Kontermann and Dubel eds., *Antibody Engineering* (2001) Springer-Verlag. New York. 790 pp.). In some embodiments, provided herein is a single domain antibody. In general, the term "antibody" when used herein encompasses an "antibody fragment". An antibody fragment generally retains the antigen-binding properties of a full-length antibody.

Antibodies and antibody portions provided herein may be in multispecific (e.g., bispecific or trispecific) formats. Such multispecific molecules specifically bind to two or more different molecular targets or epitopes. In some embodiments, an antibody or an antigen-binding portion is a bispecific molecule that binds specifically to a first antigen and a second antigen, wherein the first antigen is CD47 and the second antigen is not CD47.

In some embodiments, an antibody or an antigen-binding portion is a diabody. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al. (1993) *Proc. Natd. Acad. Sci. USA* 90:6444-6448; Poljak et al. (1994) *Structure* 2:1121-1123). In some embodiments, an antibody or an antigen-binding portion is a triabody, a tetrabody, a bis-scFv or a tandem scFv. In some embodiments, an antibody or an antigen-binding portion is a dual affinity re-targeting protein.

In some embodiments, an anti-CD47 antigen-binding portion disclosed herein is a Fab, a F(ab')$_2$, a Fab', a Fv, a scFv, a Fd, a single domain antibody, a single chain camelid antibody, a diabody, a triabody, a tetrabody or a bis-scFv.

As used herein, the terms "immunological binding" and "immunological binding properties" refer to the non-covalent interactions of the type which occur between an immunoglobulin molecule (e.g., antibody or antigen-binding portion thereof) and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See, Malmqvist, *Nature* 361: 186-187 (1993)). The ratio of $K_{off}/K_{on}$ enables the cancellation of all parameters not related to affinity, and is equal to the dissociation constant $K_d$. (See, Davies et al. (1990) *Annual Rev Biochem* 59:439-473). An antibody or antigen-binding portion provided herein is said to specifically bind CD47 when the equilibrium binding constant ($K_d$) is ≤10 µM, preferably ≤10 nM, more preferably ≤10 nM, and most preferably ≤100 pM to about 1 pM, as measured by assays such as radioligand binding assays or similar assays known to those skilled in the art.

In some embodiments, an anti-CD47 antibody or antigen-binding portion provided herein is monovalent or bivalent and comprises a single or double chain. Functionally, the binding affinity of an antibody or antigen-binding portion may be within the range of $10^{-5}$ M to $10^{-12}$ M. For example, the binding affinity of an antibody or antigen-binding portion is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-8}$ M to $10^{-11}$ M, from $10^{-9}$ M to $10^{-11}$ M, from $10^{-10}$ M to $10^{-11}$ M, from $10^{-5}$ M to $10^{-10}$ M, from $10^{-6}$ M to $10^{-10}$ M, from $10^{-7}$ M to $10^{-10}$ M, from $10^{-8}$ M to $10^{-10}$ M, from $10^{-9}$ M to $10^{-10}$ M, from $10^{-5}$ M to $10^{-9}$ M, from $10^{-6}$ M to $10^{-9}$ M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$ M to $10^{-7}$ M, from $10^{-6}$ M to $10^{-7}$ M or from $10^{-5}$ M to $10^{-6}$ M.

Provided herein is an anti-CD47 antibody or an antigen-binding portion thereof, wherein the antibody or antigen-binding portion cross-competes for binding to CD47 with antibody VH1-PTM+VL1, VH1-PTM+VL2 or VH1-PTM+VL3, or an antibody that comprises one or more amino acid sequences of antibody VH1-PTM+VL1, VH1-PTM+VL2 or VH1-PTM+VL3 (see Tables 22-24).

Provided herein is an anT-CD47 antibody or an antigen-binding portion thereof, wherein the antibody or antigen-binding portion cross-competes for binding to CD47 with antibody 41B1H9, 37H4H3, 38F1E12, 33H11F3 or 32G8H6, or an antibody that comprises one or more amino acid sequences of antibody 41B1H9, 37H4H3, 38F1E12, 33H1F3 or 32G8H6 (see Tables 2-6 and 17).

TABLE 2

Nucleotide and amino acid sequences of antibody 41B1H9

41B1H9

| Antibody name Domain or Region | Sequence | SEQ ID NO |
|---|---|---|
| Heavy chain variable domain (nucleotide) [includes signal sequence] | ATGAAATGCAGCTGGGTTATCTTCTTCCTGATGGCAGTGGTT ACAGGGGTCAATTCAGAGGTTCAGCTGCAGCAGTCTGGGACA GAACTTGTGAAGCCAGGGGCCTCAGTCAGGTTGTCCTGCACA GCTTCTGGCCTCGACATTAAAGACACCTATATGCACTGGTTG AAACAGAGGCCTGAACAGGGCCTGGAGTGGATTGGGAGGATT GATCCTGCGAGTGGCAATGCTAAACATGACCCGAAGTTCCAG GGCAAGGCCACTATAACATCAGACCCATCCTCCAACACAGCC AATTTACAGCTCACCAGCCTAACATCTGAGGACAGTGCCGTC TATTACTGTGCCTCCGGCTATGGTCACTACGTCGGTGCTATG GACTACTGGGGTCAAGGTACCTCAGTCACCGTCTCCTCA | 1 |
| Heavy chain variable domain (nucleotide) [does not include signal sequence] | GAGGTTCAGCTGCAGCAGTCTGGGACAGAACTTGTGAAGCCA GGGGCCTCAGTCAGGTTGTCCTGCACAGCTTCTGGCCTCGAC ATTAAAGACACCTATATGCACTGGTTGAAACAGAGGCCTGAA CAGGGCCTGGAGTGGATTGGGAGGATTGATCCTGCGAGTGGC AATGCTAAACATGACCCGAAGTTCCAGGGCAAGGCCACTATA ACATCAGACCCATCCTCCAACACAGCCAATTTACAGCTCACC AGCCTAACATCTGAGGACAGTGCCGTCTATTACTGTGCCTCC GGCTATGGTCACTACGTCGGTGCTATGGACTACTGGGGTCAA GGTACCTCAGTCACCGTCTCCTCA | 2 |
| Heavy chain signal sequence (nucleotide) | ATGAAATGCAGCTGGGTTATCTTCTTCCTGATGGCAGTGGTT ACAGGGGTCAATTCA | 3 |
| Heavy chain FR1 (nucleotide) | GAGGTTCAGCTGCAGCAGTCTGGGACAGAACTTGTGAAGCCA GGGGCCTCAGTCAGGTTGTCCTGCACAGCTTCTGGCCTCGAC ATTAAA | 4 |
| Heavy chain CDR1 (nucleotide) | GACACCTATATGCAC | 5 |
| Heavy chain FR2 (nucleotide) | TGGTTGAAACAGAGGCCTGAACAGGGCCTGGAGTGGATTGGG | 6 |
| Heavy chain CDR2 (nucleotide) | AGGATTGATCCTGCGAGTGGCAATGCTAAACATGACCCGAAG TTCCAGGGC | 7 |
| Heavy chain FR3 (nucleotide) | AAGGCCACTATAACATCAGACCCATCCTCCAACACAGCCAAT TTACAGCTCACCAGCCTAACATCTGAGGACAGTGCCGTCTAT TACTGTGCCTCC | 8 |
| Heavy chain CDR3 (nucleotide) | GGCTATGGTCACTACGTCGGTGCTATGGACTAC | 9 |
| Heavy chain FR4 (nucleotide) | TGGGGTCAAGGTACCTCAGTCACCGTCTCCTCA | 10 |
| Heavy chain variable domain (amino acid) [includes signal sequence] | MKCSWVIFFLMAVVTGVNSEVQLQQSGTELVKPGASVRLSCT ASGLDIKDTYMHWLKQRPEQGLEWIGRIDPASGNAKHDPKFQ GKATITSDPSSNTANLQLTSLTSEDSAVYYCASGYGHYVGAM DYWGQGTSVTVSS | 11 |
| Heavy chain variable domain (amino acid) [does not include signal sequence] | EVQLQQSGTELVKPGASVRLSCTASGLDIKDTYMHWLKQRPE QGLEWIGRIDPASGNAKHDPKFQGKATITSDPSSNTANLQLT SLTSEDSAVYYCASGYGHYVGAMDYWGQGTSVTVSS | 12 |
| Heavy chain signal sequence (amino acid) | MKCSWVIFFLMAVVTGVNS | 13 |
| Heavy chain FR1 (amino acid) | EVQLQQSGTELVKPGASVRLSCTASGLDIK | 14 |
| Heavy chain CDR1 (amino acid) | DTYMH | 15 |
| Heavy chain FR2 (amino acid) | WLKQRPEQGLEWIG | 16 |
| Heavy chain CDR2 (amino acid) | RIDPASGNAKHDPKFQG | 17 |

TABLE 2-continued

Nucleotide and amino acid sequences of antibody 41B1H9

41B1H9

| Antibody name<br>Domain or Region | Sequence | SEQ ID NO |
|---|---|---|
| Heavy chain FR3 (amino acid) | KATITSDPSSNTANLQLTSLTSEDSAVYYCAS | 18 |
| Heavy chain CDR3 (amino acid) | GYGHYVGAMDY | 19 |
| Heavy chain FR4 (amino acid) | WGQGTSVTVSS | 20 |
| Light chain variable domain (nucleotide) [includes signal sequence] | ATGAGGGTCCTTGCTGAGCTCCTGGGGCTGCTGCTGTTCTGC TTTTTAGGTGTGAGATGTGACATCCAGATGAACCAGTCTCCA TCCAGTCTGTCTGCATCCCTTGGAGACACAATTACCATCACT TGCCATGCCAGTCAGAACATTAATGTTTGGTTAAGCTGGTAC CAGCAGAAACCAGGAAATATTCCTAAACTATTGATCTATAAG GCTTCCAATTTGCACACAGGCGTCCCATCAAGGTTTAGTGGC AGTGGATCTGGAACAGGTTTCACATTAACCATCAGCAGCCTG CAGCCTGAGGACATTGCCACTTACTACTGTCAACAGAGTCGG AATTATCCGTACACGTTCGGAGGGGGGACCAAGCTGGAAATA AAA | 21 |
| Light chain variable domain (nucleotide) [does not include signal sequence] | GACATCCAGATGAACCAGTCTCCATCCAGTCTGTCTGCATCC CTTGGAGACACAATTACCATCACTTGCCATGCCAGTCAGAAC ATTAATGTTTGGTTAAGCTGGTACCAGCAGAAACCAGGAAAT ATTCCTAAACTATTGATCTATAAGGCTTCCAATTTGCACACA GGCGTCCCATCAAGGTTTAGTGGCAGTGGATCTGGAACAGGT TTCACATTAACCATCAGCAGCCTGCAGCCTGAGGACATTGCC ACTTACTACTGTCAACAGAGTCGGAATTATCCGTACACGTTC GGAGGGGGGACCAAGCTGGAAATAAAA | 22 |
| Light chain signal sequence (nucleotide) | ATGAGGGTCCTTGCTGAGCTCCTGGGGCTGCTGCTGTTCTGC TTTTTAGGTGTGAGATGT | 23 |
| Light chain FR1 (nucleotide) | GACATCCAGATGAACCAGTCTCCATCCAGTCTGTCTGCATCC CTTGGAGACACAATTACCATCACTTGC | 24 |
| Light chain CDR1 (nucleotide) | CATGCCAGTCAGAACATTAATGTTTGGTTAAGC | 25 |
| Light chain FR2 (nucleotide) | TGGTACCAGCAGAAACCAGGAAATATTCCTAAACTATTGATC TAT | 26 |
| Light chain CDR2 (nucleotide) | AAGGCTTCCAATTTGCACACA | 27 |
| Light chain FR3 (nucleotide) | GGCGTCCCATCAAGGTTTAGTGGCAGTGGATCTGGAACAGGT TTCACATTAACCATCAGCAGCCTGCAGCCTGAGGACATTGCC ACTTACTACTGT | 28 |
| Light chain CDR3 (nucleotide) | CAACAGAGTCGGAATTATCCGTACACG | 29 |
| Light chain FR4 (nucleotide) | TTCGGAGGGGGGACCAAGCTGGAAATAAAA | 30 |
| Light chain variable domain (amino acid) [includes signal sequence] | MRVLAELLGLLLFCFLGVRCDIQMNQSPSSLSASLGDTITIT CHASQNINVWLSWYQQKPGNIPKLLIYKASNLHTGVPSRFSG SGSGTGFTLTISSLQPEDIATYYCQQSRNYPYTFGGGTKLEI K | 31 |
| Light chain variable domain (amino acid) [does not include signal sequence] | DIQMNQSPSSLSASLGDTITITCHASQNINVWLSWYQQKPGN IPKLLIYKASNLHTGVPSRFSGSGSGTGFTLTISSLQPEDIA TYYCQQSRNYPYTFGGGTKLEIK | 32 |
| Light chain signal sequence (amino acid) | MRVLAELLGLLLFCFLGVRC | 33 |
| Light chain FR1 (amino acid) | DIQMNQSPSSLSASLGDTITITC | 34 |

TABLE 2-continued

Nucleotide and amino acid sequences of antibody 41B1H9

| Antibody name Domain or Region | 41B1H9 Sequence | SEQ ID NO |
|---|---|---|
| Light chain CDR1 (amino acid) | HASQNINVWLS | 35 |
| Light chain FR2 (amino acid) | WYQQKPGNIPKLLIY | 36 |
| Light chain CDR2 (amino acid) | KASNLHT | 37 |
| Light chain FR3 (amino acid) | GVPSRFSGSGSGTGFTLTISSLQPEDIATYYC | 38 |
| Light chain CDR3 (amino acid) | QQSRNYPYT | 39 |
| Light chain FR4 (amino acid) | FGGGTKLEIK | 40 |

TABLE 3

Nucleotide and amino acid sequences of antibody 37H4H3

| Antibody name Domain or Region | 37H4H3 Sequence | SEQ ID NO |
|---|---|---|
| Heavy chain variable domain (nucleotide) [includes signal sequence] | ATGGAATGGAGTTGGATATTTCTCTTTCTCCTGTCAGGAACT GCAGGTGTCCACTCTGAGGTCCAGCTGCAGCAGTCTGGACCT GAACTGGTAAAGCCTGGGGCTTCAGTGAAGCTGTCCTGCAAG GCTTCTGGATACACATTCACTAGCTCTGTTATGCACTGGGTG AAGCAGAAGCCTGGGCAGGGCCTTGAGTGGCTTGGATATATT AATCCTTATAGTGATGGAACTAAATTCAATGAGAAGTACAAA ACCAAGGCCACACTGACTTCAGACAAATCCTCCAGCACAGCC TACATGGAACTCAGCAGCCTGACCTCTGAGGACTCTGCGGTC TATTACTGTGCAAGAGGCCTTATAGGGACTAGATACGACTCC TGGTTTGCTTACTGGGGCCAAGGGACTCTGGTCACTGTCTCT GCA | 41 |
| Heavy chain variable domain (nucleotide) [does not include signal sequence] | GAGGTCCAGCTGCAGCAGTCTGGACCTGAACTGGTAAAGCCT GGGGCTTCAGTGAAGCTGTCCTGCAAGGCTTCTGGATACACA TTCACTAGCTCTGTTATGCACTGGGTGAAGCAGAAGCCTGGG CAGGGCCTTGAGTGGCTTGGATATATTAATCCTTATAGTGAT GGAACTAAATTCAATGAGAAGTACAAAACCAAGGCCACACTG ACTTCAGACAAATCCTCCAGCACAGCCTACATGGAACTCAGC AGCCTGACCTCTGAGGACTCTGCGGTCTATTACTGTGCAAGA GGCCTTATAGGGACTAGATACGACTCCTGGTTTGCTTACTGG GGCCAAGGGACTCTGGTCACTGTCTCTGCA | 42 |
| Heavy chain signal sequence (nucleotide) | ATGGAATGGAGTTGGATATTTCTCTTTCTCCTGTCAGGAACT GCAGGTGTCCACTCT | 43 |
| Heavy chain FR1 (nucleotide) | GAGGTCCAGCTGCAGCAGTCTGGACCTGAACTGGTAAAGCCT GGGGCTTCAGTGAAGCTGTCCTGCAAGGCTTCTGGATACACA TTCACT | 44 |
| Heavy chain CDR1 (nucleotide) | AGCTCTGTTATGCAC | 45 |
| Heavy chain FR2 (nucleotide) | TGGGTGAAGCAGAAGCCTGGGCAGGGCCTTGAGTGGCTTGGA | 46 |
| Heavy chain CDR2 (nucleotide) | TATATTAATCCTTATAGTGATGGAACTAAATTCAATGAGAAG TACAAAACC | 47 |
| Heavy chain FR3 (nucleotide) | AAGGCCACACTGACTTCAGACAAATCCTCCAGCACAGCCTAC ATGGAACTCAGCAGCCTGACCTCTGAGGACTCTGCGGTCTAT TACTGTGCAAGA | 48 |

TABLE 3-continued

Nucleotide and amino acid sequences of antibody 37H4H3

| Antibody name | 37H4H3 | |
|---|---|---|
| Domain or Region | Sequence | SEQ ID NO |
| Heavy chain CDR3 (nucleotide) | GGCCTTATAGGGACTAGATACGACTCCTGGTTTGCTTAC | 49 |
| Heavy chain FR4 (nucleotide) | TGGGGCCAAGGGACTCTGGTCACTGTCTCTGCA | 50 |
| Heavy chain variable domain (amino acid) [includes signal sequence] | MEWSWIFLFLLSGTAGVHSEVQLQQSGPELVKPGASVKLSCK ASGYTFTSSVMHWVKQKPGQGLEWLGYINPYSDGTKFNEKYK TKATLTSDKSSSTAYMELSSLTSEDSAVYYCARGLIGTRYDS WFAYWGQGTLVTVSA | 51 |
| Heavy chain variable domain (amino acid) [does not include signal sequence] | EVQLQQSGPELVKPGASVKLSCKASGYTFTSSVMHWVKQKPG QGLEWLGYINPYSDGTKFNEKYKTKATLTSDKSSSTAYMELS SLTSEDSAVYYCARGLIGTRYDSWFAYWGQGTLVTVSA | 52 |
| Heavy chain signal sequence (amino acid) | MEWSWIFLFLLSGTAGVHS | 53 |
| Heavy chain FR1 (amino acid) | EVQLQQSGPELVKPGASVKLSCKASGYTFT | 54 |
| Heavy chain CDR1 (amino acid) | SSVMH | 55 |
| Heavy chain FR2 (amino acid) | WVKQKPGQGLEWLG | 56 |
| Heavy chain CDR2 (amino acid) | YINPYSDGTKFNEKYKT | 57 |
| Heavy chain FR3 (amino acid) | KATLTSDKSSSTAYMELSSLTSEDSAVYYCAR | 58 |
| Heavy chain CDR3 (amino acid) | GLIGTRYDSWFAY | 59 |
| Heavy chain FR4 (amino acid) | WGQGTLVTVSA | 60 |
| Light chain variable domain (nucleotide) [includes signal sequence] | ATGTCCTCTGCTCAGTTCCTTGGTCTCCTGTTGCTCTGTTTT CAAGGTATCAGATGTGATATCCAGATGACACAGAATGCATCC TCCCTGTCTGCCTCTCTGGGAGACAGAGTCACCATCAGTTGC AGGACAAGTCAGGACATTAACAATTATTTAAATTGGTATCAG CAGAAACCAGATGGAACTGTTAAACTCCTGATCTATTACACA TCAAGATTACACTCAGGAGTCCCATCAAGGTTCAGTGGCAGT GGGTCTGGAACAGATTATTCTCTCTCCATTCGCTACCTGGAG CAAGAAGATATTGCCACTTACTTTTGCCACCAGGGTAATACA CTTCCGTACACGTTCGGAGGGGGGACCAAACTGGAAATAAAA | 61 |
| Light chain variable domain (nucleotide) [does not include signal sequence] | GATATCCAGATGACACAGAATGCATCCTCCCTGTCTGCCTCT CTGGGAGACAGAGTCACCATCAGTTGCAGGACAAGTCAGGAC ATTAACAATTATTTAAATTGGTATCAGCAGAAACCAGATGGA ACTGTTAAACTCCTGATCTATTACACATCAAGATTACACTCA GGAGTCCCATCAAGGTTCAGTGGCAGTGGGTCTGGAACAGAT TATTCTCTCTCCATTCGCTACCTGGAGCAAGAAGATATTGCC ACTTACTTTTGCCACCAGGGTAATACACTTCCGTACACGTTC GGAGGGGGGACCAAACTGGAAATAAAA | 62 |
| Light chain signal sequence (nucleotide) | ATGTCCTCTGCTCAGTTCCTTGGTCTCCTGTTGCTCTGTTTT CAAGGTATCAGATGT | 63 |
| Light chain FR1 (nucleotide) | GATATCCAGATGACACAGAATGCATCCTCCCTGTCTGCCTCT CTGGGAGACAGAGTCACCATCAGTTGC | 64 |
| Light chain CDR1 (nucleotide) | AGGACAAGTCAGGACATTAACAATTATTTAAAT | 65 |
| Light chain FR2 (nucleotide) | TGGTATCAGCAGAAACCAGATGGAACTGTTAAACTCCTGATC TAT | 66 |

TABLE 3-continued

Nucleotide and amino acid sequences of antibody 37H4H3

| Antibody name | 37H4H3 | |
|---|---|---|
| Domain or Region | Sequence | SEQ ID NO |
| Light chain CDR2 (nucleotide) | TACACATCAAGATTACACTCA | 67 |
| Light chain FR3 (nucleotide) | GGAGTCCCATCAAGGTTCAGTGGCAGTGGGTCTGGAACAGAT TATTCTCTCTCCATTCGCTACCTGGAGCAAGAAGATATTGCC ACTTACTTTTGC | 68 |
| Light chain CDR3 (nucleotide) | CACCAGGGTAATACACTTCCGTACACG | 69 |
| Light chain FR4 (nucleotide) | TTCGGAGGGGGGACCAAACTGGAAATAAAA | 70 |
| Light chain variable domain (amino acid) [includes signal sequence] | MSSAQFLGLLLLCFQGIRCDIQMTQNASSLSASLGDRVTISC RTSQDINNYLNWYQQKPDGTVKLLIYYTSRLHSGVPSRFSGS GSGTDYSLSIRYLEQEDIATYFCHQGNTLPYTFGGGTKLEIK | 71 |
| Light chain variable domain (amino acid) [does not include signal sequence] | DIQMTQNASSLSASLGDRVTISCRTSQDINNYLNWYQQKPDG TVKLLIYYTSRLHSGVPSRFSGSGSGTDYSLSIRYLEQEDIA TYFCHQGNTLPYTFGGGTKLEIK | 72 |
| Light chain signal sequence (amino acid) | MSSAQFLGLLLLCFQGIRC | 73 |
| Light chain FR1 (amino acid) | DIQMTQNASSLSASLGDRVTISC | 74 |
| Light chain CDR1 (amino acid) | RTSQDINNYLN | 75 |
| Light chain FR2 (amino acid) | WYQQKPDGTVKLLIY | 76 |
| Light chain CDR2 (amino acid) | YTSRLHS | 77 |
| Light chain FR3 (amino acid) | GVPSRFSGSGSGTDYSLSIRYLEQEDIATYFC | 78 |
| Light chain CDR3 (amino acid) | HQGNTLPY | 79 |
| Light chain FR4 (amino acid) | FGGGTKLEIK | 40 |

TABLE 4

Nucleotide and amino acid sequences of antibody 38F1E12

| Antibody name | 38F1E12 | |
|---|---|---|
| Domain or Region | Sequence | SEQ ID NO |
| Heavy chain variable domain (nucleotide) [includes signal sequence] | ATGGAATGGAGTTGGATATTTCTCTTTCTCCTGTCAGGAACT GCAGGTGTCCACTCTGAGGTCCAGCTGCAGCAGTCTGGACCT GAGCTGGTACAGCCTGGGGCTTCAGTGAGGATGTCCTGCAAG GCTTCTGGATACACGTTCACTAGCTATGTTATGCACTGGGTG AAGCAGAAGCCTGGGCAGGGCCTTGAGTGGATTGGATATATT AATCCTTACAATGATGGTACTAAGTATAATGAGAAGTTCAAA GGCAAGGCCACACTGACTTCAGACAAATCCTCCAGCACAGCC TACATGGAGCTCAGCAGCCTGACCTCTGAGGACTCTGCGGTC TATTACTGTGCAAGAGGAAGGAATAGGTACGACGGTTGGTTT ACTTACTGGGGCCAAGGGACTCTGGTCACTGTCTCTGCA | 81 |
| Heavy chain variable domain (nucleotide) [does not include | GAGGTCCAGCTGCAGCAGTCTGGACCTGAGCTGGTACAGCCT GGGGCTTCAGTGAGGATGTCCTGCAAGGCTTCTGGATACACG TTCACTAGCTATGTTATGCACTGGGTGAAGCAGAAGCCTGGG | 82 |

TABLE 4-continued

Nucleotide and amino acid sequences of antibody 38F1E12

| Antibody name | 38F1E12 | |
|---|---|---|
| Domain or Region | Sequence | SEQ ID NO |
| signal sequence] | CAGGGCCTTGAGTGGATTGGATATATTAATCCTTACAATGAT GGTACTAAGTATAATGAGAAGTTCAAAGGCAAGGCCACACTG ACTTCAGACAAATCCTCCAGCACAGCCTACATGGAGCTCAGC AGCCTGACCTCTGAGGACTCTGCGGTCTATTACTGTGCAAGA GGAAGGAATAGGTACGACGGTTGGTTTACTTACTGGGGCCAA GGGACTCTGGTCACTGTCTCTGCA | |
| Heavy chain signal sequence (nucleotide) | ATGGAATGGAGTTGGATATTTCTCTTTCTCCTGTCAGGAACT GCAGGTGTCCACTCT | 43 |
| Heavy chain FR1 (nucleotide) | GAGGTCCAGCTGCAGCAGTCTGGACCTGAGCTGGTACAGCCT GGGGCTTCAGTGAGGATGTCCTGCAAGGCTTCTGGATACACG TTCACT | 84 |
| Heavy chain CDR1 (nucleotide) | AGCTATGTTATGCAC | 85 |
| Heavy chain FR2 (nucleotide) | TGGGTGAAGCAGAAGCCTGGGCAGGGCCTTGAGTGGATTGGA | 86 |
| Heavy chain CDR2 (nucleotide) | TATATTAATCCTTACAATGATGGTACTAAGTATAATGAGAAG TTCAAAGGC | 87 |
| Heavy chain FR3 (nucleotide) | AAGGCCACACTGACTTCAGACAAATCCTCCAGCACAGCCTAC ATGGAGCTCAGCAGCCTGACCTCTGAGGACTCTGCGGTCTAT TACTGTGCAAGA | 88 |
| Heavy chain CDR3 (nucleotide) | GGAAGGAATAGGTACGACGGTTGGTTTACTTAC | 89 |
| Heavy chain FR4 (nucleotide) | TGGGGCCAAGGGACTCTGGTCACTGTCTCTGCA | 90 |
| Heavy chain variable domain (amino acid) [includes signal sequence] | MEWSWIFLFLLSGTAGVHSEVQLQQSGPELVQPGASVRMSCK ASGYTFTSYVMHWVKQKPGQGLEWIGYINPYNDGTKYNEKFK GKATLTSDKSSSTAYMELSSLTSEDSAVYYCARGRNRYDGWF TYWGQGTLVTVSA | 91 |
| Heavy chain variable domain (amino acid) [does not include signal sequence] | EVQLQQSGPELVQPGASVRMSCKASGYTFTSYVMHWVKQKPG QGLEWIGYINPYNDGTKYNEKFKGKATLTSDKSSSTAYMELS SLTSEDSAVYYCARGRNRYDGWFTYWGQGTLVTVSA | 92 |
| Heavy chain signal sequence (amino acid) | MEWSWIFLFLLSGTAGVHS | 53 |
| Heavy chain FR1 (amino acid) | EVQLQQSGPELVQPGASVRMSCKASGYTFT | 93 |
| Heavy chain CDR1 (amino acid) | SYVMH | 94 |
| Heavy chain FR2 (amino acid) | WVKQKPGQGLEWIG | 95 |
| Heavy chain CDR2 (amino acid) | YINPYNDGTKYNEKFKG | 96 |
| Heavy chain FR3 (amino acid) | KATLTSDKSSSTAYMELSSLTSEDSAVYYCAR | 58 |
| Heavy chain CDR3 (amino acid) | GRNRYDGWFTY | 98 |
| Heavy chain FR4 (amino acid) | WGQGTLVTVSA | 60 |
| Light chain variable domain (nucleotide) [includes signal sequence] | ATGTCCTCTGCTCAGTTCCTTGGTCTCCTGTTGCTCTGTTTT CAAGGTATCAGATGTGATATCCAGATGACACAGACTACATTC TCCCTGTCTGCCTCTCTGGGAGACAGAGTCACCATCAGTTGC AGGGCAAGTCAGGACATTAGTAATTATTTAAACTGGTATCAG CAGAAACCAGATGGAACTGTTAAACTCCTGATCTACTACACA TCAAGATTACACTCAGGAGTCCCATCAAGGTTCAGTGGCAGT | 100 |

TABLE 4-continued

Nucleotide and amino acid sequences of antibody 38F1E12

| Antibody name | 38F1E12 | |
|---|---|---|
| Domain or Region | Sequence | SEQ ID NO |
| | GGGTCTGGAACAGATTATTCTCTCACCATTAGCAACCTGGAG<br>CAAGAAGATATTGCCACTTACTTTTGCCAACAGGGTAATACG<br>CTTCCGTACACGTTCGGAGGGGGGACCAAGCTGGAAATAAAA | |
| Light chain variable<br>domain (nucleotide)<br>signal sequence] | GATATCCAGATGACACAGACTACATTCTCCCTGTCTGCCTCT<br>CTGGGAGACAGAGTCACCATCAGTTGCAGGGCAAGTCAGGAC<br>ATTAGTAATTATTTAAACTGGTATCAGCAGAAACCAGATGGA<br>ACTGTTAAACTCCTGATCTACTACACATCAAGATTACACTCA<br>GGAGTCCCATCAAGGTTCAGTGGCAGTGGGTCTGGAACAGAT<br>TATTCTCTCACCATTAGCAACCTGGAGCAAGAAGATATTGCC<br>ACTTACTTTTGCCAACAGGGTAATACGCTTCCGTACACGTTC<br>GGAGGGGGGACCAAGCTGGAAATAAAA | 101 |
| Light chain signal<br>sequence (nucleotide) | ATGTCCTCTGCTCAGTTCCTTGGTCTCCTGTTGCTCTGTTTT<br>CAAGGTATCAGATGT | 102 |
| Light chain FR1<br>(nucleotide) | GATATCCAGATGACACAGACTACATTCTCCCTGTCTGCCTCT<br>CTGGGAGACAGAGTCACCATCAGTTGC | 103 |
| Light chain CDR1<br>(nucleotide) | AGGGCAAGTCAGGACATTAGTAATTATTTAAAC | 104 |
| Light chain FR2<br>(nucleotide) | TGGTATCAGCAGAAACCAGATGGAACTGTTAAACTCCTGATC<br>TAC | 105 |
| Light chain CDR2<br>(nucleotide) | TACACATCAAGATTACACTCA | 67 |
| Light chain FR3<br>(nucleotide) | GGAGTCCCATCAAGGTTCAGTGGCAGTGGGTCTGGAACAGAT<br>TATTCTCTCACCATTAGCAACCTGGAGCAAGAAGATATTGCC<br>ACTTACTTTTGC | 106 |
| Light chain CDR3<br>(nucleotide) | CAACAGGGTAATACGCTTCCGTACACG | 107 |
| Light chain FR4<br>(nucleotide) | TTCGGAGGGGGGACCAAGCTGGAAATAAAA | 108 |
| Light chain variable<br>domain (amino acid)<br>[includes signal<br>sequence] | MSSAQFLGLLLLCFQGIRCDIQMTQTTFSLSASLGDRVTISC<br>RASQDISNYLNWYQQKPDGTVKLLIYYTSRLHSGVPSRFSGS<br>GSGTDYSLTISNLEQEDIATYFCQQGNTLPYTFGGGTKLEIK | 109 |
| Light chain variable<br>domain (amino acid)<br>[does not include<br>signal sequence] | DIQMTQTTFSLSASLGDRVTISCRASQDISNYLNWYQQKPDG<br>TVKLLIYYTSRLHSGVPSRFSGSGSGTDYSLTISNLEQEDIA<br>TYFCQQGNTLPYTFGGGTKLEIK | 110 |
| Light chain signal<br>sequence (amino<br>acid) | MSSAQFLGLLLLCFQGIRC | 73 |
| Light chain FR1<br>(amino acid) | DIQMTQTTFSLSASLGDRVTISC | 111 |
| Light chain CDR1<br>(amino acid) | RASQDISNYLN | 112 |
| Light chain FR2<br>(amino acid) | WYQQKPDGTVKLLIY | 113 |
| Light chain CDR2<br>(amino acid) | YTSRLHS | 77 |
| Light chain FR3<br>(amino acid) | GVPSRFSGSGSGTDYSLTISNLEQEDIATYFC | 114 |
| Light chain CDR3<br>(amino acid) | QQGNTLPYT | 115 |
| Light chain FR4<br>(amino acid) | FGGGTKLEIK | 40 |

TABLE 5

Nucleotide and amino acid sequences of antibody 33H11F3

| Antibody name | 33H11F3 | |
|---|---|---|
| Domain or Region | Sequence | SEQ ID NO |
| Heavy chain variable domain (nucleotide) [includes signal sequence] | ATGGAATGGAGTTGGATATTTCTCTTTCTCCTGTCAGGAACT GCAGGTGTCCACTCTGAGGTCCAGCTGCAGCAGTCTGGACCT GAGCTGGTAAAGCCTGGGGCTTCAGTGAAGATGTCCTGCAAG GCTTCTGGATACACATTCACTAGCTATGTTATGCACTGGGTG AAGCAGAAGCCTGGGCAGGGCCTTGAGTGGATGGGATATATT AATCCTTACAATGATGGTACTAAGTACAATGAGAAGTTCAAA GGCAAGGCCACACTGACTTCAGACAAATCCTCCAACACAGCC TACATGGAGTTCAGCAGCCTGACCTCTGAGGACTCTGCGGTC TATTACTGTGCAAGAATAGACTACGGTACTATCCACACGTCC TGGTTTGCTTACTGGGGCCAAGGGACTCTGGTCACTGTCTCT GCA | 117 |
| Heavy chain variable domain (nucleotide) [does not include signal sequence] | GAGGTCCAGCTGCAGCAGTCTGGACCTGAGCTGGTAAAGCCT GGGGCTTCAGTGAAGATGTCCTGCAAGGCTTCTGGATACACA TTCACTAGCTATGTTATGCACTGGGTGAAGCAGAAGCCTGGG CAGGGCCTTGAGTGGATGGGATATATTAATCCTTACAATGAT GGTACTAAGTACAATGAGAAGTTCAAAGGCAAGGCCACACTG ACTTCAGACAAATCCTCCAACACAGCCTACATGGAGTTCAGC AGCCTGACCTCTGAGGACTCTGCGGTCTATTACTGTGCAAGA ATAGACTACGGTACTATCCACACGTCCTGGTTTGCTTACTGG GGCCAAGGGACTCTGGTCACTGTCTCTGCA | 118 |
| Heavy chain signal sequence (nucleotide) | ATGGAATGGAGTTGGATATTTCTCTTTCTCCTGTCAGGAACT GCAGGTGTCCACTCT | 43 |
| Heavy chain FR1 (nucleotide) | GAGGTCCAGCTGCAGCAGTCTGGACCTGAGCTGGTAAAGCCT GGGGCTTCAGTGAAGATGTCCTGCAAGGCTTCTGGATACACA TTCACT | 120 |
| Heavy chain CDR1 (nucleotide) | AGCTATGTTATGCAC | 85 |
| Heavy chain FR2 (nucleotide) | TGGGTGAAGCAGAAGCCTGGGCAGGGCCTTGAGTGGATGGGA | 121 |
| Heavy chain CDR2 (nucleotide) | TATATTAATCCTTACAATGATGGTACTAAGTACAATGAGAAG TTCAAAGGC | 122 |
| Heavy chain FR3 (nucleotide) | AAGGCCACACTGACTTCAGACAAATCCTCCAACACAGCCTAC ATGGAGTTCAGCAGCCTGACCTCTGAGGACTCTGCGGTCTAT TACTGTGCAAGA | 123 |
| Heavy chain CDR3 (nucleotide) | ATAGACTACGGTACTATCCACACGTCCTGGTTTGCTTAC | 124 |
| Heavy chain FR4 (nucleotide) | TGGGGCCAAGGGACTCTGGTCACTGTCTCTGCA | 125 |
| Heavy chain variable domain (amino acid) [includes signal sequence] | MEWSWIFLFLLSGTAGVHSEVQLQQSGPELVKPGASVKMSCK ASGYTFTSYVMHWVKQKPGQGLEWMGYINPYNDGTKYNEKFK GKATLTSDKSSNTAYMEFSSLTSEDSAVYYCARIDYGTIHTS WFAYWGQGTLVTVSA | 126 |
| Heavy chain variable domain (amino acid) [does not include signal sequence] | EVQLQQSGPELVKPGASVKMSCKASGYTFTSYVMHWVKQKPG QGLEWMGYINPYNDGTKYNEKFKGKATLTSDKSSNTAYMEFS SLTSEDSAVYYCARIDYGTIHTSWFAYWGQGTLVTVSA | 127 |
| Heavy chain signal sequence (amino acid) | MEWSWIFLFLLSGTAGVHS | 53 |
| Heavy chain FR1 (amino acid) | EVQLQQSGPELVKPGASVKMSCKASGYTFT | 128 |
| Heavy chain CDR1 (amino acid) | SYVMH | 94 |
| Heavy chain FR2 (amino acid) | WVKQKPGQGLEWMG | 129 |
| Heavy chain CDR2 (amino acid) | YINPYNDGTKYNEKFKG | 96 |

TABLE 5-continued

Nucleotide and amino acid sequences of antibody 33H11F3

| Antibody name | 33H11F3 | |
|---|---|---|
| Domain or Region | Sequence | SEQ ID NO |
| Heavy chain FR3 (amino acid) | KATLTSDKSSNTAYMEFSSLTSEDSAVYYCAR | 130 |
| Heavy chain CDR3 (amino acid) | IDYGTIHTSWFAY | 131 |
| Heavy chain FR4 (amino acid) | WGQGTLVTVSA | 60 |
| Light chain variable domain (nucleotide) [includes signal sequence] | ATGICCTCTGCTCAGTTCCTIGGTCTCCIGTTGCTCTGTTTT CAAGGTACCAGATGTGATATCCAGATGACACACTACATCC TCCCTGTCTGCCTCTCTGGGAGACAGAGTCACCATCAGTTGC AGGGCAAGTCAGGACATTAGCAATTATTTAAACTGGTATCAG CAGAAACCAGATGGAACTGTTAAACTCCTGATCTACTACACA TCAAGATTACACTCAGGAGTCCCATCAAGGTTCAGTGGCAGT GGGTCTGGAACAGATTATTCTCTCACCATTAGCAACCTGGAG CAAGAAGATATTGCCACTTACTTTTGCCAACAGGGTAATACG CTTCCGTGGACGTTCGGTGGAGGCACCAAACTGGAAATCAAA | 133 |
| Light chain variable domain (nucleotide) [does not include signal sequence] | GATATCCAGATGACACACACTACATCCTCCCTGTCTGCCTCT CTGGGAGACAGAGTCACCATCAGTTGCAGGGCAAGTCAGGAC ATTAGCAATTATTTAAACTGGTATCAGCAGAAACCAGATGGA ACTGTTAAACTCCTGATCTACTACACATCAAGATTACACTCA GGAGTCCCATCAAGGTTCAGTGGCAGTGGGTCTGGAACAGAT TATTCTCTCACCATTAGCAACCTGGAGCAAGAAGATATTGCC ACTTACTTTTGCCAACAGGGTAATACGCTTCCGTGGACGTTC GGTGGAGGCACCAAACTGGAAATCAAA | 134 |
| Light chain signal sequence (nucleotide) | ATGTCCTCTGCTCAGTTCCTTGGTCTCCTGTTGCTCTGTTTT CAAGGTACCAGATGT | 135 |
| Light chain FR1 (nucleotide) | GATATCCAGATGACACACACTACATCCTCCCTGTCTGCCTCT CTGGGAGACAGAGTCACCATCAGTTGC | 136 |
| Light chain CDR1 (nucleotide) | AGGGCAAGTCAGGACATTAGCAATTATTTAAAC | 137 |
| Light chain FR2 (nucleotide) | TGGTATCAGCAGAAACCAGATGGAACTGTTAAACTCCTGATC TAC | 138 |
| Light chain CDR2 (nucleotide) | TACACATCAAGATTACACTCA | 67 |
| Light chain FR3 (nucleotide) | GGAGTCCCATCAAGGTTCAGTGGCAGTGGGTCTGGAACAGAT TATTCTCTCACCATTAGCAACCTGGAGCAAGAAGATATTGCC ACTTACTTTTGC | 140 |
| Light chain CDR3 (nucleotide) | CAACAGGGTAATACGCTTCCGTGGACG | 141 |
| Light chain FR4 (nucleotide) | TTCGGTGGAGGCACCAAACTGGAAATCAAA | 142 |
| Light chain variable domain (amino acid) [includes signal sequence] | MSSAQFLGLLLLCFQGTRCDIQMTHTTSSLSASLGDRVTISC RASQDISNYLNWYQQKPDGTVKLLIYYTSRLHSGVPSRFSGS GSGTDYSLTISNLEQEDIATYFCQQGNTLPWTFGGGTKLEIK | 143 |
| Light chain variable domain (amino acid) [does not include signal sequence] | DIQMTHTTSSLSASLGDRVTISCRASQDISNYLNWYQQKPDG TVKLLIYYTSRLHSGVPSRFSGSGSGTDYSLTISNLEQEDIA TYFCQQGNTLPWTFGGGTKLEIK | 144 |
| Light chain signal sequence (amino acid) | MSSAQFLGLLLLCFQGTRC | 145 |
| Light chain FR1 (amino acid) | DIQMTHTTSSLSASLGDRVTISC | 146 |
| Light chain CDR1 (amino acid) | RASQDISNYLN | 112 |

TABLE 5-continued

Nucleotide and amino acid sequences of antibody 33H11F3

| Antibody name | 33H11F3 | |
|---|---|---|
| Domain or Region | Sequence | SEQ ID NO |
| Light chain FR2 (amino acid) | WYQQKPDGTVKLLIY | 147 |
| Light chain CDR2 (amino acid) | YTSRLHS | 77 |
| Light chain FR3 (amino acid) | GVPSRFSGSGSGTDYSLTISNLEQEDIATYFC | 148 |
| Light chain CDR3 (amino acid) | QQGNTLPWT | 149 |
| Light chain FR4 (amino acid) | FGGGTKLEIK | 40 |

TABLE 6

Nucleotide and amino acid sequences of antibody 32G8H6

| Antibody name | 32G8H6 | |
|---|---|---|
| Domain or Region | Sequence | SEQ ID NO |
| Heavy chain variable domain (nucleotide) [includes signal sequence] | ATGGAATGGAGTTGGATATTTCTCTTTCTCCTGTCAGGAACTGCAGGTGTCCACTCTGAGGTCCAGCTGCAGCAGTCTGGACCTGAGTTGGTAAAGCCTGGGGCTTCAGTGAAGCTGTCCTGCAAGGCTTCTGGATACACATTCACTAGTTCTGTTATTCACTGGGTGAAGCAGAAGCCTGGGCAGGGCCTTGAGTGGCTTGGATATATTAATCCTTATAGTGATGGAACTAAATTCAATGAGAAGTGCAAAATCAAGGCCACACTGACTTCAGACAAATCCTCCAGCACAGCCTACATGGAACTCAGCAGCCTGACCTCTGAGGACTCTGCGGTCTATTACTGTGCAAGAGGCCTTATAGGGACTAGATACGACTCCTGGTTTGCTTACTGGGGCCAAGGGACTCTGGTCACTGTCTCTGCA | 151 |
| Heavy chain variable domain (nucleotide) [does not include signal sequence] | GAGGTCCAGCTGCAGCAGTCTGGACCTGAGTTGGTAAAGCCTGGGGCTTCAGTGAAGCTGTCCTGCAAGGCTTCTGGATACACATTCACTAGTTCTGTTATTCACTGGGTGAAGCAGAAGCCTGGGCAGGGCCTTGAGTGGCTTGGATATATTAATCCTTATAGTGATGGAACTAAATTCAATGAGAAGTGCAAAATCAAGGCCACACTGACTTCAGACAAATCCTCCAGCACAGCCTACATGGAACTCAGCAGCCTGACCTCTGAGGACTCTGCGGTCTATTACTGTGCAAGAGGCCTTATAGGGACTAGATACGACTCCTGGTTTGCTTACTGGGGCCAAGGGACTCTGGTCACTGTCTCTGCA | 152 |
| Heavy chain signal sequence (nucleotide) | ATGGAATGGAGTTGGATATTTCTCTTTCTCCTGTCAGGAACTGCAGGTGTCCACTCT | 43 |
| Heavy chain FR1 (nucleotide) | GAGGTCCAGCTGCAGCAGTCTGGACCTGAGTTGGTAAAGCCTGGGGCTTCAGTGAAGCTGTCCTGCAAGGCTTCTGGATACACATTCACT | 153 |
| Heavy chain CDR1 (nucleotide) | AGTTCTGTTATTCAC | 154 |
| Heavy chain FR2 (nucleotide) | TGGGTGAAGCAGAAGCCTGGGCAGGGCCTTGAGTGGCTTGGA | 155 |
| Heavy chain CDR2 (nucleotide) | TATATTAATCCTTATAGTGATGGAACTAAATTCAATGAGAAGTGCAAAATC | 156 |
| Heavy chain FR3 (nucleotide) | AAGGCCACACTGACTTCAGACAAATCCTCCAGCACAGCCTACATGGAACTCAGCAGCCTGACCTCTGAGGACTCTGCGGTCTATTACTGTGCAAGA | 157 |
| Heavy chain CDR3 (nucleotide) | GGCCTTATAGGGACTAGATACGACTCCTGGTTTGCTTAC | 158 |
| Heavy chain FR4 (nucleotide) | TGGGGCCAAGGGACTCTGGTCACTGTCTCTGCA | 159 |

TABLE 6-continued

Nucleotide and amino acid sequences of antibody 32G8H6

| Antibody name | 32G8H6 | |
|---|---|---|
| Domain or Region | Sequence | SEQ ID NO |
| Heavy chain variable domain (amino acid) [includes signal sequence] | MEWSWIFLFLLSGTAGVHSEVQLQQSGPELVKPGASVKLSCK ASGYTFTSSVIHWVKQKPGQGLEWLGYINPYSDGTKFNEKCK IKATLTSDKSSSTAYMELSSLTSEDSAVYYCARGLIGTRYDS WFAYWGQGTLVTVSA | 160 |
| Heavy chain variable domain (amino acid) [does not include signal sequence] | EVQLQQSGPELVKPGASVKLSCKASGYTFTSSVIHWVKQKPG QGLEWLGYINPYSDGTKFNEKCKIKATLTSDKSSSTAYMELS SLTSEDSAVYYCARGLIGTRYDSWFAYWGQGTLVTVSA | 161 |
| Heavy chain signal sequence (amino acid) | MEWSWIFLFLLSGTAGVHS | 53 |
| Heavy chain FR1 (amino acid) | EVQLQQSGPELVKPGASVKLSCKASGYTFT | 54 |
| Heavy chain CDR1 (amino acid) | SSVIH | 162 |
| Heavy chain FR2 (amino acid) | WVKQKPGQGLEWLG | 56 |
| Heavy chain CDR2 (amino acid) | YINPYSDGTKFNEKCKI | 163 |
| Heavy chain FR3 (amino acid) | KATLTSDKSSSTAYMELSSLTSEDSAVYYCAR | 58 |
| Heavy chain CDR3 (amino acid) | GLIGTRYDSWFAY | 59 |
| Heavy chain FR4 (amino acid) | WGQGTLVTVSA | 60 |
| Light chain 1 variable domain (nucleotide) [includes signal sequence] | ATGTCCTCTGCTCAGTTCCTTGGTCTCCTGTTGCTCTGTTTT CAAGGTATCAGATGTGATATCCAGATGACACAGAATGGATCC TCCCTGTCTGCCTCTCTGGGAGACAGAGTCACCATCAGTTGC AGGACAAGTCAGGACATTAACAATTATTTAAATTGGTATCAG CAGAAACAAGATGGAACTGTTAAACTCCTGATCTACTACACA TCAAGATTACACTCAGGAGTCCCATCAAGGTTCAGTGGCAGT GGGTCTGGAACAGATTATTCTCTCACCATTCGCAACCTGGAG CAAGAAGATATTGCCACTTACTTTTGCCAACAGGGTAATACG CTTCCGTACACGTTCGGAGGGGGGACCAAACTGGAAATAAAA | 164 |
| Light chain 1 variable domain (nucleotide) [does not include signal sequence] | GATATCCAGATGACACAGAATGGATCCTCCCTGTCTGCCTCT CTGGGAGACAGAGTCACCATCAGTTGCAGGACAAGTCAGGAC ATTAACAATTATTTAAATTGGTATCAGCAGAAACAAGATGGA ACTGTTAAACTCCTGATCTACTACACATCAAGATTACACTCA GGAGTCCCATCAAGGTTCAGTGGCAGTGGGTCTGGAACAGAT TATTCTCTCACCATTCGCAACCTGGAGCAAGAAGATATTGCC ACTTACTTTTGCCAACAGGGTAATACGCTTCCGTACACGTTC GGAGGGGGGACCAAACTGGAAATAAAA | 165 |
| Light chain 1 signal sequence (nucleotide) | ATGTCCTCTGCTCAGTTCCTTGGTCTCCTGTTGCTCTGTTTT CAAGGTATCAGATGT | 102 |
| Light chain 1 FR1 (nucleotide) | GATATCCAGATGACACAGAATGGATCCTCCCTGTCTGCCTCT CTGGGAGACAGAGTCACCATCAGTTGC | 166 |
| Light chain 1 CDR1 (nucleotide) | AGGACAAGTCAGGACATTAACAATTATTTAAAT | 65 |
| Light chain 1 FR2 (nucleotide) | TGGTATCAGCAGAAACAAGATGGAACTGTTAAACTCCTGATC TAC | 167 |
| Light chain 1 CDR2 (nucleotide) | TACACATCAAGATTACACTCA | 67 |
| Light chain 1 FR3 (nucleotide) | GGAGTCCCATCAAGGTTCAGTGGCAGTGGGTCTGGAACAGAT TATTCTCTCACCATTCGCAACCTGGAGCAAGAAGATATTGCC ACTTACTTTTGC | 168 |

TABLE 6-continued

Nucleotide and amino acid sequences of antibody 32G8H6

| Antibody name | 32G8H6 | |
|---|---|---|
| Domain or Region | Sequence | SEQ ID NO |
| Light chain 1 CDR3 (nucleotide) | CAACAGGGTAATACGCTTCCGTACACG | 107 |
| Light chain 1 FR4 (nucleotide) | TTCGGAGGGGGGACCAAACTGGAAATAAAA | 70 |
| Light chain 1 variable domain (amino acid) [includes signal sequence] | MSSAQFLGLLLLCFQGIRCDIQMTQNGSSLSASLGDRVTISC RTSQDINNYLNWYQQKQDGTVKLLIYYTSRLHSGVPSRFSGS GSGTDYSLTIRNLEQEDIATYFCQQGNTLPYTFGGGTKLEIK | 169 |
| Light chain 1 variable domain (amino acid) [does not include signal sequence] | DIQMTQNGSSLSASLGDRVTISCRTSQDINNYLNWYQQKQDG TVKLLIYYTSRLHSGVPSRFSGSGSGTDYSLTIRNLEQEDIA TYFCQQGNTLPYTFGGGTKLEIK | 170 |
| Light chain 1 signal sequence (amino acid) | MSSAQFLGLLLLCFQGIRC | 73 |
| Light chain 1 FR1 (amino acid) | DIQMTQNGSSLSASLGDRVTISC | 171 |
| Light chain 1 CDR1 (amino acid) | RTSQDINNYLN | 75 |
| Light chain 1 FR2 (amino acid) | WYQQKQDGTVKLLIY | 172 |
| Light chain 1 CDR2 (amino acid) | YTSRLHS | 77 |
| Light chain 1 FR3 (amino acid) | GVPSRFSGSGSGTDYSLTIRNLEQEDIATYFC | 173 |
| Light chain 1 CDR3 (amino acid) | QQGNTLPYT | 115 |
| Light chain 1 FR4 (amino acid) | FGGGTKLEIK | 40 |
| Light chain 2 variable domain (nucleotide) [includes signal sequence] | ATGAGGGTCCTTGCTGAGCTCCTGGGGCTGCTGCTGTTCTGC TTTTTAGGTGTGAGATGTGACATCCAGATGAACCAGTCTCCA TCCAGTCTGTCTGCATCCCTTGGAGACACAATTACCATCACT TGCCATGCCAGTCAGAACATTARTGTTTGGTTAAGCTGGTAC CAGCAGAAACCAGGAAATATTCCTAAACTATTGATCTATAAG GCTTCCAACTTGCACACAGGCGTCCCATCAAGATTTAGTGGC AGTGGATCTGGAACAGGTTTCACATTAACCATCAGCAGCCTG CAGCCTGAAGACATTGCCACTTACTACTGTCAACAGGGTCAA AGTTATCCTCTCACGTTCGGTGCTGGGACCAAGCTGGAGCTG AAA | 174 |
| Light chain 2 variable domain (nucleotide) [does not include signal sequence] | GACATCCAGATGAACCAGTCTCCATCCAGTCTGTCTGCATCC CTTGGAGACACAATTACCATCACTTGCCATGCCAGTCAGAAC ATTAATGTTTGGTTAAGCTGGTACCAGCAGAAACCAGGAAAT ATTCCTAAACTATTGATCTATAAGGCTTCCAACTTGCACACA GGCGTCCCATCAAGATTTAGTGGCAGTGGATCTGGAACAGGT TTCACATTAACCATCAGCAGCCTGCAGCCTGAAGACATTGCC ACTTACTACTGTCAACAGGGTCAAAGTTATCCTCTCACGTTC GGTGCTGGGACCAAGCTGGAGCTGAAA | 175 |
| Light chain 2 signal sequence (nucleotide) | ATGAGGGTCCTTGCTGAGCTCCTGGGGCTGCTGCTGTTCTGC TTTTTAGGTGTGAGATGT | 23 |
| Light chain 2 FR1 (nucleotide) | GACATCCAGATGAACCAGTCTCCATCCAGTCTGTCTGCATCC CTTGGAGACACAATTACCATCACTTGC | 24 |
| Light chain 2 CDR1 (nucleotide) | CATGCCAGTCAGAACATTAATGTTTGGTTAAGC | 25 |
| Light chain 2 FR2 (nucleotide) | TGGTACCAGCAGAAACCAGGAAATATTCCTAAACTATTGATC TAT | 26 |

TABLE 6-continued

Nucleotide and amino acid sequences of antibody 32G8H6

| Antibody name | 32G8H6 | |
|---|---|---|
| Domain or Region | Sequence | SEQ ID NO |
| Light chain 2 CDR2 (nucleotide) | AAGGCTTCCAACTTGCACACA | 176 |
| Light chain 2 FR3 (nucleotide) | GGCGTCCCATCAAGATTTAGTGGCAGTGGATCTGGAACAGGT TTCACATTAACCATCAGCAGCCTGCAGCCTGAAGACATTGCC ACTTACTACTGT | 177 |
| Light chain 2 CDR3 (nucleotide) | CAACAGGGTCAAAGTTATCCTCTCACG | 178 |
| Light chain 2 FR4 (nucleotide) | TTCGGTGCTGGGACCAAGCTGGAGCTGAAA | 179 |
| Light chain 2 variable domain (amino acid) [includes signal sequence] | MRVLAELLGLLLFCFLGVRCDIQMNQSPSSLSASLGDTITIT CHASQNINVWLSWYQQKPGNIPKLLIYKASNLHTGVPSRFSG SGSGTGFTLTISSLQPEDIATYYCQQGQSYPLTFGAGTKLEL K | 180 |
| Light chain 2 variable domain (amino acid) [does not include signal sequence] | DIQMNQSPSSLSASLGDTITITCHASQNINVWLSWYQQKPGN IPKLLIYKASNLHTGVPSRFSGSGSGTGFTLTISSLQPEDIA TYYCQQGQSYPLTFGAGTKLELK | 181 |
| Light chain 2 signal sequence (amino acid) | MRVLAELLGLLLFCFLGVRC | 33 |
| Light chain 2 FR1 (amino acid) | DIQMNQSPSSLSASLGDTITITC | 34 |
| Light chain 2 CDR1 (amino acid) | HASQNINVWLS | 35 |
| Light chain 2 FR2 (amino acid) | WYQQKPGNIPKLLIY | 36 |
| Light chain 2 CDR2 (amino acid) | KASNLHT | 37 |
| Light chain 2 FR3 (amino acid) | GVPSRFSGSGSGTGFTLTISSLQPEDIATYYC | 38 |
| Light chain 2 CDR3 (amino acid) | QQGQSYPLT | 182 |
| Light chain 2 FR4 (amino acid) | FGAGTKLEL | 183 |

The terms "cross-compete", "cross-competition", "cross-block", "cross-blocked" and "cross-blocking" are used interchangeably herein to mean the ability of an antibody or an antigen-binding portion thereof to interfere with the binding directly or indirectly through allosteric modulation of the anti-CD47 antibodies of the disclosure to the target CD47 (e.g., human CD47). The extent to which an antibody or portion thereof is able to interfere with the binding of another to the target, and therefore whether it can be said to cross-block or cross-compete, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g., His-tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g., unlabeled) antibody or fragment thereof that needs to be cross-blocked) by the potentially cross-blocking antibody or fragment thereof that is present in a given amount. In some embodiments, cross-competing antibodies or portions thereof have a recorded displacement that is between 10% and 100%, or between 50% and 100%.

Provided herein is an anti-CD47 antibody or an antigen-binding portion thereof, wherein the antibody or antigen-binding portion cross-competes for binding to CD47 with an antibody comprising a heavy chain variable (VH) domain and a light chain variable (VL) domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115.

Provided herein is an anti-CD47 antibody or an antigen-binding portion thereof, wherein the antibody or antigen-binding portion cross-competes for binding to CD47 with an antibody comprising a heavy chain variable (VH) domain and a light chain variable (VL) domain, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

Provided herein is an anti-CD47 antibody or an antigen-binding portion thereof, wherein the antibody or antigen-binding portion cross-competes for binding to CD47 with antibody 41B1H9, 37H4H3, 38F1E12, 33H11F3 or 32G8H6, or an antibody that comprises one or more amino acid sequences of antibody 41B1H9, 37H4H3, 38F1E12, 33H11F3 or 32G8H6, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR3 comprises SEQ ID NO: 19; and/or wherein the LCDR3 comprises SEQ ID NO: 39; (b) wherein the HCDR3 comprises SEQ ID NO: 59; and/or wherein the LCDR3 comprises SEQ ID NO: 79; (c) wherein the HCDR3 comprises SEQ ID NO: 98; and/or wherein the LCDR3 comprises SEQ ID NO: 115; (d) wherein the HCDR3 comprises SEQ ID NO: 131; and/or wherein the LCDR3 comprises SEQ ID NO: 149; (e) wherein the HCDR3 comprises SEQ ID NO: 59; and/or wherein the LCDR3 comprises SEQ ID NO: 115; or (f) wherein the HCDR3 comprises SEQ ID NO: 59; and/or wherein the LCDR3 comprises SEQ ID NO: 182.

Provided herein is an anti-CD47 antibody or an antigen-binding portion thereof, wherein the antibody or antigen-binding portion cross-competes for binding to CD47 with antibody VH1-PTM+VL1, VH1-PTM+VL2 or VH1-PTM+VL3, or an antibody that comprises one or more amino acid sequences of antibody VH1-PTM+VL1, VH1-PTM+VL2 or VH1-PTM+VL3, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR3 comprises SEQ ID NO: 59; and/or wherein the LCDR3 comprises SEQ ID NO: 115.

Further provided herein is an anti-CD47 antibody or an antigen-binding portion thereof, wherein the antibody or antigen-binding portion cross-competes for binding to CD47 with antibody 41B1H9, 37H4H3, 38F1E12, 33H11F3 or 32G8H6, or an antibody that comprises one or more amino acid sequences of antibody 41B1H9, 37H4H3, 38F1E12, 33H11F3 or 32G8H6, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR2 comprises SEQ ID NO: 17; and/or wherein the LCDR2 comprises SEQ ID NO: 37; (b) wherein the HCDR2 comprises SEQ ID NO: 57; and/or wherein the LCDR2 comprises SEQ ID NO: 77; (c) wherein the HCDR2 comprises SEQ ID NO: 96; and/or wherein the LCDR2 comprises SEQ ID NO: 77; (d) wherein the HCDR2 comprises SEQ ID NO: 163; and/or wherein the LCDR2 comprises SEQ ID NO: 77; or (e) wherein the HCDR2 comprises SEQ ID NO: 163; and/or wherein the LCDR2 comprises SEQ ID NO: 37.

Provided herein is an anti-CD47 antibody or an antigen-binding portion thereof, wherein the antibody or antigen-binding portion cross-competes for binding to CD47 with antibody VH1-PTM+VL1, VH1-PTM+VL2 or VH1-PTM+VL3, or an antibody that comprises one or more amino acid sequences of antibody VH1-PTM+VL1, VH1-PTM+VL2 or VH1-PTM+VL3, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR2 comprises SEQ ID NO: 216; and/or wherein the LCDR2 comprises SEQ ID NO: 77.

Provided herein is an anti-CD47 antibody or an antigen-binding portion thereof, wherein the antibody or antigen-binding portion cross-competes for binding to CD47 with antibody 41B1H9, 37H4H3, 38F1E12, 33H11F3 or 32G8H6, or an antibody that comprises one or more amino acid sequences of antibody 41B1H9, 37H4H3, 38F1E12, 33H11F3 or 32G8H6, (a) wherein the HCDR1 comprises SEQ ID NO: 15; and/or wherein the LCDR1 comprises SEQ ID NO: 35; (b) wherein the HCDR1 comprises SEQ ID NO: 55; and/or wherein the LCDR1 comprises SEQ ID NO: 75; (c) wherein the HCDR1 comprises SEQ ID NO: 94; and/or wherein the LCDR1 comprises SEQ ID NO: 112; (d) wherein the HCDR1 comprises SEQ ID NO: 162; and/or wherein the LCDR1 comprises SEQ ID NO: 75; or (e) wherein the HCDR1 comprises SEQ ID NO: 162; and/or wherein the LCDR1 comprises SEQ ID NO: 35.

Provided herein is an anti-CD47 antibody or an antigen-binding portion thereof, wherein the antibody or antigen-binding portion cross-competes for binding to CD47 with antibody VH1-PTM+VL1, VH1-PTM+VL2 or VH1-PTM+VL3, or an antibody that comprises one or more amino acid sequences of antibody VH1-PTM+VL1, VH1-PTM+VL2 or VH1-PTM+VL3, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR1 comprises SEQ ID NO:162; and/or wherein the LCDR1 comprises SEQ ID NO: 75.

Further provided herein is an anti-CD47 antibody or an antigen-binding portion thereof that comprises one or more amino acid sequences of antibody 41B1H9, 37H4H3, 38F1E12, 33H11F3 or 32G8H6. The combinations of VH domain, VL domain and CDR sequences forming these antibodies are provided in Tables 2-6 and 17. Further provided herein is an anti-CD47 antibody or an antigen-binding portion thereof that comprises one or more amino acid sequences of antibody VH1-PTM+VL1, VH1-PTM+VL2 or VH1-PTM+VL3. The combinations of VH domain, VL domain and CDR sequences forming these antibodies are provided in Tables 22-24. In some embodiments, the VH domain sequence and/or the VL domain sequence comprises a signal sequence (also known as a signal peptide) at the amino-terminus. Also provided herein is a hybridoma cell line producing antibody 41B1H9, 37H4H3, 38F1E12, 33H11F3 or 32G8H6.

Provided herein is an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3.

Provided herein is an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 15, HCDR2 of SEQ ID NO: 17 and HCDR3 of SEQ ID NO: 19, or a variant thereof having 1, 2 or 3 conservative amino acid substitutions in HCDR1, HCDR2, and/or HCDR3; and the VL domain amino acid sequence comprises LCDR1 of SEQ ID NO: 35, LCDR2 of SEQ ID NO: 37 and LCDR3 of SEQ ID NO: 39, or a variant thereof having 1, 2 or 3 conservative amino acid substitutions in LCDR1, LCDR2, and/or LCDR3; (b) the VH domain amino acid sequence comprises HCDR1 of SEQ ID NO: 55, HCDR2 of SEQ ID NO: 57 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 79, or a variant thereof having 1, 2 or 3 conservative amino acid substitutions in LCDR1, LCDR2, and/or LCDR3; (c) the VH domain amino acid sequence comprises HCDR1 of SEQ ID NO: 94, HCDR2 of SEQ ID NO: 96 and HCDR3 of SEQ ID NO: 98, or a variant thereof having 1, 2 or 3 conservative amino acid substitutions in HCDR1, HCDR2, and/or HCDR3; and the VL domain amino acid sequence comprises LCDR1 of SEQ ID NO: 112, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3; (d) the VH domain amino acid sequence comprises HCDR1 of SEQ ID NO: 94, HCDR2 of SEQ ID NO: 96 and HCDR3 of SEQ ID NO: 131, or a variant thereof having 1, 2 or 3 conservative amino acid substitutions in HCDR1, HCDR2, and/or HCDR3; and the VL domain amino acid sequence comprises LCDR1 of SEQ ID NO: 112, LCDR2 of SEQ ID NO: 77 and LCDR3 of SEQ ID NO: 149, or a variant thereof having 1, 2 or 3 conservative amino acid substitutions in LCDR1, LCDR2, and/or LCDR3; (e) the VH domain amino acid sequence comprises HCDR1 of SEQ ID NO: 162, HCDR2 of SEQ ID NO: 163 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3; or (f) the VH domain amino acid sequence comprises HCDR1 of SEQ ID NO: 162, HCDR2 of SEQ ID NO: 163 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 35, LCDR2 of SEQ ID NO: 37 and LCDR3 of SEQ ID NO: 182, or a variant thereof having 1, 2 or 3 conservative amino acid substitutions in LCDR1, LCDR2, and/or LCDR3.

Provided herein is an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115.

Also provided herein is an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

Provided herein is an anti-CD47 antibody or an antigen-binding portion thereof, wherein the antibody or antigen-binding portion comprises a VH domain and a VL domain, wherein the VH domain amino acid sequence comprises (a) SEQ ID NO: 213, or an amino acid sequence that is at least 95%, 96%, 97%, 98% or 99% identical to the amino acid sequence of SEQ ID NO: 213.

Provided herein is an anti-CD47 antibody or an antigen-binding portion thereof, wherein the antibody or antigen-binding portion comprises a VH domain and a VL domain, wherein the VH domain amino acid sequence comprises (a) SEQ ID NO: 12, or an amino acid sequence that is at least 95%, 96%, 97%, 98% or 99% identical to the amino acid sequence of SEQ ID NO: 12; (b) SEQ ID NO: 52, or an amino acid sequence that is at least 95%, 96%, 97%, 98% or 99% identical to the amino acid sequence of SEQ ID NO: 52; (c) SEQ ID NO: 92, or an amino acid sequence that is at least 95%, 96%, 97%, 98% or 99% identical to the amino acid sequence of SEQ ID NO: 92; (d) SEQ ID NO: 127, or an amino acid sequence that is at least 95%, 96%, 97%, 98% or 99% identical to the amino acid sequence of SEQ ID NO: 127; or (e) SEQ ID NO: 161, or an amino acid sequence that is at least 95%, 96%, 97%, 98% or 99% identical to the amino acid sequence of SEQ ID NO: 161.

Also provided herein is an anti-CD47 antibody or an antigen-binding portion thereof, wherein the antibody or antigen-binding portion comprises a VH domain and a VL domain, wherein the VH domain amino acid sequence comprises SEQ ID NO: 213, SEQ ID NO: 238, SEQ ID NO: 239, SEQ ID NO: 240, SEQ ID NO: 241, SEQ ID NO: 242 or SEQ ID NO: 243.

Provided herein is an anti-CD47 antibody or an antigen-binding portion thereof, wherein the antibody or antigen-binding portion comprises a VH domain and a VL domain, wherein the VL domain amino acid sequence comprises (a) SEQ ID NO: 222, or an amino acid sequence that is at least 95%, 96%, 97%, 98% or 99% identical to the amino acid sequence of SEQ ID NO: 222; (b) SEQ ID NO: 230, or an amino acid sequence that is at least 95%, 96%, 97%, 98% or 99% identical to the amino acid sequence of SEQ ID NO: 230; or (c) SEQ ID NO: 236, or an amino acid sequence that is at least 95%, 96%, 97%, 98% or 99% identical to the amino acid sequence of SEQ ID NO: 236.

Provided herein is an anti-CD47 antibody or an antigen-binding portion thereof, wherein the antibody or antigen-binding portion comprises a VH domain and a VL domain, wherein the VL domain amino acid sequence comprises (a) SEQ ID NO: 32, or an amino acid sequence that is at least 95%, 96%, 97%, 98% or 99% identical to the amino acid sequence of SEQ ID NO: 32; (b) SEQ ID NO: 72, or an amino acid sequence that is at least 95%, 96%, 97%, 98% or 99% identical to the amino acid sequence of SEQ ID NO: 72; (c) SEQ ID NO: 110, or an amino acid sequence that is at least 95%, 96%, 97%, 98% or 99% identical to the amino acid sequence of SEQ ID NO: 110; (d) SEQ ID NO: 144, or an amino acid sequence that is at least 95%, 96%, 97%, 98% or 99% identical to the amino acid sequence of SEQ ID NO: 144; (e) SEQ ID NO: 170, or an amino acid sequence that is at least 95%, 96%, 97%, 98% or 99% identical to the amino acid sequence of SEQ ID NO: 170; or (f) SEQ ID NO: 181, or an amino acid sequence that is at least 95%, 96%, 97%, 98% or 99% identical to the amino acid sequence of SEQ ID NO: 181.

Also provided herein is an anti-CD47 antibody or an antigen-binding portion thereof, wherein the antibody or antigen-binding portion comprises a VH domain and a VL domain, wherein the VL domain amino acid sequence comprises SEQ ID NO: 222, SEQ ID NO: 230, SEQ ID NO: 236 or SEQ ID NO: 244.

Provided herein is an anti-CD47 antibody or an antigen-binding portion thereof, wherein the antibody or antigen-binding portion comprises a VH domain and a VL domain, wherein (a) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 222, or an amino acid sequence that is at least 95%, 96%, 97%, 98% or 99% identical to the amino acid sequence of SEQ ID NO: 222; (b) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 230, or an amino acid sequence that is at least 95%, 96%, 97%, 98% or 99% identical to the amino acid sequence of SEQ ID NO: 230; or (c) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 236, or an amino acid sequence that is at least 95%, 96%, 97%, 98% or 99% identical to the amino acid sequence of SEQ ID NO: 236.

Also provided herein is an anti-CD47 antibody or an antigen-binding portion thereof, wherein the antibody or antigen-binding portion comprises a VH domain and a VL domain, wherein (a) the VH domain amino acid sequence comprises SEQ ID NO: 12, or an amino acid sequence that is at least 95%, 96%, 97%, 98% or 99% identical to the amino acid sequence of SEQ ID NO: 12; and the VL domain amino acid sequence comprises SEQ ID NO: 32, or an amino acid sequence that is at least 95%, 96%, 97%, 98% or 99% identical to the amino acid sequence of SEQ ID NO: 32; (b) the VH domain amino acid sequence comprises SEQ ID NO: 52, or an amino acid sequence that is at least 95%, 96%, 97%, 98% or 99% identical to the amino acid sequence of SEQ ID NO: 52; and the VL domain amino acid sequence comprises SEQ ID NO: 72, or an amino acid sequence that is at least 95%, 96%, 97%, 98% or 99% identical to the amino acid sequence of SEQ ID NO: 72; (c) the VH domain amino acid sequence comprises SEQ ID NO: 92, or an amino acid sequence that is at least 95%, 96%, 97%, 98% or 99% identical to the amino acid sequence of SEQ ID NO: 92; and the VL domain amino acid sequence comprises SEQ ID NO: 110, or an amino acid sequence that is at least 95%, 96%, 97%, 98% or 99% identical to the amino acid sequence of SEQ ID NO: 110; (d) the VH domain amino acid sequence comprises SEQ ID NO: 127, or an amino acid sequence that is at least 95%, 96%, 97%, 98% or 99% identical to the amino acid sequence of SEQ ID NO: 127; and the VL domain amino acid sequence comprises SEQ ID NO: 144, or an amino acid sequence that is at least 95%, 96%, 97%, 98% or 99% identical to the amino acid sequence of SEQ ID NO: 144; (e) the VH domain amino acid sequence comprises SEQ ID NO: 161, or an amino acid sequence that is at least 95%, 96%, 97%, 98% or 99% identical to the amino acid sequence of SEQ ID NO: 161; and the VL domain amino acid sequence comprises SEQ ID NO: 170, or an amino acid sequence that is at least 95%, 96%, 97%, 98% or 99% identical to the amino acid sequence of SEQ ID NO: 170; or (f) the VH domain amino acid sequence comprises SEQ ID NO: 161, or an amino acid sequence that is at least 95%, 96%, 97%, 98% or 99% identical to the amino acid sequence of SEQ ID NO: 161; and the VL domain amino acid sequence comprises SEQ ID NO: 181, or an amino acid sequence that is at least 95%, 96%, 97%, 98% or 99% identical to the amino acid sequence of SEQ ID NO: 181.

Provided herein is an anti-CD47 antibody or an antigen-binding portion thereof, wherein the antibody or antigen-binding portion comprises a VH domain and a VL domain, wherein (a) the VH domain amino acid sequence comprises SEQ ID NO: 213; and the VL domain amino acid sequence comprises SEQ ID NO: 222, with 1, 2 or 3 conservative amino acid substitutions in the VH domain sequence, the VL domain sequence, or both the VH domain and the VL domain sequences; (b) the VH domain amino acid sequence comprises SEQ ID NO: 213; and the VL domain amino acid sequence comprises SEQ ID NO: 230, with 1, 2 or 3 conservative amino acid substitutions in the VH domain sequence, the VL domain sequence, or both the VH domain and the VL domain sequences; or (c) the VH domain amino acid sequence comprises SEQ ID NO: 213; and the VL domain amino acid sequence comprises SEQ ID NO: 236, with 1, 2 or 3 conservative amino acid substitutions in the VH domain sequence, the VL domain sequence, or both the VH domain and the VL domain sequences. Provided herein is an anti-CD47 antibody or an antigen-binding portion thereof, wherein the antibody or antigen-binding portion comprises a VH domain and a VL domain, wherein (a) the VH domain amino acid sequence comprises SEQ ID NO: 12; and the VL domain amino acid sequence comprises SEQ ID NO: 32, with 1, 2 or 3 conservative amino acid substitutions in the VH domain sequence, the VL domain sequence, or both the VH domain and the VL domain sequences; (b) the VH domain amino acid sequence comprises SEQ ID NO: 52; and the VL domain amino acid sequence comprises SEQ ID NO: 72, with 1, 2 or 3 conservative amino acid substitutions in the VH domain sequence, the VL domain sequence, or both the VH domain and the VL domain sequences; (c) the VH domain amino acid sequence comprises SEQ ID NO: 92; and the VL domain amino acid sequence comprises SEQ ID NO: 110, with 1, 2 or 3 conservative amino acid substitutions in the VH domain sequence, the VL domain sequence, or both the VH domain and the VL domain sequences; (d) the VH domain amino acid sequence comprises SEQ ID NO: 127; and the VL domain amino acid sequence comprises SEQ ID NO: 144, with 1, 2 or 3 conservative amino acid substitutions in the VH domain sequence, the VL domain sequence, or both the VH domain and the VL domain sequences; (e) the VH domain amino acid sequence comprises SEQ ID NO: 161; and the VL domain amino acid sequence comprises SEQ ID NO: 170, with 1, 2 or 3 conservative amino acid substitutions in the VH domain sequence, the VL domain sequence, or both the VH domain and the VL domain sequences; or (f) the VH domain amino acid sequence comprises SEQ ID NO: 161; and the VL domain amino acid sequence comprises SEQ ID NO: 181, with 1, 2 or 3 conservative amino acid substitutions in the VH domain sequence, the VL domain sequence, or both the VH domain and the VL domain sequences. In some embodiments, conservative amino acid substitutions are made only in the FR sequences and not in the CDR sequences of an antibody or antigen-binding portion.

As used herein, the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4 |

Calculations of sequence homology or identity (the terms are used interchangeably herein) between sequences may be performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman et al. ((1970) *J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In some embodiments, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) is a BLOSUM 62 scoring matrix with a gap penalty of 12, a gap extend penalty of 4, and a frameshift gap penalty of 5.

In some embodiments, the percent identity between two amino acid or nucleotide sequences can be determined using the algorithm of Meyers et al. ((1989) CABIOS 4:11-17) which has been incorporated into the ALIGN program (version 2.0), using a PAM120 weight residue table, a gap length penalty of 12 and a gap penalty of 4.

Provided herein is an anti-CD47 antibody or an antigen-binding portion thereof, wherein the antibody or antigen-binding portion comprises a VH domain and a VL domain, wherein (a) the VH domain amino acid sequence comprises SEQ ID NO: 213; and the VL domain amino acid sequence comprises SEQ ID NO: 222; (b) the VH domain amino acid sequence comprises SEQ ID NO: 213; and the VL domain amino acid sequence comprises SEQ ID NO: 230; or (c) the VH domain amino acid sequence comprises SEQ ID NO: 213; and the VL domain amino acid sequence comprises SEQ ID NO: 236.

Provided herein is an anti-CD47 antibody or an antigen-binding portion thereof, wherein the antibody or antigen-binding portion comprises a VH domain and a VL domain, wherein (a) the VH domain amino acid sequence comprises SEQ ID NO: 12; and the VL domain amino acid sequence comprises SEQ ID NO: 32; (b) the VH domain amino acid sequence comprises SEQ ID NO: 52; and the VL domain amino acid sequence comprises SEQ ID NO: 72; (c) the VH domain amino acid sequence comprises SEQ ID NO: 92; and the VL domain amino acid sequence comprises SEQ ID NO: 110; (d) the VH domain amino acid sequence comprises SEQ ID NO: 127; and the VL domain amino acid sequence comprises SEQ ID NO: 144; (e) the VH domain amino acid sequence comprises SEQ ID NO: 161; and the VL domain amino acid sequence comprises SEQ ID NO: 170; or (f) the VH domain amino acid sequence comprises SEQ ID NO: 161; and the VL domain amino acid sequence comprises SEQ ID NO: 181.

In some embodiments, an anti-CD47 antibody or antigen-binding portion provided herein is monoclonal.

In some embodiments, an anti-CD47 antibody or antigen-binding portion provided herein is chimeric. The term "chimeric" is intended to refer to an antibody molecule, or an antigen-binding portion thereof, in which the variable domain sequences are derived from one species and at least one constant region sequence is derived from another species. For example, one or all the variable domains of the light chain(s) and/or one or all the variable domains of the heavy chain(s) of a mouse antibody (e.g., a mouse monoclonal antibody) may each be joined to a human constant region, such as, without limitation an IgG1 or an IgG4 human constant region. Examples of chimeric antibodies and suitable techniques for their generation are provided in U.S. Pat. Nos. 4,816,567; 4,975,369; and 4,816,397, each of which is incorporated herein by reference in its entirety. In some embodiments, an anti-CD47 antibody or an antigen-binding portion provided herein comprises: (a) a VH domain amino acid sequence comprising SEQ ID NO: 213; a VL domain amino acid sequence comprising SEQ ID NO: 222 and a human constant region; (b) a VH domain amino acid sequence comprising SEQ ID NO: 213, a VL domain amino acid sequence comprising SEQ ID NO: 230 and a human constant region; or (c) a VH domain amino acid sequence comprising SEQ ID NO: 213, a VL domain amino acid sequence comprising SEQ ID NO: 236 and a human constant region. In some embodiments, an anti-CD47 antibody or an antigen-binding portion provided herein comprises: (a) a VH domain amino acid sequence comprising SEQ ID NO: 12; a VL domain amino acid sequence comprising SEQ ID NO: 32 and a human constant region; (b) a VH domain amino acid sequence comprising SEQ ID NO: 52, a VL domain amino acid sequence comprising SEQ ID NO: 72 and a human constant region; (c) a VH domain amino acid sequence comprising SEQ ID NO: 92, a VL domain amino acid sequence comprising SEQ ID NO: 110 and a human constant region; (d) a VH domain amino acid sequence comprising SEQ ID NO: 127, a VL domain amino acid sequence comprising SEQ ID NO: 144 and a human constant region; (e) a VH domain amino acid sequence comprising SEQ ID NO: 161, a VL domain amino acid sequence comprising SEQ ID NO: 170 and a human constant region; or (f) a VH domain amino acid sequence comprising SEQ ID NO: 161, a VL domain amino acid sequence comprising SEQ ID NO: 181 and a human constant region.

In some embodiments, an anti-CD47 antibody or antigen-binding portion provided herein is humanized. The term "humanized" is intended to refer to an antibody, or an antigen-binding portion thereof, that has been engineered to comprise one or more human framework regions in the variable domain together with non-human (e.g., mouse, rat, or hamster) CDRs of the heavy and/or light chain. In some embodiments, a humanized antibody comprises sequences that are entirely human except for the CDRs. In some embodiments, the VH domain, the VL domain, or both the VH domain and the VL domain of an anti-CD47 antibody or antigen-binding portion provided herein comprise one or more human framework region amino acid sequences. In some embodiments, a humanized antibody comprises sequences that are entirely human except for the CDRs, which are the CDRs of antibody 32G8H6. Examples of humanized antibodies and suitable techniques for their generation are provided in Hwang et al., Methods 36:35, 2005; Queen et al., Proc. Nati. *Acad. Sci.* USA, 86:10029-10033, 1989; Jones et al., *Nature,* 321:522-25, 1986; Riechmann et al., *Nature,* 332:323-27, 1988; Verhoeyen et al., *Science,* 239:1534-36, 1988; Orlandi et al., *Proc. Natl. Acad. Sci. USA,* 86:3833-37, 1989; U.S. Pat. Nos. 5,225,539; 5,530,101; 5,585,089; 5,693,761; 5,693,762; 6,180,370; and WO 90/07861, each of which is incorporated herein by reference in its entirety.

In some embodiments, humanization comprises removal of post-translational modification (PTM) sites in the variable domain sequences (e.g., in the CDR or framework sequences) of a non-human antibody. For example, one or more PTM sites in CDR sequences may be removed by substituting certain amino acid residues. In some embodiments, humanization comprises CDR grafting and back mutation. An exemplary list of procedures for humanization of an antibody is shown in Table 32. Antibodies VH1-PTM+ VL1, VH1-PTM+VL2 or VH1-PTM+VL3 (whose sequences are provided in Tables 22-24) are examples of humanized antibodies produced by CDR grafting, back mutation and PTM site removal.

Further provided herein is an anti-CD47 antibody or an antigen-binding portion thereof, wherein the antibody or antigen-binding portion comprises a VH domain, a VL domain and one or more human framework region sequences, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115.

Also provided herein is an anti-CD47 antibody or an antigen-binding portion thereof, wherein the antibody or antigen-binding portion comprises a VH domain, a VL domain and one or more human framework region sequences, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

Provided herein is an anti-CD47 antibody or an antigen-binding portion thereof, wherein the antibody or antigen-binding portion comprises a VH domain, a VL domain and human framework region sequences, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115.

Also provided herein is an anti-CD47 antibody or an antigen-binding portion thereof, wherein the antibody or antigen-binding portion comprises a VH domain, a VL domain and human framework region sequences, wherein: (a) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (b) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

In some embodiments, an anti-CD47 antibody or an antigen-binding portion thereof comprises an immunoglobulin constant region. In some embodiments, the immunoglobulin constant region is IgG, IgE, IgM, IgD, IgA or IgY. In some embodiments, the immunoglobulin constant region is IgG1, IgG2, IgG3, IgG4, IgA1 or IgA2. In some embodiments, the immunoglobulin constant region is immunologically inert. In some embodiments, the immunoglobulin constant region comprises one or more mutations to reduce or prevent FcγR binding, antibody-dependent cell-mediated cytotoxicity activity, and/or complement-dependent cytotoxicity activity. In some embodiments, the immunoglobulin constant region is a wild-type human IgG1 constant region, a wild-type human IgG2 constant region, a wild-type human IgG4 constant region, a human IgG1 constant region comprising the amino acid substitutions L234A, L235A and G237A, a human IgG1 constant region comprising the amino acid substitutions L234A, L235A, G237A and P331S or a human IgG4 constant region comprising the amino acid substitution S228P, wherein numbering is according to the EU numbering system. In some embodiments, a position of an amino acid residue in a constant region of an immunoglobulin molecule is numbered according to EU nomenclature (Ward et al., 1995 *Therap. Immunol.* 2:77-94).

In some embodiments, an anti-CD47 antibody or an antigen-binding portion thereof may comprise an immunoglobulin light chain constant region that is a kappa light chain constant region or a lambda light chain constant region.

In some embodiments, an anti-CD47 antibody or an antigen-binding portion thereof may comprise a human IgG4 constant region comprising the amino acid substitution S228P and a kappa light chain constant region.

In some embodiments, an anti-CD47 antibody or an antigen-binding portion provided herein inhibits or reduces the binding of CD47 to thrombospondin 1 (TSP-1). In some embodiments, the inhibition or reduction of binding of CD47 to TSP-1 in the presence of an anti-CD47 antibody or antigen-binding portion provided herein may be analyzed by ELISA, Western blot, immunoprecipitation or FACS.

Further provided herein is an immunoconjugate comprising an anti-CD47 antibody or an antigen-binding portion linked to a therapeutic agent. In some embodiments, the therapeutic agent is a small molecule drug.

Pharmaceutical Compositions

The anti-CD47 antibodies and antigen-binding portions provided herein (also referred to herein as "active compounds") can be incorporated into pharmaceutical compositions suitable for administration. Such compositions typically comprise an anti-CD47 antibody or antigen-binding portion (or an immunoconjugate comprising said antibody or portion), and a pharmaceutically acceptable carrier, diluent or excipient. As used herein, the term "pharmaceutically acceptable" refers to molecular entities and compositions that do not generally produce allergic or other serious adverse reactions when administered using routes well known in the art. Molecular entities and compositions approved by a regulatory agency of the U.S. federal or state government or listed in the U.S. Pharmacopeia or other generally recognized pharmacopeia for use in animals, and more particularly in humans are considered to be "pharmaceutically acceptable." As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Some examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Provided herein is a pharmaceutical composition comprising (i) an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; and (ii) a pharmaceutically acceptable carrier, diluent or excipient.

Provided herein is a pharmaceutical composition comprising (i) an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182; and (ii) a pharmaceutically acceptable carrier, diluent or excipient.

A pharmaceutical composition disclosed herein may be formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL® (castor oil polyoxyethylene ether) (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOJEL® (sodium starch glycolate), or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical agents can also be prepared in the form of suppositories (e.g., with conventional suppository bases such as cocoa butter and other glycerides) or retention enemas for rectal delivery.

In some embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions can also be used as pharmaceutically acceptable carriers.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions provided herein can be included in a container, pack, or dispenser together with instructions for administration.

Nucleic Acid Molecules, Vectors, Host Cells and Methods of Producing Antibodies

Provided herein is a nucleic acid molecule (e.g., an isolated nucleic acid molecule) encoding an amino acid sequence of an anti-CD47 antibody or anti-CD47 antigen-binding portion described herein (or an amino acid sequence of a (i) VH domain, (ii) a VL domain, or (iii) both a VH domain and a VL domain of an antibody or antigen-binding portion). Further provided herein is a nucleic acid molecule (e.g., an isolated nucleic acid molecule) encoding (i) a heavy chain, (ii) a light chain, or (iii) both a heavy chain and a light chain of an anti-CD47 antibody or anti-CD47 antigen-binding portion described herein. In some embodiments, a nucleic acid molecule encoding a VH domain, a VL domain, a heavy chain or a light chain comprises a signal sequence.

In some embodiments, a nucleic acid molecule encoding a VH domain, a VL domain, a heavy chain or a light chain does not comprise a signal sequence.

In some embodiments, a nucleic acid molecule encodes an amino acid sequence of a VH domain and a VL domain of an anti-CD47 antibody or an antigen-binding portion thereof, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115. In some embodiments, a nucleic acid molecule further encodes a human framework region amino acid sequence.

In some embodiments, a nucleic acid molecule encodes an amino acid sequence of a VH domain and a VL domain of an anti-CD47 antibody or an antigen-binding portion thereof, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182. In some embodiments, a nucleic acid molecule further encodes a human framework region amino acid sequence.

In some embodiments, the nucleic acid molecule comprises SEQ ID NO: 1, SEQ ID NO: 2, SEQ ID NO: 21, SEQ ID NO: 22, SEQ ID NO: 41, SEQ ID NO: 42, SEQ ID NO: 61, SEQ ID NO: 62, SEQ ID NO: 81, SEQ ID NO: 82, SEQ ID NO: 100, SEQ ID NO: 101, SEQ ID NO: 117, SEQ ID NO: 118, SEQ ID NO: 133, SEQ ID NO: 134, SEQ ID NO: 151, SEQ ID NO: 152, SEQ ID NO: 164, SEQ ID NO: 165, SEQ ID NO: SEQ ID NO: 174 or SEQ ID NO: 175. In some embodiments, the nucleic acid molecule comprises SEQ ID NO: 210, SEQ ID NO: 211, SEQ ID NO: 219, SEQ ID NO: 220, SEQ ID NO: 227, SEQ ID NO: 228, SEQ ID NO: 233 or SEQ ID NO: 234. In some embodiments, the nucleic acid molecule comprises SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 206, SEQ ID NO: 207, SEQ ID NO: 208 or SEQ ID NO: 209.

In some embodiments, the nucleic acid molecule comprises (a) SEQ ID NO: 1 and SEQ ID NO: 21; (b) SEQ ID NO: 2 and SEQ ID NO: 22; (c) SEQ ID NO: 41 and SEQ ID NO: 61; (d) SEQ ID NO: 42 and SEQ ID NO: 62; (e) SEQ ID NO: 81 and SEQ ID NO: 100; (f) SEQ ID NO: 82 and SEQ ID NO: 101; (g) SEQ ID NO: 117 and SEQ ID NO: 133; (h) SEQ ID NO: 118 and SEQ ID NO: 134; (i) SEQ ID NO: 151 and SEQ ID NO: 164; (j) SEQ ID NO: 152 and SEQ ID NO: 165; (k) SEQ ID NO: 151 and SEQ ID NO: 174; or (l) SEQ ID NO: 152 and SEQ ID NO: 175. In some embodiments, the nucleic acid molecule comprises (a) SEQ ID NO: 210 and SEQ ID NO: 219; (b) SEQ ID NO: 211 and SEQ ID NO: 220; (c) SEQ ID NO: 210 and SEQ ID NO: 227; (d) SEQ ID NO: 211 and SEQ ID NO: 228; (e) SEQ ID NO: 210 and SEQ ID NO: 233; or (f) SEQ ID NO: 211 and SEQ ID NO: 234.

Also provided herein is an expression vector comprising a nucleic acid molecule described herein. In certain vectors, a nucleic acid molecule is operatively linked to one or more regulatory sequences suitable for expression of the nucleic acid segment in a host cell. In some cases, an expression vector comprises sequences that mediate replication and comprises one or more selectable markers. As used herein, "vector" means a construct that is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Provided herein is a recombinant host cell comprising an expression vector or a nucleic acid molecule disclosed herein. A "host cell" includes an individual cell, a cell line or cell culture that can be or has been a recipient for vector(s) for incorporation of polynucleotide inserts. Host cells include progeny of a single host cell. The progeny may not necessarily be completely identical (in morphology or in genomic DNA complement) to the original parent cell due to natural, accidental, or deliberate mutation. An expression vector can be transfected into a host cell by standard techniques. Non-limiting examples include electroporation, calcium-phosphate precipitation, DEAE-dextran transfection and the like. In some embodiments, a recombinant host cell comprises a single vector or a single nucleic acid molecule encoding both a VH domain and a VL domain of an anti-CD47 antibody or an antigen-binding portion thereof. In some embodiments, a recombinant host cell comprises (i) a first vector or a first nucleic acid molecule encoding a VH domain of an anti-CD47 antibody or an antigen-binding portion thereof and (ii) a second vector or a second nucleic acid molecule encoding a VL domain of an anti-CD47 antibody or an antigen-binding portion thereof.

Further provided herein is a method for producing an anti-CD47 antibody or an antigen-binding portion thereof, the method comprising: culturing a recombinant host cell comprising an expression vector described herein under conditions whereby the nucleic acid segment is expressed, thereby producing the anti-CD47 antibody or antigen-binding portion. The antibody or antigen-binding portion may then be isolated from the host cell or culture. Anti-CD47 antibodies and antigen-binding portions thereof can be produced by any of a variety of methods known to those skilled in the art. In certain embodiments, anti-CD47 antibodies and antigen-binding portions thereof can be produced recombinantly. For example, nucleic acid sequences encoding one or more of SEQ ID NO: 1, SEQ ID NO: 2, SEQ ID NO: 21, SEQ ID NO: 22, SEQ ID NO: 41, SEQ ID NO: 42, SEQ ID NO: 61, SEQ ID NO: 62, SEQ ID NO: 81, SEQ ID NO: 82, SEQ ID NO: 100, SEQ ID NO: 101, SEQ ID NO: 117, SEQ ID NO: 118, SEQ ID NO: 133, SEQ ID NO: 134, SEQ ID NO: 151, SEQ ID NO: 152, SEQ ID NO: 164, SEQ ID NO: 165, SEQ ID NO: 174, SEQ ID NO: 175, SEQ ID NO: 210, SEQ ID NO: 211, SEQ ID NO: 219, SEQ ID NO: 220, SEQ ID NO: 227, SEQ ID NO: 228, SEQ ID NO: 233, SEQ ID NO: 234, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 206, SEQ ID NO: 207, SEQ ID NO: 208 or SEQ ID NO: 209, or portions thereof, may be introduced into a bacterial cell (e.g., *E. coli, B. subtilis*) or a eukaryotic cell (e.g., a yeast such as *S. cerevisiae*, or a mammalian cell such as a CHO cell line, various Cos cell lines, a HeLa cell, a HEK293 cell, various myeloma cell lines, or a transformed B-cell or hybridoma), or into an in vitro translation system, and the translated polypeptide may be isolated. In some embodiments, antibody light chain proteins and heavy chain proteins are produced in a cell with a signal sequence that is removed upon production of a mature anti-CD47 antibody or antigen-binding portion thereof.

Those skilled in the art will be able to determine whether an antibody or antigen-binding portion comprising a given polypeptide sequence binds to CD47 protein without undue experimentation using standard methodologies, for example, Western blots, ELISA, and the like.

Uses of Antibodies

Provided herein are methods and uses of the anti-CD47 antibodies, anti-CD47 antigen-binding portions, immunoconjugates and pharmaceutical compositions described herein for providing a therapeutic benefit to a subject with an inherited disorder or disease of red blood cells (for example, sickle cell disease (SCD)).

Provided herein is a method for inhibiting or reducing the binding of a CD47-expressing cell to TSP-1, the method comprising contacting the CD47-expressing cell with an anti-CD47 antibody or an anti-CD47 antigen-binding portion, an immunoconjugate or a pharmaceutical composition described herein. In some embodiments, the CD47-expressing cell is a CD47-expressing red blood cell (RBC). In some embodiments, the CD47-expressing cell is a CD47-expressing sickle cell. In some embodiments, the CD47-expressing RBC is a CD47-expressing RBC from a subject with SCD. In some embodiments, the binding of a CD47-expressing cell to TSP-1 is reduced by about 10%, about 20%, about 30%, about 40%, about 50%, about 60%, about 70%, about 80%, about 90% or about 95% in the presence of an anti-CD47 antibody or an anti-CD47 antigen-binding portion, an immunoconjugate or a pharmaceutical composition described herein, as compared to the binding in the absence of the anti-CD47 antibody, anti-CD47 antigen-binding portion, immunoconjugate or pharmaceutical composition. Binding of a CD47-expressing to TSP-1 protein may be measured by methods known in the art, for example, ELISA, FACS, Western blot or immunoprecipitation.

Further provided herein is a method for treating or reducing the severity of SCD in a subject, the method comprising administering to the subject a therapeutically effective amount of an anti-CD47 antibody or an anti-CD47 antigen-binding portion, an immunoconjugate or a pharmaceutical composition described herein. Provided herein is a method for treating or reducing the severity of SCD in a subject, the method comprising administering to the subject a therapeutically effective amount of an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; thereby treating or reducing the severity of SCD in the subject. Provided herein is a method for treating or reducing the severity of SCD in a subject, the method comprising administering to the subject a therapeutically effective amount of an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182; thereby treating or reducing the severity of SCD in the subject.

Provided herein is a method for ameliorating, treating or reducing the severity of a symptom of SCD in a subject, the method comprising administering to the subject a therapeutically effective amount of an anti-CD47 antibody or an anti-CD47 antigen-binding portion, an immunoconjugate or a pharmaceutical composition described herein. Provided herein is a method for ameliorating, treating or reducing the severity of a symptom of SCD in a subject, the method comprising administering to the subject a therapeutically effective amount of an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; thereby ameliorating, treating or reducing the severity of the symptom of SCD in the subject.

Provided herein is a method for ameliorating, treating or reducing the severity of a symptom of SCD in a subject, the method comprising administering to the subject a therapeutically effective amount of an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182; thereby ameliorating, treating or reducing the severity of the symptom of SCD in the subject.

Symptoms and complications of SCD include, without limitation, pain, fatigue, anemia, infection (e.g., bacterial and/or viral infection), swelling of extremities (hands and feet), stroke, vision loss, gallstones, splenic sequestration, avascular necrosis, leg ulcer, deep vein thrombosis, pulmonary embolism, vaso-occlusive crisis and acute chest syndrome.

Also provided herein is a method for ameliorating, treating or reducing the severity of a vaso-occlusive crisis or acute chest syndrome in a subject with SCD, the method comprising administering to the subject a therapeutically effective amount of an anti-CD47 antibody or an anti-CD47 antigen-binding portion, an immunoconjugate or a pharmaceutical composition described herein. Provided herein is a method for ameliorating, treating or reducing the severity of a vaso-occlusive crisis or acute chest syndrome in a subject with SCD, the method comprising administering to the subject a therapeutically effective amount of an anti-CD47 antibody or an antigen-binding portion thereof, wherein the antibody or antigen-binding portion comprises a VH domain and a VL domain, wherein: (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; thereby ameliorating, treating or reducing the severity of a vaso-occlusive crisis or acute chest syndrome in the subject.

Provided herein is a method for ameliorating, treating or reducing the severity of a vaso-occlusive crisis or acute chest syndrome in a subject with SCD, the method comprising administering to the subject a therapeutically effective amount of an anti-CD47 antibody or an antigen-binding portion thereof, wherein the antibody or antigen-binding portion comprises a VH domain and a VL domain, wherein:

(a) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39; (b) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79; (c) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115; (d) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149; (e) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182; thereby ameliorating, treating or reducing the severity of a vaso-occlusive crisis or acute chest syndrome in the subject.

In some embodiments, the VH domain, the VL domain, or both the VH domain and the VL domain of an anti-CD47 antibody or antigen-binding portion used in the methods provided herein comprise one or more human framework region amino acid sequences.

As used herein, the term "effective amount" or "therapeutically effective amount" refers to the amount of a pharmaceutical agent, e.g., an anti-CD47 antibody or an antigen-binding portion thereof, which is sufficient to reduce or ameliorate the severity and/or duration of a disorder, e.g., SCD, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another SCD-related therapy (e.g., prophylactic or therapeutic agent).

In some embodiments, a subject is a human, a non-human primate, a pig, a horse, a cow, a dog, a cat, a guinea pig, a mouse or a rat. In some embodiments, a subject is an adult human. In some embodiments, a subject is a pediatric human.

In some embodiments, a subject is homozygous for the HbS mutation (substituting thymine for adenine in the sixth codon of the beta-chain gene to replace GAG with GTG). This type of SCD is also known as HBSS or sickle cell anemia. In some embodiments, a subject is heterozygous for the HbS mutation. In some embodiments, the subject has the HbS mutation in one hemoglobin beta gene and a mutation producing a different abnormal beta-globin in the other hemoglobin beta gene. In some embodiments, a subject has Hemoglobin Sβ0 thalassemia (HbSB®) or Hemoglobin Sβ+ thalassemia (HbSB+). In sickle beta thalassemia, the subject has the HbS mutation in one hemoglobin beta gene and a mutation producing a reduced amount of normal hemoglobin in the other hemoglobin beta gene. In HbSB®, a subject has no normal hemoglobin. In HbSB+, a subject has a reduced amount of normal hemoglobin. In some embodiments, a subject has Hemoglobin SC disease (HbSC). In HbSC, one beta-globin subunit in hemoglobin is replaced with hemoglobin S, and the other beta-globin subunit is replaced with hemoglobin C.

In some embodiments, a subject may be treated with an anti-CD47 antibody or an anti-CD47 antigen-binding portion, an immunoconjugate or a pharmaceutical composition described herein and an additional therapeutic agent or therapy that is used to SCD or a symptom or complication of SCD. In some embodiments, the additional therapeutic agent hydroxyurea, voxelotor, crizanlizumab-tmca or blood transfusion. In some embodiments, the additional therapeutic agent is a small molecule drug. In some embodiments, the additional therapy is blood transfusion.

In some embodiments, the subject was previously treated with myoeloablative therapy. In some embodiments, the subject was previously treated with hydroxyurea, voxelotor, crizanlizumab-tmca or blood transfusion.

Further provided herein is an anti-CD47 antibody or an anti-CD47 antigen-binding portion, an immunoconjugate or a pharmaceutical composition described herein, for use in the treatment of SCD.

Provided herein is an anti-CD47 antibody or an anti-CD47 antigen-binding portion, an immunoconjugate or a pharmaceutical composition described herein, for use as a medicament.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously.

The disclosure will be further clarified by the following examples, which are intended to be purely exemplary of the disclosure and in no way limiting.

EXAMPLES

Example 1: Generation of Mouse Hybridomas Producing Monoclonal Anti-CD47 Antibodies Balb/c mice (4-6 mice per group) were immunized with the extracellular domain of human CD47 and immune adjuvant. Immune boosts were performed 3-5 times. Serum collection and titer evaluation by ELISA against target immunogen were performed.

Spleens were extracted surgically from the highest titer mouse or mice. Mouse spleen cells were fused with rat myeloma cells facilitated by PEG. Fused cells were seeded into 96-well plates in the presence of HAT Fusion medium. Three consecutive rounds of clone testing were performed by ELISA using the immunogen for positive screening to identify and validate the positive hybridoma clones. Hybridoma cell lines producing the most suitable antibodies were subcloned and expanded for monoclonal antibody production and cell storage. The following hybridoma cell lines were generated: 41B1H9, 37H4H3, 38F1E12, 33H11F3 and 32G8H6.

Example 2: Sequencing of Variable Domains of Anti-CD47 Antibodies Produced by Mouse Hybridomas Total RNA was isolated from cells of hybridoma cell lines 41B1H9, 37H4H3, 38F1E12, 33H11F3 and 32G8H6, following the technical manual of RNEASY® Plus Micro Kit (RNA purification kit) (QIAGEN©, Cat. No. 74034). Total RNA was then reverse-transcribed into cDNA using either isotype-specific anti-sense primers or universal primers following the technical manual of SMARTSCRIBE™ Reverse Transcriptase (TaKaRa, Cat. No. 639536). Antibody fragments of heavy chain and light chain were amplified by rapid amplification of cDNA ends (RACE). Amplified antibody fragments were cloned into a standard cloning vector separately. Colony PCR was performed to screen for clones with inserts of correct sizes. The consensus sequence was provided. Information about the clones sequenced and IMGT analysis of V(D)J junctions for each antibody is provided in Tables 7-16. For antibody 32G8H6, one VH sequence and two VL sequences were obtained. Variable domain sequences are provided in Tables 2-6 and 17.

TABLE 7

Sequencing information for antibody 41B1H9

| Sequence | Clones Sequenced | Clones with >99% Sequence with identity |
|---|---|---|
| $V_H$ | 5 | 5 |
| $V_L$ | 5 | 5 |

TABLE 8

IMGT analysis of V(D)J junctions for antibody 41B1H9

| Sequence | V-GENE and allele | Functio-nality | V-REGION identity % (nt) | J-GENE and allele | D-GENE and allele | AA Junction | Junction Frame |
|---|---|---|---|---|---|---|---|
| $V_H$ | Musmus IGHV14-3*02 F | productive | 92.71% (267/288 nt) | MusMus IGHJ4*01 F | Musmus IGHD2-1*01 F | CASGYG HYVGAM DYW (SEQ ID NO: 97) | in-frame |
| $V_L$ | Musmus IGKV15-103*01 ORF | productive | 97.85% (273/279 nt) | Musmus IGKJ2*01 F | — | CQQSRN YPTF (SEQ ID NO: 99) | in-frame |

"nt" = nucleotides

TABLE 9

Sequencing information for antibody 37H4H3

| Sequence | Clones Sequenced | Clones with >99% Sequence with identity |
|---|---|---|
| $V_H$ | 5 | 5 |
| $V_L$ | 5 | 5 |

TABLE 10

IMGT analysis of V(D)J junctions for antibody 37H4H3

| Sequence | V-GENE and allele | Functio-nality | V-REGION identity % (nt) | J-GENE and allele | D-GENE and allele | AA Junction | Junction Frame |
|---|---|---|---|---|---|---|---|
| $V_H$ | Musmus IGHV1-14*01 F | productive | 94.76% (263/288 nt) | MusMus IGHJ3*01 F | Musmus IGHD2-12*01 F | CARGLIG TRYDSW FAYW (SEQ ID NO: 116) | in-frame |
| $V_L$ | Musmus IGKV10-96*01 F | productive | 96.06% (268/279 nt) | Musmus IGKJ2*01 F | — | CHQGNT LPYTF (SEQ ID NO: 119) | in-frame |

"nt" = nucleotides

TABLE 11

Sequencing information for antibody 38F1E12

| Sequence | Clones Sequenced | Clones with >99% Sequence with identity |
|---|---|---|
| $V_H$ | 5 | 5 |
| $V_L$ | 5 | 5 |

TABLE 12

IMGT analysis of V(D)J junctions for antibody 38F1E12

| Sequence | V-GENE and allele | Functio-nality | V-REGION identity % (nt) | J-GENE and allele | D-GENE and allele | AA Junction | Junction Frame |
|---|---|---|---|---|---|---|---|
| VH | Musmus IGHV1-14*01 F | productive | 97.92% (282/288 nt) | Musmus IGHJ3*01 F | Musmus IGHD2-14*01 F | CARGRN RYDGWF TYW (SEQ ID NO: 132) | in-frame |
| VL | Musmus IGKV10-96*01 F | productive | 99.28% (277/279 nt) | Musmus IGKJ2*01 F | — | CQQGNT LPYTF (SEQ ID NO: 139) | in-frame |

"nt" = nucleotides

TABLE 13

Sequencing information for antibody 33H11F3

| Sequence | Clones Sequenced | Clones with >99% Sequence with identity |
|---|---|---|
| $V_H$ | 5 | 5 |
| $V_L$ | 5 | 5 |

TABLE 14

IMGT analysis of V(D)J junctions for antibody 33H11F3

| Sequence | V-GENE and allele | Functio-nality | V-REGION identity % (nt) | J-GENE and allele | D-GENE and allele | AA Junction | Junction Frame |
|---|---|---|---|---|---|---|---|
| VH | Musmus IGHV1-14*01 F | productive | 98.26% (282/288 nt) | Musmus IGHJ3*01 F | Musmus IGHD1-1*01 F | CARIDY GTIHTS WFAYW (SEQ ID NO: 150) | in-frame |
| VL | Musmus IGKV10-96*01 F | productive | 99.64% (278/279 nt) | Musmus IGKJ1*01 F | — | CQQGNT LPWTF (SEQ ID NO: 184) | in-frame |

"nt" = nucleotides

TABLE 15

Sequencing information for antibody 32G8H6

| Sequence | Clones Sequenced | Clones with >99% Sequence with identity |
|---|---|---|
| V$_H$ | 5 | 5 |
| V$_{L1}$ | 10 | 9 |
| V$_{L2}$ | | 1 |

TABLE 16

IMGT analysis of V(D)J junctions for antibody 32G8H6

| Sequence | V-GENE and allele | Functio-nality | V-REGION identity % (nt) | J-GENE and allele | D-GENE and allele | AA Junction | Junction Frame |
|---|---|---|---|---|---|---|---|
| V$_H$ | Musmus IGHV14 3*92 f | productive | 92.71% (267/288 nt) | Musmus IGHJ4*01 F | Musmus IGHD2-1*01 F | CASGYG HYVGAM DYW (SEQ ID NO: 185) | in-frame |
| V$_{L1}$ | Musmus IGKV15-103*01 ORF | productive | 97.85% (273/279 nt) | Musmus IGKJ2*01 F | — | CQQSRN YPYTF (SEQ ID NO: 184) | in-frame |
| V$_{L2}$ | Musmus IGKV15-103*01 ORF | productive | 99.64% (278/279 nt) | Musmus IGKJ5*01 F | — | CQQGQSYPYTF (SEQ ID NO: 187) | in-frame |

"nt" = nucleotides

TABLE 17

Annotated variable domain sequences of anti-CD47 antibodies

41B1H9 VH nucleotidesequence (417 base pairs (bp))
(SEQ ID NO: 1)
ATGAAATGCAGCTGGGTTATCTTCTTCCTGATGGCAGTGGTTACAGGGGTCAATTCA

GAGGTTCAGCTGCAGCAGTCTGGGACAGAACTTGTGAAGCCAGGGGCCTCAGTCAGG

TTGTCCTGCACAGCTTCTGGCCTCGACATTAAAGACACCTATATGCACTGGTTGAAA

CAGAGGCCTGAACAGGGCCTGGAGTGGATTGGGAGGATTGATCCTGCGAGTGGCAAT

GCTAAACATGACCCGAAGTTCCAGGGCAAGGCCACTATAACATCAGACCCATCCTCC

AACACAGCCAATTTACAGCTCACCAGCCTAACATCTGAGGACAGTGCCGTCTATTAC

TGTGCCTCCGGCTATGGTCACTACGTCGGTGCTATGGACTACTGGGGTCAAGGTACC

TCAGTCACCGTCTCCTCA

41B1H9 VH amino acid sequence (139 amino acids (aa))

MKCSWVIFFLMAVVTGVNSEVQLQQSGTELVKPGASVRLSCTASGLDIKDTYMHWLK

QRPEQGLEWIGRIDPASGNAKHDPKFQGKATITSDPSSNTANLQLTSLTSEDSAVYY

CASGYGHYVGAMDYWGQGTSVTVSS (SEQ ID NO: 11)

41B1H9 VL nucleotide sequence (381 bp)
(SEQ ID NO: 21)
ATGAGGGTCCTTGCTGAGCTCCTGGGGCTGCTGCTGTTCTGCTTTTTAGGTGTGAGA

TGTGACATCCAGATGAACCAGTCTCCATCCAGTCTGTCTGCATCCCTTGGAGACACA

ATTACCATCACTTGCCATGCCAGTCAGAACATTATGTTTGGTTAAGCTGGTACCAG

CAGAAACCAGGAAATATTCCTAAACTATTGATCTATAAGGCTTCCAATTTGCACACA

TABLE 17-continued

Annotated variable domain sequences of anti-CD47 antibodies

GGCGTCCCATCAAGGTTTAGTGGCAGTGGATCTGGAACAGGTTTCACATTAACCATC

AGCAGCCTGCAGCCTGAGGACATTGCCACTTACTACTGTCAACAGAGTCGGAATTAT

CCGTACACGTTCGGAGGGGGGACCAAGCTGGAAATAAAA

41B1H9 VL amino acid sequence (127 aa)
(SEQ ID NO: 31)
MRVLAELLGLLLFCFLGVRCDIQMNQSPSSLSASLGDTIIITCHASQNINVWLSWYQQ

KPGNIPKLLIYKASNLHTGVPSRFSGSGSGTGFTLTISSLQPEDIATYYCQQSRNYPY

TFGGGTKLEIK

37H4H3 VH nucleotide sequence (423 bp)
(SEQ ID NO: 41)
ATGGAATGGAGTTGGATATTTCTCTTTCTCCTGTCAGGAACTGCAGGTGTCCACTCT

GAGGTCCAGCTGCAGCAGTCTGGACCTGAACTGGTAAAGCCTGGGGCTICAGTGAAG

CTGTCCTGCAAGGCTTCTGGATACACATTCACTAGCTCTGTTATGCACTGGGTGAAG

CAGAAGCCTGGGCAGGGCCTTGAGTGGCTTGGATATATTATCCITATAGTGATGGA

ACTAAATTCAATGAGAAGTACAAAACCAAGGCCACACTGACTTCAGACAAATCCTCC

AGCACAGCCTACATGGAACTCAGCAGCCTGACCTCTGAGGACTCTGCGGTCTATTAC

TGTGCAAGAGGCCTTATAGGGACTAGATACGACTCCIGGTTTGCTTACTGGGGCCAA

GGGACTCTGGTCACTGTCTCTGCA

37H4H3 VH amino acid sequence (141 aa)
(SEQ ID NO: 51)
MEWSWIFLFLLSGTAGVHSEVQLQQSGPELVKPGASVKLSCKASGYTFTSSVMHWVK

QKPGQGLEWLGYINPYSDGTKFNEKYKTKATLTSDKSSSTAYMELSSLTSEDSAVYY

CARGLIGTRYDSWFAYWGQGTLVTVSA

37H4H3 VL nucleotide sequence (378 bp)
(SEQ ID NO: 61)
ATGTCCTCTGCTCAGTTCCTTGGTCTCCTGTTGCTCTGTTTTCAAGGTATCAGATGT

GATATCCAGATGACACAGAATGCATCCTCCCTGTCTGCCTCTCTGGGAGACAGAGTC

ACCATCAGTTGCAGGACAAGTCAGGACATTAACAATTATTTAAATTGGTATCAGCAG

AAACCAGATGGAACTGTTAAACTCCTGATCTATTACACATCAAGATTACACTCAGGA

GTCCCATCAAGGTTCAGTGGCAGTGGGTCTGGAACAGATTATTCTCTCTCCATTCGC

TACCTGGAGCAAGAAGATATTGCCACTTACTTTTGCCACCAGGGTAATACACTTCCG

TACACGTTCGGAGGGGGGACCAAACTGGAAATAAAA

37H4H3 VL amino acid sequence (126 aa)
(SEQ ID NO: 71)
MSSAQFLGLLLLCFQGIRCDIQMTQNASSLSASLGDRVTISCRTSQDINNYLNWYQQ

KPDGTVKLLIYYTSRLHSGVPSRFSGSGSGTDYSLSIRYLEQEDIATYFCHQGNTLP

YTFGGGTKLEIK

38F1E12 VH nucleotide sequence(417 bp)
(SEQ ID NO: 81)
ATGGAATGGAGTTGGATATTTCTCTTTCTCCTGTCAGGAACTGCAGGTGTCCACTCT

GAGGTCCAGCTGCAGCAGTCTGGACCTGAGCTGGTACAGCCTGGGGCTTCAGTGAGG

ATGTCCTGCAAGGCTTCTGGATACACGTTCACTAGCTATGTTATGCACTGGGTGAAG

CAGAAGCCTGGGCAGGGCCTTGAGTGGATTGGATATATTATCCITACAATGATGGT

ACTAAGTATAATGAGAAGTTCAAAGGCAAGGCCACACTGACTTCAGACAAATCCTCC

AGCACAGCCTACATGGAGCTCAGCAGCCTGACCTCTGAGGACTCTGCGGTCTATTAC

TABLE 17-continued

Annotated variable domain sequences of anti-CD47 antibodies

TGTGCAAG<u>AGGAAGGAATAGGTACGACGGTTGGTTTACTTAC</u>TGGGGCCAAGGGACT

CTGGTCACTGTCTCTGCA

38F1E12 VH amino acid sequence (139 aa)
(SEQ ID NO: 91)
MEWSWIFLFLLSGTAGVHSEVQLQQSGPELVQPGASVRMSCKASGYTFT<u>SYVMH</u>WVK QKPGQGLEWIG<u>YINPYNDGTKYNEKFKG</u>KATLTSDKSSTAYMELSSLTSEDSAVYY CAR<u>GRNRYDGWFTY</u>WGQGTLVTVSA 38F1E12 VL nucleotide sequence (378 bp)
(SEQ ID NO: 100)
ATGTCCTCTGCTCAGTTCCTTGGTCTCCTGTTGCTCTGTTTTCAAGGTATCAGATGT

GATATCCAGATGACACAGACTACATTCTCCCTGTCTGCCTCTCTGGGAGACAGAGTC

ACCATCAGTTGC<u>AGGGCAAGTCAGGACATTAGTATTATTTAAAC</u>TGGTATCAGCAG

AAACCAGATGGAACTGTTAAACTCCTGATCTACTACACATCAAGATTACACTCAGGA

GTCCCATCAAGGTTCAGTGGCAGTGGGTCTGGAACAGATTATTCTCTCACCATTAGC

AACCTGGAGCAAGAAGATATTGCCACTTACTTTTGC<u>CAACAGGGTAATACGCTTCCG</u>

<u>TACACG</u>TTCGGAGGGGGGACCAAGCTGGAAATAAAA

38F1E12 VL amino acid sequence (126 aa)
(SEQ ID NO: 109)
MSSAQFLGLLLLCFQGIRCDIQMTQTTFSLSASLGDRVTISC<u>RASQDISNYLN</u>WYQQ KPDGTVKLLIYYTSRLHSGVPSRFSGSGSGTDYSLTISNLEQEDIATYFC<u>QQGNTLP</u>

<u>YT</u>FGGGTKLEIK

33H11F3 VH nucleotide sequence (423 bp)
(SEQ ID NO: 117)
ATGGAATGGAGTTGGATATTTCTCTTTCTCCTGTCAGGAACTGCAGGTGTCCACTCT

GAGGTCCAGCTGCAGCAGTCTGGACCTGAGCTGGTAAAGCCTGGGGCTTCAGTGAAG

ATGTCCTGCAAGGCTTCTGGATACACATTCACT<u>AGCTATGTTATGCAC</u>TGGGTGAAG

CAGAAGCCTGGGCAGGGCCTTGAGTGGATGGGA<u>TATATTAATCCTTACAATGATGGT</u>

<u>ACTAAGTACAATGAGAAGTTCAAAGG</u>CAAGGCCACACTGACTTCAGACAAATCCTCC

AACACAGCCTACATGGAGTTCAGCAGCCTGACCTCTGAGGACTCTGCGGTCTATTAC

TGTGCAAG<u>AATAGACTACGGTACTATCCACACGTCCTGGTTTGCTTAC</u>TGGGGCCAA

GGGACTCTGGTCACTGTCTCTGCA

33H11F3 VH amino acids equence (141 aa)
(SEQ ID NO: 126)
MEWSWIFLFLLSGTAGVHSEVQLQQSGPELVKPGASVKMSCKASGYTFT<u>SYVMH</u>WVK QKPGQGLEWMG<u>YINPYNDGTKYNEKFKG</u>KATLTSDKSSNTAYMEFSSLTSEDSAVYY CAR<u>IDYGTIHTSWFAY</u>WGQGTLVTVSA 33H11F3 VL nucleotide sequence (378 bp)
(SEQ ID NO: 133)
ATGTCCTCTGCTCAGTTCCTTGGTCTCCTGTTGCTCTGTTTTCAAGGTACCAGATGT

GATATCCAGATGACACACACTACATCCTCCCTGTCTGCCTCTCTGGGAGACAGAGTC

ACCATCAGTTGC<u>AGGGCAAGTCAGGACATTAGCAATTATTTAAAC</u>TGGTATCAGCAG

AAACCAGATGGAACTGTTAAACTCCTGATCTACTACACATCAAGATTACACTCAGGA

GTCCCATCAAGGTTCAGTGGCAGTGGGTCTGGAACAGATTATTCTCTCACCATTAGC

AACCTGGAGCAAGAAGATATTGCCACTTACTTTTGC<u>CAACAGGGTAATACGCTTCCG</u>

<u>TGGACG</u>TTCGGTGGAGGCACCAAACTGGAAATCAAA

TABLE 17-continued

Annotated variable domain sequences of anti-CD47 antibodies

33H11F3 VL amino acid sequence (126 aa)
(SEQ ID NO: 143)
MSSAQFLGLLLLCFQGTRCDIQMTHTTSSLSASLGDRVTISC<u>RASQDISNYLN</u>WYQQ KPDGTVKLLIY<u>YTSRLHS</u>GVPSRFSGSGSGTDYSLTISNLEQEDIATYFC<u>QQGNTLP</u>

<u>WT</u>FGGGTKLEIK

32G8H6 VH nucleotide sequence (423 bp)
(SEQ ID NO: 151)
ATGGAATGGAGTTGGATATTTCTCTTTCTCCTGTCAGGAACTGCAGGTGTCCACTCT

GAGGTCCAGCTGCAGCAGTCTGGACCTGAGTTGGTAAAGCCTGGGGCTTCAGTGAAG

CTGTCCTGCAAGGCTTCTGGATACACATTCACT<u>AGTTCTGTTATTCAC</u>TGGGTGAAG

CAGAAGCCTGGGCAGGGCCTTGAGTGGCTTGGA<u>TATATTATCCITATAGTGATGGA</u>

<u>ACTAAATTCAATGAGAAGTGCAAA</u>ATCAAGGCCACACTGACTTCAGACAAATCCTCC

AGCACAGCCTACATGGAACTCAGCAGCCTGACCTCTGAGGACTCTGCGGTCTATTAC

TGTGCAAGA<u>GGCCTTATAGGGACTAGATACGACTCCIGGTTTGCTTAC</u>TGGGGCCAA

GGGACTCTGGTCACTGTCTCTGCA

32G8H6 VH amino acid sequence (141 aa)
(SEQ ID NO: 160)
MEWSWIFLFLLSGTAGVHSEVQLQQSGPELVKPGASVKLSCKASGYTFT<u>SSVIH</u>WVK QKPGQGLEWLGY<u>INPYSDGTKFNEKCKI</u>KATLTSDKSSSTAYMELSSLTSEDSAVYY CAR<u>GLIGTRYDSWFAY</u>WGQGTLVTVSA 32G8H6 VL-1 nucleotide sequence (378 bp)
(SEQ ID NO: 164)
ATGTCCTCTGCTCAGTTCCTTGGTCTCCTGTTGCTCTGTTTTCAAGGTATCAGATGT

GATATCCAGATGACACAGAATGGATCCTCCCTGTCTGCCTCTCTGGGAGACAGAGTC

ACCATCAGTTGC<u>AGGACAAGTCAGGACATTAACAATTATTTAAAT</u>TGGTATCAGCAG

AAACAAGATGGAACTGTTAAACTCCTGATCTAC<u>TACACATCAAGATTACACTCAGGA</u>

GTCCCATCAAGGTTCAGTGGCAGTGGGTCTGGAACAGATTATTCTCTCACCATTCGC

AACCTGGAGCAAGAAGATATTGCCACITACTITTGC<u>CAACAGGGTAATACGCTICCG</u>

<u>TACACG</u>TTCGGAGGGGGGACCAAACTGGAAATAAAA

32G8H6 VL-1 amino acid sequence (126 aa)
(SEQ ID NO: 169)
MSSAQFLGLLLLCFQGIRCDIQMTQNGSSLSASLGDRVTISC<u>RTSQDINNYLN</u>WYQQ KQDGTVKLLIY<u>YTSRLHS</u>GVPSRFSGSGSGTDYSLTIRNLEQEDIATYFC<u>QQGNTLP</u>

<u>YT</u>FGGGTKLEIK

32G8H6 VL-2 nucleotide sequence (381 bp)
(SEQ ID NO: 174)
ATGAGGGTCCTTGCTGAGCTCCTGGGGCTGCTGCTGTTCTGCTTTTTAGGTGTGAGAT

GTGACATCCAGATGAACCAGTCTCCATCCAGTCTGTCTGCATCCCTTGGAGACACAAT

TACCATCACTTGC<u>CATGCCAGTCAGAACATTAATGTTTGGTTAAGC</u>TGGTACCAGCAG

AAACCAGGAAATATTCCTAAACTATTGATCTATAAGGCTTCCAACTTGCACACAGGCG

TCCCATCAAGATTTAGTGGCAGTGGATCTGGAACAGGTTTCACATTAACCATCAGCAG

CCTGCAGCCTGAAGACATTGCCACTTACTACTGT<u>CAACAGGGICAAAGTTATCCTCTC</u>

<u>ACG</u>TTCGGTGCTGGGACCAAGCTGGAGCTGAAA

TABLE 17-continued

Annotated variable domain sequences of anti-CD47 antibodies

32G8H6 VL-2 amino acid sequence (126 aa)
(SEQ ID NO: 180)
MRVLAELLGLLLFCFLGVRCDIQMNQSPSSLSASLGDTITITC<u>HASQNINVWLS</u>WYQQ KPGNIPKLLIY<u>KASNLHT</u>GVPSRFSGSGSGTGFTLTISSLQPEDIATYYC<u>QQGQSYPL</u>

TFGAGTKLELK

In all variable domain sequences, components of the sequence are shown in the following amino-terminus to carboxyl-terminus order: signal sequence-FR1-CDR1-FR2-CDR2-FR3-CDR3-FR4.
Signal sequence is in bold font and underlined.
CDRs are underlined.
FRs are in plain font.

Example 3: Humanization of Anti-CD47 Antibodies

Mouse monoclonal anti-CD47 antibodies generated and sequenced in Examples 1 and 2 (e.g., antibody 32G8H6) are humanized using CDR grafting and back mutation. Briefly, the following protocols are used.

Chimeric antibody binding confirmation: Based on the variable domain sequences provided in Example 2, IgG expression constructs are made for the parent antibody (mouse-human chimera) production. The chimeric antibody is transiently expressed in HEK293 cells. The full-length IgG is purified using protein A affinity chromatography. The binding between antigen (human CD47) and the chimeric antibody is tested using BIACORE™ 8K (surface plasmon resonance system) or FACS. If the interaction is confirmed, the next step is performed.

Antibody developability assessment (sequence Post-Translational Modification (PTM) analysis): Post-translational modifications and chemical degradation in grafted sequence including deamidation, isomerization, oxidation and glycosylation, etc. are analyzed through developability assessment. PTM hotspots on the surface in the structural model like N-glycosylation sites, deamidation site, isomerization site, oxidation site and unpaired cysteine residues, etc. that may affect the binding activity and manufacturability of the grafted antibody are identified.

Humanization by rational design and sequence synthesis: Variable domain sequences of the selected antibody are analyzed. CDRs, HV loops and FRs are identified. Homology modeling to obtain the modeled structure of the mouse antibody. Calculate the solvent accessible surface area of framework residues is performed. Based on the result, framework residues that are buried (i.e., with solvent accessible surface area of <15%) are identified. One (1) human acceptor for VH and VL that share the highest sequence identities to the mouse counterparts is selected. The CDRs of the mouse antibody are directly grafted to the human acceptor frameworks to obtain the sequence of the grafted antibody without any back mutation. These are referred to as VH1 and VL1. The critical residues previously identified in the sequences of the grafted VH1 and VL1 and the mouse VH and VL are compared. The critical residues that are different in the grafted and mouse antibody framework sequences (i.e., putative back mutation sites) are identified. Stepwise incorporation of one or more back mutations in the grafted antibody sequence is designed according to the following guidelines:

Buried residues which have less chance of elicit immune response should be selected for back mutation.

Buried residues that are also in the proximity of CDRs should be selected for higher priority back mutation;

The other buried FR residues should be selected for lower priority back mutation.

This gives a series of humanized VHs and VLs. These are referred to as VH2/3/4 and VL2/3/4. The DNA sequences encoding the humanized light and heavy chains (one grafted and three back-mutated molecules for each chain) are synthesized. These chains are paired to make sixteen full-length antibody expression plasmids (4 heavy chains×4 light chains).

Humanized antibody production and affinity ranking: The humanized antibodies are expressed in HEK293 cell culture. The cells are spun down, and the supernatant obtained. Affinity ranking using the supernatant is performed by BIACORE™ 8K (surface plasmon resonance system). The humanized antibodies are ranked according to their dissociation rate constants (kd) or FACS EC50. Selection of one or more humanized IgGs is performed for further analysis.

Humanized antibody production and affinity determination: Selected humanized IgGs are transiently expressed in HEK293 cells. IgGs are purified using protein A affinity chromatography. The kinetics and binding affinity between antigen protein and chimeric and humanized antibodies are measured using BIACORE™ 8K (surface plasmon resonance system) or FACS EC50.

Example 4: Humanization of Murine 32G8H6 Anti-CD47 Antibody

Humanization of mouse monoclonal antibody (mAb) 32G8H6 was performed using CDR grafting plus back mutation method without sacrificing the binding affinity of the parental (chimeric) antibody. The chimeric antibody comprised the mouse variable domains of antibody 32G8H6 and human immunoglobulin constant regions.

Methods

A summary of processes for humanization of anti-CD47 antibodies is provided in Table 32 and described in more detail below.

Construction and production of chimeric antibody. The DNA sequences encoding the chimeric antibody heavy and light chains were synthesized and inserted into pcDNA3.4 vector to construct expression plasmids of full-length IgGs. Expression of chimeric antibody was conducted in EXPI293F™ (human kidney cells) cell culture and the supernatants were purified with protein A affinity column. The purified antibody was buffer-exchanged into PBS using PD-10 desalting column. The concentration and purity of the purified protein were determined by OD280 and SDS-PAGE, respectively.

Binding confirmation of chimeric antibody. The affinity of chimeric antibody to human CD47 antigen was determined using a Surface Plasmon Resonance (SPR) biosensor, BIACORE™ T200/8K (surface plasmon resonance system). Antibody was immobilized on the sensor chip through Fc capture method. Human CD47 protein was used as the analyte. The data of dissociation (kd) and association (ka) rate constants were obtained using BIACORE™ T200/8K (surface plasmon resonance system) evaluation software. The equilibrium dissociation constants (KD) were calculated from the ratio of kd over ka.

Production and affinity ranking of clones with post-translational modification (PTM) site removal. The designed plasmids of heavy chain and light chain sequences were sent for 10 mL transfection following GENSCRIPT™'s standard operating procedures (SOP). For affinity ranking, antibodies were immobilized on the sensor chip through Fc capture method. Anti-human CD47 was used as the analyte. The surface was regenerated before the injection of another antibody. The process was repeated until all antibodies were analyzed. The off-rates of antibodies were obtained from fitting the experimental data locally to 1:1 interaction model using the BIACORE™ (surface plasmon resonance system) evaluation software. The antibodies were ranked by their dissociation rate constants (off-rates, kd). Based on the ranking result, the top 3 clones were selected. The sequences of chimeric heavy chain and variable domain sequences with PTM sites removed are shown in Tables 18, 19 and 25.

Antibody humanization by CDR grafting plus back mutation. The structure of the parental antibody was modelled by a computer-aided homology modelling program. Humanized antibodies were designed using CDR grafting. Briefly, the CDRs of the parental antibody were grafted into the human acceptors to obtain humanized light chains and humanized heavy chains for each parental antibody. 5 heavy chains (VH1, VH2, VH3, VH4 and VH5) and 3 light chains (VL1, VL2 and VL3) were paired with each other for the affinity ranking experiment. The sequences of humanized heavy and light chains and variable domains are shown in Tables 18-26.

Production and affinity ranking of humanized antibodies. The designed plasmids of heavy chain and light chain were sent for 3 mL transfection following GENSCRIPT™'s SOP. For affinity ranking, Antibodies were captured on the sensor chip through Fc capture method. Human CD47 protein was used as the analyte. The surface was regenerated before the injection of another antibody. The process was repeated until all antibodies were analyzed. The off-rates of antibodies were obtained from fitting the experimental data locally to 1:1 interaction model using the BIACORE™ T200/8K (surface plasmon resonance system) evaluation software. The antibodies were ranked by their dissociation rate constants (off-rates, kd). Based on the ranking result, the top 3 clones were selected.

Construction and production of selected humanized IgGs. The top 3 binders were selected to express in EXPI293™ (human kidney cells) cell culture. The recombinant IgGs secreted to the medium were purified using protein A affinity chromatography following GENSCRIPT™'s SOP. The purified antibody was buffer-exchanged into PBS using PD-10 desalting column. The concentration and purity of the purified protein were determined by OD280 and SDS-PAGE, respectively.

Affinity measurement of purified humanized IgGs. The affinity of purified antibody binding to human CD47 was individually determined using a Surface Plasmon Resonance (SPR) biosensor, BIACORE™ T200/8K (surface plasmon resonance system) (GE Healthcare). Antibodies were captured on the sensor chip through Fc capture method. Human CD47 protein was used as the analyte. The data of dissociation (kd) and association (ka) rate constants were obtained using BIACORE™ T200/8K (surface plasmon resonance system) evaluation software. The equilibrium dissociation constants (KD) were calculated from the ratio of kd over ka.

Results

Figure 1B:
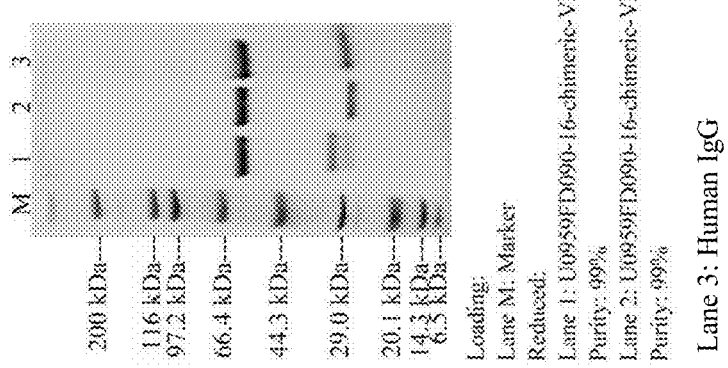

Chimeric antibody production. The purified IgG migrated as a ~150 kDa band in SDS-PAGE under non-reducing condition, and a ~50 kDa band under reducing condition. Evaluating by the SDS-PAGE result, the purity of IgG was >98% (FIG. 1A and FIG. 1B).

Figure 2:
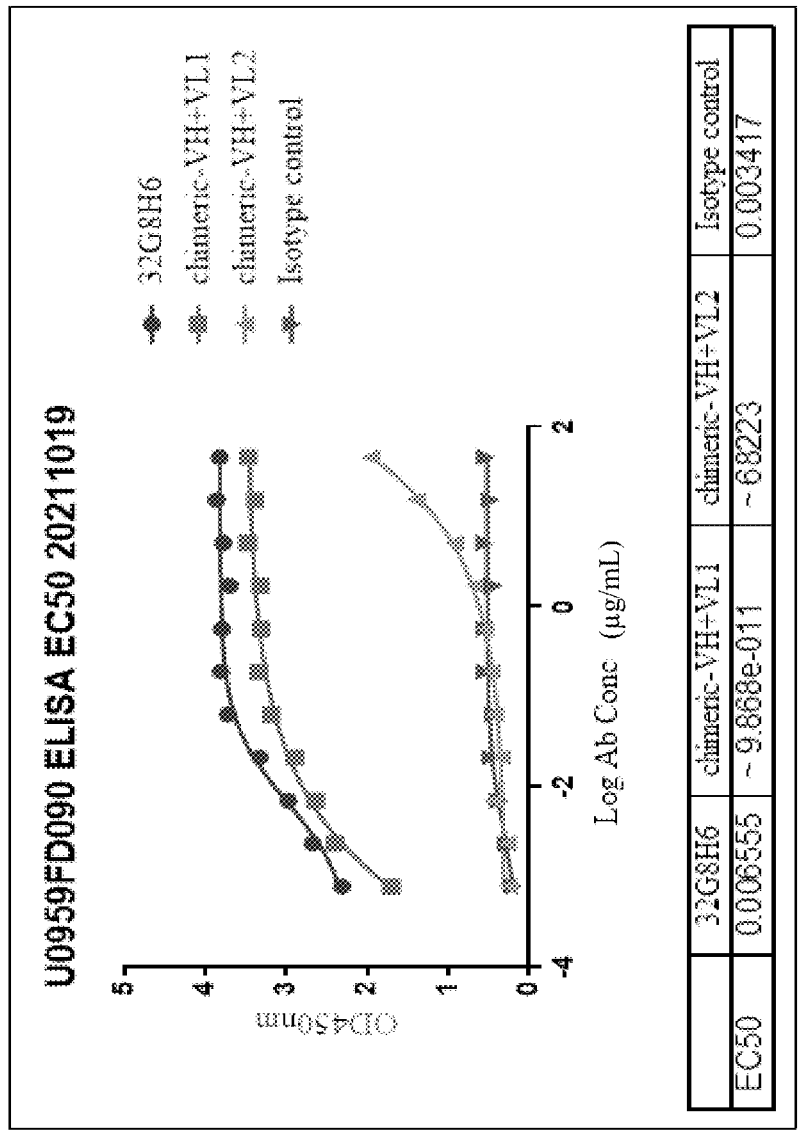
FIG. 2 is an ELISA EC50 plot of parent mAb (32G8H6), Chimeric-VH+VL1 and Chimeric-VH+VL2 binding to human CD47 protein.

Binding confirmation of chimeric antibody. The results indicate that chimeric antibody can bind to human CD47 protein. The affinity and kinetics of human CD47 protein to chimeric (VH+VL1 and VH+VL2) IgG are summarized in the table within FIG. 2, and EC50 values are shown in FIG. 2. Additional results from ELISA testing are shown in Table 27.

Figure 3A:
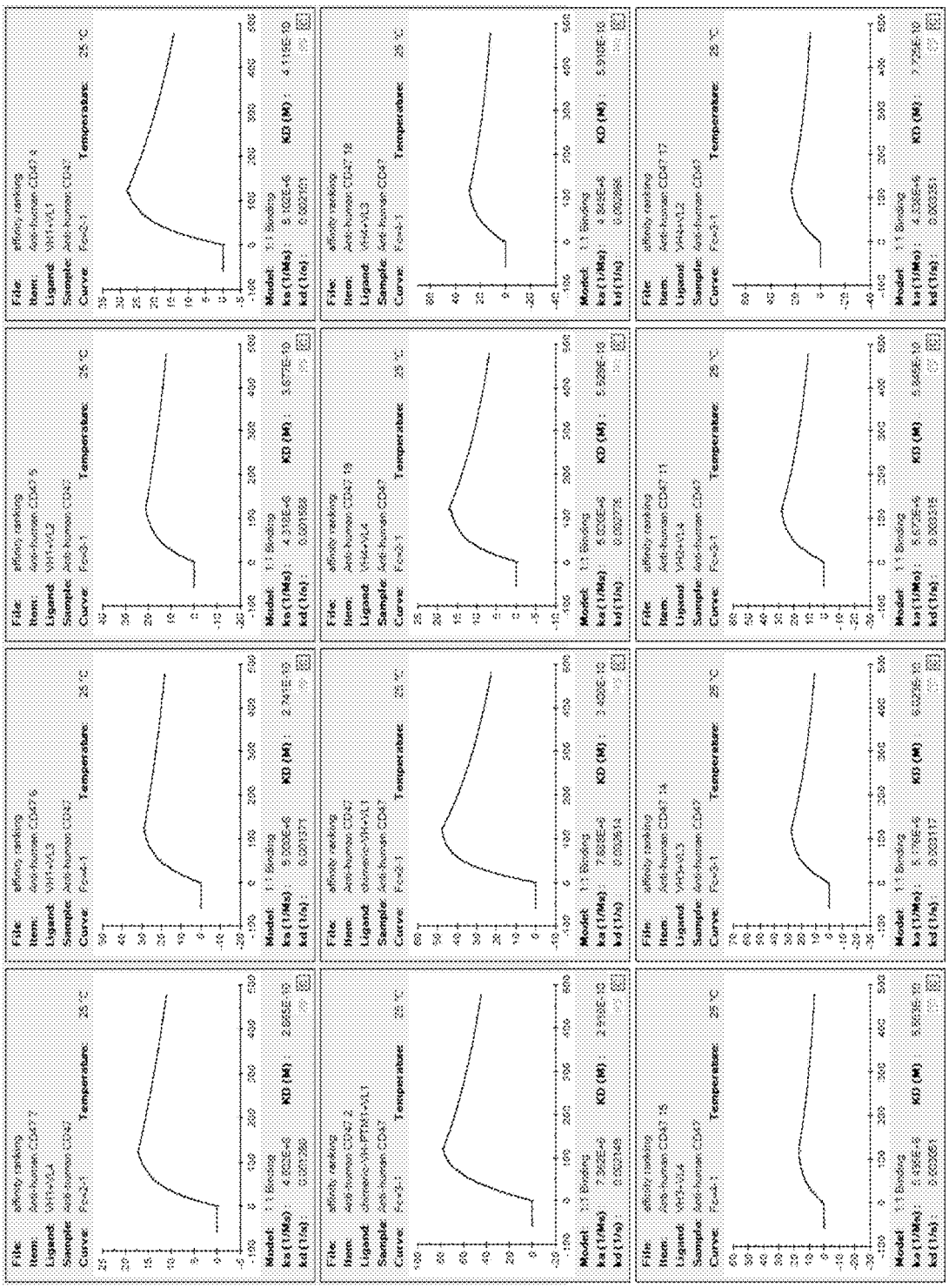
FIG. 3A and FIG. 3B show sensor-grams showing affinity measurement of human CD47 and humanized anti-CD47 antibodies.
Figure 3B:
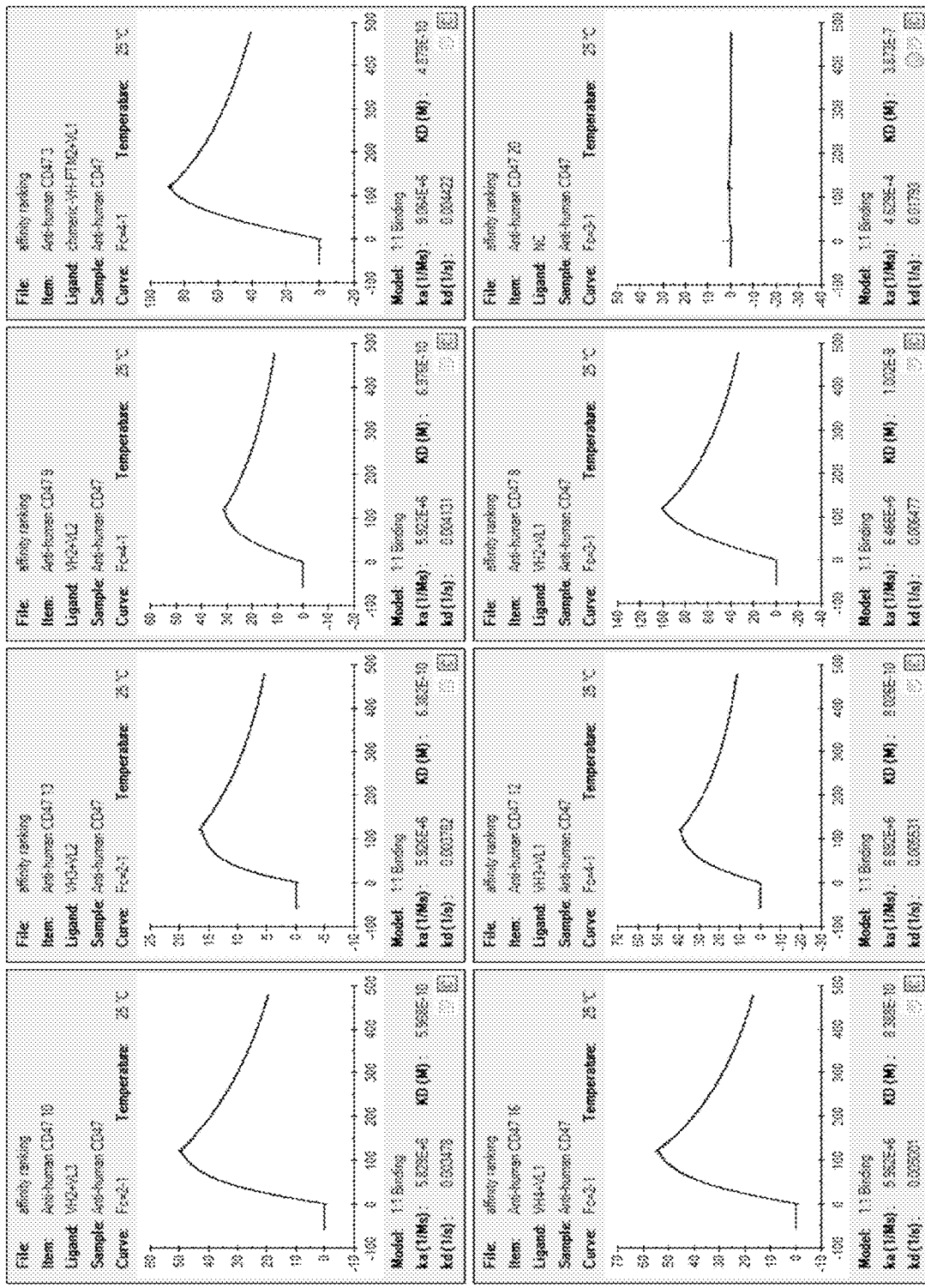

Affinity ranking of PTM site removal and humanized antibodies. The affinity of human CD47 protein to humanized Abs from supernatant is summarized in Tables 28 and 29. The sensor-grams are shown in FIG. 3A and FIG. 3B. Three humanized antibodies (VH1+VL1, VH1+VL2 and VH1+VL3) were selected to be expressed and purified according to GENSCRIPT™'s respective SOPs. These antibodies were selected for PTM site removal based on their similar binding affinity to the chimeric antibody. The PTM1 sequence (see Table 18) was used with these humanized antibodies.

Figure 4:
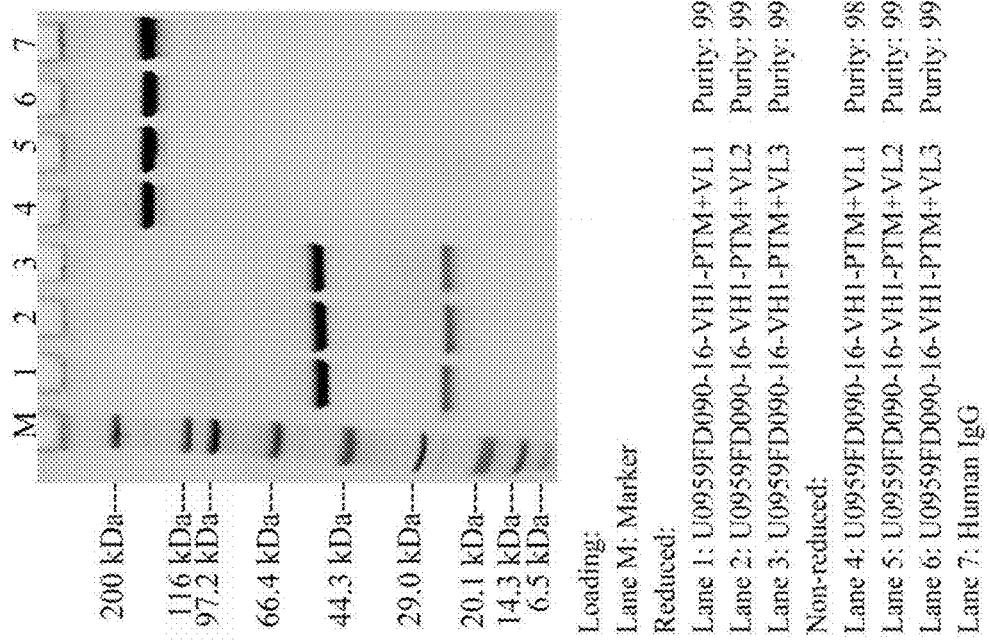
FIG. 4 shows SDS-PAGE results of selected anti-CD47 antibodies under reduced and non-reduced conditions.
Figure 5A:
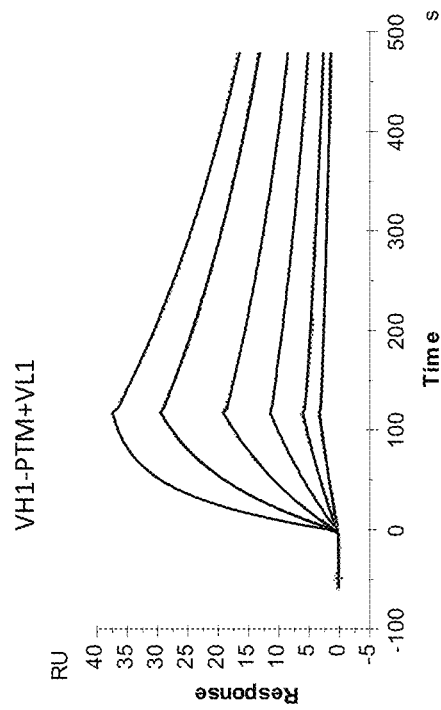
FIG. 5A-FIG. 5D show sensor-grams showing affinity measurement of human CD47 and selected chimeric and humanized anti-CD47 antibodies.
Figure 5B:
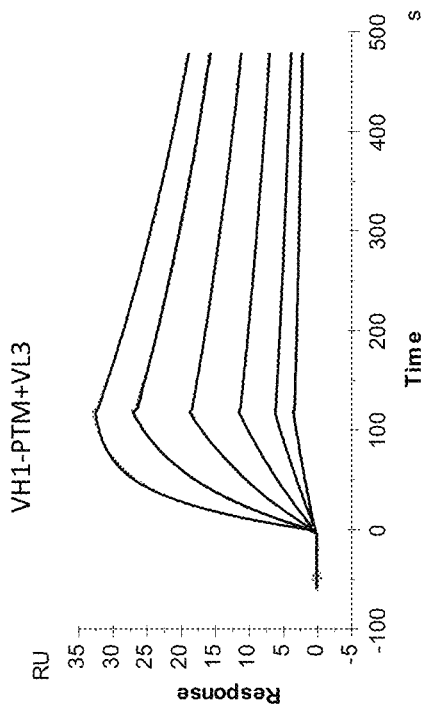
Figure 5C:
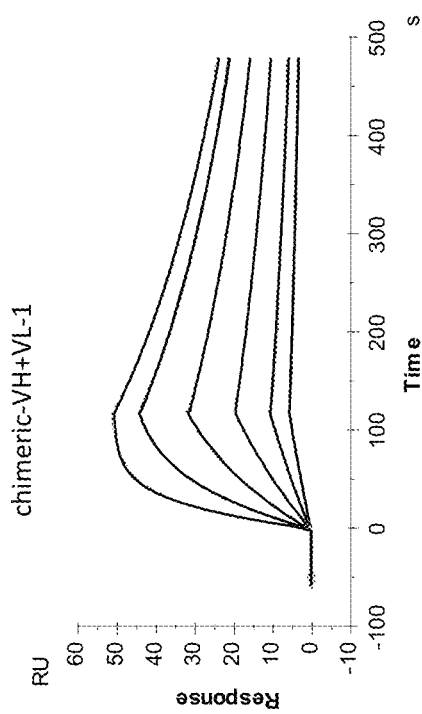
Figure 5D:
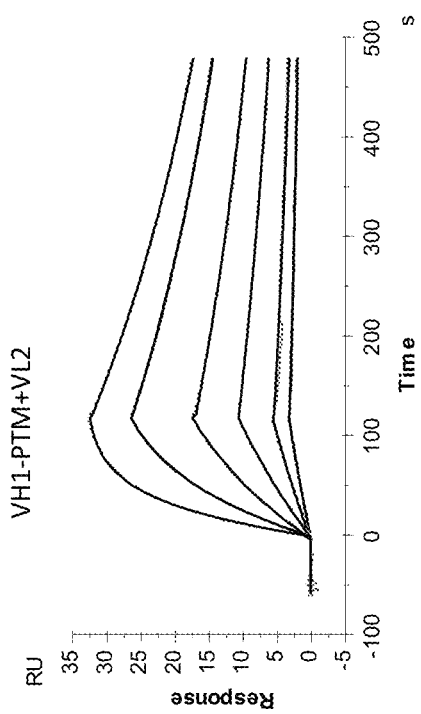

Production of purified hIgGs. The 3 selected humanized antibodies with PTM site removal were expressed and purified according to GENSCRIPT™'s respective SOPs. The sequences of these antibodies (VH1-PTM+VL1; VH1-PTM+VL2; and VH1-PTM+VL3) are provided in Tables 22-24. The purified IgG migrated as ~150 kDa band in SDS-PAGE under non-reducing condition, ~50 kDa band under reducing condition. Evaluating by the SDS-PAGE result, the purity of IgG is >98% (FIG. 4).

Affinity measurement of purified hIgGs. The affinity validation and binding kinetics of anti-CD47 antibodies are summarized in Tables 30 and 31. The sensor-grams are shown in FIG. 5A-FIG. 5D.

NUMBERED EMBODIMENTS

Notwithstanding the appended claims, the disclosure sets forth the following numbered embodiments:

1. An anti-CD47 antibody or an antigen-binding portion thereof, wherein the antibody or antigen-binding portion comprises a VH domain and a VL domain, wherein:
   (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115;
   (b) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39;
   (c) the VH domain amino acid sequence comprises HCDR1 of SEQ ID NO: 55, HCDR2 of SEQ ID NO:

57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79;
(d) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115;
(e) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149;
(f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or
(g) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

2. An anti-CD47 antibody or an antigen-binding portion thereof, wherein the antibody or antigen-binding portion cross-competes for binding to CD47 with an antibody comprising a heavy chain variable (VH) domain and a light chain variable (VL) domain, wherein:
(a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115;
(b) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39;
(c) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79;
(d) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115;
(e) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149;
(f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or
(g) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

3. The antibody or antigen-binding portion of embodiment 2, wherein the antibody or antigen-binding portion comprises a VH domain comprising an HCDR1, an HCDR2 and an HCDR3, and a VL domain comprising an LCDR1, an LCDR2 and an LCDR3, (a) wherein the HCDR3 comprises SEQ ID NO: 19; and/or wherein the LCDR3 comprises SEQ ID NO: 39;
(b) wherein the HCDR3 comprises SEQ ID NO: 59; and/or wherein the LCDR3 comprises SEQ ID NO: 79;
(c) wherein the HCDR3 comprises SEQ ID NO: 98; and/or wherein the LCDR3 comprises SEQ ID NO: 115;
(d) wherein the HCDR3 comprises SEQ ID NO: 131; and/or wherein the LCDR3 comprises SEQ ID NO: 149;
(e) wherein the HCDR3 comprises SEQ ID NO: 59; and/or wherein the LCDR3 comprises SEQ ID NO: 115; or
(f) wherein the HCDR3 comprises SEQ ID NO: 59; and/or wherein the LCDR3 comprises SEQ ID NO: 182.

4. The antibody or antigen-binding portion of embodiment 2 or 3, (a) wherein the HCDR2 comprises SEQ ID NO: 216; and/or wherein the LCDR2 comprises SEQ ID NO: 77;
(b) wherein the HCDR2 comprises SEQ ID NO: 17; and/or wherein the LCDR2 comprises SEQ ID NO: 37;
(c) wherein the HCDR2 comprises SEQ ID NO: 57; and/or wherein the LCDR2 comprises SEQ ID NO: 77;
(d) wherein the HCDR2 comprises SEQ ID NO: 96; and/or wherein the LCDR2 comprises SEQ ID NO: 77;
(e) wherein the HCDR2 comprises SEQ ID NO: 163; and/or wherein the LCDR2 comprises SEQ ID NO: 77; or
(f) wherein the HCDR2 comprises SEQ ID NO: 163; and/or wherein the LCDR2 comprises SEQ ID NO: 37.

5. The antibody or antigen-binding portion of any one of embodiments 2-4, (a) wherein the HCDR1 comprises SEQ ID NO: 15; and/or wherein the LCDR1 comprises SEQ ID NO: 35;
(b) wherein the HCDR1 comprises SEQ ID NO: 55; and/or wherein the LCDR1 comprises SEQ ID NO: 75;
(c) wherein the HCDR1 comprises SEQ ID NO: 94; and/or wherein the LCDR1 comprises SEQ ID NO: 112;
(d) wherein the HCDR1 comprises SEQ ID NO: 162; and/or wherein the LCDR1 comprises SEQ ID NO: 75; or
(e) wherein the HCDR1 comprises SEQ ID NO: 162; and/or wherein the LCDR1 comprises SEQ ID NO: 35.

6. An anti-CD47 antibody or an antigen-binding portion thereof, wherein the antibody or antigen-binding portion comprises a VH domain and a VL domain, wherein:
(a) the VH domain amino acid sequence comprises HCDR1 of SEQ ID NO: 162, HCDR2 of SEQ ID NO: 216 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3;
(b) the VH domain amino acid sequence comprises HCDR1 of SEQ ID NO: 15, HCDR2 of SEQ ID NO: 17 and HCDR3 of SEQ ID NO: 19, or a variant thereof having 1, 2 or 3 conservative amino acid substitutions in HCDR1, HCDR2, and/or HCDR3; and the VL domain amino acid sequence comprises LCDR1 of SEQ ID NO: 35, LCDR2 of SEQ ID NO: 37 and LCDR3 of SEQ ID NO: 39, or a variant thereof having 1, 2 or 3 conservative amino acid substitutions in LCDR1, LCDR2, and/or LCDR3;
(c) the VH domain amino acid sequence comprises HCDR1 of SEQ ID NO: 55, HCDR2 of SEQ ID NO: 57 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 79, or a variant thereof having 1, 2 or 3 conservative amino acid substitutions in LCDR1, LCDR2, and/or LCDR3;
(d) the VH domain amino acid sequence comprises HCDR1 of SEQ ID NO: 94, HCDR2 of SEQ ID NO: 96 and HCDR3 of SEQ ID NO: 98, or a variant thereof having 1, 2 or 3 conservative amino acid substitutions in HCDR1, HCDR2, and/or HCDR3; and the VL domain amino acid sequence comprises LCDR1 of SEQ ID NO: 112, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3;
(e) the VH domain amino acid sequence comprises HCDR1 of SEQ ID NO: 94, HCDR2 of SEQ ID NO: 96 and HCDR3 of SEQ ID NO: 131, or a variant thereof having 1, 2 or 3 conservative amino acid substitutions in HCDR1, HCDR2, and/or HCDR3; and the VL domain amino acid sequence comprises LCDR1 of SEQ ID NO: 112, LCDR2 of SEQ ID NO: 77 and LCDR3 of SEQ ID NO: 149, or a variant thereof having 1, 2 or 3 conservative amino acid substitutions in LCDR1, LCDR2, and/or LCDR3;
(f) the VH domain amino acid sequence comprises HCDR1 of SEQ ID NO: 162, HCDR2 of SEQ ID NO: 163 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 75, LCDR2 of SEQ ID NO: 77 and LCDR3 of SEQ ID NO: 115, or a variant thereof having 1, 2 or 3 conservative amino acid substitutions in LCDR1, LCDR2, and/or LCDR3; or
(g) the VH domain amino acid sequence comprises HCDR1 of SEQ ID NO: 162, HCDR2 of SEQ ID NO: 163 and HCDR3 of SEQ ID NO: 59, or a variant thereof having 1, 2 or 3 conservative amino acid substitutions in HCDR1, HCDR2, and/or HCDR3; and the VL domain amino acid sequence comprises LCDR1 of SEQ ID NO: 35, LCDR2 of SEQ ID NO: 37 and LCDR3 of SEQ ID NO: 182, or a variant thereof having 1, 2 or 3 conservative amino acid substitutions in LCDR1, LCDR2, and/or LCDR3.

7. The antibody or antigen-binding portion of any one of embodiments 1-6, wherein the VH domain amino acid sequence comprises (a) SEQ ID NO: 213, or an amino acid sequence that is at least 95%, 96%, 97%, 98% or 99% identical to the amino acid sequence of SEQ ID NO: 213;
(b) SEQ ID NO: 12, or an amino acid sequence that is at least 95%, 96%, 97%, 98% or 99% identical to the amino acid sequence of SEQ ID NO: 12;
(c) SEQ ID NO: 52, or an amino acid sequence that is at least 95%, 96%, 97%, 98% or 99% identical to the amino acid sequence of SEQ ID NO: 52;
(d) SEQ ID NO: 92, or an amino acid sequence that is at least 95%, 96%, 97%, 98% or 99% identical to the amino acid sequence of SEQ ID NO: 92;
(e) SEQ ID NO: 127, or an amino acid sequence that is at least 95%, 96%, 97%, 98% or 99% identical to the amino acid sequence of SEQ ID NO: 127; or
(f) SEQ ID NO: 161, or an amino acid sequence that is at least 95%, 96%, 97%, 98% or 99% identical to the amino acid sequence of SEQ ID NO: 161.

8. The antibody or antigen-binding portion of any one of embodiments 1-7, wherein the VL domain amino acid sequence comprises
(a) SEQ ID NO: 222, or an amino acid sequence that is at least 95%, 96%, 97%, 98% or 99% identical to the amino acid sequence of SEQ ID NO: 222;
(b) SEQ ID NO: 230, or an amino acid sequence that is at least 95%, 96%, 97%, 98% or 99% identical to the amino acid sequence of SEQ ID NO: 230;
(c) SEQ ID NO: 236, or an amino acid sequence that is at least 95%, 96%, 97%, 98% or 99% identical to the amino acid sequence of SEQ ID NO: 236;
(d) SEQ ID NO: 32, or an amino acid sequence that is at least 95%, 96%, 97%, 98% or 99% identical to the amino acid sequence of SEQ ID NO: 32;
(e) SEQ ID NO: 72, or an amino acid sequence that is at least 95%, 96%, 97%, 98% or 99% identical to the amino acid sequence of SEQ ID NO: 72;
(f) SEQ ID NO: 110, or an amino acid sequence that is at least 95%, 96%, 97%, 98% or 99% identical to the amino acid sequence of SEQ ID NO: 110;
(g) SEQ ID NO: 144, or an amino acid sequence that is at least 95%, 96%, 97%, 98% or 99% identical to the amino acid sequence of SEQ ID NO: 144;
(h) SEQ ID NO: 170, or an amino acid sequence that is at least 95%, 96%, 97%, 98% or 99% identical to the amino acid sequence of SEQ ID NO: 170; or
(i) SEQ ID NO: 181, or an amino acid sequence that is at least 95%, 96%, 97%, 98% or 99% identical to the amino acid sequence of SEQ ID NO: 181.

9. The antibody or antigen-binding portion of any one of embodiments 1-8, wherein
(a) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 222, or an amino acid sequence that is at least 95%, 96%, 97%, 98% or 99% identical to the amino acid sequence of SEQ ID NO: 222;
(b) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 230, or an amino acid sequence that is at least 95%, 96%, 97%, 98% or 99% identical to the amino acid sequence of SEQ ID NO: 230;

(c) the VH domain amino acid sequence comprises SEQ ID NO: 213, or an amino acid sequence that is at least 95%, 96%, 97%, 98% or 99% identical to the amino acid sequence of SEQ ID NO: 213; and the VL domain amino acid sequence comprises SEQ ID NO: 236, or an amino acid sequence that is at least 95%, 96%, 97%, 98% or 99% identical to the amino acid sequence of SEQ ID NO: 236;

(d) the VH domain amino acid sequence comprises SEQ ID NO: 12, or an amino acid sequence that is at least 95%, 96%, 97%, 98% or 99% identical to the amino acid sequence of SEQ ID NO: 12; and the VL domain amino acid sequence comprises SEQ ID NO: 32, or an amino acid sequence that is at least 95%, 96%, 97%, 98% or 99% identical to the amino acid sequence of SEQ ID NO: 32;

(e) the VH domain amino acid sequence comprises SEQ ID NO: 52, or an amino acid sequence that is at least 95%, 96%, 97%, 98% or 99% identical to the amino acid sequence of SEQ ID NO: 52; and the VL domain amino acid sequence comprises SEQ ID NO: 72, or an amino acid sequence that is at least 95%, 96%, 97%, 98% or 99% identical to the amino acid sequence of SEQ ID NO: 72;

(f) the VH domain amino acid sequence comprises SEQ ID NO: 92, or an amino acid sequence that is at least 95%, 96%, 97%, 98% or 99% identical to the amino acid sequence of SEQ ID NO: 92; and the VL domain amino acid sequence comprises SEQ ID NO: 110, or an amino acid sequence that is at least 95%, 96%, 97%, 98% or 99% identical to the amino acid sequence of SEQ ID NO: 110;

(g) the VH domain amino acid sequence comprises SEQ ID NO: 127, or an amino acid sequence that is at least 95%, 96%, 97%, 98% or 99% identical to the amino acid sequence of SEQ ID NO: 127; and the VL domain amino acid sequence comprises SEQ ID NO: 144, or an amino acid sequence that is at least 95%, 96%, 97%, 98% or 99% identical to the amino acid sequence of SEQ ID NO: 144;

(h) the VH domain amino acid sequence comprises SEQ ID NO: 161, or an amino acid sequence that is at least 95%, 96%, 97%, 98% or 99% identical to the amino acid sequence of SEQ ID NO: 161; and the VL domain amino acid sequence comprises SEQ ID NO: 170, or an amino acid sequence that is at least 95%, 96%, 97%, 98% or 99% identical to the amino acid sequence of SEQ ID NO: 170; or (i) the VH domain amino acid sequence comprises SEQ ID NO: 161, or an amino acid sequence that is at least 95%, 96%, 97%, 98% or 99% identical to the amino acid sequence of SEQ ID NO: 161; and the VL domain amino acid sequence comprises SEQ ID NO: 181, or an amino acid sequence that is at least 95%, 96%, 97%, 98% or 99% identical to the amino acid sequence of SEQ ID NO: 181.

10. The antibody or antigen-binding portion of any one of embodiments 1-9, wherein (a) the VH domain amino acid sequence comprises SEQ ID NO: 213; and the VL domain amino acid sequence comprises SEQ ID NO: 222;

(b) the VH domain amino acid sequence comprises SEQ ID NO: 213; and the VL domain amino acid sequence comprises SEQ ID NO: 230;

(c) the VH domain amino acid sequence comprises SEQ ID NO: 213; and the VL domain amino acid sequence comprises SEQ ID NO: 236;

(d) the VH domain amino acid sequence comprises SEQ ID NO: 12; and the VL domain amino acid sequence comprises SEQ ID NO: 32;

(e) the VH domain amino acid sequence comprises SEQ ID NO: 52; and the VL domain amino acid sequence comprises SEQ ID NO: 72;

(f) the VH domain amino acid sequence comprises SEQ ID NO: 92; and the VL domain amino acid sequence comprises SEQ ID NO: 110;

(g) the VH domain amino acid sequence comprises SEQ ID NO: 127; and the VL domain amino acid sequence comprises SEQ ID NO: 144;

(h) the VH domain amino acid sequence comprises SEQ ID NO: 161; and the VL domain amino acid sequence comprises SEQ ID NO: 170; or (i) the VH domain amino acid sequence comprises SEQ ID NO: 161; and the VL domain amino acid sequence comprises SEQ ID NO: 181.

11. The antibody or antigen-binding portion of any one of embodiments 1-10, wherein the CD47 is human CD47.

12. The antibody or antigen-binding portion of any one of embodiments 1-11, wherein the antibody is monoclonal.

13. The antibody or antigen-binding portion of any one of embodiments 1-12, wherein the antibody or antigen-binding portion is chimeric or humanized.

14. The antibody or antigen-binding portion of any one of embodiments 1-8 and 11-13, wherein the VH domain, the VL domain, or both the VH domain and the VL domain comprise one or more human framework region amino acid sequences.

15. The antigen-binding portion of any one of embodiments 1-14, wherein the antigen-binding portion is a Fab, a F(ab')2, a Fab', a Fv, a scFv, a Fd, a diabody, a triabody, a tetrabody or a bis-scFv.

16. The antibody or antigen-binding portion of any one of embodiments 1-15, wherein the antibody or antigen-binding portion is multispecific.

17. The antibody or antigen-binding portion of embodiment 16, wherein the antibody or antigen-binding portion is bispecific.

18. The antibody or antigen-binding portion of any one of embodiments 1-17, wherein the antibody or antigen-binding portion comprises an immunoglobulin constant region.

19. The antibody or antigen-binding portion of embodiment 18, wherein the immunoglobulin constant region is IgG, IgE, IgM, IgD, IgA or IgY.

20. The antibody or antigen-binding portion of embodiment 18, wherein the immunoglobulin constant region is IgG1, IgG2, IgG3, IgG4, IgA1 or IgA2.

21. The antibody or antigen-binding portion of embodiment 18, wherein the immunoglobulin constant region is immunologically inert.

22. The antibody or antigen-binding portion of embodiment 18, wherein the immunoglobulin constant region is a wild-type human IgG1 constant region, a wild-type human IgG2 constant region, a wild-type human IgG4 constant region, a human IgG1 constant region comprising the amino acid substitutions L234A, L235A and G237A, a human IgG1 constant region comprising the amino acid substitutions L234A, L235A, G237A and P331S or a human IgG4 constant region comprising the amino acid substitution S228P, wherein numbering is according to the EU numbering system.

23. The antibody or antigen-binding portion of any one of embodiments 1-22, wherein the antibody or antigen-binding portion inhibits or reduces the binding of CD47 to thrombospondin 1 (TSP-1).

24. An immunoconjugate comprising the antibody or antigen-binding portion of any one of embodiments 1-23 linked to a therapeutic agent.

25. The immunoconjugate of embodiment 24, wherein the therapeutic agent is a small molecule drug.

26. A pharmaceutical composition comprising the antibody or antigen-binding portion of any one of embodiments 1-23 or the immunoconjugate of embodiment 24 or 25, and a pharmaceutically acceptable carrier, diluent or excipient.

27. A nucleic acid molecule encoding:
(a) the VH domain amino acid sequence;
(b) the VL domain amino acid sequence; or
(c) both the VH domain and the VL domain amino acid sequences, of the antibody or antigen-binding portion of any one of embodiments 1-23.

28. The nucleic acid molecule of embodiment 27, wherein the nucleic acid molecule comprises SEQ ID NO: 1, SEQ ID NO: 2, SEQ ID NO: 21, SEQ ID NO: 22, SEQ ID NO: 41, SEQ ID NO: 42, SEQ ID NO: 61, SEQ ID NO: 62, SEQ ID NO: 81, SEQ ID NO: 82, SEQ ID NO: 100, SEQ ID NO: 101, SEQ ID NO: 117, SEQ ID NO: 118, SEQ ID NO: 133, SEQ ID NO: 134, SEQ ID NO: 151, SEQ ID NO: 152, SEQ ID NO: 164, SEQ ID NO: 165, SEQ ID NO: SEQ ID NO: 174, SEQ ID NO: 175, SEQ ID NO: 210, SEQ ID NO: 211, SEQ ID NO: 219, SEQ ID NO: 220, SEQ ID NO: 227, SEQ ID NO: 228, SEQ ID NO: 233 or SEQ ID NO: 234.

29. An expression vector comprising the nucleic acid molecule of embodiment 27 or 28.

30. A recombinant host cell comprising the nucleic acid molecule of embodiment 27 or 28 or the expression vector of embodiment 29.

31. A method of producing an anti-CD47 antibody or an antigen-binding portion thereof, the method comprising:
culturing a recombinant host cell comprising the expression vector of embodiment 29 under conditions whereby the nucleic acid molecule is expressed, thereby producing the antibody or antigen-binding portion; and isolating the antibody or antigen-binding portion from the host cell or culture.

32. A method for treating or reducing the severity of sickle cell disease (SCD) in a subject, the method comprising administering to the subject a therapeutically effective amount of the antibody or antigen-binding portion of any one of embodiments 1-23, the immunoconjugate of embodiment 24 or 25 or the pharmaceutical composition of embodiment 26.

33. A method for ameliorating, treating or reducing the severity of a symptom of SCD in a subject, the method comprising administering to the subject a therapeutically effective amount of the antibody or antigen-binding portion of any one of embodiments 1-23, the immunoconjugate of embodiment 24 or 25 or the pharmaceutical composition of embodiment 26.

34. The method of embodiment 33, wherein the symptom is pain, fatigue, anemia, infection or swelling of extremities.

35. A method for ameliorating, treating or reducing the severity of a vaso-occlusive crisis or acute chest syndrome in a subject with SCD, the method comprising administering to the subject a therapeutically effective amount of the antibody or antigen-binding portion of any one of embodiments 1-23, the immunoconjugate of embodiment 24 or 25 or the pharmaceutical composition of embodiment 26.

36. The method of any one of embodiments 32-35, wherein the method comprises administering to the subject an additional therapeutic agent.

37. The method of embodiment 36, wherein the additional therapeutic agent is a small molecule drug.

38. The method of any one of embodiments 32-37, wherein the subject was previously treated with myoeloablative therapy.

39. A method for inhibiting or reducing the binding of a CD47-expressing cell to TSP-1, the method comprising contacting the CD47-expressing cell with the antibody or antigen-binding portion of any one of embodiments 1-23, the immunoconjugate of embodiment 24 or 25 or the pharmaceutical composition of embodiment 26.

40. The method of embodiment 39, wherein the CD47-expressing cell is a CD47-expressing red blood cell (RBC).

41. The method of embodiment 40, wherein the CD47-expressing RBC is a CD47-expressing RBC from a subject with SCD.

42. The antibody or antigen-binding portion of any one of embodiments 1-23, the immunoconjugate of embodiment 24 or 25 or the pharmaceutical composition of embodiment 26, for use in the treatment of SCD.

43. The antibody or antigen-binding portion of any one of embodiments 1-23, the immunoconjugate of embodiment 24 or 25 or the pharmaceutical composition of embodiment 26, for use as a medicament.

TABLE 18

Annotated amino acid sequences of exemplary chimeric and humanized anti-CD47 antibody heavy chains U0959FD090-chimeric-VH-PTM1

(SEQ ID NO: 188)

MGWSCIILFLVATATGVHSEVQLQQSGPELVKPGASVKLSCKASGYTFT<u>SSVIHWVKQ</u>

KPGQGLEWLG<u>YINPYSEGTKFNEKSKI</u>KATLTSDKSSSTAYMELSSLTSEDSAVYYCA

R<u>GLIGTRYDSWFAY</u>WGQGTLVTVSAastkgpsvfplapcsrstsestaalgclvkdyf pepvtvswnsgaltsgvhtfpavlqssglyslssvvtvpssslgtktytcnvdhkpsn tkvdkrveskygppcppcpapeflggpsvflfppkpkdtlmisrtpevtcvvvdvsqe dpevqfnwyvdgvevhnaktkpreeqfnstyrvvsvltvlhqdwlngkeykckvsnkg TABLE 18-continued Annotated amino acid sequences of exemplary chimeric and humanized anti-CD47 antibody heavy chains lpssiektiskakgqprepqvytlppsqeemtknqvsltclvkgfypsdiavewesng
qpennykttppvldsdgsfflysrltvdksrwqegnvfscsvmhealhnhytqkslsl
slgk**

U0959FD090-chimeric-VH-PTM2 (SEQ ID NO: 189)

MGWSCIILFLVATATGVHSEVQLQQSGPELVKPGASVKLSCKASGYTFT<u>SSVIH</u>WVKQ
KPGQGLEWLG<u>YINPYSDATKFNEKSKI</u>KATLTSDKSSTAYMELSSLTSEDSAVYYCA
R<u>GLIGTRYDSWFAY</u>WGQGTLVTVSAastkgpsvfplapcsrstsestaalgclvkdyf
pepvtvswnsgaltsgvhtfpavlqssglyslssvvtvpssslgtktytcnvdhkpsn
tkvdkrveskygppcppcpapeflggpsvflfppkpkdtlmisrtpevtcvvvdvsqe
dpevqfnwyvdgvevhnaktkpreeqfnstyrvvsvltvlhqdwlngkeykckvsnkg
lpssiektiskakgqprepqvytlppsqeemtknqvsltclvkgfypsdiavewesng
qpennykttppvldsdgsfflysrltvdksrwqegnvfscsvmhealhnhytqkslsl
slgk**

U0959FD090-VH1 (SEQ ID NO: 190)

MGWSCIILFLVATATGVHSQVQLVQSGAEVKKPGASVKVSCKASGYTFT<u>SSVIH</u>WVRQ
APGQGLEWMG<u>YINPYSDGTKFNEKCKI</u>RVTMTRDTSISTAYMELSRLRSDDTAVYYCA
R<u>GLIGTRYDSWFAY</u>WGQGTLVTVSSastkgpsvfplapcsrstsestaalgclvkdyf
pepvtvswnsgaltsgvhtfpavlqssglyslssvvtvpssslgtktytcnvdhkpsn
tkvdkrveskygppcppcpapeflggpsvflfppkpkdtlmisrtpevtcvvvdvsqe
dpevqfnwyvdgvevhnaktkpreeqfnstyrvvsvltvlhqdwlngkeykckvsnkg
lpssiektiskakgqprepqvytlppsqeemtknqvsltclvkgfypsdiavewesng
qpennykttppvldsdgsfflysrltvdksrwqegnvfscsvmhealhnhytqkslsl
slgk**

U0959FD090-VH1-PTM (SEQ ID NO: 191)

MGWSCIILFLVATATGVHSQVQLVQSGAEVKKPGASVKVSCKASGYTFT<u>SSVIH</u>WVRQ
APGQGLEWMG<u>YINPYSEGTKFNEKSKI</u>RVTMTRDTSISTAYMELSRLRSDDTAVYYCA
R<u>GLIGTRYDSWFAY</u>WGQGTLVTVSSastkgpsvfplapcsrstsestaalgclvkdyf
pepvtvswnsgaltsgvhtfpavlqssglyslssvvtvpssslgtktytcnvdhkpsn
tkvdkrveskygppcppcpapeflggpsvflfppkpkdtlmisrtpevtcvvvdvsqe
dpevqfnwyvdgvevhnaktkpreeqfnstyrvvsvltvlhqdwlngkeykckvsnkg
lpssiektiskakgqprepqvytlppsqeemtknqvsltclvkgfypsdiavewesng
qpennykttppvldsdgsfflysrltvdksrwqegnvfscsvmhealhnhytqkslsl
slgk**

U0959FD090-VH2 (SEQ ID NO: 192)

MGWSCIILFLVATATGVHSQVQLVQSGAEVKKPGASVKVSCKASGYTFT<u>SSVIH</u>WVRQ
APGQGLEWLG<u>YINPYSDGTKFNEKCKI</u>RATMTSDTSISTAYMELSRLRSDDTAVYYCA
R<u>GLIGTRYDSWFAY</u>WGQGTLVTVSSastkgpsvfplapcsrstsestaalgclvkdyf
pepvtvswnsgaltsgvhtfpavlqssglyslssvvtvpssslgtktytcnvdhkpsn TABLE 18-continued Annotated amino acid sequences of exemplary chimeric and humanized anti-CD47 antibody heavy chains tkvdkrveskygppcppcpapeflggpsvflfppkpkdtlmisrtpevtcvvvdsqe dpevqfnwyvdgvevhnaktkpreeqfnstyrvvsvltvlhqdwlngkeykckvsnkg lpssiektiskakgqprepqvytlppsqeemtknqvsltclvkgfypsdiavewesng qpennykttppvldsdgsfflysrltvdksrwqegnvfscsvmhealhnhytqkslsl slgk**

U0959FD090-VH3 (SEQ ID NO: 193)

MGWSCIILFLVATATGVHSQVQLVQSGAEVKKPGASVKVSCKASGYTFT<u>SSVIH</u>WVKQ

APGQGLEWLG<u>YINPYSDGTKFNEKCKI</u>RVTLTSDTSISTAYMELSRLRSDDTAVYYCA

R<u>GLIGTRYDSWFAY</u>WGQGTLVTVSSastkgpsvfplapcsrstsestaalgclvkdyf pepvtvswnsgaltsgvhtfpavlqssglyslssvvtvpssslgtktytcnvdhkpsn tkvdkrveskygppcppcpapeflggpsvflfppkpkdtlmisrtpevtcvvvdsqe dpevqfnwyvdgvevhnaktkpreeqfnstyrvvsvltvlhqdwlngkeykckvsnkg lpssiektiskakgqprepqvytlppsqeemtknqvsltclvkgfypsdiavewesng qpennykttppvldsdgsfflysrltvdksrwqegnvfscsvmhealhnhytqkslsl slgk**

U0959FD090-VH4 (SEQ ID NO: 194)

MGWSCIILFLVATATGVHSQVQLVQSGAEVKKPGASVKVSCKASGYTFT<u>SSVIH</u>WVKQ

APGQGLEWLG<u>YINPYSDGTKFNEKCKI</u>RATMTSDKSISTAYMELSRLRSDDTAVYYCA

R<u>GLIGTRYDSWFAY</u>WGQGTLVTVSSastkgpsvfplapcsrstsestaalgclvkdyf pepvtvswnsgaltsgvhtfpavlqssglyslssvvtvpssslgtktytcnvdhkpsn tkvdkrveskygppcppcpapeflggpsvflfppkpkdtlmisrtpevtcvvvdsqe dpevqfnwyvdgvevhnaktkpreeqfnstyrvvsvltvlhqdwlngkeykckvsnkg lpssiektiskakgqprepqvytlppsqeemtknqvsltclvkgfypsdiavewesng qpennykttppvldsdgsfflysrltvdksrwqegnvfscsvmhealhnhytqkslsl slgk**

Leader sequence is in bold font and underlined.
Variable domain sequence is capitalized.
In the variable domains, CDR1, CDR2 and CDR3 (from left to right) sequences are underlined.
hIgG4CH (S228P) is in lower case font.
** = stop codon.

TABLE 19

Annotated nucleotide sequences of exemplary chimeric and humanized anti-CD47 antibody heavy chains U0959FD090-chimeric-VH-PTM1 (SEQ ID NO: 195)

ATGGGCTGGTCTTGTATTATTCTGTTTCTGGTCGCAACTGCTACAGGCGTGCATTCTG

AAGTGCAGCTGCAGCAGAGCGGCCCAGAGCTCGTCAAACCTGGAGCCAGCGTGAAGCT

GAGCTGTAAAGCTTCTGGATACACCTTTACCAGCTCTGTGATCCACTGGGTGAAGCAG

AAGCCTGGCCAGGGCCTGGAATGGCTGGGCTACATCAACCCCTACAGCGAGGGCACAA

AGTTCAACGAGAAGTCCAAGATCAAGGCCACCCTGACCTCCGATAAGAGCAGCAGCAC

CGCCTATATGGAACTGAGCAGCCTGACATCTGAGGACAGCGCCGTGTACTACTGCGCC

TABLE 19-continued

Annotated nucleotide sequences of exemplary chimeric and humanized anti-CD47 antibody heavy chains

CGGGGCCTGATCGGCACAAGATACGACTCTTGGTTCGCCTACTGGGGACAAGGCACCC

TGGTGACCGTGTCCGCTgccagcaccaagggcccttccgtgtttcccctggcccttg ctcccggtccacatctgagagcaccgccgccctgggctgtctggtgaaggactacttc ccagagcccgtgaccgtgagctggaacagcggcgccctgacaagcggcgtgcacacat tcccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc ctgccctcctctatcgagaagacaatctctaaggctaagggccagccaagagagcctc aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacaccccctgtgctggactctgatggcagcttct ttctgtattccaggctgaccgtggataagtctcggtggcaggagggcaacgtgttcag ctgctctgtgatgcacgaagccctgcataatcactatactcagaaaagtctgtcactg tcactgggaaag*TGATAA*

U0959FD090-chimeric-VH-PTM2

(SEQ ID NO: 196)

ATGGGCTGGTCTTGTATTATTCTGTTTCTGGTCGCAACTGCTACAGGCGTGCATTCTG

AGGTGCAGCTGCAGCAGAGCGGACCTGAGCTGGTGAAGCCAGGCGCCAGCGTGAAACT

GAGCTGTAAAGCTTCTGGCTACACCTTCACCAGCTCTGTGATCCACTGGGTCAAGCAG

AAGCCTGGACAAGGCCTGGAATGGCTGGGCTACATCAACCCCTACAGCGACGCCACCA

AGTTCAACGAGAAGAGCAAGATCAAGGCCACACTGACCTCTGATAAGTCCAGCTCCAC

CGCCTACATGGAACTGTCTAGCCTGACAAGCGAGGACAGCGCCGTGTACTACTGCGCC

AGAGGCCTCATCGGCACCCGGTACGACAGCTGGTTTGCCTATTGGGGCCAGGGCACAC

TGGTTACAGTGTCCGCTgccagcaccaagggcccttccgtgtttcccctggcccttg ctcccggtccacatctgagagcaccgccgccctgggctgtctggtgaaggactacttc ccagagcccgtgaccgtgagctggaacagcggcgccctgacaagcggcgtgcacacat tcccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc ctgccctcctctatcgagaagacaatctctaaggctaagggccagccaagagagcctc TABLE 19-continued Annotated nucleotide sequences of exemplary chimeric and humanized anti-CD47 antibody heavy chains aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacaccccctgtgctggactctgatggcagcttct ttctgtattccaggctgaccgtggataagtctcggtggcaggagggcaacgtgttcag ctgctctgtgatgcacgaagccctgcataatcactatactcagaaaagtctgtcactg tcactgggaaag*TGATAA*

U0959FD090-VH1

(SEQ ID NO: 197)

ATGGGCTGGTCTTGTATTATTCTGTTTCTGGTCGCAACTGCTACAGGCGTGCATTCTC

AAGTGCAGCTGGTTCAGAGCGGCGCCGAGGTGAAGAAACCTGGAGCTTCCGTGAAAGT

GTCCTGCAAGGCCTCTGGCTACACCTTCACCAGCAGCGTGATCCACTGGGTGCGGCAG

GCCCCTGGCCAGGGCCTGGAATGGATGGGCTACATCAACCCCTACAGCGATGGCACAA

AGTTCAACGAGAAGTGCAAGATCCGGGTGACCATGACCAGAGATACATCTATCAGCAC

CGCTTATATGGAACTGAGCAGACTGAGAAGCGACGACACCGCCGTGTACTACTGTGCC

AGAGGCCTGATCGGCACACGCTACGACAGCTGGTTTGCCTACTGGGGCCAGGGAACAC

TGGTCACCGTGTCTAGCgccagcaccaagggcccttccgtgtttcccctggccccttg ctcccggtccacatctgagagcaccgccgccctgggctgtctggtgaaggactacttc ccagagcccgtgaccgtgagctggaacagcggcgccctgacaagcggcgtgcacacat tccccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggcccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc ctgccctcctctatcgagaagacaatctctaaggctaagggccagccaagagagcctc aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacaccccctgtgctggactctgatggcagcttct ttctgtattccaggctgaccgtggataagtctcggtggcaggagggcaacgtgttcag ctgctctgtgatgcacgaagccctgcataatcactatactcagaaaagtctgtcactg tcactgggaaag*TGATAA*

U0959FD090-VH1-PTM (SEQ ID NO: 198)

ATGGGCTGGTCTTGTATTATTCTGTTTCTGGTCGCAACTGCTACAGGCGTGCATTCTC

AAGTGCAGCTGGTCCAGAGCGGCGCCGAGGTGAAAAAGCCTGGCGCTTCTGTGAAGGT

GTCCTGCAAGGCCTCTGGCTACACCTTCACCAGCAGCGTGATCCACTGGGTGCGGCAG

GCCCCTGGACAGGGCCTGGAATGGATGGGCTACATCAACCCCTACAGCGAGGGCACAA

AGTTCAACGAGAAAAGCAAGATCAGAGTGACCATGACCAGAGATACCTCCATCAGCAC

TABLE 19-continued

Annotated nucleotide sequences of exemplary chimeric and humanized anti-CD47 antibody heavy chains

AGCTTACATGGAACTGAGCCGCCTGCGGAGCGACGACACCGCCGTGTACTACTGTGCC

AGAGGCCTGATCGGCACAAGATACGACAGCTGGTTTGCCTATTGGGGCCAGGGAACCC

TGGTTACAGTGTCTAGCgccagcaccaagggcccttccgtgtttcccctggcccttg ctcccggtccacatctgagagcaccgccgccctgggctgtctggtgaaggactacttc ccagagcccgtgaccgtgagctggaacagcggcgccctgacaagcggcgtgcacacat tcccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc ctgccctcctctatcgagaagacaatctctaaggctaagggccagccaagagagcctc aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacacccctgtgctggactctgatggcagcttct ttctgtattccaggctgaccgtggataagtctcggtggcaggagggcaacgtgttcag ctgctctgtgatgcacgaagcctgcataatcactatactcagaaaagtctgtcactg tcactgggaaag*TGATAA*

U0959FD090-VH2

(SEQ ID NO: 199)

ATGGGCTGGTCTTGTATTATTCTGTTTCTGGTCGCAACTGCTAGAGGCGTGCATTCTC

AAGTGCAGCTGGTCCAGAGCGGCGCCGAGGTGAAGAAGCCTGGCGCTTCTGTGAAAGT

GTCTTGTAAAGCCTCTGGATACACCTTCACCAGCAGCGTGATCCACTGGGTGCGGCAG

GCCCCTGGACAGGGCCTGGAATGGCTGGGCTACATCAACCCCTACAGCGATGGCACAA

AGTTCAACGAGAAGTGCAAGATCCGGGCCACAATGACCTCCGATACAAGCATCAGCAC

CGCTTATATGGAACTGAGCAGACTGAGAAGCGACGACACCGCCGTGTACTACTGCGCC

AGAGGCCTGATCGGCACAAGATACGACAGCTGGTTTGCCTACTGGGGCCAGGGCACCC

TGGTGACCGTGTCCAGCgccagcaccaagggcccttccgtgtttcccctggcccttg ctcccggtccacatctgagagcaccgccgccctgggctgtctggtgaaggactacttc ccagagcccgtgaccgtgagctggaacagcggcgccctgacaagcggcgtgcacacat tcccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc TABLE 19-continued Annotated nucleotide sequences of exemplary chimeric and humanized anti-CD47 antibody heavy chains ctgccctcctctatcgagaagacaatctctaaggctaagggccagccaagagagcctc aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacaccccctgtgctggactctgatggcagcttct ttctgtattccaggctgaccgtggataagtctcggtggcaggagggcaacgtgttcag ctgctctgtgatgcacgaagccctgcataatcactatactcagaaaagtctgtcactg tcactgggaaag*TGATAA*

U0959FD090-VH3

(SEQ ID NO: 200)

ATGGGCTGGTCTTGTATTATTCTGTTTCTGGTCGCAACTGCTAGAGGCGTGCATTCTC

AAGTGCAGCTCGTGCAGAGCGGCGCCGAGGTGAAAAAGCCTGGCGCTTCTGTGAAGGT

GTCTTGTAAAGCCTCTGGCTACACCTTCACCAGCAGCGTGATCCACTGGGTTAAGCAG

GCCCCTGGACAGGGCCTGGAATGGCTGGGCTACATCAACCCCTACAGCGATGGCACAA

AGTTCAACGAGAAGTGCAAGATCCGGGTGACCCTGACCTCCGATACAAGCATCAGCAC

CGCTTATATGGAACTGAGCAGACTGCGGAGCGACGACACCGCCGTGTACTACTGCGCC

AGAGGCCTGATCGGAACAAGATACGACAGCTGGTTTGCCTACTGGGGCCAGGGCACAC

TGGTCACCGTGTCCAGCgccagcaccaagggcccttccgtgtttcccctggccccttg ctcccggtccacatctgagagcaccgccgccctgggctgtctggtgaaggactacttc ccagagcccgtgaccgtgagctggaacagcggcgccctgacaagcggcgtgcacacat tcccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggcccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc ctgccctcctctatcgagaagacaatctctaaggctaagggccagccaagagagcctc aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacaccccctgtgctggactctgatggcagcttct ttctgtattccaggctgaccgtggataagtctcggtggcaggagggcaacgtgttcag ctgctctgtgatgcacgaagccctgcataatcactatactcagaaaagtctgtcactg tcactgggaaag*TGATAA*

U0959FD090-VH4

(SEQ ID NO: 201)

ATGGGCTGGTCTTGTATTATTCTGTTTCTGGTCGCAACTGCTACAGGCGTGCATTCTC

AAGTGCAGCTGGTTCAGAGCGGCGCCGAGGTGAAAAAGCCTGGCGCTTCTGTGAAGGT

GTCTTGTAAAGCCTCTGGCTACACCTTCACCAGCAGCGTGATCCACTGGGTCAAGCAG

GCCCCTGGACAGGGACTGGAATGGCTGGGCTACATCAACCCCTACAGCGATGGCACAA

TABLE 19-continued

Annotated nucleotide sequences of exemplary chimeric and humanized anti-CD47 antibody heavy chains

AGTTCAACGAGAAGTGCAAGATCCGGGCCACAATGACCTCCGATAAGAGCATCAGCAC

CGCTTATATGGAACTGAGCAGACTGCGGAGCGACGACACCGCCGTGTACTACTGCGCC

AGAGGCCTGATCGGCACAAGATACGACAGCTGGTTTGCCTACTGGGGCCAGGGCACCC

TGGTGACCGTGTCCAGCgccagcaccaagggcccttccgtgtttcccctggccccttg ctcccggtccacatctgagagcaccgccgccctgggctgtctggtgaaggactacttc ccagagcccgtgaccgtgagctggaacagcggcgccctgacaagcggcgtgcacacat tcccgccgtgctgcagagctccggcctgtactccctgtctagcgtggtgacagtgcc ttcctctagcctgggcaccaagacatatacctgtaacgtggaccacaagccaagcaat accaaggtggataagcgggtggagtctaagtacggccctccttgccctccatgtcctg ctccagagtttctgggcggccttccgtgttcctgtttccacccaaaccaaaggacac actgatgatctctagaacaccagaggtgacctgcgtggtggtggacgtgagccaggag gatcccgaggtgcagttcaactggtacgtggatggcgtggaggtgcacaatgccaaga ccaagccaagagaggagcagtttaactctacatacagggtggtgagcgtgctgaccgt gctgcaccaggattggctcaacggcaaggagtataagtgcaaggtgtccaataagggc ctgcccctcctctatcgagaagacaatctctaaggctaagggccagccaagagagcctc aggtgtacaccctgcctccaagccaggaggagatgacaaagaaccaggtgtccctgac atgtctggtgaagggcttctatccctccgacatcgccgtggagtgggagtctaatggc cagcctgagaacaattacaagaccacacccctgtgctggactctgatggcagcttct ttctgtattccaggctgaccgtggataagtctcggtggcaggagggcaacgtgttcag ctgctctgtgatgcacgaagccctgcataatcactatactcagaaaagtctgtcactg tcactgggaaag*TGATAA*

Leader sequence is in bold font and underlined.
Variable domain sequence is capitalized.
hIgG4CH (S228P) is in lower case font.
Stop codon is in italic font.

TABLE 20

Annotated amino acid sequences of exemplary humanized anti-CD47 antibody light chains U0959FD090-VL1
(SEQ ID NO: 202)
MGWSCIILFLVATATGVHSDIQMTQSPSSLSASVGDRVTITCRTSQDINNYLNWYQQK

PGKAPKLLIYYTSRLHSGVPSRFSGSGSGTDFTFTISSLQPEDIATYYCQQGNTLPYT

FGGGTKVEIKrtvaapsvfifppsdeqlksgtasvvclinnfypreakvqwkvdnalq sgnsclesvtecldskdstyslsstltlskadyekhkvyacevthqglsspvtksfnrge c\*\*

U0959FD090-VL2
(SEQ ID NO: 203)
MGWSCIILFLVATATGVHSDIQMTQSPSSLSASVGDRVTITCRTSQDINNYLNWYQQK

PGKAVKLLIYYTSRLHSGVPSRFSGSGSGTDFTFTISSLQPEDIATYFCQQGNTLPYT

TABLE 20-continued

Annotated amino acid sequences of exemplary humanized anti-CD47 antibody light chains FGGGTKVEIKrtvaapsvfifppsdeqlksgtasvvclinnfypreakvqwkvdnalq sgnsclesvtecldskdstyslsstltlskadyekhkvyacevthqglsspvtksfnrge c**

U0959FD090-VL3 (SEQ ID NO: 204)
MGWSCIILFLVATATGVHSDIQMTQSPSSLSASVGDRVTITC<u>RTSQDINNYLNWYQQK</u>

PGKAVKLLIY<u>YTSRLHS</u>GVPSRFSGSGSGTDYTFTISSLQPEDIATYFC<u>QQGNTLPYT</u>

FGGGTKVEIKrtvaapsvfifppsdeqlksgtasvvclinnfypreakvqwkvdnalq sgnsclesvtecldskdstyslsstltlskadyekhkvyacevthqglsspvtksfnrge c**

U0959FD090-VL4 (SEQ ID NO: 205)
MGWSCIILFLVATATGVHSDIQMTQSPSSLSASVGDRVTISC<u>RTSQDINNYLNWYQQK</u>

PGKTVKLLIY<u>YTSRLHS</u>GVPSRFSGSGSGTDYTFTISSLQPEDIATYFC<u>QQGNTLPYT</u>

FGGGTKVEIKrtvaapsvfifppsdeqlksgtasvvclinnfypreakvqwkvdnalq sgnsclesvtecldskdstyslsstltlskadyekhkvyacevthqglsspvtksfnrge c**

Leader sequence is in bold font and underlined.
Variable domain sequence is capitalized.
In the variable domains, CDR1, CDR2 and CDR3 (from left to right) sequences are underlined.
hIgkappaCL is in lower case font.
** = stop codon.

TABLE 21

Annotated nucleotide sequences of exemplary humanized anti-CD47 antibody light chains U0959FD090-VL1 (SEQ ID NO: 206)
ATGGGCTGGTCATGTATTATTCTGTTTCTGGTCGCAACTGCTACAGGGGTCCATAGTG

ATATTCAGATGACACAGAGCCCCTCTTCTCTGAGCGCTAGCGTGGGCGATAGAGTGAC

CATCACATGTAGAACCTCCCAGGACATCAACAACTACCTGAACTGGTACCAGCAGAAA

CCAGGCAAGGCCCCTAAGCTGCTGATCTACTACACCAGCCGGCTGCACAGCGGCGTCC

CCAGCAGATTCAGCGGCTCCGGATCTGGCACCGACTTCACCTTTACCATCAGCAGCCT

GCAGCCTGAGGACATCGCCACCTACTACTGCCAGCAAGGCAATACCCTGCCTTATACA

TTCGGCGGCGGAACAAAGGTGGAAATCAAGaggacagtggccgccccaagcgtgttca tctttccccttccgacgagcagctgaagtctggcaccgccagcgtggtgtgcctgct gaacaacttctaccctcgggaggccaaggtccagtggaaggtggataacgccctgcag tctggcaatagccaggagtccgtgaccgagcaggactctaaggatagcacatattccc tgtctagcaccctgacactgagcaaggccgattacgagaagcacaaggtgtatgcctg tgaagtcacccatcagggcgtcatcacccgtcactaagtcattcaatcgcggagaa tgc*TGATAA*

U0959FD090-VL2 (SEQ ID NO: 207)
ATGGGCTGGTCATGTATTATTCTGTTTCTGGTCGCAACTGCTACAGGGGTCCATAGTG

ATATTCAGATGACCCAGAGCCCCTCCTCCCTGAGCGCTTCTGTGGGCGATAGAGTGAC

TABLE 21-continued

Annotated nucleotide sequences of exemplary humanized anti-CD47 antibody light chains

CATCACCTGTAGAACAAGCCAGGACATCAACAACTACCTGAACTGGTACCAGCAGAAA

CCIGGCAAGGCCGTCAAGCTGCTGATCTACTACACCAGCCGGCTGCACAGCGGAGTGC

CATCTAGATTCAGCGGCTCTGGCAGCGGCACCGACTTCACCTTTACCATCAGCAGCCT

GCAGCCTGAGGACATCGCCACATACTTCTGCCAGCAAGGCAATACCCTGCCTTATACA

TTCGGCGGCGGAACAAAGGTGGAAATCAAGaggacagtggccgccccaagcgtgttca tctttccccttccgacgagcagctgaagtctggcaccgccagcgtggtgtgcctgct gaacaacttctaccctcgggaggccaaggtccagtggaaggtggataacgccctgcag tctggcaatagccaggagtccgtgaccgagcaggactctaaggatagcacatattccc tgtctagcaccctgacactgagcaaggccgattacgagaagcacaaggtgtatgcctg tgaagtcacccatcaggggctgtcatcacccgtcactaagtcattcaatcgcggagaa tgc*TGATAA*

U0959FD090-VL3

(SEQ ID NO: 208)

ATGGGCTGGTCATGTATTATTCTGTTTCTGGTCGCAACTGCTACAGGGGTCCATAGTG

ATATTCAGATGACCCAGTCCCCATCTAGCCTGAGCGCCAGCGTGGGCGATAGAGTGAC

CATCACCTGTAGAACCAGCCAGGACATCAACAACTACCTGAACTGGTATCAGCAGAAA

CCIGGCAAGGCCGTGAAGCTGCTGATCTACTACACATCTAGACTGCACAGCGGCGTCC

CCAGCCGGTTCAGCGGATCTGGCAGCGGCACCGACTACACATTTACCATCAGCTCCCT

GCAGCCTGAGGACATCGCTACATACTTCTGCCAGCAAGGCAATACCCTGCCTTACACC

TTCGGCGGAGGCACAAAGGIGGAAATCAAGaggacagtggccgccccaagcgtgttca tctttccccttccgacgagcagctgaagtctggcaccgccagcgtggtgtgcctgct gaacaacttctaccctcgggaggccaaggtccagtggaaggtggataacgccctgcag tctggcaatagccaggagtccgtgaccgagcaggactctaaggatagcacatattccc tgtctagcaccctgacactgagcaaggccgattacgagaagcacaaggtgtatgcctg tgaagtcacccatcaggggctgtcatcacccgtcactaagtcattcaatcgcggagaa tgc*TGATAA*

U0959FD090-VL4

(SEQ ID NO: 209)

ATGGGCTGGTCATGTATTATTCTGTTTCTGGTCGCAACTGCTACAGGGGTCCATAGTG

ATATTCAGATGACCCAGTCCCCATCTTCCCTGAGCGCCAGCGTGGGCGATAGAGTGAC

CATCTCTTGTAGAACAAGCCAGGACATCAACAACTACCTGAACTGGTATCAGCAGAAA

CCTGGCAAGACCGTGAAGCTGCTGATCTACTACACCAGCCGGCTGCACAGCGGCGTCC

CCAGCAGATTCAGCGGATCTGGCAGCGGCACCGACTACACATTTACCATCAGCAGCCT

GCAGCCTGAGGACATCGCCACATACTTCTGCCAGCAAGGCAATACCCTGCCTTACACC

TTCGGCGGAGGCACAAAGGTGGAAATCAAGaggacagtggccgccccaagcgtgttca tctttccccttccgacgagcagctgaagtctggcaccgccagcgtggtgtgcctgct gaacaacttctaccctcgggaggccaaggtccagtggaaggtggataacgccctgcag tctggcaatagccaggagtccgtgaccgagcaggactctaaggatagcacatattccc TABLE 21-continued Annotated nucleotide sequences of exemplary humanized anti-CD47 antibody light chains tgtctagcaccctgacactgagcaaggccgattacgagaagcacaaggtgtatgcctg tgaagtcacccatcaggggctgtcatcacccgtcactaagtcattcaatcgcggagaa tgc*TGATAA*

Leader sequence is in bold font and underlined.
Variable domain sequence is capitalized.
hIgkappaCL is in lower case font.
Stop codon is in italic font.

TABLE 22

Nucleotide and amino acid sequences of antibody VH1 - PTM + VL1

| Antibody name | VH1 - PTM + VL1 | |
|---|---|---|
| Domain or Region | Sequence | SEQ ID NO |
| Heavy chain variable domain (nucleotide) [includes signal sequence] | ATGGGCTGGTCTTGTATTATTCTGTTTCTGGTCGCAACTGCT ACAGGCGTGCATTCTCAAGTGCAGCTGGTCCAGAGCGGCGCC GAGGTGAAAAAGCCTGGCGCTTCTGTGAAGGTGTCCTGCAAG GCCTCTGGCTACACCTTCACCAGCAGCGTGATCCACTGGGTG CGGCAGGCCCCTGGACAGGGCCTGGAATGGATGGGCTACATC AACCCCTACAGCGAGGGCACAAAGTTCAACGAGAAAAGCAAG ATCAGAGTGACCATGACCAGAGATACCTCCATCAGCACAGCT TACATGGAACTGAGCCGCCTGCGGAGCGACGACACCGCCGTG TACTACTGTGCCAGAGGCCTGATCGGCACAAGATACGACAGC TGGTTTGCCTATTGGGGCCAGGGAACCCTGGTTACAGTGTCT AGC | 210 |
| Heavy chain variable domain (nucleotide) [does not include signal sequence] | CAAGTGCAGCTGGTCCAGAGCGGCGCCGAGGTGAAAAAGCCT GGCGCTTCTGTGAAGGTGTCCTGCAAGGCCTCTGGCTACACC TTCACCAGCAGCGTGATCCACTGGGTGCGGCAGGCCCCTGGA CAGGGCCTGGAATGGATGGGCTACATCAACCCCTACAGCGAG GGCACAAAGTTCAACGAGAAAAGCAAGATCAGAGTGACCATG ACCAGAGATACCTCCATCAGCACAGCTTACATGGAACTGAGC CGCCTGCGGAGCGACGACACCGCCGTGTACTACTGTGCCAGA GGCCTGATCGGCACAAGATACGACAGCTGGTTTGCCTATTGG GGCCAGGGAACCCTGGTTACAGTGTCTAGC | 211 |
| Heavy chain variable domain (amino acid) [includes signal sequence] | MGWSCIILFLVATATGVHSQVQLVQSGAEVKKPGASVKVSCK ASGYTFTSSVIHWVRQAPGQGLEWMGYINPYSEGTKFNEKSK IRVTMRDTSISTAYMELSRLRSDDTAVYYCARGLIGTRYDS WFAYWGQGTLVTVSS | 212 |
| Heavy chain variable domain (amino acid) [does not include signal sequence] | QVQLVQSGAEVKKPGASVKVSCKASGYTFTSSVIHWVRQAPG QGLEWMGYINPYSEGTKFNEKSKIRVIMIRDTSISTAYMELS RLRSDDTAVYYCARGLIGTRYDSWFAYWGQGTLVTVSS | 213 |
| Heavy chain FR1 (amino acid) | QVQLVQSGAEVKKPGASVKVSCKASGYTFT | 214 |
| Heavy chain CDR1 (amino acid) | SSVIH | 162 |
| Heavy chain FR2 (amino acid) | WVRQAPGQGLEWMG | 215 |
| Heavy chain CDR2 (amino acid) | YINPYSEGTKFNEKSKI | 216 |
| Heavy chain FR3 (amino acid) | RVIMIRDTSISTAYMELSRLRSDDTAVYYCAR | 217 |
| Heavy chain CDR3 (amino acid) | GLIGTRYDSWFAY | 59 |
| Heavy chain FR4 (amino acid) | WGQGTLVTVSS | 218 |
| Light chain variable domain (nucleotide) | ATGGGCTGGTCATGTATTATTCTGTTTCTGGTCGCAACTGCT ACAGGGGTCCATAGTGATATTCAGATGACACAGAGCCCCTCT | 219 |

TABLE 22-continued

Nucleotide and amino acid sequences of antibody VH1 - PTM + VL1

| Antibody name | VH1 - PTM + VL1 | |
|---|---|---|
| Domain or Region | Sequence | SEQ ID NO |
| [includes signal sequence] | TCTCTGAGCGCTAGCGTGGGCGATAGAGTGACCATCACATGT AGAACCTCCCAGGACATCAACAACTACCTGAACTGGTACCAG CAGAAACCAGGCAAGGCCCCTAAGCTGCTGATCTACTACACC AGCCGGCTGCACAGCGGCGTCCCCAGCAGATTCAGCGGCTCC GGATCTGGCACCGACTTCACCTTTACCATCAGCAGCCTGCAG CCTGAGGACATCGCCACCTACTACTGCCAGCAAGGCAATACC CTGCCTTATACATTCGGCGGCGGAACAAAGGTGGAAATCAAG | |
| Light chain variable domain (nucleotide) [does not include signal sequence] | GATATTCAGATGACACAGAGCCCCTCTTCTCTGAGCGCTAGC GTGGGCGATAGAGTGACCATCACATGTAGAACCTCCCAGGAC ATCAACAACTACCTGAACTGGTACCAGCAGAAACCAGGCAAG GCCCCTAAGCTGCTGATCTACTACACCAGCCGGCTGCACAGC GGCGTCCCCAGCAGATTCAGCGGCTCCGGATCTGGCACCGAC TTCACCTTTACCATCAGCAGCCTGCAGCCTGAGGACATCGCC ACCTACTACTGCCAGCAAGGCAATACCCTGCCTTATACATTC GGCGGCGGAACAAAGGTGGAAATCAAG | 220 |
| Light chain variable domain (amino acid) [includes signal sequence] | MGWSCIILFLVATATGVHSDIQMTQSPSSLSASVGDRVTITC RTSQDINNYLNWYQQKPGKAPKLLIYYTSRLHSGVPSRFSGS GSGTDFTFTISSLQPEDIATYYCQQGNTLPYTFGGGTKVEIK | 221 |
| Light chain variable domain (amino acid) [does not include signal sequence] | DIQMTQSPSSLSASVGDRVTITCRTSQDINNYLNWYQQKPGK APKLLIYYTSRLHSGVPSRFSGSGSGTDFTFTISSLQPEDIA TYYCQQGNTLPYTFGGGTKVEIK | 222 |
| Light chain FR1 (amino acid) | DIQMTQSPSSLSASVGDRVTITC | 223 |
| Light chain CDR1 (amino acid) | RTSQDINNYLN | 75 |
| Light chain FR2 (amino acid) | WYQQKPGKAPKLLIY | 224 |
| Light chain CDR2 (amino acid) | YTSRLHS | 77 |
| Light chain FR3 (amino acid) | GVPSRFSGSGSGTDFTFTISSLQPEDIATYYC | 225 |
| Light chain CDR3 (amino acid) | QQGNTLPYT | 115 |
| Light chain FR4 (amino acid) | FGGGTKVEIK | 226 |

TABLE 23

Nucleotide and amino acid sequences of antibody VH1 - PTM + VL2

| Antibody name | VH1 - PTM + VL2 | |
|---|---|---|
| Domain or Region | Sequence | SEQ ID NO |
| Heavy chain variable domain (nucleotide) [includes signal sequence] | ATGGGCTGGTCTTGTATTATTCTGTTTCTGGTCGCAACTGCT ACAGGCGTGCATTCTCAAGTGCAGCTGGTCCAGAGCGGCGCC GAGGTGAAAAAGCCTGGCGCTTCTGTGAAGGTGTCCTGCAAG GCCTCTGGCTACACCTTCACCAGCAGCGTGATCCACTGGGTG CGGCAGGCCCCTGGACAGGGCCTGGAATGGATGGGCTACATC AACCCCTACAGCGAGGGCACAAAGTTCAACGAGAAAAGCAAG ATCAGAGTGACCATGACCAGAGATACCTCCATCAGCACAGCT TACATGGAACTGAGCCGCCTGCGGAGCGACGACACCGCCGTG TACTACTGTGCCAGAGGCCTGATCGGCACAAGATACGACAGC TGGTTTGCCTATTGGGGCCAGGGAACCCTGGTTACAGTGTCT AGC | 210 |
| Heavy chain variable domain (nucleotide) [does not include | CAAGTGCAGCTGGTCCAGAGCGGCGCCGAGGTGAAAAAGCCT GGCGCTTCTGTGAAGGTGTCCTGCAAGGCCTCTGGCTACACC TTCACCAGCAGCGTGATCCACTGGGTGCGGCAGGCCCCTGGA | 211 |

TABLE 23-continued

Nucleotide and amino acid sequences of antibody VH1 – PTM + VL2

| Antibody name | VH1 – PTM + VL2 | |
|---|---|---|
| Domain or Region | Sequence | SEQ ID NO |
| signal sequence] | CAGGGCCTGGAATGGATGGGCTACATCAACCCCTACAGCGAG GGCACAAAGTTCAACGAGAAAAGCAAGATCAGAGTGACCATG ACCAGAGATACCTCCATCAGCACAGCTTACATGGAACTGAGC CGCCTGCGGAGCGACGACACCGCCGTGTACTACTGTGCCAGA GGCCTGATCGGCACAAGATACGACAGCTGGTTTGCCTATTGG GGCCAGGGAACCCTGGTTACAGTGTCTAGC | |
| Heavy chain variable domain (amino acid) [includes signal sequence] | MGWSCIILFLVATATGVHSQVQLVQSGAEVKKPGASVKVSCK ASGYTFTSSVIHWVRQAPGQGLEWMGYINPYSEGTKFNEKSK IRVTMTRDTSISTAYMELSRLRSDDTAVYYCARGLIGTRYDS WFAYWGQGTLVTVSS | 212 |
| Heavy chain variable domain (amino acid) [does not include signal sequence] | QVQLVQSGAEVKKPGASVKVSCKASGYTFTSSVIHWVRQAPG QGLEWMGYINPYSEGTKFNEKSKIRVIMIRDTSISTAYMELS RLRSDDTAVYYCARGLIGTRYDSWFAYWGQGTLVTVSS | 213 |
| Heavy chain FR1 (amino acid) | QVQLVQSGAEVKKPGASVKVSCKASGYTFT | 214 |
| Heavy chain CDR1 (amino acid) | SSVIH | 162 |
| Heavy chain FR2 (amino acid) | WVRQAPGQGLEWMG | 215 |
| Heavy chain CDR2 (amino acid) | YINPYSEGTKFNEKSKI | 216 |
| Heavy chain FR3 (amino acid) | RVIMIRDTSISTAYMELSRLRSDDTAVYYCAR | 217 |
| Heavy chain CDR3 (amino acid) | GLIGTRYDSWFAY | 59 |
| Heavy chain FR4 (amino acid) | WGQGTLVTVSS | 218 |
| Light chain variable domain (nucleotide) [includes signal sequence] | ATGGGCTGGTCATGTATTATTCTGTTTCTGGTCGCAACTGCT ACAGGGGTCCATAGTGATATTCAGATGACCCAGAGCCCCTCC TCCCTGAGCGCTTCTGTGGGCGATAGAGTGACCATCACCTGT AGAACAAGCCAGGACATCAACAACTACCTGAACTGGTACCAG CAGAAACCTGGCAAGGCCGTCAAGCTGCTGATCTACTACACC AGCCGGCTGCACAGCGGAGTGCCATCTAGATTCAGCGGCTCT GGCAGCGGCACCGACTTCACCTTTACCATCAGCAGCCTGCAG CCTGAGGACATCGCCACATACTTCTGCCAGCAAGGCAATACC CTGCCTTATACATTCGGCGGCGGAACAAAGGTGGAAATCAAG | 227 |
| Light chain variable domain (nucleotide) [does not include signal sequence] | GATATTCAGATGACCCAGAGCCCCTCCTCCCTGAGCGCTTCT GTGGGCGATAGAGTGACCATCACCTGTAGAACAAGCCAGGAC ATCAACAACTACCTGAACTGGTACCAGCAGAAACCTGGCAAG GCCGTCAAGCTGCTGATCTACTACACCAGCCGGCTGCACAGC GGAGTGCCATCTAGATTCAGCGGCTCTGGCAGCGGCACCGAC TTCACCTTTACCATCAGCAGCCTGCAGCCTGAGGACATCGCC ACATACTTCTGCCAGCAAGGCAATACCCTGCCTTATACATTC GGCGGCGGAACAAAGGTGGAAATCAAG | 228 |
| Light chain variable domain (amino acid) [includes signal sequence] | MGWSCIILFLVATATGVHSDIQMTQSPSSLSASVGDRVTITC RTSQDINNYLNWYQQKPGKAVKLLIYYTSRLHSGVPSRFSGS GSGTDFTFTISSLQPEDIATYFCQQGNTLPYTFGGGTKVEIK | 229 |
| Light chain variable domain (amino acid) [does not include signal sequence] | DIQMTQSPSSLSASVGDRVTITCRTSQDINNYLNWYQQKPGK AVKLLIYYTSRLHSGVPSRFSGSGSGTDFTFTISSLQPEDIA TYFCQQGNTLPYTFGGGTKVEIK | 230 |
| Light chain FR1 (amino acid) | DIQMTQSPSSLSASVGDRVTITC | 223 |
| Light chain CDR1 (amino acid) | RTSQDINNYLN | 75 |

TABLE 23-continued

Nucleotide and amino acid sequences of antibody VH1 – PTM + VL2

| Antibody name | VH1 – PTM + VL2 | |
|---|---|---|
| Domain or Region | Sequence | SEQ ID NO |
| Light chain FR2 (amino acid) | WYQQKPGKAVKLLIY | 231 |
| Light chain CDR2 (amino acid) | YTSRLHS | 77 |
| Light chain FR3 (amino acid) | GVPSRFSGSGSGTDFTFTISSLQPEDIATYFC | 232 |
| Light chain CDR3 (amino acid) | QQGNTLPYT | 115 |
| Light chain FR4 (amino acid) | FGGGTKVEIK | 226 |

TABLE 24

Nucleotide and amino acid sequences of antibody VH1 – PTM + VL3

| Antibody name | VH1 – PTM + VL3 | |
|---|---|---|
| Domain or Region | Sequence | SEQ ID NO |
| Heavy chain variable domain (nucleotide) [includes signal sequence] | ATGGGCTGGTCTTGTATTATTCTGTTTCTGGTCGCAACTGCT ACAGGCGTGCATTCTCAAGTGCAGCTGGTCCAGAGCGGCGCC GAGGTGAAAAAGCCTGGCGCTTCTGTGAAGGTGTCCTGCAAG GCCTCTGGCTACACCTTCACCAGCAGCGTGATCCACTGGGTG CGGCAGGCCCCTGGACAGGGCCTGGAATGGATGGGCTACATC AACCCCTACAGCGAGGGCACAAAGTTCAACGAGAAAAGCAAG ATCAGAGTGACCATGACCAGAGATACCTCCATCAGCACAGCT TACATGGAACTGAGCCGCCTGCGGAGCGACGACACCGCCGTG TACTACTGTGCCAGAGGCCTGATCGGCACAAGATACGACAGC TGGTTTGCCTATTGGGGCCAGGGAACCCTGGTTACAGTGTCT AGC | 210 |
| Heavy chain variable domain (nucleotide) [does not include signal sequence] | CAAGTGCAGCTGGTCCAGAGCGGCGCCGAGGTGAAAAAGCCT GGCGCTTCTGTGAAGGTGTCCTGCAAGGCCTCTGGCTACACC TTCACCAGCAGCGTGATCCACTGGGTGCGGCAGGCCCCTGGA CAGGGCCTGGAATGGATGGGCTACATCAACCCCTACAGCGAG GGCACAAAGTTCAACGAGAAAAGCAAGATCAGAGTGACCATG ACCAGAGATACCTCCATCAGCACAGCTTACATGGAACTGAGC CGCCTGCGGAGCGACGACACCGCCGTGTACTACTGTGCCAGA GGCCTGATCGGCACAAGATACGACAGCTGGTTTGCCTATTGG GGCCAGGGAACCCTGGTTACAGTGTCTAGC | 211 |
| Heavy chain variable domain (amino acid) [includes signal sequence] | MGWSCIILFLVATATGVHSQVQLVQSGAEVKKPGASVKVSCK ASGYTFTSSVIHWVRQAPGQGLEWMGYINPYSEGTKFNEKSK IRVTMTRDTSISTAYMELSRLRSDDTAVYYCARGLIGTRYDS WFAYWGQGTLVTVSS | 212 |
| Heavy chain variable domain (amino acid) [does not include signal sequence] | QVQLVQSGAEVKKPGASVKVSCKASGYTFTSSVIHWVRQAPG QGLEWMGYINPYSEGTKFNEKSKIRVIMIRDTSISTAYMELS RLRSDDTAVYYCARGLIGTRYDSWFAYWGQGTLVTVSS | 213 |
| Heavy chain FR1 (amino acid) | QVQLVQSGAEVKKPGASVKVSCKASGYTFT | 214 |
| Heavy chain CDR1 (amino acid) | SSVIH | 162 |
| Heavy chain FR2 (amino acid) | WVRQAPGQGLEWMG | 215 |
| Heavy chain CDR2 (amino acid) | YINPYSEGTKFNEKSKI | 216 |
| Heavy chain FR3 (amino acid) | RVIMIRDTSISTAYMELSRLRSDDTAVYYCAR | 217 |

TABLE 24-continued

Nucleotide and amino acid sequences of antibody VH1 – PTM + VL3

| Antibody name | VH1 – PTM + VL3 | |
|---|---|---|
| Domain or Region | Sequence | SEQ ID NO |
| Heavy chain CDR3 (amino acid) | GLIGTRYDSWFAY | 59 |
| Heavy chain FR4 (amino acid) | WGQGTLVTVSS | 218 |
| Light chain variable domain (nucleotide) [includes signal sequence] | ATGGGCTGGTCATGTATTATTCTGTTTCTGGTCGCAACTGCT ACAGGGGTCCATAGTGATATTCAGATGACCCAGTCCCCATCT AGCCTGAGCGCCAGCGTGGGCGATAGAGTGACCATCACCTGT AGAACCAGCCAGGACATCAACAACTACCTGAACTGGTATCAG CAGAAACCTGGCAAGGCCGTGAAGCTGCTGATCTACTACACA TCTAGACTGCACAGCGGCGTCCCCAGCCGGTTCAGCGGATCT GGCAGCGGCACCGACTACACATTTACCATCAGCTCCCTGCAG CCTGAGGACATCGCTACATACTTCTGCCAGCAAGGCAATACC CTGCCTTACACCTTCGGCGGAGGCACAAAGGTGGAAATCAAG GATATTCAGATGACCCAGTCCCCATCTAGCCTGAGCGCCAGC | 233 |
| Light chain variable domain (nucleotide) [does not include signal sequence] | GTGGGCGATAGAGTGACCATCACCTGTAGAACCAGCCAGGAC ATCAACAACTACCTGAACTGGTATCAGCAGAAACCTGGCAAG GCCGTGAAGCTGCTGATCTACTACACATCTAGACTGCACAGC GGCGTCCCCAGCCGGTTCAGCGGATCTGGCAGCGGCACCGAC TACACATTTACCATCAGCTCCCTGCAGCCTGAGGACATCGCT ACATACTTCTGCCAGCAAGGCAATACCCTGCCTTACACCTTC GGCGGAGGCACAAAGGTGGAAATCAAG | 234 |
| Light chain variable domain (amino acid) [includes signal sequence] | MGWSCIILFLVATATGVHSDIQMTQSPSSLSASVGDRVTITC RTSQDINNYLNWYQQKPGKAVKLLIYYTSRLHSGVPSRFSGS GSGTDYTFTISSLQPEDIATYFCQQGNTLPYTFGGGTKVEIK | 235 |
| Light chain variable domain (amino acid) [does not include signal sequence] | DIQMTQSPSSLSASVGDRVTITCRTSQDINNYLNWYQQKPGK AVKLLIYYTSRLHSGVPSRFSGSGSGTDYTFTISSLQPEDIA TYFCQQGNTLPYTFGGGTKVEIK | 236 |
| Light chain FR1 (amino acid) | DIQMTQSPSSLSASVGDRVTITC | 223 |
| Light chain CDR1 (amino acid) | RTSQDINNYLN | 75 |
| Light chain FR2 (amino acid) | WYQQKPGKAVKLLIY | 231 |
| Light chain CDR2 (amino acid) | YTSRLHS | 77 |
| Light chain FR3 (amino acid) | GVPSRFSGSGSGTDYTFTISSLQPEDIATYFC | 237 |
| Light chain CDR3 (amino acid) | QQGNTLPYT | 115 |
| Light chain FR4 (amino acid) | FGGGTKVEIK | 226 |

TABLE 25

Amino acid sequences of exemplary chimeric and humanized anti-CD47 antibody heavy chain variable domains U0959FD090-chimeric-VH-PTM1 (SEQ ID NO: 238)
EVQLQQSGPELVKPGASVKLSCKASGYTFT<u>SSVIH</u>WVKQKPGQGLEWLG<u>YINPYSEGT
KFNEKSKI</u>KATLTSDKSSSTAYMELSSLTSEDSAVYYC<u>ARGLIGTRYDSWFAY</u>WGQGT
LVTVSA U0959FD090-chimeric-VH-PTM2 (SEQ ID NO: 239)
EVQLQQSGPELVKPGASVKLSCKASGYTFT<u>SSVIH</u>WVKQKPGQGLEWLG<u>YINPYSDAT
KFNEKSKI</u>KATLTSDKSSSTAYMELSSLTSEDSAVYYC<u>ARGLIGTRYDSWFAY</u>WGQGT
LVTVSA U0959FD090-VH1 (SEQ ID NO: 240)
QVQLVQSGAEVKKPGASVKVSCKASGYTFT<u>SSVIH</u>WVRQAPGQGLEWMG<u>YINPYSDGT
KFNEKCKI</u>RVTMTRDTSISTAYMELSRLRSDDTAVYYC<u>ARGLIGTRYDSWFAY</u>WGQGT
LVTVSS U0959FD090-VH1-PTM (SEQ ID NO: 213)
QVQLVQSGAEVKKPGASVKVSCKASGYTFT<u>SSVIH</u>WVRQAPGQGLEWMG<u>YINPYSEGT
KFNEKSKI</u>RVTMTRDTSISTAYMELSRLRSDDTAVYYC<u>ARGLIGTRYDSWFAY</u>WGQGT
LVTVSS U0959FD090-VH2 (SEQ ID NO: 241)
QVQLVQSGAEVKKPGASVKVSCKASGYTFT<u>SSVIH</u>WVRQAPGQGLEWLG<u>YINPYSDGT
KFNEKCKI</u>RATMTSDTSISTAYMELSRLRSDDTAVYYC<u>ARGLIGTRYDSWFAY</u>WGQGT
LVTVSS U0959FD090-VH3 (SEQ ID NO: 242)
QVQLVQSGAEVKKPGASVKVSCKASGYTFT<u>SSVIH</u>WVKQAPGQGLEWLG<u>YINPYSDGT
KFNEKCKI</u>RVTLTSDTSISTAYMELSRLRSDDTAVYYC<u>ARGLIGTRYDSWFAY</u>WGQGT
LVTVSS U0959FD090-VH4 (SEQ ID NO: 243)
QVQLVQSGAEVKKPGASVKVSCKASGYTFT<u>SSVIH</u>WVKQAPGQGLEWLG<u>YINPYSDGT
KFNEKCKI</u>RATMTSDKSISTAYMELSRLRSDDTAVYYC<u>ARGLIGTRYDSWFAY</u>WGQGT
LVTVSS In the variable domains, CDR1, CDR2 and CDR3 (from left to right) sequences are underlined.

TABLE 26

Amino acid sequences of exemplary humanized anti-CD47 antibody light chain variable domains U0959FD090-VL1 (SEQ ID NO: 222)
DIQMTQSPSSLSASVGDRVTITC<u>RTSQDINNYLN</u>WYQQKPGKAPKLLIY<u>YTSRLHS</u>GV
PSRFSGSGSGTDFTFTISSLQPEDIATYYC<u>QQGNTLPYT</u>FGGGTKVEIK U0959FD090-VL2 (SEQ ID NO: 230)
DIQMTQSPSSLSASVGDRVTITC<u>RTSQDINNYLN</u>WYQQKPGKAVKLLIY<u>YTSRLHS</u>GV
PSRFSGSGSGTDFTFTISSLQPEDIATYFC<u>QQGNTLPYT</u>FGGGTKVEIK

U0959FD090-VL3 (SEQ ID NO: 236)

TABLE 26-continued

Amino acid sequences of exemplary humanized anti-CD47 antibody light chain variable domains DIQMTQSPSSLSASVGDRVTITC<u>RTSQDINNYLN</u>WYQQKPGKAVKLLIY<u>YTSRLHS</u>GV
PSRFSGSGSGTDYTFTISSLQPEDIATYFC<u>QQGNTLPYT</u>FGGGTKVEIK
U0959FD090-VL4
(SEQ ID NO: 244)

DIQMTQSPSSLSASVGDRVTISC<u>RTSQDINNYLN</u>WYQQKPGKTVKLLIY<u>YTSRLHS</u>GV
PSRFSGSGSGTDYTFTISSLQPEDIATYFC<u>QQGNTLPYT</u>FGGGTKVEIK

In the variable domains, CDR1, CDR2 and CDR3 (from left to right) sequences are underlined.

TABLE 27

ELISA EC50 plot of parent mAb (32G8H6), Chimeric-VH + VL1 and Chimeric-VH + VL2

| Log Abs Conc. | Abs Conc (μg/ml) | 32G8H6 (mAb) | chimeric-VH + VL1 | chimeric-VH + VL2 | Isotype control |
|---|---|---|---|---|---|
| 1.65 | 45 | 3.826 | 3.479 | 1.95 | 0.543 |
| 1.18 | 15 | 3.865 | 3.387 | 1.393 | 0.49 |
| 0.70 | 5.00E+00 | 3.78 | 3.483 | 0.918 | 0.562 |
| 0.22 | 1.67E+00 | 3.707 | 3.321 | 0.663 | 0.454 |
| −0.26 | 5.56E−01 | 3.797 | 3.317 | 0.56 | 0.553 |
| −0.73 | 1.85E−01 | 3.814 | 3.343 | 0.475 | 0.551 |
| −1.21 | 6.17E−02 | 3.727 | 3.189 | 0.435 | 0.445 |
| −1.69 | 2.06E−02 | 3.333 | 2.898 | 0.342 | 0.48 |
| −2.16 | 6.86E−03 | 2.98 | 2.644 | 0.44 | 0.387 |
| −2.64 | 2.29E−03 | 2.682 | 2.403 | 0.276 | 0.287 |
| −3.12 | 7.62E−04 | 2.316 | 1.705 | 0.255 | 0.211 |
|  | 0 | 0.086 | 0.162 | 0.251 | 0.275 |

TABLE 28

Parameter details of affinity validation

| Immobilization | |
|---|---|
| Ligand | antibodies |
| Capture time (s) | 15 |
| Flow rate (μl/min) | 10 |
| Association & Dissociation | |
| Association contact time (s) | 120 |
| Dissociation contact time (s) | 360 |
| Flow rate (μl/min) | 30 |
| Sample concentrations (nM) | 5 |
| Surface regeneration | |
| Regeneration buffer | 10 mM Glycine-HCl |
| Contact time (s) | 30 |
| Flow rate (μl/min) | 30 |

TABLE 29

Binding kinetics of human CD47 to anti-CD47 antibodies isolated from supernatant of a eukaryotic expression system

| Ligand | Analyte | ka (1/Ms) | kd (1/s) | KD (M) | Rmax (RU) | Chi$^2$ (RU$^2$) |
|---|---|---|---|---|---|---|
| VH1 + VL4 | human CD47 | 4.80E+06 | 1.28E−03 | 2.66E−10 | 19.2 | 0.00884 |
| VH1 + VL3 | human CD47 | 5.00E+06 | 1.37E−03 | 2.74E−10 | 32.4 | 0.208 |
| VH1 + VL2 | human CD47 | 4.32E+06 | 1.59E−03 | 3.68E−10 | 24.5 | 0.184 |
| VH1 + VL1 | human CD47 | 5.10E+06 | 2.10E−03 | 4.12E−10 | 31.9 | 0.00955 |
| chimeric-VH − PTM1 + VL-1 | human CD47 | 7.36E+06 | 2.15E−03 | 2.92E−10 | 85.9 | 0.0839 |
| chimeric-VH + VL-1 | human CD47 | 7.69E+06 | 2.61E−03 | 3.40E−10 | 52.1 | 0.0196 |
| VH4 + VL4 | human CD47 | 5.02E+06 | 2.78E−03 | 5.53E−10 | 19.9 | 0.0175 |
| VH4 + VL3 | human CD47 | 4.85E+06 | 2.87E−03 | 5.91E−10 | 34.1 | 1.26 |
| VH3 + VL4 | human CD47 | 5.49E+06 | 3.05E−03 | 5.55E−10 | 19.9 | 1.07 |
| VH3 + VL3 | human CD47 | 5.18E+06 | 3.12E−03 | 6.02E−10 | 32.7 | 0.958 |
| VH2 + VL4 | human CD47 | 5.67E+06 | 3.32E−03 | 5.85E−10 | 33.1 | 0.511 |
| VH4 + VL2 | human CD47 | 4.34E+06 | 3.35E−03 | 7.72E−10 | 29.1 | 1.07 |
| VH2 + VL3 | human CD47 | 5.83E+06 | 3.48E−03 | 5.97E−10 | 58.6 | 0.0315 |
| VH3 + VL2 | human CD47 | 5.93E+06 | 3.78E−03 | 6.38E−10 | 19.3 | 0.0189 |
| VH2 + VL2 | human CD47 | 5.92E+06 | 4.13E−03 | 6.98E−10 | 37.5 | 0.423 |
| chimeric-VH − PTM2 + VL-1 | human CD47 | 9.06E+06 | 4.42E−03 | 4.88E−10 | 102.7 | 0.0746 |
| VH4 + VL1 | human CD47 | 5.96E+06 | 5.00E−03 | 8.39E−10 | 67.5 | 0.0486 |
| VH3 + VL1 | human CD47 | 6.89E+06 | 5.53E−03 | 8.03E−10 | 47.2 | 0.614 |
| VH2 + VL1 | human CD47 | 6.47E+06 | 6.48E−03 | 1.00E−09 | 133.7 | 0.422 |
| NC | human CD47 | 4.63E+04 | 1.79E−02 | 3.87E−07 | 104 | 1.6 |

TABLE 30

Parameter details of affinity validation

Immobilization

| | |
|---|---|
| Ligand | antibodies |
| Capture time (s) | 12 |
| Flow rate (μl/min) | 10 |

Association & Dissociation

| | |
|---|---|
| Association contact time (s) | 120 |
| Dissociation contact time (s) | 360 |
| Flow rate (μl/min) | 30 |
| Sample concentrations (nM) | 10, 5, 2.5, 1.25, 0.625, 0.3125 |

Surface regeneration

| | |
|---|---|
| Regeneration buffer | 10 mM Glycine-HCl |
| Contact time (s) | 30 |
| Flow rate (μl/min) | 30 |

TABLE 31

Binding kinetics of selected antibodies to human CD47

| Ligand | Analyte | ka (1/Ms) | kd (1/s) | KD (M) | Rmax (RU) | Chi$^2$ (RU$^2$) |
|---|---|---|---|---|---|---|
| chimeric-VH + VL-1 | human CD47 | 5.30E+06 | 2.55E−03 | 4.82E−10 | 52.84 | 0.0243 |
| VH1 − PTM + VL1 | human CD47 | 2.64E+06 | 2.30E−03 | 8.72E−10 | 41.3 | 0.0163 |
| VH1 − PTM + VL2 | human CD47 | 3.46E+06 | 1.93E−03 | 5.56E−10 | 34.55 | 0.0155 |
| VH1 − PTM + VL3 | human CD47 | 3.49E+06 | 1.60E−03 | 4.58E−10 | 34.19 | 0.00844 |

TABLE 32

Summary of procedures for humanization of anti-CD47 antibodies

| Antibody development | Procedures |
|---|---|
| Humanization | Chimeric antibody production with constant region: Human IgG4 (mutant S228P) |
| | Antigen binding confirmation of Chimeric antibody (with Biacore ®) |
| | Chimeric antibody characterization (IC50) |
| | PTM analysis |
| | PTM removal for selected chimeric sequence |
| | Express humanization by rational design and sequence synthesis |
| | Humanized antibody production and affinity ranking |
| | Humanized antibody production (including PTM removal or not) and affinity determination |
| | Humanized antibody characterization |

What is claimed is:

1. An anti-CD47 antibody or an antigen-binding portion thereof, wherein the antibody or antigen-binding portion comprises a heavy chain variable (VH) domain and a light chain variable (VL) domain, wherein:
   (a) the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115;
   (b) the VH domain amino acid sequence comprises HCDR1 of SEQ ID NO: 15, HCDR2 of SEQ ID NO: 17 and HCDR3 of SEQ ID NO: 19; and the VL domain amino acid sequence comprises LCDR1 of SEQ ID NO: 35, LCDR2 of SEQ ID NO: 37 and LCDR3 of SEQ ID NO: 39;
   (c) the VH domain amino acid sequence comprises HCDR1 of SEQ ID NO: 55, HCDR2 of SEQ ID NO: 57 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 79;
   (d) the VH domain amino acid sequence comprises HCDR1 of SEQ ID NO: 94, HCDR2 of SEQ ID NO: 96 and HCDR3 of SEQ ID NO: 98; and the VL domain amino acid sequence comprises LCDR1 of SEQ ID NO: 112, LCDR2 of SEQ ID NO: 77 and LCDR3 of SEQ ID NO: 115;
   (e) the VH domain amino acid sequence comprises HCDR1 of SEQ ID NO: 94, HCDR2 of SEQ ID NO: 96 and HCDR3 of SEQ ID NO: 131; and the VL domain amino acid sequence comprises LCDR1 of SEQ ID NO: 112, LCDR2 of SEQ ID NO: 77 and LCDR3 of SEQ ID NO: 149;
   (f) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115; or (g) the VH domain amino acid sequence comprises HCDR1 of SEQ ID NO: 162, HCDR2 of SEQ ID NO: 163 and HCDR3 of SEQ ID NO: 59; and the VL domain amino acid sequence comprises LCDR1 of SEQ ID NO: 35, LCDR2 of SEQ ID NO: 37 and LCDR3 of SEQ ID NO: 182.

2. The antibody or antigen-binding portion of claim 1, wherein the VH domain amino acid sequence comprises:
(a) SEQ ID NO: 213, or an amino acid sequence that is at least 95%, identical to the amino acid sequence of SEQ ID NO: 213;
(b) SEQ ID NO: 12, or an amino acid sequence that is at least 95%, identical to the amino acid sequence of SEQ ID NO: 12;
(c) SEQ ID NO: 52, or an amino acid sequence that is at least 95%, identical to the amino acid sequence of SEQ ID NO: 52;
(d) SEQ ID NO: 92, or an amino acid sequence that is at least 95%, identical to the amino acid sequence of SEQ ID NO: 92;
(e) SEQ ID NO: 127, or an amino acid sequence that is at least 95%, identical to the amino acid sequence of SEQ ID NO: 127; or
(f) SEQ ID NO: 161, or an amino acid sequence that is at least 95%, identical to the amino acid sequence of SEQ ID NO: 161.

3. The antibody or antigen-binding portion of claim 1, wherein the VL domain amino acid sequence comprises:
(a) SEQ ID NO: 222, or an amino acid sequence that is at least 95%, identical to the amino acid sequence of SEQ ID NO: 222;
(b) SEQ ID NO: 230, or an amino acid sequence that is at least 95%, identical to the amino acid sequence of SEQ ID NO: 230;
(c) SEQ ID NO: 236, or an amino acid sequence that is at least 95%, identical to the amino acid sequence of SEQ ID NO: 236;
(d) SEQ ID NO: 32, or an amino acid sequence that is at least 95%, identical to the amino acid sequence of SEQ ID NO: 32;
(e) SEQ ID NO: 72, or an amino acid sequence that is at least 95%, identical to the amino acid sequence of SEQ ID NO: 72;
(f) SEQ ID NO: 110, or an amino acid sequence that is at least 95%, identical to the amino acid sequence of SEQ ID NO: 110;
(g) SEQ ID NO: 144, or an amino acid sequence that is at least 95%, identical to the amino acid sequence of SEQ ID NO: 144;
(h) SEQ ID NO: 170, or an amino acid sequence that is at least 95%, identical to the amino acid sequence of SEQ ID NO: 170; or
(i) SEQ ID NO: 181, or an amino acid sequence that is at least 95%, identical to the amino acid sequence of SEQ ID NO: 181.

4. The antibody or antigen-binding portion of claim 1, wherein:
(a) the VH domain amino acid sequence comprises SEQ ID NO: 213, or an amino acid sequence that is at least 95%, identical to the amino acid sequence of SEQ ID NO: 213; and the VL domain amino acid sequence comprises SEQ ID NO: 222, or an amino acid sequence that is at least 95%, identical to the amino acid sequence of SEQ ID NO: 222;
(b) the VH domain amino acid sequence comprises SEQ ID NO: 213, or an amino acid sequence that is at least 95%, identical to the amino acid sequence of SEQ ID NO: 213; and the VL domain amino acid sequence comprises SEQ ID NO: 230, or an amino acid sequence that is at least 95%, identical to the amino acid sequence of SEQ ID NO: 230;
(c) the VH domain amino acid sequence comprises SEQ ID NO: 213, or an amino acid sequence that is at least 95%, identical to the amino acid sequence of SEQ ID NO: 213; and the VL domain amino acid sequence comprises SEQ ID NO: 236, or an amino acid sequence that is at least 95%, identical to the amino acid sequence of SEQ ID NO: 236;
(d) the VH domain amino acid sequence comprises SEQ ID NO: 12, or an amino acid sequence that is at least 95%, identical to the amino acid sequence of SEQ ID NO: 12; and the VL domain amino acid sequence comprises SEQ ID NO: 32, or an amino acid sequence that is at least 95%, identical to the amino acid sequence of SEQ ID NO: 32;
(e) the VH domain amino acid sequence comprises SEQ ID NO: 52, or an amino acid sequence that is at least 95%, identical to the amino acid sequence of SEQ ID NO: 52; and the VL domain amino acid sequence comprises SEQ ID NO: 72, or an amino acid sequence that is at least 95%, identical to the amino acid sequence of SEQ ID NO: 72;
(f) the VH domain amino acid sequence comprises SEQ ID NO: 92, or an amino acid sequence that is at least 95%, identical to the amino acid sequence of SEQ ID NO: 92; and the VL domain amino acid sequence comprises SEQ ID NO: 110, or an amino acid sequence that is at least 95%, identical to the amino acid sequence of SEQ ID NO: 110;
(g) the VH domain amino acid sequence comprises SEQ ID NO: 127, or an amino acid sequence that is at least 95%, identical to the amino acid sequence of SEQ ID NO: 127; and the VL domain amino acid sequence comprises SEQ ID NO: 144, or an amino acid sequence that is at least 95%, identical to the amino acid sequence of SEQ ID NO: 144;
(h) the VH domain amino acid sequence comprises SEQ ID NO: 161, or an amino acid sequence that is at least 95%, identical to the amino acid sequence of SEQ ID NO: 161; and the VL domain amino acid sequence comprises SEQ ID NO: 170, or an amino acid sequence that is at least 95%, identical to the amino acid sequence of SEQ ID NO: 170; or
(i) the VH domain amino acid sequence comprises SEQ ID NO: 161, or an amino acid sequence that is at least 95%, identical to the amino acid sequence of SEQ ID NO: 161; and the VL domain amino acid sequence comprises SEQ ID NO: 181, or an amino acid sequence that is at least 95%, identical to the amino acid sequence of SEQ ID NO: 181.

5. The antibody or antigen-binding portion of claim 1, wherein:
(a) the VH domain amino acid sequence comprises SEQ ID NO: 213; and the VL domain amino acid sequence comprises SEQ ID NO: 222;
(b) the VH domain amino acid sequence comprises SEQ ID NO: 213; and the VL domain amino acid sequence comprises SEQ ID NO: 230;
(c) the VH domain amino acid sequence comprises SEQ ID NO: 213; and the VL domain amino acid sequence comprises SEQ ID NO: 236;
(d) the VH domain amino acid sequence comprises SEQ ID NO: 12; and the VL domain amino acid sequence comprises SEQ ID NO: 32;

(e) the VH domain amino acid sequence comprises SEQ ID NO: 52; and the VL domain amino acid sequence comprises SEQ ID NO: 72;

(f) the VH domain amino acid sequence comprises SEQ ID NO: 92; and the VL domain amino acid sequence comprises SEQ ID NO: 110;

(g) the VH domain amino acid sequence comprises SEQ ID NO: 127; and the VL domain amino acid sequence comprises SEQ ID NO: 144;

(h) the VH domain amino acid sequence comprises SEQ ID NO: 161; and the VL domain amino acid sequence comprises SEQ ID NO: 170; or (i) the VH domain amino acid sequence comprises SEQ ID NO: 161; and the VL domain amino acid sequence comprises SEQ ID NO: 181.

6. An anti-CD47 antibody or an antigen-binding portion thereof, wherein the antibody or antigen-binding portion comprises a VH domain and a VL domain, wherein: the VH domain amino acid sequence comprises HCDR1 of SEQ ID NO: 162, HCDR2 of SEQ ID NO: 216 and HCDR3 of SEQ ID NO: 59; and the VL domain amino acid sequence comprises LCDR1 of SEQ ID NO: 75, LCDR2 of SEQ ID NO: 77 and LCDR3 of SEQ ID NO: 115.

7. The antibody or antigen-binding portion of claim 1, wherein the antibody or antigen-binding portion inhibits or reduces the binding of CD47 to thrombospondin 1 (TSP-1).

8. The antibody or antigen-binding portion of claim 1, wherein the VH domain, the VL domain, or both the VH domain and the VL domain comprise one or more human framework region amino acid sequences.

9. The antibody or antigen-binding portion of claim 1, wherein the anti-CD47 antibody is an anti-human CD47 antibody.

10. The antibody or antigen-binding portion of claim 1, wherein the antibody is monoclonal.

11. The antibody or antigen-binding portion of claim 1, wherein the antibody or antigen-binding portion is chimeric or humanized.

12. The antibody or antigen-binding portion of claim 1, wherein the antibody or antigen-binding portion is multi-specific.

13. The antibody or antigen-binding portion of claim 12, wherein the antibody or antigen-binding portion is bispecific.

14. The antibody or antigen-binding portion of claim 1, wherein the antigen-binding portion is a Fab, a F(ab')$_2$, a Fab', a Fv, a scFv, a Fd, a diabody, a triabody, a tetrabody or a bis-scFv.

15. The antibody or antigen-binding portion of claim 1, wherein the antibody or antigen-binding portion comprises an immunoglobulin constant region.

16. The antibody or antigen-binding portion of claim 15, wherein the immunoglobulin constant region is IgG, IgE, IgM, IgD, IgA or IgY.

17. The antibody or antigen-binding portion of claim 15, wherein the immunoglobulin constant region is IgG1, IgG2, IgG3, IgG4, IgA1 or IgA2.

18. The antibody or antigen-binding portion of claim 15, wherein the immunoglobulin constant region is immunologically inert.

19. The antibody or antigen-binding portion of claim 15, wherein the immunoglobulin constant region is a wild-type human IgG1 constant region, a wild-type human IgG2 constant region, a wild-type human IgG4 constant region, a human IgG1 constant region comprising the amino acid substitutions L234A, L235A and G237A, a human IgG1 constant region comprising the amino acid substitutions L234A, L235A, G237A and P331S or a human IgG4 constant region comprising the amino acid substitution S228P, wherein numbering is according to the EU numbering system.

20. A pharmaceutical composition comprising the antibody or antigen-binding portion of claim 1, and a pharmaceutically acceptable carrier, diluent or excipient.

21. An immunoconjugate comprising the antibody or antigen-binding portion of claim 1 linked to a therapeutic agent.

22. The immunoconjugate of claim 21, wherein the therapeutic agent is a small molecule drug.

\* \* \* \* \*